US011634737B2

(12) United States Patent
Tsakraklides et al.

(10) Patent No.: US 11,634,737 B2
(45) Date of Patent: Apr. 25, 2023

(54) OLEIC ACID PRODUCTION IN YEAST

(71) Applicant: Ginkgo Bioworks, Inc., Boston, MA (US)

(72) Inventors: Vasiliki Tsakraklides, Lexington, MA (US); Elena E. Brevnova, Belmont, MA (US); Jonathan Friedlander, Cambridge, MA (US); Annapurna Kamineni, Arlington, MA (US); Arthur J. Shaw, IV, Belmont, MA (US)

(73) Assignee: Ginkgo Bioworks, Inc., Boston, MA (US)

( * ) Notice: Subject to any disclaimer, the term of this patent is extended or adjusted under 35 U.S.C. 154(b) by 0 days.

(21) Appl. No.: 15/534,818

(22) PCT Filed: Dec. 9, 2015

(86) PCT No.: PCT/US2015/064710
§ 371 (c)(1),
(2) Date: Jun. 9, 2017

(87) PCT Pub. No.: WO2016/094520
PCT Pub. Date: Jun. 16, 2016

(65) Prior Publication Data

US 2017/0369910 A1 Dec. 28, 2017

Related U.S. Application Data

(60) Provisional application No. 62/090,169, filed on Dec. 10, 2014.

(51) Int. Cl.
*C12N 1/16* (2006.01)
*C12P 7/6463* (2022.01)
(Continued)

(52) U.S. Cl.
CPC .............. *C12P 7/6463* (2013.01); *C12N 1/16* (2013.01); *C12N 9/1029* (2013.01); *C12N 15/80* (2013.01);
(Continued)

(58) Field of Classification Search
None
See application file for complete search history.

(56) References Cited

U.S. PATENT DOCUMENTS

2004/0006792 A1* 1/2004 Fillatti ................. C12N 9/0083 800/281
2006/0094091 A1 5/2006 Macool et al. ............... 435/134
(Continued)

FOREIGN PATENT DOCUMENTS

WO WO-2009/129583 A1 10/2009

OTHER PUBLICATIONS

UniProt Accession No. A0A060TAX1_BLAAD, published Sep. 3, 2014 (Year: 2014).*
(Continued)

*Primary Examiner* — Richard C Ekstrom
(74) *Attorney, Agent, or Firm* — Foley Hoag LLP; Janine S. Ladislaw; Mohanad Mossalam

(57) ABSTRACT

Disclosed are transformed cells comprising one or more genetic modifications that affect the lipid content of the cell, e.g., by increasing the concentration of oleic acid in the cell relative to an unmodified cell of the same type. Also disclosed are methods for modifying the lipid content of a cell by increasing the activity of one or more proteins in the cell and/or by decreasing the activity of one or more proteins in the same cell.

22 Claims, 18 Drawing Sheets

Specification includes a Sequence Listing.

(51) Int. Cl.

| | |
|---|---|
| ***C12N 9/10*** | (2006.01) |
| ***C12N 15/80*** | (2006.01) |

(52) U.S. Cl.

CPC . *C12Y 203/0102* (2013.01); *C12Y 203/01015* (2013.01); *C12Y 203/01158* (2013.01); *C12Y 203/01199* (2015.07); *Y02E 50/10* (2013.01)

(56) References Cited

U.S. PATENT DOCUMENTS

| | | | | |
|---|---|---|---|---|
| 2011/0314725 | A1 | 12/2011 | Petrie et al. | |
| 2013/0123361 | A1 | 5/2013 | Damude | 514/560 |
| 2013/0247451 | A1 | 9/2013 | Vanhercke et al. | |
| 2013/0323823 | A1* | 12/2013 | Franklin | C12N 9/0071 435/257.2 |
| 2014/0335578 | A1* | 11/2014 | San | C12P 7/649 435/134 |
| 2017/0191073 | A1* | 7/2017 | Brevnova | C07K 14/39 |
| 2017/0369910 | A1* | 12/2017 | Tsakraklides | C12P 7/6463 |

OTHER PUBLICATIONS

UniProt Accession No. Q6C5M4_YARLI, published Aug. 16, 2004 (Year: 2004).*

UniProt Accession No. Q6CF55_YARLI, published Aug. 16, 2004 (Year: 2004).*

UniProt Accession No. GPT2_YEAST, published Jun. 1, 1994 (Year: 1994).*

NCBI Reference Sequence XP_003326562.1, published Sep. 6, 2012 (Year: 2012).*

UniProt Accession No. A0A060TGR1_BLAAD, published Sep. 3, 2014 (Year: 2014).*

GenBank Accession No. CAG83378.1, published Mar. 16, 2012 (Year: 2012).*

NCBI Reference Sequence No. XP_502557.1, published Oct. 29, 2008 (Year: 2008).*

International Search Report and Written Opinion in International Application No. PCT/US2015/064710 dated Apr. 19, 2016.

Genbank Accession No. CDR46911.1 RHTO0S13e03246g1_1 Rhodosporidium toroloides, retrieved from the internet: <URL: http://www.ncbi.nlm.nih.gov/protein/647400993?sat=18&satkey=24121726> accessed Jul. 11, 2017.

International Preliminary Report on Patentability in International Application No. PCT/US2015/064710 dated Jun. 13, 2017.

Cai et al., "A conserved evolutionary mechanism permits Δ9 desaturation of very-long-chain fatty acyl lipids," Journal of Biological Chemistry, 295(32): 11337-11345 (2020).

Dar et al., "The FAD2 Gene in Plants: Occurrence, Regulation, and Role," Frontiers in Plant Science, 8: Article 1789 (2017).

Muto et al., "Identification and Functional Analysis of Delta-9 Desaturase, a Key Enzyme in PUFA Synthesis, Isolated from the Oleaginous Diatom Fistulifera," Plos One, 8(9): e73507 (2013).

Sakuradani et al., "Δ9-Fatty acid desaturase from arachidonic acid-producing fungus Unique gene sequence and its heterologous expression in a fungus, Aspergillus," European Journal of Biochemistry, 260(1): 208-216 (1999).

Sheng et al., "Metabolic engineering of yeast to produce fatty acid-derived biofuels: bottlenecks and solutions," Frontiers in Microbiology, 6: Article 554 (2015).

Yilmaz et al., "Determination of Substrate Preferences for Desaturases and Elongases for Production of Docosahexaenoic Acid from Oleic Acid in Engineered Canola," Lipids, 52(3): 207-222 (2017).

EPO Third Party Observations for EP Application No. 17193531.5 dated Sep. 9, 2022.

Kajiwara, "Overexpression of the OL£1 gene enhances ethanol fermentation by *Saccharomyces cerevisiae*" Applied Microbiology Biotechnology, 53:568-574 (2000).

Yamada et al., "High Expression of Unsaturated Fatty Acid Synthesis Gene OLE1 in Sake Yeasts", Journal of Bioscience and Bioengineering 99(5): 512-516 (2005).

* cited by examiner

Figure 15
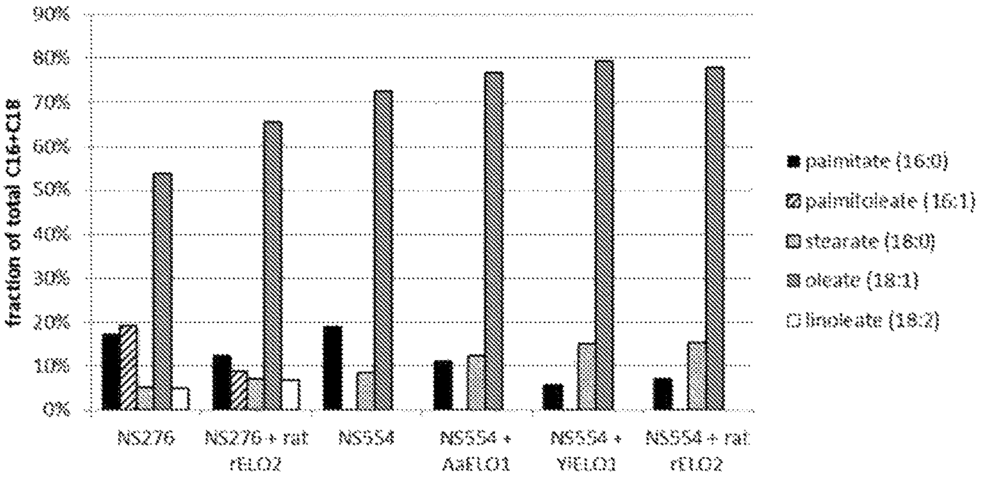
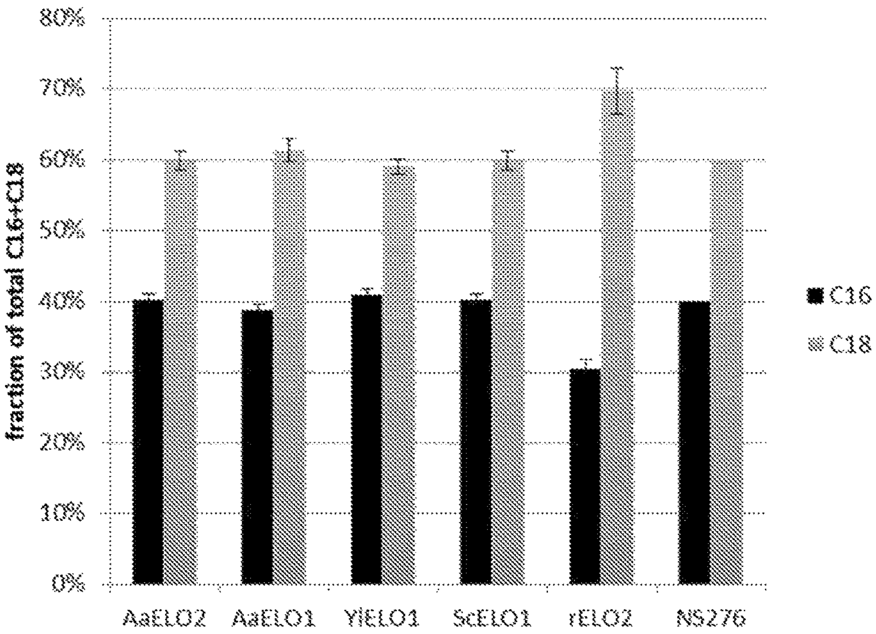
Figure 16

SEQUENCE LISTING

```
<160> NUMBER OF SEQ ID NOS: 168

<210> SEQ ID NO 1
<211> LENGTH: 419
<212> TYPE: PRT
<213> ORGANISM: Yarrowia lipolytica

<400> SEQUENCE: 1

Met Asp Ser Thr Thr Gln Thr Asn Thr Gly Thr Gly Lys Val Ala Val
1               5                   10                  15

Gln Pro Pro Thr Ala Phe Ile Lys Pro Ile Glu Lys Val Ser Glu Pro
            20                  25                  30
```

-continued

```
Val Tyr Asp Thr Phe Gly Asn Glu Phe Thr Pro Pro Asp Tyr Ser Ile
        35                  40                  45

Lys Asp Ile Leu Asp Ala Ile Pro Gln Glu Cys Tyr Lys Arg Ser Tyr
    50                  55                  60

Val Lys Ser Tyr Ser Tyr Val Ala Arg Asp Cys Phe Phe Ile Ala Val
65                  70                  75                  80

Phe Ala Tyr Met Ala Tyr Ala Tyr Leu Pro Leu Ile Pro Ser Ala Ser
                85                  90                  95

Gly Arg Ala Val Ala Trp Ala Met Tyr Ser Ile Val Gln Gly Leu Phe
            100                 105                 110

Gly Thr Gly Leu Trp Val Leu Ala His Glu Cys Gly His Ser Ala Phe
        115                 120                 125

Ser Asp Ser Asn Thr Val Asn Asn Val Thr Gly Trp Val Leu His Ser
    130                 135                 140

Ser Met Leu Val Pro Tyr Tyr Ala Trp Lys Leu Thr His Ser Met His
145                 150                 155                 160

His Lys Ser Thr Gly His Leu Thr Arg Asp Met Val Phe Val Pro Lys
                165                 170                 175

Asp Arg Lys Glu Phe Met Glu Asn Arg Gly Ala His Asp Trp Ser Glu
            180                 185                 190

Leu Ala Glu Asp Ala Pro Leu Met Thr Leu Tyr Gly Leu Ile Thr Gln
        195                 200                 205

Gln Val Phe Gly Trp Pro Leu Tyr Leu Leu Ser Asn Val Thr Gly Gln
    210                 215                 220

Lys Tyr Pro Lys Leu Asn Lys Trp Ala Val Asn His Phe Asn Pro Asn
225                 230                 235                 240

Ala Pro Leu Phe Glu Lys Lys Asp Trp Phe Asn Ile Trp Ile Ser Asn
                245                 250                 255

Val Gly Ile Gly Ile Thr Met Ser Val Ile Ala Tyr Ser Ile Asn Arg
            260                 265                 270

Trp Gly Leu Ala Ser Val Thr Leu Tyr Tyr Leu Ile Pro Tyr Leu Trp
        275                 280                 285

Val Asn His Trp Leu Val Ala Ile Thr Tyr Leu Gln His Thr Asp Pro
    290                 295                 300

Thr Leu Pro His Tyr His Ala Asp Gln Trp Asn Phe Thr Arg Gly Ala
305                 310                 315                 320

Ala Ala Thr Ile Asp Arg Glu Phe Gly Phe Ile Gly Ser Phe Cys Phe
                325                 330                 335

His Asp Ile Ile Glu Thr His Val Leu His His Tyr Val Ser Arg Ile
            340                 345                 350

Pro Phe Tyr Asn Ala Arg Ile Ala Thr Glu Lys Ile Lys Lys Val Met
        355                 360                 365

Gly Lys His Tyr Arg His Asp Asp Thr Asn Phe Ile Lys Ser Leu Tyr
    370                 375                 380

Thr Val Ala Arg Thr Cys Gln Phe Val Glu Gly Lys Glu Gly Ile Gln
385                 390                 395                 400

Met Phe Arg Asn Val Asn Gly Val Gly Val Ala Pro Asp Gly Leu Pro
                405                 410                 415

Ser Lys Lys


<210> SEQ ID NO 2
<211> LENGTH: 1260
<212> TYPE: DNA
<213> ORGANISM: Yarrowia lipolytica
```

-continued

<400> SEQUENCE: 2

```
atggattcga ccacgcagac caacaccggc accggcaagg tggccgtgca gccccccacg      60
gccttcatta agcccattga gaaggtgtcc gagcccgtct acgacacctt tggcaacgag     120
ttcactcctc cagactactc tatcaaggat attctggatg ccattcccca ggagtgctac     180
aagcggtcct acgttaagtc ctactcgtac gtggcccgag actgcttctt tatcgccgtt     240
tttgcctaca tggcctacgc gtacctgcct cttattccct cggcttccgg ccgagctgtg     300
gcctgggcca tgtactccat tgtccagggt ctgtttggca ccggtctgtg ggttcttgcc     360
cacgagtgtg gccactctgc tttctccgac tctaacaccg tcaacaacgt caccggatgg     420
gttctgcact cctccatgct ggtcccttac tacgcctgga agctgaccca ctccatgcac     480
cacaagtcca ctggtcacct cacccgtgat atggtgtttg tgcccaagga ccgaaaggag     540
tttatggaga accgaggcgc ccatgactgg tctgagcttg ctgaggacgc tcccctcatg     600
accctctacg gcctcatcac ccagcaggtg tttggatggc ctctgtatct gctgtctaac     660
gttaccggac agaagtaccc caagctcaac aaatgggctg tcaaccactt caaccccaac     720
gccccgctgt ttgagaagaa ggactggttc aacatctgga tctctaacgt cggtattggt     780
atcaccatgt ccgtcatcgc atactccatc aaccgatggg gcctggcttc cgtcaccctc     840
tactacctga tcccctacct gtgggtcaac cactggctcg tggccatcac ctacctgcag     900
cacaccgacc ccactctgcc ccactaccac gccgaccagt ggaacttcac ccgaggagcc     960
gccgccacca tcgaccgaga gtttggcttc atcggctcct tctgcttcca tgacatcatc    1020
gagacccacg ttctgcacca ctacgtgtct cgaattccct tctacaacgc ccgaatcgcc    1080
actgagaaga tcaagaaggt catgggcaag cactaccgac acgacgacac caacttcatc    1140
aagtctcttt acactgtcgc ccgaacctgc cagtttgttg aaggtaagga aggcattcag    1200
atgtttagaa acgtcaatgg agtcggagtt gctcctgacg gcctgccttc taaaaagtag    1260
```

<210> SEQ ID NO 3
<211> LENGTH: 482
<212> TYPE: PRT
<213> ORGANISM: Yarrowia lipolytica

<400> SEQUENCE: 3

```
Met Val Lys Asn Val Asp Gln Val Asp Leu Ser Gln Val Asp Thr Ile
1               5                   10                  15

Ala Ser Gly Arg Asp Val Asn Tyr Lys Val Lys Tyr Thr Ser Gly Val
            20                  25                  30

Lys Met Ser Gln Gly Ala Tyr Asp Asp Lys Gly Arg His Ile Ser Glu
        35                  40                  45

Gln Pro Phe Thr Trp Ala Asn Trp His Gln His Ile Asn Trp Leu Asn
    50                  55                  60

Phe Ile Leu Val Ile Ala Leu Pro Leu Ser Ser Phe Ala Ala Ala Pro
65                  70                  75                  80

Phe Val Ser Phe Asn Trp Lys Thr Ala Ala Phe Ala Val Gly Tyr Tyr
                85                  90                  95

Met Cys Thr Gly Leu Gly Ile Thr Ala Gly Tyr His Arg Met Trp Ala
            100                 105                 110

His Arg Ala Tyr Lys Ala Ala Leu Pro Val Arg Ile Ile Leu Ala Leu
        115                 120                 125

Phe Gly Gly Gly Ala Val Glu Gly Ser Ile Arg Trp Trp Ala Ser Ser
    130                 135                 140
```

```
His Arg Val His His Arg Trp Thr Asp Ser Asn Lys Asp Pro Tyr Asp
145                 150                 155                 160

Ala Arg Lys Gly Phe Trp Phe Ser His Phe Gly Trp Met Leu Leu Val
                165                 170                 175

Pro Asn Pro Lys Asn Lys Gly Arg Thr Asp Ile Ser Asp Leu Asn Asn
            180                 185                 190

Asp Trp Val Val Arg Leu Gln His Lys Tyr Tyr Val Tyr Val Leu Val
        195                 200                 205

Phe Met Ala Ile Val Leu Pro Thr Leu Val Cys Gly Phe Gly Trp Gly
    210                 215                 220

Asp Trp Lys Gly Gly Leu Val Tyr Ala Gly Ile Met Arg Tyr Thr Phe
225                 230                 235                 240

Val Gln Gln Val Thr Phe Cys Val Asn Ser Leu Ala His Trp Ile Gly
                245                 250                 255

Glu Gln Pro Phe Asp Asp Arg Arg Thr Pro Arg Asp His Ala Leu Thr
            260                 265                 270

Ala Leu Val Thr Phe Gly Glu Gly Tyr His Asn Phe His His Glu Phe
        275                 280                 285

Pro Ser Asp Tyr Arg Asn Ala Leu Ile Trp Tyr Gln Tyr Asp Pro Thr
    290                 295                 300

Lys Trp Leu Ile Trp Thr Leu Lys Gln Val Gly Leu Ala Trp Asp Leu
305                 310                 315                 320

Gln Thr Phe Ser Gln Asn Ala Ile Glu Gln Gly Leu Val Gln Gln Arg
                325                 330                 335

Gln Lys Lys Leu Asp Lys Trp Arg Asn Asn Leu Asn Trp Gly Ile Pro
            340                 345                 350

Ile Glu Gln Leu Pro Val Ile Glu Phe Glu Glu Phe Gln Glu Gln Ala
        355                 360                 365

Lys Thr Arg Asp Leu Val Leu Ile Ser Gly Ile Val His Asp Val Ser
    370                 375                 380

Ala Phe Val Glu His His Pro Gly Gly Lys Ala Leu Ile Met Ser Ala
385                 390                 395                 400

Val Gly Lys Asp Gly Thr Ala Val Phe Asn Gly Gly Val Tyr Arg His
                405                 410                 415

Ser Asn Ala Gly His Asn Leu Leu Ala Thr Met Arg Val Ser Val Ile
            420                 425                 430

Arg Gly Gly Met Glu Val Glu Val Trp Lys Thr Ala Gln Asn Glu Lys
        435                 440                 445

Lys Asp Gln Asn Ile Val Ser Asp Glu Ser Gly Asn Arg Ile His Arg
    450                 455                 460

Ala Gly Leu Gln Ala Thr Arg Val Glu Asn Pro Gly Met Ser Gly Met
465                 470                 475                 480

Ala Ala
```

<210> SEQ ID NO 4
<211> LENGTH: 1449
<212> TYPE: DNA
<213> ORGANISM: Yarrowia lipolytica

<400> SEQUENCE: 4

```
atggtgaaaa acgtggacca agtggatctc tcgcaggtcg acaccattgc ctccggccga      60

gatgtcaact acaaggtcaa gtacacctcc ggcgttaaga tgagccaggg cgcctacgac     120

gacaagggcc gccacatttc cgagcagccc ttcacctggg ccaactggca ccagcacatc     180
```

-continued

```
aactggctca acttcattct ggtgattgcg ctgcctctgt cgtcctttgc tgccgctccc    240

ttcgtctcct tcaactggaa gaccgccgcg tttgctgtcg gctattacat gtgcaccggt    300

ctcggtatca ccgccggcta ccaccgaatg tgggcccatc gagcctacaa ggccgctctg    360

cccgttcgaa tcatccttgc tctgtttgga ggaggagctg tcgagggctc catccgatgg    420

tgggcctcgt ctcaccgagt ccaccaccga tggaccgact ccaacaagga cccttacgac    480

gcccgaaagg gattctggtt ctcccacttt ggctggatgc tgcttgtgcc caaccccaag    540

aacaagggcc gaactgacat ttctgacctc aacaacgact gggttgtccg actccagcac    600

aagtactacg tttacgttct cgtcttcatg gccattgttc tgcccaccct cgtctgtggc    660

tttggctggg gcgactggaa gggaggtctt gtctacgccg gtatcatgcg atacaccttt    720

gtgcagcagg tgactttctg tgtcaactcc cttgcccact ggattggaga gcagcccttc    780

gacgaccgac gaactccccg agaccacgct cttaccgccc tggtcacctt tggagagggc    840

taccacaact tccaccacga gttcccctcg gactaccgaa acgccctcat ctggtaccag    900

tacgacccca ccaagtggct catctggacc ctcaagcagg ttggtctcgc ctgggacctc    960

cagaccttct cccagaacgc catcgagcag ggtctcgtgc agcagcgaca gaagaagctg   1020

gacaagtggc gaaacaacct caactggggt atccccattg agcagctgcc tgtcattgag   1080

tttgaggagt tccaagagca ggccaagacc cgagatctgg ttctcatttc tggcattgtc   1140

cacgacgtgt ctgcctttgt cgagcaccac cctggtggaa aggccctcat tatgagcgcc   1200

gtcggcaagg acggtaccgc tgtcttcaac ggaggtgtct accgacactc caacgctggc   1260

cacaacctgc ttgccaccat gcgagtttcg gtcattcgag gcggcatgga ggttgaggtg   1320

tggaagactg cccagaacga aaagaaggac cagaacattg tctccgatga gagtggaaac   1380

cgaatccacc gagctggtct ccaggccacc cgggtcgaga accccggtat gtctggcatg   1440

gctgcttag                                                           1449
```

<210> SEQ ID NO 5
<211> LENGTH: 304
<212> TYPE: PRT
<213> ORGANISM: Yarrowia lipolytica

<400> SEQUENCE: 5

```
Met Leu Ser Ser Ile Ser Pro Asp Leu Tyr Ser Ser Phe Ser Phe Lys
1               5                   10                  15

Asn Ser Leu Ala Glu Ala Met Pro Ser Val Pro His Glu Leu Ile Asn
            20                  25                  30

Ser Lys Thr Leu Ser Trp Met Tyr Asn Ala Ser Leu Asp Ile Arg Val
        35                  40                  45

Pro Leu Thr Ile Gly Thr Ile Tyr Ala Val Ser Val His Leu Thr Asn
    50                  55                  60

Ser Ser Glu Arg Ile Lys Lys Arg Gln Pro Ile Ala Phe Ala Lys Thr
65                  70                  75                  80

Ala Leu Phe Lys Trp Leu Cys Val Leu His Asn Ala Gly Leu Cys Leu
                85                  90                  95

Tyr Ser Ala Trp Thr Phe Val Gly Ile Leu Asn Ala Val Lys His Ala
            100                 105                 110

Tyr Gln Ile Thr Gly Asp Ser Ser Ala Pro Phe Ser Phe Asn Thr Leu
        115                 120                 125

Trp Gly Ser Phe Cys Ser Arg Asp Ser Leu Trp Val Thr Gly Leu Asn
    130                 135                 140
```

```
Tyr Tyr Gly Tyr Trp Phe Tyr Leu Ser Lys Phe Tyr Glu Val Val Asp
145                 150                 155                 160

Thr Met Ile Ile Leu Ala Lys Gly Lys Pro Ser Ser Met Leu Gln Thr
                165                 170                 175

Tyr His His Thr Gly Ala Met Phe Ser Met Trp Ala Gly Ile Arg Phe
            180                 185                 190

Ala Ser Pro Pro Ile Trp Ile Phe Val Val Phe Asn Ser Leu Ile His
        195                 200                 205

Thr Ile Met Tyr Phe Tyr Tyr Thr Leu Thr Thr Leu Lys Ile Lys Val
    210                 215                 220

Pro Lys Ile Leu Lys Ala Ser Leu Thr Thr Ala Gln Ile Thr Gln Ile
225                 230                 235                 240

Val Gly Gly Gly Ile Leu Ala Ala Ser His Ala Phe Ile Tyr Tyr Lys
                245                 250                 255

Asp His Gln Thr Glu Thr Val Cys Ser Cys Leu Thr Thr Gln Gly Gln
            260                 265                 270

Phe Phe Ala Leu Ala Val Asn Val Ile Tyr Leu Ser Pro Leu Ala Tyr
        275                 280                 285

Leu Phe Ile Ala Phe Trp Ile Arg Ser Tyr Leu Lys Ala Lys Ser Asn
    290                 295                 300
```

<210> SEQ ID NO 6
<211> LENGTH: 915
<212> TYPE: DNA
<213> ORGANISM: Yarrowia lipolytica

<400> SEQUENCE: 6

```
atgctctcgt caatctcgcc cgacctatac tcgtccttct cgttcaaaaa ctcgctcgcc     60

gaggccatgc cctccgtgcc acacgaactc atcaactcaa aaacactctc atggatgtac    120

aatgcctctc tggacattcg ggttcctctg actatcggaa ccatctacgc cgtctccgtg    180

cacctgacca actcatctga acgaatcaag aaacgccagc ccattgcctt tgccaagacc    240

gcactcttca agtggctctg tgtcctccac aatgcaggtc tgtgtctcta ctcagcatgg    300

acctttgtcg gtatcctcaa cgccgtcaaa cacgcctacc aaatcacagg agacagctcc    360

gcccccttct ccttcaacac cctctgggga tcgttttgtt cacgtgactc cctctgggtc    420

accggcctca actactacgg atactggttc tatctgtcca aattctacga agtggtggac    480

accatgatca tcctcgcaaa gggaaaaccg tcctcaatgc tccagacata ccaccacacc    540

ggcgccatgt tctccatgtg ggccggcatc cgattcgcct ctccccccat ctggatcttt    600

gtggttttca actccctcat ccacacaatc atgtactttt actacaccct caccaccctc    660

aagatcaagg ttcccaagat cctcaaggca tctctgacca ccgcccagat cacccagatt    720

gtcggaggtg gcatcctggc tgcctcccac gcctttattt attacaagga ccaccagact    780

gagaccgtct gttcttgtct cactacccag ggtcagtttt tcgctctcgc cgtcaatgtc    840

atctatctga gtcctctggc ctatctcttt attgccttct ggattcgatc ttacttgaag    900

gccaagtcca actag                                                      915
```

<210> SEQ ID NO 7
<211> LENGTH: 486
<212> TYPE: PRT
<213> ORGANISM: Arxula adeninivorans

<400> SEQUENCE: 7

-continued

```
Met Asn Gly Pro Glu Glu Val Asn Leu Glu Glu Val Gln Ala Ile Ala
1               5                   10                  15

Ser Gly Ala Glu Val Arg Ala Lys Val Asn Ile Asn Arg Arg Arg Gln
            20                  25                  30

Glu Glu Gln Ala Ala Ala Ala Ala Ala Ser Ser Gly Ser Thr Lys Thr
        35                  40                  45

His Ile Ser Glu Gln Ala Phe Thr Leu Ala Asn Trp His Lys His Phe
    50                  55                  60

Asn Trp Ile Asn Thr Thr Ile Ile Ala Ile Ile Pro Ala Ile Gly Phe
65                  70                  75                  80

Leu Ser Val Pro Phe Ile Pro Val His Gly Lys Thr Leu Ala Trp Ala
                85                  90                  95

Phe Val Tyr Tyr Phe Leu Thr Gly Leu Gly Ile Thr Ala Gly Tyr His
            100                 105                 110

Arg Leu Trp Ala His Arg Ala Tyr Ser Ala Ser Trp Pro Leu Arg Val
        115                 120                 125

Phe Leu Ala Leu Leu Gly Ala Gly Ala Gly Glu Gly Ser Val Lys Trp
    130                 135                 140

Trp Ser Asn Gly His Arg Thr His His Arg Tyr Thr Asp Thr Asp Lys
145                 150                 155                 160

Asp Pro Tyr Asn Ala Lys Arg Gly Phe Trp Phe Ser His Met Gly Trp
                165                 170                 175

Met Met Phe Lys Gln Asn Pro Lys Leu Lys Gly Arg Cys Asp Ile Ser
            180                 185                 190

Asp Leu Ile Cys Asp Pro Ile Ile Arg Trp Gln His Arg His Tyr Ile
        195                 200                 205

Trp Ile Met Ala Ala Met Ser Phe Val Phe Pro Ser Val Val Ala Gly
    210                 215                 220

Leu Gly Trp Gly Asp Tyr Leu Gly Gly Phe Val Phe Ala Gly Ile Leu
225                 230                 235                 240

Arg Gln Phe Val Val His Gln Ser Thr Phe Cys Val Asn Ser Leu Ala
                245                 250                 255

His Trp Leu Gly Glu Gln Pro Phe Asp Asp Asn Arg Ser Pro Arg Asp
            260                 265                 270

His Val Leu Thr Ala Phe Ala Thr Leu Gly Glu Gly Tyr His Asn Phe
        275                 280                 285

His His Glu Phe Pro Ser Asp Tyr Arg Asn Ala Ile Lys Trp Tyr Gln
    290                 295                 300

Tyr Asp Pro Thr Lys Ile Phe Ile Trp Thr Met Lys Gln Leu Gly Leu
305                 310                 315                 320

Ala Ser Asn Leu Gln Thr Phe Ser Gln Asn Ala Ile Glu Gln Gly Leu
                325                 330                 335

Val Gln Gln Lys Gln Lys Lys Leu Asp Arg Trp Arg Ala Arg Leu Asn
            340                 345                 350

Trp Gly Val Pro Ile Glu Gln Leu Pro Val Ile Glu Tyr Asp Asp Phe
        355                 360                 365

Lys Asp Glu Ser Ser Ser Arg Ser Leu Val Leu Ile Ser Gly Ile Val
    370                 375                 380

His Asp Val Thr Asp Phe Ile Asp Lys His Pro Gly Gly Lys Ala Leu
385                 390                 395                 400

Ile Lys Ser Ala Ile Gly Lys Asp Gly Thr Ala Val Phe Asn Gly Gly
                405                 410                 415

Val Tyr Lys His Ser Asn Ala Ala His Asn Leu Leu Ala Thr Met Arg
```

-continued

```
            420                 425                 430

Val Ala Val Ile Arg Gly Gly Met Glu Val Glu Val Trp Lys Arg Ala
        435                 440                 445

Gln Gly Glu Lys Lys Asp Val Asp Pro Val Ala Asp Ser Ala Gly Asp
    450                 455                 460

Arg Ile Leu Arg Ala Gly Asp Gln Pro Ser Arg Val Pro Glu Ala Arg
465                 470                 475                 480

Val Ser Gly Arg Ala Ala
                485


<210> SEQ ID NO 8
<211> LENGTH: 1461
<212> TYPE: DNA
<213> ORGANISM: Arxula adeninivorans

<400> SEQUENCE: 8

atgaacggtc ccgaagaggt gaatctcgaa gaagtccagg ccattgcgtc tggagccgaa      60

gttcgagcta aggtcaacat caaccgacga aggcaagagg agcaggctgc cgccgctgct     120

gcctccagcg gttcgacaaa gactcatatc tccgagcagg ctttcaccct cgccaactgg     180

cacaagcatt tcaattggat caacacaacc atcattgcca ttatcccagc aatcggcttt     240

ttgtcggtgc ctttcattcc tgtgcacggc aagacattag cgtgggcatt cgtctactac     300

tttttgaccg gtctgggaat caccgccgga taccaccgtc tgtgggctca ccgggcttac     360

agtgcatcat ggcccctgcg agtgttcttg gcacttttgg gtgctggagc cggtgagggt     420

tcagtaaagt ggtggtctaa tggacaccgc actcaccacc gttacactga cactgacaag     480

gatccttaca atgccaagcg aggattctgg ttctcccaca tgggctggat gatgttcaag     540

cagaacccca agctcaaggg acgatgcgac atttccgatc ttatctgcga ccctattatt     600

cgatggcagc accgacacta catttggatc atggcagcaa tgtcgtttgt attcccttct     660

gtagttgctg gactgggctg gggagactac ctgggaggat ttgtgtttgc aggaatcctg     720

cgacagtttg ttgtccacca gtcgaccttc tgtgtcaact cgcttgccca ctggctggga     780

gagcagcctt ttgacgacaa ccgatctcct cgagaccacg ttctgactgc gtttgctact     840

ctgggtgagg gttaccacaa cttccaccac gagttcccct ccgactaccg taacgctatc     900

aagtggtacc agtacgaccc taccaagatc ttcatctgga ccatgaagca gcttggtctg     960

gcctctaacc tgcagacttt ctcccagaat gctattgagc agggtctggt acagcagaag    1020

cagaagaagc tggaccgatg gagagctcgt ctcaactggg gagtgcctat tgagcagctt    1080

cctgtaattg agtacgacga cttcaaggac gagtcatctt cccgatcttt ggtcctcatt    1140

tctggaattg tccacgatgt taccgacttt attgacaagc accctggtgg aaaggctctc    1200

atcaagagcg ccattggcaa ggacggaact gccgtgttca acggaggtgt gtacaagcac    1260

tccaacgctg ctcacaacct gctggccact atgcgtgtag ctgtcattcg aggaggaatg    1320

gaagtcgagg tctggaagcg tgcccagggc gagaagaagg atgttgaccc tgtcgccgat    1380

tccgctggtg accgtatcct gcgagctggc gaccagcctt ctcgtgttcc tgaggcccgt    1440

gtctctggcc gcgctgctta a                                               1461


<210> SEQ ID NO 9
<211> LENGTH: 545
<212> TYPE: PRT
<213> ORGANISM: Rhodosporidium toruloides

<400> SEQUENCE: 9
```

-continued

```
Met Thr Ala Ser Ser Ala Leu Glu Thr Ser Leu Pro His Ser Val Gly
1               5                   10                  15

Pro Glu Ala Ala Thr Thr Thr Ala Lys Pro Pro Arg Ala Pro Leu Arg
            20                  25                  30

Met Arg His Pro Asp Tyr Thr Gln Thr Asp Val Leu Asp Ser Ser Asp
        35                  40                  45

Ser Asp Ala Ala Ser Asp Ser Glu Gly Glu Thr Thr Ala Val Asp Asp
    50                  55                  60

Gly Thr Tyr Glu Asp Asp Asn Tyr Val Arg Lys Val Leu Ser Lys Glu
65                  70                  75                  80

Lys Pro Leu Pro Pro Ile Thr Trp Lys Asn Ile His Arg Asn Ile Gln
                85                  90                  95

Trp Ile Ser Thr Leu Ala Leu Thr Ile Val Pro Leu Leu Ala Ile Tyr
            100                 105                 110

Gly Ala Phe Thr Thr Pro Leu Lys Trp Gln Thr Ala Val Trp Ser Val
        115                 120                 125

Val Tyr Tyr Tyr Tyr Thr Gly Leu Gly Ile Thr Ala Gly Tyr His Arg
    130                 135                 140

Leu Trp Ala His Arg Ser Tyr Thr Ala Ser Leu Pro Leu Gln Tyr Phe
145                 150                 155                 160

Leu Ala Leu Gly Gly Ser Gly Ala Val Glu Gly Ser Val Lys Trp Trp
                165                 170                 175

Ser Arg Gly His Arg Ala His His Arg Tyr Thr Asp Thr Asp Leu Asp
            180                 185                 190

Pro Tyr Ser Ala Gln Lys Gly Phe Trp Trp Ala His Leu Gly Trp Met
        195                 200                 205

Ile Val Lys Pro Arg Arg Arg Pro Gly Val Ala Asp Val Ser Asp Leu
    210                 215                 220

Asn Asn Asn Pro Val Val Lys Trp Gln His Arg Tyr Tyr Leu Pro Leu
225                 230                 235                 240

Ile Leu Gly Met Gly Phe Val Phe Pro Thr Ile Val Ala Gly Leu Gly
                245                 250                 255

Trp Gly Asp Phe Arg Gly Gly Phe Phe Phe Ala Gly Ala Ala Arg Leu
            260                 265                 270

Leu Phe Val His His Ser Thr Phe Cys Val Asn Ser Leu Ala His Trp
        275                 280                 285

Leu Gly Glu Thr Pro Phe Asp Asp Lys His Thr Pro Lys Asp His Trp
    290                 295                 300

Leu Thr Ala Leu Ala Thr Val Gly Glu Gly Tyr His Asn Phe His His
305                 310                 315                 320

Glu Phe Pro Ser Asp Tyr Arg Asn Ala Leu Arg Trp Trp Gln Tyr Asp
                325                 330                 335

Pro Thr Lys Leu Phe Ile Trp Thr Met Ser Lys Leu Gly Leu Ala Ser
            340                 345                 350

Gln Leu Lys Thr Phe Pro Asp Asn Glu Ile Lys Lys Gly Gln Tyr Ala
        355                 360                 365

Met Thr Leu Lys Ala Val Ala Arg Glu Ala Glu Asn Ile Glu Trp Pro
    370                 375                 380

Lys Ser Ser Asn His Leu Pro Val Leu Thr Trp Asp Glu Phe Gln Asp
385                 390                 395                 400

Ala Cys Lys Thr Arg Gln Leu Leu Val Val Ala Gly Phe Ile His Asp
                405                 410                 415
```

-continued

```
Val Ser Thr Phe Ile Asp Gln His Pro Gly Gly Ala Gly Leu Ile Lys
            420                 425                 430

Thr Arg Leu Gly Arg Asp Ala Thr Thr Ala Phe Tyr Gly Gly Tyr Tyr
        435                 440                 445

Asp His Ser Asn Gly Ala Ala Asn Leu Leu Ala Gln Tyr Arg Val Gly
    450                 455                 460

Val Ile Glu Gly Gly Tyr Glu Val Glu His Met Lys Lys Tyr Ser Glu
465                 470                 475                 480

Val Val Glu Asn Leu Lys Lys His Gly Ala Asp Gly Val Ala Gly Lys
                485                 490                 495

Ser Ala Asp Leu Val Lys Gly Pro Lys Gln Thr Ser Val Ile Lys Gly
            500                 505                 510

Asp Pro Gln Leu Lys Ser Ala Pro Leu Glu Thr Leu Ala Lys Pro Pro
        515                 520                 525

Thr Phe Ser Glu Thr Asn Leu Leu Gly Gly Leu Ser Leu Lys Val Lys
    530                 535                 540

Ala
545


<210> SEQ ID NO 10
<211> LENGTH: 1638
<212> TYPE: DNA
<213> ORGANISM: Rhodosporidium toruloides

<400> SEQUENCE: 10

atgactgcct cttcggcact cgagacctcg ctcccgcact ctgtcgggcc cgaggctgcg      60

accaccacag caaagccgcc ccgtgcgccg ctcaggatgc gtcaccccga ctacactcag     120

accgacgtcc tcgattcgtc ggactcggat gcagcgtcgg attctgaggg cgagacgacg     180

gcggtcgacg atgggaccta cgaggacgac aactacgtcc gcaaggtcct cagcaaggag     240

aagccgctcc cgcccatcac ctggaagaac atccaccgca acatccagtg gatctcgacc     300

ctcgccctca ccatcgtgcc cctcctcgcc atctacggag cgttcacgac gcccttgaag     360

tggcagacgg cggtctggag tgtcgtctac tactactaca ccggacttgg tatcacggca     420

ggctaccaca ggctgtgggc ccacaggtcc tacaccgcct ctctgcctct ccagtacttc     480

ttggcacttg gaggaagcgg cgcagtcgag gggagcgtga aatggtggtc taggggacac     540

cgcgcacacc atcgctacac cgacacagac ctcgacccgt attcggcgca gaagggcttc     600

tggtgggctc accttggctg gatgatcgtc aagccgcgcc gtcgtcccgg tgtcgccgac     660

gtttccgacc tcaacaacaa cccggtcgtc aagtggcagc accgctacta tctcccgctc     720

atcctcggca tgggcttcgt cttccctacc atcgtcgctg gactcggctg gggcgacttc     780

cgcggcggat tcttcttcgc cggcgccgct cgcctcctct tcgtccacca ctcgacgttc     840

tgcgtcaact cgcttgcgca ctggctgggc gagacgccct tcgacgacaa gcacacgccg     900

aaggatcact ggctcacggc gctcgcgact gtcggtgagg gctaccacaa cttccaccac     960

gagttcccct ccgactaccg caacgcactt cgatggtggc agtacgaccc gactaagctc    1020

ttcatctgga cgatgtcgaa gctcggattg gcgtcgcagc tcaagacgtt ccccgacaac    1080

gagatcaaga agggccagta cgcgatgacg ctcaaggctg tcgcgcgcga ggccgagaac    1140

atcgagtggc ccaagtcgtc gaaccatttg cctgtgctca cttgggacga gttccaggac    1200

gcctgcaaga cccgtcagct ccttgttgtc gccggtttca tccacgatgt cagcacgttc    1260

atcgaccagc accccggcgg tgccggcttg atcaagactc gtctcggtcg cgacgcgacg    1320
```

-continued

```
actgccttct acggtggcta ctacgaccac tcgaacggcg cagccaacct gctcgcccag   1380

taccgtgtcg gtgtcatcga aggcggctac gaggtcgagc acatgaagaa gtattcggag   1440

gtcgtcgaga acctcaagaa gcacggcgcc gatggcgtgg ccggcaagag cgccgacctc   1500

gtcaagggcc cgaagcagac gtcggtcatc aagggcgacc ctcagctgaa gagcgcgccg   1560

ctcgagacgc tcgccaagcc gcccaccttc agcgaaacca acctcttggg cggtctcagc   1620

ctgaaggtca aggcgtaa                                                 1638
```

<210> SEQ ID NO 11
<211> LENGTH: 546
<212> TYPE: PRT
<213> ORGANISM: Microbotryum violaceum

<400> SEQUENCE: 11

```
Met Ser Val Thr Ala Ser Ala Ser His Lys Leu Ala Ala Ser Leu Pro
1               5                   10                  15

His Gly Asp Gly Gln Val Ser Ala Ser Thr Thr Ala Arg Ser Thr Ala
            20                  25                  30

Pro Leu Arg Met Arg His Pro Asp Lys Gly Glu Ala Ser Asp Ser Asp
        35                  40                  45

Ser Asp His Gly Thr Asp Ser Asp Gly Glu Thr Thr Ala Val Asp Asp
    50                  55                  60

Gly Tyr Ala Glu Asp Asn Tyr Val Arg Lys Val Leu Ala Lys Glu Arg
65                  70                  75                  80

Pro Leu Pro Pro Ile Thr Leu Lys Thr Leu Pro Gln Asn Ile Gln Val
                85                  90                  95

Val Ser Thr Leu Ala Leu Thr Leu Val Pro Leu Leu Ala Val Tyr Gly
            100                 105                 110

Ala Phe Thr Thr Glu Ile Lys Trp Gln Thr Met Val Trp Ser Val Val
        115                 120                 125

Tyr Tyr Phe Phe Thr Gly Leu Gly Ile Thr Ala Gly Tyr His Arg Leu
    130                 135                 140

Trp Ala His Arg Ser Tyr Thr Ala Ser Arg Pro Leu Gln Tyr Phe Leu
145                 150                 155                 160

Ala Leu Gly Gly Ser Gly Ala Val Glu Gly Ser Ile Lys Trp Trp Ala
                165                 170                 175

Arg Gly His Arg Ala His His Arg Tyr Thr Asp Thr Asp Leu Asp Pro
            180                 185                 190

Tyr Ser Ala Gln Lys Gly Phe Leu His Ala His Leu Leu Trp Met Val
        195                 200                 205

Leu Lys Pro Arg Arg Ala Pro Gly Thr Ala Asp Val Ser Asp Leu Ser
    210                 215                 220

Ser Asn Glu Val Val Lys Trp Gln His Arg Phe Tyr Leu Pro Leu Ile
225                 230                 235                 240

Val Gly Met Gly Phe Val Phe Pro Thr Val Val Ala Gly Leu Gly Trp
                245                 250                 255

Gly Asp Trp Arg Gly Gly Tyr Phe Phe Ala Gly Ala Ala Arg Leu Thr
            260                 265                 270

Phe Val His His Ser Thr Phe Cys Val Asn Ser Leu Ala His Trp Leu
        275                 280                 285

Gly Glu Thr Pro Phe Asp Asp Lys His Thr Pro Lys Asp His Phe Leu
    290                 295                 300

Thr Ala Leu Val Thr Val Gly Glu Gly Tyr His Asn Phe His His Glu
305                 310                 315                 320
```

-continued

```
Phe Pro Ser Asp Phe Arg Asn Ala Ile Lys Trp Tyr Gln Tyr Asp Pro
                325                 330                 335

Thr Lys Trp Phe Ile Phe Thr Met Tyr Lys Leu Gly Leu Ala Ser Asn
            340                 345                 350

Leu Gln Thr Phe Pro Asp Ser Glu Leu Ala Arg Gly Gln Phe Asn Met
        355                 360                 365

Lys Leu Lys Lys Leu Ala Ala Ser Ala Ser Asn Leu Pro Trp Pro Lys
    370                 375                 380

Ser Ser Asn Asp Leu Pro Val Leu Thr Trp Glu Ser Phe Gln Glu Glu
385                 390                 395                 400

Ala Lys Ser Arg Asp Leu Leu Val Ile Gly Gly Phe Ile His Asp Val
                405                 410                 415

Ser Gln Phe Met Asp Asp His Pro Gly Gly Arg Gly Leu Ile Lys Ser
            420                 425                 430

Arg Leu Gly Arg Asp Ala Thr Thr Ala Phe Tyr Gly Gly Tyr Tyr Asp
        435                 440                 445

His Ser Asn Ala Ala Gly Asn Val Leu Ala Arg Leu Arg Val Gly Cys
    450                 455                 460

Ile Glu Gly Gly Tyr Glu Val Glu Ala Leu Lys Lys Tyr Ser Gln Ile
465                 470                 475                 480

Ile Glu Asp Ile Lys Arg Tyr Gly Gly Asp Gly Val Ala Gly Lys Thr
                485                 490                 495

Ala Asp Met Gly Ser Ser Ala Arg Ala Thr Val Ala Ile Lys Gly Asp
            500                 505                 510

Pro Ala His Arg Gly Ser Lys Leu Asp Thr Leu Lys Asp Tyr Pro Thr
        515                 520                 525

Phe Lys Pro Glu Val Leu Pro Leu Asn Gly Gly Leu Thr Gln Ser Leu
    530                 535                 540

Phe Glu
545
```

<210> SEQ ID NO 12
<211> LENGTH: 1641
<212> TYPE: DNA
<213> ORGANISM: Microbotryum violaceum

<400> SEQUENCE: 12

```
atgtccgtca cggcctctgc tagtcacaag cttgccgcct cgctgcccca tggcgacggt     60

caggttagtg cttcgaccac cgcgcgctcg acagccccgc ttcgcatgcg ccacccagat    120

aagggtgaag cttccgactc ggactcggac catggtaccg acagcgacgg cgaaacgact    180

gccgtcgacg acgggtacgc tgaggacaac tatgtccgca aggttctcgc caaggaacga    240

cctctgccgc ccatcacgct caagactttg ccacagaaca tccaagtcgt ttcgactctc    300

gcgttgacac tagtgccgct cctggccgtc tacggtgcct ttacgacgga gattaagtgg    360

caaacgatgg tatggtctgt tgtttactac ttcttcaccg gccttggcat taccgcgggc    420

tatcatcgac tctgggcgca ccgatcttac actgcctcga ggccgctgca gtactttttg    480

gcgcttggtg gctcgggtgc tgtcgaaggt tcaatcaaat ggtgggcacg tggccaccgc    540

gcgcatcatc gctacaccga caccgacctg gacccgtact ccgcgcagaa gggcttcctt    600

cacgcccact tgctttggat ggtcctcaag cctcgccgtg caccgggaac cgccgacgtt    660

tctgatttgt cgtcgaacga agtcgtcaag tggcagcatc ggttttacct ccccctcatt    720

gtcggcatgg gctttgtctt ccccactgtg gtggccggac tgggttgggg agactggcgc    780
```

-continued

```
ggaggctact tctttgcggg tgcggctcga cttaccttcg tccatcactc gaccttctgc    840

gtcaactcct tggcgcattg gcttggcgaa actccttttg atgacaagca cacgcccaag    900

gaccacttcc tcactgcgct cgtcaccgtc ggcgagggat accacaactt ccaccacgag    960

tttccctcgg acttccgcaa tgccatcaaa tggtaccagt acgatccgac taagtggttt   1020

atcttcacca tgtacaagct tggtctggcg tcaaatcttc aaacattccc cgattcggaa   1080

ctcgcgcggg gtcaattcaa catgaagctg aagaaacttg ctgcctccgc gtcgaatctc   1140

ccttggccca agagctccaa cgatcttccc gttcttacgt gggaatcatt ccaggaagag   1200

gccaaatcgc gcgatttgct cgtcattggc ggcttcattc atgacgtttc gcagtttatg   1260

gatgaccatc ccggtggacg aggcctgatc aaaagtcgtc ttggtcgcga cgccactacc   1320

gcgttctacg gcgggtacta cgaccacagc aatgccgctg gcaacgtact tgcccgattg   1380

cgtgtcggct gcatcgaagg tggctatgaa gtagaggcgc tcaagaagta ttctcaaatc   1440

atcgaagaca taaagagata cggcggtgat ggtgtggctg gcaagactgc tgatatgggc   1500

tcctccgctc gtgctacggt ggccatcaaa ggtgatcctg cgcaccgcgg gtcgaagctg   1560

gacaccctca aggactaccc cactttcaag cccgaggttc tccctttgaa tggcggttta   1620

acccagtccc tctttgaata g                                             1641
```

<210> SEQ ID NO 13
<211> LENGTH: 507
<212> TYPE: PRT
<213> ORGANISM: Puccinia graminis

<400> SEQUENCE: 13

```
Met Ser Lys Pro Ser Pro Ser Thr Pro Ala Thr Ala Pro His Leu Arg
1               5                   10                  15

Gln Arg Gln Arg Lys Asn Leu Pro Asp Tyr Asp Pro Asp Ser Asp Leu
            20                  25                  30

Ser Glu Ser Glu Gly Leu Gly Gly Leu Arg Ser Gln Val Gly Asn Thr
        35                  40                  45

Trp Glu Asp Asp Glu Glu Thr Ala Val Asp Asp Asp Ser Tyr Val Gln
    50                  55                  60

Arg Thr Leu Arg Lys Glu Lys Pro Leu Pro Pro Ile Thr Trp Cys Asn
65                  70                  75                  80

Phe Tyr Arg Glu Ile Asn Met Ile Ser Thr Leu Ala Leu Thr Val Val
                85                  90                  95

Pro Ile Leu Ala Ile Tyr Gly Ala Phe Thr Thr Pro Leu Tyr Arg Ser
            100                 105                 110

Thr Leu Ala Trp Ser Ile Leu Tyr Tyr Tyr Phe Thr Gly Leu Gly Ile
        115                 120                 125

Thr Ala Gly Tyr His Arg Leu Trp Ala His Arg Ser Tyr Asn Ala Ser
    130                 135                 140

Leu Pro Leu Gln Tyr Phe Leu Ala Leu Gly Gly Ser Gly Ala Val Glu
145                 150                 155                 160

Gly Ser Ile Arg Trp Trp Ala Arg Gly His Arg Ala His His Arg Tyr
                165                 170                 175

Thr Asp Thr Asp Leu Asp Pro Tyr Ser Ala His Lys Gly Leu Leu Trp
            180                 185                 190

Ser His Val Gly Trp Met Ile Val Lys Pro Arg Arg Lys Pro Gly Val
        195                 200                 205

Ala Asp Val Ser Asp Leu Ser Arg Asn Gln Val Val Arg Trp Gln His
```

-continued

```
    210                 215                 220

Arg Trp Tyr Leu Pro Leu Ile Phe Gly Met Gly Phe Phe Phe Pro Thr
225                 230                 235                 240

Leu Val Ala Gly Leu Gly Trp Gly Asp Trp Arg Gly Gly Phe Phe Tyr
                245                 250                 255

Ala Gly Ala Ala Arg Leu Leu Phe Val His His Ser Thr Phe Cys Val
            260                 265                 270

Asn Ser Leu Ala His Trp Leu Gly Glu Ala Pro Phe Asp Asp Lys His
        275                 280                 285

Thr Pro Arg Asp His Ile Ile Thr Ala Phe Val Thr Ile Gly Glu Gly
    290                 295                 300

Tyr His Asn Phe His His Glu Phe Pro Gln Asp Phe Arg Asn Ala Ile
305                 310                 315                 320

Arg Trp Tyr Gln Tyr Asp Pro Thr Lys Trp Phe Ile Ala Val Ala Ala
                325                 330                 335

Phe Leu Gly Leu Ala Ser Glu Leu Lys Thr Phe Pro Asp Asn Glu Val
            340                 345                 350

Arg Lys Gly Gln Tyr Ser Met Lys Leu Lys Glu Leu Gln Arg Asp Phe
        355                 360                 365

Arg Asp Val Lys Trp Pro Lys Ser Ser Asn Asp Leu Pro Ile Val Thr
    370                 375                 380

Trp Glu Gln Phe Val Glu Glu Ala Asp Lys Lys Asn Gly Arg Asp Leu
385                 390                 395                 400

Ile Val Val Gly Gly Phe Ile His Asp Val Thr Glu Phe Ile Asp Glu
                405                 410                 415

His Pro Gly Gly Arg Ala Leu Ile Lys Thr Arg Leu Gly Lys Asp Ala
            420                 425                 430

Thr Thr Ala Phe His Gly Gly Val Tyr Asp His Ser Asn Ala Ala His
        435                 440                 445

Asn Leu Leu Ala Met Leu Arg Val Gly Val Ile Glu Gly Gly Tyr Glu
    450                 455                 460

Val Glu His Leu Lys Lys Lys Val Gly Val Phe Arg Lys Glu Gln Gln
465                 470                 475                 480

Ile Pro Ile Cys Gly Pro Lys Ser Leu Gly Thr Ile Ser Thr Pro Glu
                485                 490                 495

Ser Pro Val Val Glu Val Lys Pro Ile Tyr Thr
            500                 505


<210> SEQ ID NO 14
<211> LENGTH: 1524
<212> TYPE: DNA
<213> ORGANISM: Puccinia graminis

<400> SEQUENCE: 14

atgtccaaac cctcaccttc aactcccgcc accgcccctc atctccgtca gcgccaacgc      60

aagaacttgc cggattatga tcccgattcc gatcttagcg agtcagaggg cttgggaggc     120

ctcagatctc aagttggtaa tacttgggaa gatgatgagg aaactgcggt ggatgatgat     180

agctacgttc aacgcacctt gcgcaaggaa aagccactcc ctccaatcac ctggtgcaac     240

ttttatcgtg agatcaatat gatctccact ttggccttga ccgtcgtccc catcctggcc     300

atctacggtg ctttcactac gcccctctat cgttcaacct tggcctggtc gattctctac     360

tactacttca ccggtctcgg catcaccgcc ggttatcatc gtctttgggc ccatcgatcc     420

tacaatgcct cccttccgct ccaatatttc ctcgctctcg gtggctctgg cgccgttgag     480
```

-continued

```
ggtagtatcc gttggtgggc tcgtgggcat cgagctcatc atcgttacac tgacaccgat    540

ctagacccct actcggctca caaaggactc ctatggagtc atgtgggctg gatgattgtc    600

aaacctcgac gaaaacccgg cgtggccgat gtctctgatc tatctcgcaa tcaagtcgtc    660

agatggcagc atcgttggta tctgcctttg attttcggca tgggattctt cttccccact    720

cttgtcgctg gactcggatg gggtgattgg agaggcggat ttttctacgc tggggccgct    780

agattattgt ttgttcacca ctcgactttc tgtgtgaact ctctggctca ctggcttgga    840

gaggctccct ttgatgataa acacactcca agggatcaca tcattaccgc ctttgtcaca    900

attggagaag gttatcacaa cttccatcac gaatttcctc aggacttccg aaatgccatt    960

cgatggtacc aatacgaccc aaccaaatgg ttcatcgctg tcgctgcctt cctcggacta   1020

gcttctgagc tcaaaacctt cccggataac gaggttcgca aaggtcaata cagtatgaaa   1080

cttaaggaac tccagcgaga tttccgagac gtcaagtggc ccaagtcttc caacgacctt   1140

ccgatcgtta catgggaaca atttgtcgaa gaggctgata aaaagaacgg acgtgatttg   1200

atcgttgtcg gggtttcat ccatgatgtg actgagttta tcgacgagca tcccggaggt   1260

cgggcactca tcaaaacccg acttggtaaa gatgccacca cggccttcca tggtggagtt   1320

tacgatcatt ccaacgccgc gcacaacttg ttggctatgc tgcgagttgg tgtgatcgag   1380

ggtggctacg aggttgaaca tctgaagaaa aaagtagggg tctttcgaaa ggaacaacag   1440

atccctatct gtggtcctaa gagcttagga accatttcta cccctgaaag tccagtggta   1500

gaagtcaagc cgatctatac ttga                                          1524
```

<210> SEQ ID NO 15
<211> LENGTH: 476
<212> TYPE: PRT
<213> ORGANISM: Gloeophyllum trabeum

<400> SEQUENCE: 15

```
Met Ala Thr Tyr Thr Pro Pro Leu Thr Pro Pro Ser Glu Pro Thr Lys
1               5                   10                  15

Arg Leu Lys Asn Leu Glu Pro Glu Pro Ile Asp Ile Asn Ile Pro Asp
            20                  25                  30

Asn Tyr Val Gln His Thr Leu Lys Thr Gln Lys Glu Leu Pro Pro Ile
        35                  40                  45

Thr Trp Ser Asn Trp Tyr Arg Glu Leu Gln Trp Ile Ser Val Leu Ala
    50                  55                  60

Leu Thr Ile Thr Pro Ala Leu Ala Ile Tyr Gly Ala Phe Thr Thr Lys
65                  70                  75                  80

Leu Thr Trp Gln Thr Gly Leu Phe Ser Val Phe Tyr Tyr Tyr Val Thr
                85                  90                  95

Gly Leu Gly Ile Thr Ala Gly Tyr His Arg Leu Trp Ala His Arg Ser
            100                 105                 110

Tyr Asn Ala Ser Lys Pro Leu Gln Tyr Phe Leu Ala Leu Ala Gly Ser
        115                 120                 125

Gly Ala Val Glu Gly Ser Ile Lys Trp Trp Ser Arg Gly His Arg Ala
    130                 135                 140

His His Arg Tyr Thr Asp Thr Glu Leu Asp Pro Tyr Ser Ala Gln Lys
145                 150                 155                 160

Gly Phe Trp Trp Ser His Val Gly Trp Met Leu Phe Lys Pro Arg Arg
                165                 170                 175

Lys Pro Gly Val Ala Asp Val Ser Asp Leu Ser Arg Asn Glu Val Val
```

-continued

```
            180                 185                 190

Arg Trp Gln His Arg Trp Tyr Val Trp Leu Ile Leu Gly Met Gly Phe
        195                 200                 205

Gly Leu Pro Thr Val Val Pro Gly Leu Leu Trp Gly Asp Trp Trp Gly
    210                 215                 220

Gly Phe Phe Tyr Ala Gly Ala Leu Arg Leu Thr Phe Val His His Ser
225                 230                 235                 240

Thr Phe Cys Val Asn Ser Leu Ala His Trp Leu Gly Glu Thr Pro Phe
                245                 250                 255

Asp Asp Lys His Thr Pro Arg Asp His Val Ile Thr Ala Leu Val Thr
            260                 265                 270

Ile Gly Glu Gly Tyr His Asn Phe His His Gln Phe Pro Met Asp Tyr
        275                 280                 285

Arg Asn Ala Ile Lys Trp Tyr Gln Tyr Asp Pro Thr Lys Trp Phe Ile
    290                 295                 300

Met Ala Cys Gln Trp Val Gly Leu Ala Ser His Leu Lys Thr Phe Pro
305                 310                 315                 320

Asp Asn Glu Val Arg Lys Gly Gln Leu Thr Met Gln Leu Lys Arg Leu
                325                 330                 335

Arg Glu Thr Gln Glu Lys Leu Thr Trp Ala Pro Asp Ser Asn Asp Leu
            340                 345                 350

Pro Ile Val Ser Trp Asp Ser Phe Gln Glu Gln Ser Ala Lys Arg Pro
        355                 360                 365

Leu Ile Leu Ile Ala Gly Phe Ile His Asp Val Ala Ser Phe Leu Asp
    370                 375                 380

Glu His Pro Gly Gly Arg His Leu Leu Val Lys Tyr Ile Gly Lys Asp
385                 390                 395                 400

Ala Thr Thr Ala Phe Phe Gly Gly Val Tyr Asp His Ser Asn Ala Ala
                405                 410                 415

His Asn Leu Leu Ser Met His Arg Val Gly Ile Leu Gln His Gly Tyr
            420                 425                 430

Arg Gln Ser Leu Asp Asp Lys Ala Ile Pro Pro Ala Gln Arg Leu Arg
        435                 440                 445

Ile Ala Arg Tyr Asn Glu Leu Gly Ser Ser Thr Ala Val Ser Asp Ala
    450                 455                 460

Glu Thr Leu Val Gly Glu Lys Glu Glu Lys Glu Ala
465                 470                 475
```

<210> SEQ ID NO 16
<211> LENGTH: 1431
<212> TYPE: DNA
<213> ORGANISM: Gloeophyllum trabeum

<400> SEQUENCE: 16

```
atggcgacct acacgccgcc gctgacgccg ccgtccgagc ccaccaagcg gctcaaaaat      60

ctcgagccgg agcccatcga catcaacatc cccgacaact acgtccagca cacgctcaag     120

acgcagaagg agctcccgcc tatcacctgg agcaactggt accgcgagct gcagtggatc     180

agcgtcctcg cgctcacgat cacacctgca cttgcgatct acggcgcgtt tacgaccaag     240

ctcacatggc agacgggcct cttcagcgtc ttctactact acgtgactgg cctcggtatc     300

accgccggat accaccgtct gtgggcgcac cggtcgtaca acgcctccaa gccgttgcag     360

tacttcctcg cgctcgcggg ctcgggcgcc gtcgagggct ccatcaaatg gtggtcgcgc     420

ggccaccgtg cgcaccatcg ctacaccgac accgaactcg acccgtactc ggcccagaag     480
```

```
ggcttctggt ggtcgcacgt cggctggatg ctcttcaagc cgcgccgcaa gcccggcgtc    540

gccgacgtca gcgacctcag ccgcaacgag gtcgtcaggt ggcagcaccg ctggtatgtc    600

tggctcatcc ttggcatggg cttcgggctc ccgactgttg tcccgggcct gctctggggt    660

gactggtggg gcgggttctt ctacgcgggt gctctgcgcc tgacgttcgt gcaccattcg    720

acgttctgtg tcaactccct agcgcactgg ctgggagaga cgccgttcga cgacaagcac    780

acgcccaggg accacgttat caccgcgctc gtcaccatcg gcgagggcta ccacaacttc    840

caccaccagt tccccatgga ctaccgcaac gccatcaagt ggtaccagta cgacccgaca    900

aagtggttca tcatggcctg ccagtgggtc ggcctcgcgt cacatctcaa gacgttccct    960

gataacgaag tccgcaaagg ccagctgact atgcagctca agcggctccg ggaaacgcag   1020

gagaagctca cctgggcacc ggatagcaac gacctgccca ttgtctcttg ggacagcttc   1080

caggaacagt cggcgaagcg tccgctgatc ttgattgctg gcttcatcca cgatgtcgcg   1140

tccttcttgg acgagcaccc tggcggccgg catctgctcg tgaagtacat cggcaaggac   1200

gctacgacgg cgttcttcgg cggtgtctac gatcactcca acgccgcgca taacctgctc   1260

tcgatgcacc gcgttggcat cctgcaacac ggctaccgcc agagcttgga cgataaggcc   1320

atcccgcccg cgcagcgcct gcggattgcg cggtacaacg agctcgggtc atcgacggcc   1380

gtgtcggatg cggagacgct agtgggggag aaggaggaga aggaagcgta g             1431
```

<210> SEQ ID NO 17
<211> LENGTH: 727
<212> TYPE: PRT
<213> ORGANISM: Yarrowia lipolytica

<400> SEQUENCE: 17

```
Met Ser Glu Thr Asp His Leu Leu Ala Ala Glu Pro Val Ala Glu Tyr
1               5                   10                  15

Pro Gln Tyr Thr Pro Trp Pro Asn Ser Arg Lys Ser Val Asp Thr Glu
            20                  25                  30

Phe Ser Ala Thr Ser Trp Ile Tyr Asp Leu Val Leu Trp Ile Phe Thr
        35                  40                  45

Ala Cys Phe Asp Ile Phe Phe Arg Glu Ile Arg Pro Arg Gly Ala Phe
    50                  55                  60

Arg Ile Pro Arg Lys Gly Pro Val Leu Phe Val Ala Ala Pro His Ala
65                  70                  75                  80

Asn Gln Phe Val Asp Pro Val Ile Leu Met Asn Gln Val Lys Gln Glu
                85                  90                  95

Ala Gly Arg Arg Ile Ser Phe Leu Val Ala Glu Lys Ser Met Arg Arg
            100                 105                 110

Ala Ala Val Gly Arg Met Ala Arg Ser Met Asn Ser Ile Pro Val Val
        115                 120                 125

Arg Ala Gln Asp Asn Ala Lys Lys Gly Glu Gly Lys Ile Tyr Val Asp
    130                 135                 140

Ala Glu Asp Pro Thr Lys Ile His Gly Ile Gly Thr Gln Phe Thr Lys
145                 150                 155                 160

Gln Cys Glu Val Arg Gly Leu Val Val Cys Ser Ser Ser Val Gly Ser
                165                 170                 175

Ile Asp Val Ala Glu Ile Val Ser Asp Thr Leu Leu Ile Ala Arg Lys
            180                 185                 190

Glu Phe Lys Gly Pro Lys Ala Lys Glu Ala Leu Lys Glu Ser Asn Gly
        195                 200                 205
```

-continued

```
Gly Ile Thr Tyr Lys Tyr Ala Asp Tyr Val Asn Gln Ala Thr Val Tyr
    210                 215                 220

Arg Ser Val Phe Asp Lys Leu His His Gly Gly Cys Val Gly Ile Phe
225                 230                 235                 240

Pro Glu Gly Gly Ser His Asp Arg Thr Glu Leu Leu Pro Leu Lys Ala
                245                 250                 255

Gly Val Ala Ile Met Ala Leu Gly Ala Leu Ala Glu Asp Pro Ser Cys
            260                 265                 270

Gly Val Arg Ile Val Pro Cys Gly Leu Asn Tyr Phe His Ala His Lys
        275                 280                 285

Phe Arg Ser Arg Ala Val Val Glu Phe Gly Ser Pro Ile Ala Ile Pro
    290                 295                 300

Pro Asp Leu Val Glu Lys Tyr Lys Ala Gly Gly Glu Ala Lys Arg Glu
305                 310                 315                 320

Ala Val Lys Thr Val Leu Asp Ile Thr Ala Ala Gly Leu Lys Ser Val
                325                 330                 335

Thr Val Gln Val Gln Asp Phe Asp Thr Leu Met Leu Ile Gln Ala Ile
            340                 345                 350

Arg Arg Leu Tyr Arg Pro Pro Gly Lys Lys Ile Pro Leu Pro Met Val
        355                 360                 365

Val Glu Leu Asn Arg Arg Leu Val Tyr Ala Tyr Asn His Tyr Lys Asp
    370                 375                 380

Asp Pro Arg Ile Glu Glu Met Lys Gln Glu Ile Arg Lys Tyr Asn Lys
385                 390                 395                 400

Phe Leu Gln Ala Met Gly Leu Lys Asp His Gln Val Glu Lys Ala Arg
                405                 410                 415

Ile Ser Lys Ile Glu Ile Leu Gly Arg Leu Leu Tyr Arg Ser Ile Lys
            420                 425                 430

Leu Val Phe Leu Ser Ile Gly Cys Leu Pro Gly Leu Leu Leu Phe Ser
        435                 440                 445

Pro Ile Phe Ile Ile Ser Lys Ser Ile Ser Lys Thr Lys Ala Lys Glu
    450                 455                 460

Ala Leu Lys Ala Ser Ser Val Lys Ile Lys Ala Asn Asp Val Val Ala
465                 470                 475                 480

Thr Trp Lys Val Leu Val Ala Met Gly Leu Thr Pro Val Leu Tyr Ile
                485                 490                 495

Leu Tyr Ser Leu Val Gly Ser Val Val Ile Arg Lys Leu Asp Leu Ile
            500                 505                 510

Ser Trp Phe Pro Thr Ile Leu Leu Pro Gly Leu Val Leu Ser Ile Ile
        515                 520                 525

Ile Thr Thr Ser Tyr Ala Ala Leu Ala Met Gly Glu Ala Gly Met Asp
    530                 535                 540

Ile Phe Lys Ser Leu Arg Pro Leu Ala Leu Ala Leu Asn Pro Ser Thr
545                 550                 555                 560

Lys Asn Ser Leu Leu Lys Leu Gln Asn Glu Arg Lys Arg Leu Val Leu
                565                 570                 575

Lys Ser Ser Glu Leu Val Thr Ser Leu Gly Pro Glu Leu Phe Pro Asp
            580                 585                 590

Phe Pro Glu Asn Ser Ile Leu Gln Gly Ser Asp Lys Phe Glu Asp Glu
        595                 600                 605

Glu Asn Tyr Glu Asn Glu Lys Arg Ser His Ser Arg Ser Thr Ser Ala
    610                 615                 620
```

-continued

```
Thr Ser Leu Ser Ala Met Ser Glu Gly Asp Gly Asp Glu Leu Val Arg
625                 630                 635                 640

Glu Val Arg Lys Gly Ala Ser Tyr Phe Pro Val Ser Thr Ile Ser Glu
                645                 650                 655

Asp Glu Asp Gln Ala Ile Ser Arg Val Gly Ser Glu Ala Ser Leu Ala
            660                 665                 670

Asp Ile Pro Leu Phe Gly Met Ser Arg Ser Gln Ser Gly Ala Ser Leu
        675                 680                 685

Ser Glu Ala Ser Thr His Gly Ser Ser Thr Gly Ala Asp Ala Glu Glu
    690                 695                 700

Ala Lys Thr Glu Val Thr Arg Arg Ile Ala Leu Ala Met Glu Glu Lys
705                 710                 715                 720

Arg Arg Glu Gln Asp Glu Glu
                725


<210> SEQ ID NO 18
<211> LENGTH: 2184
<212> TYPE: DNA
<213> ORGANISM: Yarrowia lipolytica

<400> SEQUENCE: 18

atgtccgaaa ccgaccatct gctggccgcc gagcccgtgg ctgagtaccc ccagtacacg     60

ccttggccca actcccgaaa atcagtggac acggagtttt ccgcaacctc gtggatttac    120

gacttggttc tgtggatttt cacggcttgc tttgacattt ttttcagaga aatccggcca    180

cgtggtgcct tccgaatccc cagaaagggc cccgtgctgt tcgtggctgc cccccacgca    240

aaccagtttg tggaccccgt catcctcatg aaccaggtca aacaggaggc cggacgacga    300

atctccttcc ttgtggccga gaagtccatg cgacgagctg cagtcggacg aatggcccga    360

agcatgaact caattcctgt cgtgcgagct caggacaatg caaaaaaggg agagggaaag    420

atttacgtcg acgcagagga ccccacaaag atccacggaa tcggcaccca gttcacgaag    480

cagtgcgagg tgcgaggcct cgtggtctgc tcgtcctctg tcggctcaat tgacgtggct    540

gagattgtgt ccgacactct gctcattgca agaaaggaat tcaagggccc caaagccaag    600

gaggctctca aggaatccaa cggaggaatc acatacaagt acgccgacta cgtcaaccag    660

gccacagtct accgatccgt attcgacaaa ttgcaccatg gaggctgtgt gggtatcttc    720

ccagagggag gatctcatga ccgaaccgaa ctgctgcccc ttaaggccgg tgttgctatc    780

atggctctgg gggctctcgc agaggacccc tcttgtggtg tgcgaatcgt cccctgtggt    840

ctcaactact tccacgccca caagttccga tctcgggccg tggtggagtt tggctctcct    900

attgccattc ctccggatct cgtggagaag tacaaggcag gaggagaggc caagcgggag    960

gctgtcaaga ccgttctaga cattactgcc gctggtctca agtctgtgac tgttcaggtg   1020

caggatttcg acaccctgat gctgatccag gccattcgac gactctaccg acctcccgga   1080

aagaagattc ctctgcccat ggttgtagag ctcaaccgtc gacttgtata cgcctacaac   1140

cactacaagg acgatccccg tatcgaggag atgaagcagg agattcgaaa gtacaacaag   1200

ttcctgcagg ccatgggtct caaggaccat caggtagaga aggcccgaat ctccaagatt   1260

gagattctgg gccggcttct gtaccggtcc atcaagcttg tgttcttgtc cattggctgt   1320

ctccccggtc tgcttttgtt ttctcccatc ttcatcattt ctaagtccat ttccaaaacc   1380

aaggccaagg aggctctcaa ggcctccagt gtcaaaatca aggctaacga tgtggttgcc   1440

acttggaagg tgctggttgc aatgggtctg accccagttc tttacattct ctattcactg   1500
```

```
gttggatctg tggtgattcg aaagctcgat ctcatctcct ggttccccac aattcttctt   1560

cccggcctcg ttttaagcat catcatcaca acctcatacg ccgccctggc tatgggagag   1620

gccggtatgg acattttcaa gtctcttcga ccacttgcat tggctctcaa cccttccacc   1680

aaaaactctc tgctcaagct gcaaaatgaa cgaaagcgac ttgtgctcaa gtcttccgag   1740

ctcgttacct ctttgggccc tgagctgttc cccgacttcc ccgagaactc cattctgcag   1800

ggaagcgata agtttgagga cgaggagaac tacgaaaacg agaagcgatc gcattccaga   1860

tccacttctg ccacttctct atctgccatg agcgagggag acggtgatga gcttgttcgg   1920

gaggtccgaa agggtgctag ctacttccct gtgagtacca tttctgagga cgaagaccaa   1980

gccatctcgc gagtgggctc tgaggcatct cttgctgaca ttcctctgtt tggtatgtcc   2040

cgatcacaat ctggagcttc tctttcggaa gcctccacac acggctcttc tactggagct   2100

gatgccgagg aggctaagac ggaggtgact cgcagaattg cattggcgat ggaggaaaaa   2160

cgacgagagc aggatgagga ataa                                          2184
```

<210> SEQ ID NO 19
<211> LENGTH: 514
<212> TYPE: PRT
<213> ORGANISM: Yarrowia lipolytica

<400> SEQUENCE: 19

```
Met Thr Ile Asp Ser Gln Tyr Tyr Lys Ser Arg Asp Lys Asn Asp Thr
1               5                   10                  15

Ala Pro Lys Ile Ala Gly Ile Arg Tyr Ala Pro Leu Ser Thr Pro Leu
            20                  25                  30

Leu Asn Arg Cys Glu Thr Phe Ser Leu Val Trp His Ile Phe Ser Ile
        35                  40                  45

Pro Thr Phe Leu Thr Ile Phe Met Leu Cys Cys Ala Ile Pro Leu Leu
    50                  55                  60

Trp Pro Phe Val Ile Ala Tyr Val Val Tyr Ala Val Lys Asp Asp Ser
65                  70                  75                  80

Pro Ser Asn Gly Gly Val Val Lys Arg Tyr Ser Pro Ile Ser Arg Asn
                85                  90                  95

Phe Phe Ile Trp Lys Leu Phe Gly Arg Tyr Phe Pro Ile Thr Leu His
            100                 105                 110

Lys Thr Val Asp Leu Glu Pro Thr His Thr Tyr Tyr Pro Leu Asp Val
        115                 120                 125

Gln Glu Tyr His Leu Ile Ala Glu Arg Tyr Trp Pro Gln Asn Lys Tyr
    130                 135                 140

Leu Arg Ala Ile Ile Thr Thr Ile Glu Tyr Phe Leu Pro Ala Phe Met
145                 150                 155                 160

Lys Arg Ser Leu Ser Ile Asn Glu Gln Glu Gln Pro Ala Glu Arg Asp
                165                 170                 175

Pro Leu Leu Ser Pro Val Ser Pro Ser Ser Pro Gly Ser Gln Pro Asp
            180                 185                 190

Lys Trp Ile Asn His Asp Ser Arg Tyr Ser Arg Gly Glu Ser Ser Gly
        195                 200                 205

Ser Asn Gly His Ala Ser Gly Ser Glu Leu Asn Gly Asn Gly Asn Asn
    210                 215                 220

Gly Thr Thr Asn Arg Arg Pro Leu Ser Ser Ala Ser Ala Gly Ser Thr
225                 230                 235                 240

Ala Ser Asp Ser Thr Leu Leu Asn Gly Ser Leu Asn Ser Tyr Ala Asn
                245                 250                 255
```

```
Gln Ile Ile Gly Glu Asn Asp Pro Gln Leu Ser Pro Thr Lys Leu Lys
            260                 265                 270

Pro Thr Gly Arg Lys Tyr Ile Phe Gly Tyr His Pro His Gly Ile Ile
        275                 280                 285

Gly Met Gly Ala Phe Gly Gly Ile Ala Thr Glu Gly Ala Gly Trp Ser
    290                 295                 300

Lys Leu Phe Pro Gly Ile Pro Val Ser Leu Met Thr Leu Thr Asn Asn
305                 310                 315                 320

Phe Arg Val Pro Leu Tyr Arg Glu Tyr Leu Met Ser Leu Gly Val Ala
                325                 330                 335

Ser Val Ser Lys Lys Ser Cys Lys Ala Leu Leu Lys Arg Asn Gln Ser
            340                 345                 350

Ile Cys Ile Val Val Gly Gly Ala Gln Glu Ser Leu Leu Ala Arg Pro
        355                 360                 365

Gly Val Met Asp Leu Val Leu Leu Lys Arg Lys Gly Phe Val Arg Leu
    370                 375                 380

Gly Met Glu Val Gly Asn Val Ala Leu Val Pro Ile Met Ala Phe Gly
385                 390                 395                 400

Glu Asn Asp Leu Tyr Asp Gln Val Ser Asn Asp Lys Ser Ser Lys Leu
                405                 410                 415

Tyr Arg Phe Gln Gln Phe Val Lys Asn Phe Leu Gly Phe Thr Leu Pro
            420                 425                 430

Leu Met His Ala Arg Gly Val Phe Asn Tyr Asp Val Gly Leu Val Pro
        435                 440                 445

Tyr Arg Arg Pro Val Asn Ile Val Val Gly Ser Pro Ile Asp Leu Pro
    450                 455                 460

Tyr Leu Pro His Pro Thr Asp Glu Glu Val Ser Glu Tyr His Asp Arg
465                 470                 475                 480

Tyr Ile Ala Glu Leu Gln Arg Ile Tyr Asn Glu His Lys Asp Glu Tyr
                485                 490                 495

Phe Ile Asp Trp Thr Glu Glu Gly Lys Gly Ala Pro Glu Phe Arg Met
            500                 505                 510

Ile Glu


<210> SEQ ID NO 20
<211> LENGTH: 1545
<212> TYPE: DNA
<213> ORGANISM: Yarrowia lipolytica

<400> SEQUENCE: 20

atgactatcg actcacaata ctacaagtcg cgagacaaaa acgacacggc acccaaaatc     60

gcgggaatcc gatatgcccc gctatcgaca ccattactca accgatgtga gaccttctct    120

ctggtctggc acattttcag cattcccact ttcctcacaa ttttcatgct atgctgcgca    180

attccactgc tctggccatt tgtgattgcg tatgtagtgt acgctgttaa agacgactcc    240

ccgtccaacg gaggagtggt caagcgatac tcgcctattt caagaaactt cttcatctgg    300

aagctctttg gccgctactt ccccataact ctgcacaaga cggtggatct ggagcccacg    360

cacacatact accctctgga cgtccaggag tatcacctga ttgctgagag atactggccg    420

cagaacaagt acctccgagc aatcatctcc accatcgagt actttctgcc cgccttcatg    480

aaacggtctc tttctatcaa cgagcaggag cagcctgccg agcgagatcc tctcctgtct    540

cccgtttctc ccagctctcc gggttctcaa cctgacaagt ggattaacca cgacagcaga    600
```

-continued

```
tatagccgtg gagaatcatc tggctccaac ggccacgcct cgggctccga acttaacggc    660

aacggcaaca atggcaccac taaccgacga cctttgtcgt ccgcctctgc tggctccact    720

gcatctgatt ccacgcttct taacgggtcc ctcaactcct acgccaacca gatcattggc    780

gaaaacgacc cacagctgtc gcccacaaaa ctcaagccca ctggcagaaa atacatcttc    840

ggctaccacc cccacggcat tatcggcatg ggagcctttg gtggaattgc caccgaggga    900

gctggatggt ccaagctctt tccgggcatc cctgtttctc ttatgactct caccaacaac    960

ttccgagtgc ctctctacag agagtacctc atgagtctgg gagtcgcttc tgtctccaag   1020

aagtcctgca aggccctcct caagcgaaac cagtctatct gcattgtcgt tggtggagca   1080

caggaaagtc ttctggccag acccggtgtc atggacctgg tgctactcaa gcgaaagggt   1140

tttgttcgac ttggtatgga ggtcggaaat gtcgcccttg ttcccatcat ggcctttggt   1200

gagaacgacc tctatgacca ggttagcaac gacaagtcgt ccaagctgta ccgattccag   1260

cagtttgtca agaacttcct tggattcacc cttcctttga tgcatgcccg aggcgtcttc   1320

aactacgatg tcggtcttgt cccctacagg cgacccgtca acattgtggt tggttccccc   1380

attgacttgc cttatctccc acaccccacc gacgaagaag tgtccgaata ccacgaccga   1440

tacatcgccg agctgcagcg aatctacaac gagcacaagg atgaatattt catcgattgg   1500

accgaggagg gcaaaggagc cccagagttc cgaatgattg agtaa                   1545
```

<210> SEQ ID NO 21
<211> LENGTH: 348
<212> TYPE: PRT
<213> ORGANISM: Rhodosporidium toruloides

<400> SEQUENCE: 21

```
Met Gly Gln Gln Ala Thr Pro Glu Glu Leu Tyr Thr Arg Ser Glu Ile
1               5                   10                  15

Ser Lys Ile Lys Phe Ala Pro Phe Gly Val Pro Arg Ser Arg Arg Leu
            20                  25                  30

Gln Thr Phe Ser Val Phe Ala Trp Thr Thr Ala Leu Pro Ile Leu Leu
        35                  40                  45

Gly Val Phe Phe Leu Leu Cys Ser Phe Pro Pro Leu Trp Pro Ala Val
    50                  55                  60

Ile Ala Tyr Leu Thr Trp Val Phe Phe Ile Asp Gln Ala Pro Ile His
65                  70                  75                  80

Gly Gly Arg Ala Gln Ser Trp Leu Arg Lys Ser Arg Ile Trp Val Trp
                85                  90                  95

Phe Ala Gly Tyr Tyr Pro Val Ser Leu Ile Lys Ser Ala Asp Leu Pro
            100                 105                 110

Pro Asp Arg Lys Tyr Val Phe Gly Tyr His Pro His Gly Val Ile Gly
        115                 120                 125

Met Gly Ala Ile Ala Asn Phe Ala Thr Asp Ala Thr Gly Phe Ser Thr
    130                 135                 140

Leu Phe Pro Gly Leu Asn Pro His Leu Leu Thr Leu Gln Ser Asn Phe
145                 150                 155                 160

Lys Leu Pro Leu Tyr Arg Glu Leu Leu Leu Ala Leu Gly Ile Cys Ser
                165                 170                 175

Val Ser Met Lys Ser Cys Gln Asn Ile Leu Arg Gln Gly Pro Gly Ser
            180                 185                 190

Ala Leu Thr Ile Val Val Gly Gly Ala Ala Glu Ser Leu Ser Ala His
        195                 200                 205
```

```
Pro Gly Thr Ala Asp Leu Thr Leu Lys Arg Arg Lys Gly Phe Ile Lys
    210                 215                 220

Leu Ala Ile Arg Gln Gly Ala Asp Leu Val Pro Val Phe Ser Phe Gly
225                 230                 235                 240

Glu Asn Asp Ile Phe Gly Gln Leu Arg Asn Glu Arg Gly Thr Arg Leu
                245                 250                 255

Tyr Lys Leu Gln Lys Arg Phe Gln Gly Val Phe Gly Phe Thr Leu Pro
            260                 265                 270

Leu Phe Tyr Gly Arg Gly Leu Phe Asn Tyr Asn Val Gly Leu Met Pro
        275                 280                 285

Tyr Arg His Pro Ile Val Ser Val Val Gly Arg Pro Ile Ser Val Glu
    290                 295                 300

Gln Lys Asp His Pro Thr Thr Ala Asp Leu Glu Glu Val Gln Ala Arg
305                 310                 315                 320

Tyr Ile Ala Glu Leu Lys Arg Ile Trp Glu Glu Tyr Lys Asp Ala Tyr
                325                 330                 335

Ala Lys Ser Arg Thr Arg Glu Leu Asn Ile Ile Ala
            340                 345
```

<210> SEQ ID NO 22
<211> LENGTH: 1047
<212> TYPE: DNA
<213> ORGANISM: Rhodosporidium toruloides

<400> SEQUENCE: 22

```
atgggccagc aggcgacgcc cgaggagcta tacacacgct cagagatctc caagatcaag      60

ttcgcaccct ttggcgtccc gcggtcgcgc cggctgcaga ccttctccgt ctttgcctgg     120

acgacggcac tgcccatcct actcggcgtc ttcttcctcc tctgctcgtt cccaccgctc     180

tggccggctg tcattgccta cctcacctgg gtctttttca ttgaccaggc gccgattcac     240

ggtggacggg cgcagtcttg gctgcggaag agtcggatat gggtctggtt tgcaggatac     300

tatcccgtca gcttgatcaa gagcgccgac ttgccgcctg accggaagta cgtctttggc     360

taccacccgc acggcgtcat aggcatgggc gccatcgcca acttcgcgac cgacgcaacc     420

ggcttctcga cactcttccc cggcttgaac cctcacctcc tcaccctcca aagcaacttc     480

aagctcccgc tctaccgcga gttgctgctc gctctcggca tatgctccgt ctcgatgaag     540

agctgtcaga acattctgcg acaaggtcct ggctcggctc tcactatcgt cgtcggtggc     600

gccgccgaga gcttgagtgc gcatcccgga accgccgatc ttacgctcaa gcgacgaaaa     660

ggcttcatca aactcgcgat ccggcaaggc gccgaccttg tgcccgtctt ttcgttcggc     720

gagaacgaca tctttggcca gctgcgaaac gagcgaggaa cgcggctgta caagttgcag     780

aagcgtttcc aaggcgtgtt tggcttcacc ctccctctct tctacggccg gggactcttc     840

aactacaacg tcggattgat gccgtatcgc catccgatcg tctctgtcgt cggtcgacca     900

atctcggtag agcagaagga ccacccgacc acggcggacc tcgaagaagt tcaggcgcgg     960

tatatcgcag aactcaagcg gatctgggaa gaatacaagg acgcctacgc caaaagtcgc    1020

acgcgggagc tcaatattat cgcctga                                        1047
```

<210> SEQ ID NO 23
<211> LENGTH: 410
<212> TYPE: PRT
<213> ORGANISM: Lipomyces starkeyi

<400> SEQUENCE: 23

-continued

```
Met Ser Glu Lys Ala Glu Ile Glu Val Pro Pro Gln Lys Ser Thr Phe
1               5                   10                  15

Pro Arg Ser Val His Phe Ala Pro Leu His Ile Pro Leu Glu Arg Arg
            20                  25                  30

Leu Gln Thr Leu Ala Val Leu Phe His Thr Val Ala Leu Pro Tyr Cys
        35                  40                  45

Ile Gly Leu Phe Phe Leu Met Leu Ala Phe Pro Pro Phe Trp Pro Leu
    50                  55                  60

Leu Val Met Tyr Val Ile Tyr Ala Tyr Gly Phe Asp His Ser Ser Ser
65                  70                  75                  80

Asn Gly Glu Ile Ser Arg Arg Arg Ser Pro Leu Phe Arg Arg Leu Pro
                85                  90                  95

Leu Phe Arg Leu Tyr Cys Asp Tyr Phe Pro Ile His Ile His Arg Glu
            100                 105                 110

Val Pro Leu Glu Pro Thr Phe Pro Gly Arg Leu Arg Glu Pro Ser Gly
        115                 120                 125

Leu Val Glu Arg Trp Ile Ala Lys Met Phe Gly Val Gln Asp Ala Val
    130                 135                 140

Val Glu Gly Asn Glu Ser Asp Val Lys Ala Thr Ala Asn Gly Asn Gly
145                 150                 155                 160

Thr Thr Lys Glu Ile Gly Pro Thr Tyr Val Phe Gly Tyr His Pro His
                165                 170                 175

Gly Ile Val Ser Leu Gly Ala Phe Gly Ala Ile Gly Thr Glu Gly Ala
            180                 185                 190

Gly Trp Glu Lys Leu Phe Pro Gly Ile Pro Val Ser Leu Leu Thr Leu
        195                 200                 205

Glu Thr Asn Phe Ser Leu Pro Phe Tyr Arg Glu Tyr Leu Leu Ser Leu
    210                 215                 220

Gly Ile Ala Ser Val Ser Arg Arg Ser Cys Thr Asn Leu Leu Lys His
225                 230                 235                 240

Asp Gln Ser Ile Cys Ile Val Ile Gly Gly Ala Gln Glu Ser Leu Leu
                245                 250                 255

Ala Glu Pro Gly Thr Leu Asp Leu Ile Leu Val Lys Arg Arg Gly Phe
            260                 265                 270

Val Lys Leu Ala Met Ser Thr Ala Arg Val Ser Asp Gln Pro Ile Cys
        275                 280                 285

Leu Val Pro Ile Leu Ser Phe Gly Glu Asn Asp Val Tyr Asp Gln Val
    290                 295                 300

Arg Gly Asp Arg Ser Ser Lys Leu Tyr Lys Ile Gln Thr Phe Ile Lys
305                 310                 315                 320

Lys Ala Ala Gly Phe Thr Leu Pro Leu Met Tyr Ala Arg Gly Ile Phe
                325                 330                 335

Asn Tyr Asp Phe Gly Leu Met Pro Tyr Arg Arg Gln Met Thr Leu Val
            340                 345                 350

Val Gly Lys Pro Ile Ala Val Pro Tyr Val Ala Gln Pro Thr Glu Ala
        355                 360                 365

Glu Ile Glu Val Tyr His Lys Gln Tyr Met Asp Glu Leu Arg Arg Leu
    370                 375                 380

Trp Asp Thr Tyr Lys Asp Asp Tyr Phe Val Asp His Lys Gly Lys Gly
385                 390                 395                 400

Val Lys Asn Ser Glu Met Arg Phe Val Glu
                405                 410
```

<210> SEQ ID NO 24
<211> LENGTH: 1233
<212> TYPE: DNA
<213> ORGANISM: Lipomyces starkeyi

<400> SEQUENCE: 24
atgagtgaga aggcagagat cgaggttccg ccgcaaaaat cgacattccc tcgcagtgtg 60
cacttcgctc cacttcatat tccactggag agacgcctac agactttggc agtcttattc 120
cacactgtcg cgctaccata ctgcatcggt ctgttctttc tcatgctcgc gttccctcct 180
ttttggccat tattggtaat gtatgtcata tacgcatacg ggttcgacca ctcgagctcg 240
aacggagaga tctcccgccg gcgatcgccg ctgtttcgaa gactcccgtt gttcaggctg 300
tattgtgatt acttccccat ccacattcac cgggaggttc cgctcgagcc gacgtttcct 360
ggtcgccttc gcgaaccgag tggccttgtc gagcggtgga ttgcgaagat gttcggcgtg 420
caggacgctg ttgtcgaggg aaatgaatct gacgttaagg ccacggccaa cggcaatggg 480
acgacgaaag aaatcggacc gacgtatgtt ttcggctatc atccgcatgg aattgttagc 540
ttgggtgcgt ttggtgctat tggtacggaa ggcgctggat gggagaagct ctttcctggg 600
atcccggtgt cactgctgac tctcgaaaca aatttcagcc ttccatttta cagagagtat 660
ttgctgtcac ttgggattgc ttcagtatct cgacggtctt gtaccaatct cctcaaacac 720
gaccaatcca tctgcatcgt tatcggcggc gcccaagagt cgctcttagc ggaaccaggc 780
actctagatc tgatcctcgt taaacgtcgc ggttttgtca aacttgcaat gtcaacggcg 840
cgggtatctg accaaccgat ttgtcttgtt ccgatcctca gtttcggcga gaacgacgtg 900
tacgaccaag tccgcgggga ccgatcgtcg aagttgtata agatccagac ttttatcaag 960
aaagcggccg ggtttacgct accattgatg tatgcgcgcg gtatatttaa ttacgacttt 1020
gggctgatgc cgtaccgcag gcaaatgacg ctcgtggtcg gcaagccgat tgcagtgccg 1080
tacgtggccc agcctacgga ggctgaaatc gaagtgtatc acaagcagta catggatgaa 1140
ttgaggaggt tatgggacac gtataaggac gactattttg tagaccacaa gggcaagggg 1200
gtcaagaatt ccgagatgcg ttttgtggag taa 1233

<210> SEQ ID NO 25
<211> LENGTH: 380
<212> TYPE: PRT
<213> ORGANISM: Aspergillus terreus

<400> SEQUENCE: 25

Met Pro Arg Asn Thr His Pro Pro Ala Asn Asn Ala Gly Pro Asn Ala
1 5 10 15

Ser His Lys Lys Asp Arg Lys Arg Gln Gly Arg Leu Phe Gln His Thr
20 25 30

Val Pro Asn Lys Tyr Ser Arg Ile Arg Trp Ala Pro Leu Asn Ile Gly
35 40 45

Leu Glu Arg Arg Leu Gln Thr Leu Val Val Leu Cys His Thr Leu Thr
50 55 60

Ile Ala Leu Phe Leu Ala Phe Phe Phe Phe Thr Cys Ala Ile Pro Leu
65 70 75 80

Thr Trp Pro Leu Leu Phe Pro Tyr Leu Val Tyr Ile Thr Leu Phe Ser
85 90 95

Thr Ala Pro Thr Ser Gly Thr Leu Lys Gly Arg Ser Asp Phe Leu Arg
100 105 110

Ser Leu Pro Ile Trp Lys Leu Tyr Thr Ala Tyr Phe Pro Ala Lys Leu

-continued

```
        115                 120                 125

His Arg Ser Glu Pro Leu Leu Pro Thr Arg Lys Tyr Ile Phe Gly Tyr
    130                 135                 140

His Pro His Gly Ile Ile Ser His Gly Ala Phe Ala Ala Phe Ala Thr
145                 150                 155                 160

Asp Ala Leu Gly Phe Ser Lys Leu Phe Pro Gly Ile Thr Asn Thr Leu
                165                 170                 175

Leu Thr Leu Asp Ser Asn Phe Arg Ile Pro Phe Tyr Arg Glu Tyr Ala
            180                 185                 190

Met Ala Met Gly Val Ala Ser Val Ser Arg Glu Ser Cys Glu Asn Leu
        195                 200                 205

Leu Thr Lys Gly Gly Ala Asp Gly Glu Gly Met Gly Arg Ala Ile Thr
    210                 215                 220

Ile Val Val Gly Gly Ala Arg Glu Ser Leu Asp Ala Leu Pro His Thr
225                 230                 235                 240

Met Arg Leu Val Leu Lys Arg Arg Lys Gly Phe Ile Lys Leu Ala Ile
                245                 250                 255

Arg Thr Gly Ala Asp Leu Val Pro Val Leu Ala Phe Gly Glu Asn Asp
            260                 265                 270

Leu Tyr Glu Gln Val Arg Ser Asp Gln His Pro Leu Ile Tyr Lys Val
        275                 280                 285

Gln Met Leu Val Lys Arg Phe Leu Gly Phe Thr Val Pro Leu Phe His
    290                 295                 300

Ala Arg Gly Ile Phe Asn Tyr Asp Val Gly Leu Met Pro Tyr Arg Arg
305                 310                 315                 320

Pro Leu Asn Ile Val Val Gly Arg Pro Ile Gln Val Val Arg Gln Gln
                325                 330                 335

Asp Arg Asp Lys Ile Asp Asp Glu Tyr Ile Asp Arg Leu His Ala Glu
            340                 345                 350

Tyr Val Arg Glu Leu Glu Ser Leu Trp Asp Gln Trp Lys Asp Val Tyr
        355                 360                 365

Ala Lys Asp Arg Ile Ser Glu Leu Glu Ile Val Ala
    370                 375                 380
```

<210> SEQ ID NO 26
<211> LENGTH: 1143
<212> TYPE: DNA
<213> ORGANISM: Aspergillus terreus

<400> SEQUENCE: 26

```
atgccccgaa acacccaccc ccccgccaac aacgccggac ctaacgcctc tcacaagaag     60

gaccgaaagc gacagggacg actctttcag cacaccgttc ctaacaagta ctctcgaatc    120

cgatgggccc ccctcaacat tggcctggag cgacgactgc agaccctcgt cgtgctgtgc    180

catacctca ctatcgccct gttcctcgct ttctttttct ttacttgtgc cattcccctg    240

acctggcctc tgctcttccc ctacctcgtg tacatcaccc tgttttcgac cgctcctact    300

tccggtaccc tgaagggacg atctgacttc ctccgatcgc tgcctatttg gaagctctac    360

actgcctact ttcccgctaa gctgcaccga tccgagcctc tgctccctac ccgaaagtac    420

atcttcggct accacccccca tggtatcatt tcccatggag ccttcgccgc ttttgccact    480

gacgctctcg gcttctctaa gctgtttcct ggtatcacca acactctgct caccctggat    540

tcgaacttcc gaattccctt ttaccgagag tacgccatgg ctatgggagt ggcttccgtt    600

tctcgagagt cgtgcgagaa cctgctcact aagggaggtg ctgacggaga gggaatgggc    660
```

```
cgagctatca ccattgttgt cggaggcgcc cgagagtccc tcgatgctct gcctcacact    720

atgcgactgg tcctcaagcg acgaaagggt ttcatcaagc tggccattcg aaccggagct    780

gacctcgttc ccgtcctggc cttcggcgag aacgacctct acgagcaggt gcgatctgat    840

cagcaccctc tgatctacaa ggtccagatg ctcgtgaagc gattcctggg ttttaccgtg    900

cccctgttcc atgctcgagg aatttttaac tacgacgttg gcctcatgcc ttaccgacga    960

cccctgaaca tcgtggttgg tcgacccatt caggtcgtgc gacagcagga ccgagataag   1020

atcgacgatg agtacattga ccgactccac gccgagtacg tccgagagct cgagtccctg   1080

tgggaccagt ggaaggatgt ttacgccaag gaccgaatct ctgagctgga gattgtcgct   1140

taa                                                                 1143
```

<210> SEQ ID NO 27
<211> LENGTH: 437
<212> TYPE: PRT
<213> ORGANISM: Claviceps purpurea

<400> SEQUENCE: 27

```
Met Ala Ala Val Gln Val Ala Arg Pro Val Pro Pro His His His Asp
1               5                   10                  15

Gly Ala Gly Arg Glu His Lys Gly Glu Arg Ala His Ser Pro Glu Arg
            20                  25                  30

Gly Glu Lys Thr Val His Asn Gly Tyr Gly Leu Ala Glu Thr His Glu
        35                  40                  45

Pro Leu Glu Leu Asn Gly Ser Ala Val Gln Asp Gly Lys His Asp Ser
    50                  55                  60

Asp Glu Thr Ile Thr Asn Gly Asp Tyr Ser Pro Tyr Pro Glu Leu Asp
65                  70                  75                  80

Cys Gly Lys Glu Arg Ala Ala His Glu Lys Glu Ala Trp Thr Ala Gly
                85                  90                  95

Gly Val Arg Phe Ala Pro Leu Arg Val Pro Phe Lys Arg Arg Met Gln
            100                 105                 110

Thr Ala Ala Val Leu Phe His Cys Met Ser Ile Ile Leu Ile Ser Ser
        115                 120                 125

Cys Phe Trp Phe Ser Leu Ala Asn Pro Ile Thr Trp Pro Ile Leu Val
    130                 135                 140

Pro Tyr Leu Val His Leu Ser Leu Ser Asn Ala Ser Thr Asp Gly Lys
145                 150                 155                 160

Leu Ser Tyr Arg Ser Glu Trp Leu Arg Ser Leu Pro Leu Trp Arg Leu
                165                 170                 175

Phe Ala Gly Tyr Phe Pro Ala Lys Leu His Lys Thr Phe Asp Leu Pro
            180                 185                 190

Pro Asn Arg Lys Tyr Ile Phe Gly Tyr His Pro His Gly Ile Ile Ser
        195                 200                 205

His Gly Ala Trp Cys Ala Phe Ala Thr Asn Ala Leu Gly Phe Val Glu
    210                 215                 220

Lys Phe Pro Gly Ile Thr Asn Ser Leu Leu Thr Leu Asp Ser Asn Phe
225                 230                 235                 240

Arg Val Pro Phe Tyr Arg Asp Trp Ile Leu Ala Met Gly Ile Arg Ser
                245                 250                 255

Val Ser Arg Glu Ser Ile Arg Asn Ile Leu Ser Lys Gly Gly Pro Asp
            260                 265                 270

Ser Asn Gly Gln Gly Arg Ala Val Thr Ile Val Ile Gly Gly Ala Arg
```

-continued

```
        275                 280                 285

Glu Ser Leu Glu Ala Gln Pro Gly Thr Leu Arg Leu Ile Leu Gln Gly
    290                 295                 300

Arg Lys Gly Phe Ile Lys Val Ala Leu Arg Ala Gly Ala Asp Leu Val
305                 310                 315                 320

Pro Val Ile Gly Phe Gly Glu Asn Asp Leu Tyr Asp Gln Leu Ser Pro
                325                 330                 335

Lys Thr His Pro Leu Val His Lys Ile Gln Met Phe Phe Leu Lys Val
            340                 345                 350

Phe Lys Phe Thr Ile Pro Ala Leu His Gly Arg Gly Leu Leu Asn Tyr
        355                 360                 365

Asp Val Gly Leu Leu Pro Tyr Arg Arg Ala Val Asn Ile Val Val Gly
    370                 375                 380

Arg Pro Ile Gln Ile Asp Glu Thr Tyr Gly Glu Gln Pro Pro Gln Glu
385                 390                 395                 400

Val Ile Asp Arg Tyr His Glu Leu Tyr Val Gln Glu Val Glu Arg Leu
                405                 410                 415

Tyr Ala Ala Tyr Lys Glu Gln Phe Ser Asn Gly Lys Lys Thr Pro Glu
            420                 425                 430

Leu Gln Ile Leu Ser
        435


<210> SEQ ID NO 28
<211> LENGTH: 1314
<212> TYPE: DNA
<213> ORGANISM: Claviceps purpurea

<400> SEQUENCE: 28

atggctgctg ttcaggttgc ccgacccgtt cccccccacc accacgatgg cgctggccga      60

gagcacaagg gagagcgagc ccattcccct gagcgaggag agaagaccgt ccacaacggc     120

tacggtctgg ccgagactca tgagcccctg gagctcaacg gttctgctgt gcaggacgga     180

aagcacgact cggatgagac catcactaac ggtgactact ctccctaccc tgagctcgat     240

tgcggaaagg agcgagccgc tcatgagaag gaggcttgga ccgctggagg tgtgcgattc     300

gctcctctgc gagttccttt taagcgacga atgcagactg ccgctgtcct cttccactgc     360

atgtccatca ttctgatttc ctcttgtttc tggttttctc tcgccaaccc catcacctgg     420

cctattctcg ttccctacct ggtccacctg tcgctctcca acgcttctac tgacggcaag     480

ctctcctacc gatctgagtg gctgcgatcc ctgcctctct ggcgactgtt cgccggttac     540

tttcccgcta agctccacaa gaccttcgat ctgcccccta accgaaagta catctttggt     600

taccaccccc atggaatcat ttcccatggc gcctggtgtg ccttcgctac caacgctctg     660

ggcttcgttg agaagtttcc tggtattacc aactcgctgc tcactctcga ctccaacttc     720

cgagtgccct tttaccgaga ttggatcctg gccatgggca ttcgatctgt ttcgcgagag     780

tctatccgaa acattctctc gaagggagga cctgactcca acggacaggg ccgagctgtg     840

accatcgtta ttggtggagc ccgagagtct ctggaggctc agcccggaac tctgcgactc     900

attctgcagg gccgaaaggg cttcattaag gtggctctcc gagctggagc tgacctggtt     960

cccgtcatcg gtttcggaga gaacgacctc tacgatcagc tgtcccctaa gacccacccc    1020

ctcgttcata agatccagat gttctttctg aaggtcttca agtttactat tcctgctctg    1080

cacggacgag gtctgctcaa ctacgacgtc ggtctgctcc cttaccgacg agctgtgaac    1140

atcgtcgtgg gacgacccat ccagattgac gagacctacg gcgagcagcc ccctcaggag    1200
```

gtcatcgatc gataccacga gctctacgtc caggaggtgg agcgactgta cgccgcttac 1260
aaggagcagt tctcgaacgg aaagaagacc cccgagctcc agatcctgtc ctaa 1314

<210> SEQ ID NO 29
<211> LENGTH: 351
<212> TYPE: PRT
<213> ORGANISM: Aurantiochytrium limacinum

<400> SEQUENCE: 29

Met Leu Ala Trp Met Pro Val Leu Ile Ala Leu Pro Arg Arg Lys Gln
1 5 10 15

Thr Ala Val Val Leu Leu Phe Val Met Leu Leu Pro Met Ile Met Val
20 25 30

Val Tyr Ser Trp Thr Leu Ile Leu Leu Ile Phe Pro Leu Thr Thr Leu
35 40 45

Pro Thr Leu Ser Tyr Leu Ile Trp Ile Met Tyr Ile Asp Lys Ser His
50 55 60

Glu Thr Gly Lys Arg Lys Pro Phe Met Arg Tyr Trp Lys Met Trp Arg
65 70 75 80

His Phe Ala Asn Tyr Phe Pro Leu Arg Leu Ile Arg Thr Thr Pro Leu
85 90 95

Asp Pro Arg Arg Lys Tyr Val Phe Cys Tyr His Pro His Gly Ile Ile
100 105 110

Ser Leu Gly Ala Phe Gly Asn Phe Ala Thr Asp Ser Thr Gly Phe Ser
115 120 125

Arg Lys Phe Pro Gly Ile Asp Leu Arg Leu Leu Thr Leu Gln Ile Asn
130 135 140

Phe Tyr Cys Pro Ile Ile Arg Glu Leu Leu Leu Tyr Met Gly Leu Cys
145 150 155 160

Ser Ala Ala Lys Lys Ser Cys Asn Gln Ile Leu Gln Arg Gly Pro Gly
165 170 175

Ser Ala Ile Met Leu Val Val Gly Gly Ala Ala Glu Ser Leu Asp Ser
180 185 190

Gln Pro Gly Thr Tyr Arg Leu Thr Leu Gly Arg Lys Gly Phe Val Arg
195 200 205

Val Ala Leu Asp Asn Gly Ala Asp Leu Val Pro Val Leu Gly Phe Gly
210 215 220

Glu Asn Asp Val Phe Asp Thr Val Tyr Leu Pro Pro Asn Ser Trp Ala
225 230 235 240

Arg Asn Val Gln Glu Phe Val Arg Lys Lys Leu Gly Phe Ala Thr Pro
245 250 255

Ile Phe Ser Gly Arg Gly Ile Phe Gln Tyr Asn Met Gly Leu Met Pro
260 265 270

His Arg Lys Pro Ile Ile Val Val Val Gly Lys Pro Ile Lys Ile Pro
275 280 285

Lys Ile Pro Asp Glu Leu Lys Gly Arg Ala Leu Ser Thr Thr Ala Glu
290 295 300

Gly Val Ala Leu Val Asp Lys Tyr His Glu Lys Tyr Val Arg Ala Leu
305 310 315 320

Arg Glu Leu Trp Asn Leu Tyr Lys Glu Glu Tyr Ala Thr Glu Pro Lys
325 330 335

Ala Ala Tyr Leu Glu Pro Asn Ser Ile Arg Lys Asn Gln Asn Val
340 345 350

<210> SEQ ID NO 30
<211> LENGTH: 1056
<212> TYPE: DNA
<213> ORGANISM: Aurantiochytrium limacinum

<400> SEQUENCE: 30
atgctcgcct ggatgcctgt cctcattgcc ctcccccgac gaaagcagac cgctgttgtt 60
ctcctgtttg tgatgctcct ccctatgatc atggtcgtgt actcctggac cctgatcctg 120
ctcattttcc ccctcaccac tctgcctact ctctcctacc tgatctggat tatgtacatt 180
gacaagtctc acgagaccgg aaagcgaaag ccctttatgc gatactggaa gatgtggcga 240
catttcgcca actactttcc tctccgactg atccgaacca ctcccctgga ccctcgacga 300
aagtacgtgt tctgctacca cccccatggc atcatttccc tcggagcctt cggcaacttt 360
gctaccgact cgactggctt ctcccgaaag tttcccggta tcgatctgcg actgctcacc 420
ctccagatta acttctactg tcctatcatt cgagagctgc tcctgtacat gggtctgtgc 480
tctgccgcta agaagtcgtg taaccagatc ctccagcgag gacccggctc tgctattatg 540
ctggttgtcg gcggtgccgc tgagtccctc gactctcagc ctggcaccta ccgactcact 600
ctgggtcgaa agggattcgt gcgagttgcc ctggacaacg gtgctgatct ggtccccgtg 660
ctcggtttcg gagagaacga cgtgtttgat accgtttacc tgccccctaa ctcgtgggcc 720
cgaaacgtcc aggagttcgt gcgaaagaag ctcggattcg ctacccccat cttttccggc 780
cgaggtattt ttcagtacaa catgggtctg atgccccacc gaaagcctat cattgtggtt 840
gtcggaaagc ccatcaagat tcccaagatc cctgacgagc tgaagggacg agccctctct 900
accactgccg agggcgttgc tctggtcgat aagtaccatg agaagtacgt tcgagccctc 960
cgagagctgt ggaacctcta caaggaggag tacgctaccg agcccaaggc cgcttacctc 1020
gagcctaact cgattcgaaa gaaccagaac gtctaa 1056

<210> SEQ ID NO 31
<211> LENGTH: 697
<212> TYPE: PRT
<213> ORGANISM: Rhodosporidium toruloides

<400> SEQUENCE: 31

Met Thr Glu Arg Ser Leu Pro Val Thr Leu Pro Leu Pro Arg Asn Phe
1 5 10 15

Ala Leu Thr Pro His Gln Met Ala Ser Pro Asp Pro Pro Leu Pro Gly
20 25 30

Pro Ala Asn Leu Val Asp Asp Ala Leu Arg His Pro Asp Ser Ala Pro
35 40 45

Pro Ile Ser Pro Asp Ser Ala Pro Pro Ser Thr Ala Thr Arg Pro Ser
50 55 60

Ala Leu Ser Arg Gly Glu Leu Ser Thr Ala Ser Ser Tyr Ala Ser Glu
65 70 75 80

Val Ser Thr Arg Glu Gly Thr Pro Asp Leu Ala Asn Gly Gln Gly Val
85 90 95

Thr Thr Thr Ile Thr Thr Val Thr Gly Lys Gly Gly Lys Ala Val Thr
100 105 110

Gln Thr Leu Thr His Val Gly Ala Ala Ser Val Asp Ala Arg Phe Ser
115 120 125

Ser Thr Thr Asn Ser Ile Thr Leu Arg Pro Ile Pro Ala Arg Gly Gly
130 135 140

```
Asp Pro Lys Lys Ile Lys Val Leu Arg Ser Arg Arg Thr His Phe Ala
145                 150                 155                 160

Pro Arg Thr Ser His Phe Asp Arg His Asn Leu Thr Ser Ala Ser Asp
                165                 170                 175

Pro Phe Arg Gly Leu Tyr Thr Leu Phe Trp Ile Val Ile Phe Val Gly
            180                 185                 190

Ala Leu Lys Thr Val Tyr His Arg Phe Ala Glu Gln Gly Gly Trp Gly
        195                 200                 205

Gly Glu Trp Arg Phe Ala Ala Leu Ile Ser Arg Asp Gly Trp Val Leu
    210                 215                 220

Ala Val Ser Asp Ala Val Leu Val Ser Ala Ser Leu Leu Cys Val Pro
225                 230                 235                 240

Tyr Ala Lys Leu Leu Val His Gly Trp Ile Arg Tyr His Gly Ala Gly
                245                 250                 255

Val Ile Ile Gln His Ile Cys Gln Thr Leu Tyr Leu Ala Ile Ala Ile
            260                 265                 270

Arg Trp Thr Phe His Arg Asn Trp Pro Trp Val Gln Ser Gly Phe Met
        275                 280                 285

Thr Leu His Ala Leu Ser Met Leu Met Lys Ile His Ser Tyr Cys Ser
    290                 295                 300

Leu Asn Gly Glu Leu Ser Glu Arg Arg Arg Gln Leu Lys Lys Asp Glu
305                 310                 315                 320

Lys Arg Leu Glu Glu Val Leu Glu Glu Met Gly Gly Arg Arg Lys Ala
                325                 330                 335

Glu Arg Glu Ala Arg Glu Glu Trp Glu Arg Gln Cys Gly Glu Ala Ala
            340                 345                 350

Arg Ala Lys Glu Gly Glu Ala Gly Val Ser Glu Gly Glu Lys Glu Ala
        355                 360                 365

Ala Ala Thr Leu Ser Ser Thr Asp Ala Ser Asn Ser Ala Leu Ser Ser
    370                 375                 380

Glu Asp Glu Ala Ala Ala Ala Leu Leu Arg His Arg Gln Pro Thr Ala
385                 390                 395                 400

Arg Arg Arg Ser Ile Ser Pro Ser Ala Ser Arg Thr Gly Ser Ser Ser
                405                 410                 415

Ala Pro Ser Ala Thr Leu Ala Pro Ser Arg Ala Glu Glu Pro Gln Glu
            420                 425                 430

Gly Val Glu Thr Leu Thr Trp His Pro Ser Asp Gln Val Ser Lys Leu
        435                 440                 445

Ala Ile Ala Ile Cys Glu Ala Lys Asp Leu Leu Thr Ser Asn Gly Lys
    450                 455                 460

Lys Pro Val Thr Phe Pro Glu Asn Val Thr Phe Ala Asn Phe Ile Asp
465                 470                 475                 480

Tyr Leu Leu Val Pro Thr Leu Val Tyr Glu Leu Glu Tyr Pro Arg Thr
                485                 490                 495

Asp Ser Ile Arg Pro Leu Tyr Ile Leu Glu Lys Thr Leu Ala Thr Phe
            500                 505                 510

Gly Thr Phe Ser Ile Leu Val Leu Ile Val Asp Ser Phe Ile Leu Pro
        515                 520                 525

Val Thr Ser Arg Thr Asp Thr Pro Leu Phe Gly Phe Val Leu Asp Leu
    530                 535                 540

Ala Leu Pro Phe Thr Leu Ala Tyr Leu Leu Ile Phe Tyr Val Ile Phe
545                 550                 555                 560

Glu Gly Val Cys Asn Gly Phe Ala Glu Leu Thr Arg Phe Ala Asp Arg
```

-continued

```
                565                 570                 575

Asn Phe Phe Asp Asp Trp Trp Asn Ser Cys Thr Phe Asp Glu Phe Ser
            580                 585                 590

Arg Lys Trp Asn Arg Pro Val His Ala Phe Leu Leu Arg His Val Tyr
        595                 600                 605

Ala Glu Thr Met Ala Ser Tyr Lys Leu Ser Lys Leu Ser Ala Ala Phe
    610                 615                 620

Val Thr Phe Leu Phe Ser Ala Cys Val His Glu Leu Val Met Ala Val
625                 630                 635                 640

Val Thr Lys Lys Leu Arg Leu Tyr Leu Phe Ser Met Gln Met Ala Gln
                645                 650                 655

Leu Pro Leu Ile Met Val Gly Arg Ala Lys Ile Phe Arg Gln Tyr Pro
            660                 665                 670

Ala Leu Gly Asn Leu Phe Phe Trp Leu Ala Leu Leu Ser Gly Phe Pro
        675                 680                 685

Leu Leu Gly Thr Leu Tyr Leu Arg Tyr
    690                 695
```

```
<210> SEQ ID NO 32
<211> LENGTH: 2094
<212> TYPE: DNA
<213> ORGANISM: Rhodosporidium toruloides

<400> SEQUENCE: 32

atgacggagc gatcccttcc agtgacgctc cctcttcctc gaaactttgc gctcacaccg      60

caccagatgg cctcgccaga cccgccactc ccaggcccag ccaacctcgt cgacgacgca     120

ctccgacacc cagactcggc gccgcccatc tcgcccgact ccgcgcctcc ttcgactgcg     180

actcggccct ctgctctctc gcgcggagag ctctcgaccg cttcgagcta cgcgagcgag     240

gtgtcgacga gggaggggac accggatctg gcgaatgggc aaggggttac gacgaccatc     300

acgactgtca caggcaaagg cggaaaggcc gtcacccaga ccctcaccca cgtcggcgcc     360

gcctccgtcg acgcccgctt ctcctccacc acaaactcca tcactctccg ccctatcccc     420

gcccgtggcg gcgacccgaa aaagatcaaa gtcctccgct ctcgtcggac ccacttcgcc     480

ccacgcacct cacacttcga ccgtcacaac ctcacctccg cctctgaccc gttccgcgga     540

ctgtacacgt tgttctggat cgtgatcttc gttggggcac tcaagactgt gtatcatcgg     600

tttgcggaac agggtgggtg gggtggagaa tggaggtttg cggcgttgat tagtcgcgat     660

gggtgggttc tggcggttag tgatgcggtg ttggttagcg cgtcgttgtt gtgcgtgccg     720

tatgcaaagc tcctcgtaca cggctggatc cggtaccacg gcgcaggcgt catcatccaa     780

cacatctgtc aaacgctcta cctcgccatc gcgatccgct ggaccttcca ccgcaactgg     840

ccctgggtcc aaagcggttt catgaccctc cacgccctct cgatgctcat gaagatccat     900

agctactgtt ctctgaacgg cgagctttcg gagcggcgga gacagttgaa gaaggacgag     960

aagcggttgg aggaggtgct ggaggagatg ggtggacgga ggaaggcgga gagggaggcg    1020

agggaggagt gggagaggca gtgtggggag gcggcgaggg ccaaggaggg tgaggcggga    1080

gtgagcgagg gggagaagga ggcggcggcg actctatctt cgacggatgc gtcgaattcg    1140

gccctttcgt cggaggacga ggcggctgcg gcgctgttgc ggcatcgaca gccgactgct    1200

cgacgacgat ccatctcgcc ctctgcctca cgcaccggtt cctcctccgc cccctccgct    1260

accctcgccc cctctcgcgc cgaagaaccc caagaaggcg ttgagacgct cacctggcac    1320

ccatccgacc aagtcagcaa actcgctatc gccatctgcg aggcaaagga cctcctcacg    1380
```

-continued

```
agtaacggca agaagcccgt cacgttcccc gagaacgtca cctttgcgaa ctttatcgac   1440

tacttgcttg tgccgacgtt ggtgtacgag ttggagtacc ctcggacgga ttccatccgg   1500

cccctctaca tcctcgaaaa gaccctcgca accttcggca ccttctccat tctcgtcctc   1560

atcgtcgact cgttcatcct ccccgtcacc tcgcgcaccg acacgcccct cttcgggttc   1620

gtcctcgacc tcgccctgcc gttcacgctc gcgtacctcc tcatcttcta cgtcatcttt   1680

gagggcgtgt gcaatgggtt tgcggagttg acgaggtttg cggatcggaa tttcttcgac   1740

gattggtgga actcgtgcac gttcgacgag ttctcgcgca agtggaatcg ccccgtccac   1800

gccttcctcc tccgccacgt ttacgccgaa acgatggctt cttacaagct ctcgaagctc   1860

tcggctgcgt tcgtcacgtt cttgttcagc gcctgcgtgc acgaactcgt catggcggtc   1920

gtgacgaaga agcttcggct gtacctgttc tcgatgcaga tggcccagct cccgctcatc   1980

atggtgggcc gcgccaagat cttccgacag tatccagcgc tcggcaacct cttcttctgg   2040

ctcgcccttc tctcgggatt cccgcttctc gggacgctgt atctgcggta ctga         2094
```

<210> SEQ ID NO 33
<211> LENGTH: 555
<212> TYPE: PRT
<213> ORGANISM: Lipomyces starkeyi

<400> SEQUENCE: 33

```
Met Ser Thr Ala Ala Gln Ser Asp Thr Asp Asn Glu Asp Ile Ser Thr
1               5                   10                  15

Val Asp Leu Val Asp Ser Arg Ala Asp Thr His Thr Ser Ser Asn Val
            20                  25                  30

Met Leu Gln Gln Gln Lys Ser Arg Arg Arg Leu Ile Gly Lys Asp Ala
        35                  40                  45

Glu Pro Arg Thr Gln His Pro Ser Gly Gly Lys Ser Glu Lys Glu Glu
    50                  55                  60

Leu Thr Lys Pro Asp Asp Ser Lys Gly Pro Ile Lys Leu Ser His Ile
65                  70                  75                  80

Tyr Pro Ile His Ala Val Ser Arg Gly Ser Ile Leu Ser Arg Glu Ser
                85                  90                  95

Thr Thr Pro Thr Pro Ser Phe Val Gly Phe Arg Asn Leu Ala Met Ile
            100                 105                 110

Val Leu Gly Lys Leu Gln Tyr Ser Leu Phe Phe Trp Cys Asp Arg Ala
        115                 120                 125

Asn Ile Pro Thr Ala Val Ser Asn Leu Arg Leu Val Ile Glu Asn Tyr
    130                 135                 140

Ser Lys Tyr Gly Val Leu Ile Arg Phe Ala Arg Leu Gly Ile Ser Gln
145                 150                 155                 160

Lys Asp Ile Leu Tyr Cys Ile Phe Leu Thr Ala Thr Ile Pro Leu His
                165                 170                 175

Leu Phe Ile Ala Ile Val Ile Glu Arg Leu Val Ala Ile Pro Thr Val
            180                 185                 190

Asn Tyr Val Ala Ser Leu Ser Glu Ser Glu Asp Lys Lys Arg Ser Asn
        195                 200                 205

Pro Lys Met Gly Arg Lys Gly Gly Ser Ile Ser Ile Leu Arg Pro Lys
    210                 215                 220

Pro Lys Tyr Met Trp Arg Leu Ile Val Leu Leu His Ser Ile Asn Ala
225                 230                 235                 240

Met Ala Cys Leu Trp Val Thr Thr Val Val Val Tyr Asn Ser Ile Tyr
```

-continued

```
                245                 250                 255

His Pro Leu Ile Gly Thr Ala Cys Glu Phe His Ala Val Ile Val Cys
            260                 265                 270

Leu Lys Val Ala Ser Phe Ala Leu Thr Asn Arg Asp Leu Arg Glu Ser
        275                 280                 285

Met Leu Asn Ser Gln Pro Val Pro Ala Ile Tyr Asn Leu Ala Pro Tyr
    290                 295                 300

Pro Lys Asn Leu Thr Leu Lys Asn Leu Ser Tyr Phe Trp Trp Ala Pro
305                 310                 315                 320

Thr Leu Val Tyr Gln Pro Val Tyr Pro Arg Ser Pro Ser Phe Arg Pro
                325                 330                 335

Leu Phe Phe Val Lys Arg Ile Leu Glu Met Val Gly Leu Ser Phe Leu
            340                 345                 350

Ile Trp Phe Leu Ser Ala Gln Tyr Ala Val Pro Thr Leu Glu Asn Ser
        355                 360                 365

Leu Val His Phe His Ser Leu Gln Phe Met Gly Ile Met Glu Arg Leu
    370                 375                 380

Met Lys Leu Ala Ser Ile Ser Met Ala Ile Trp Leu Ala Gly Phe Phe
385                 390                 395                 400

Cys Ile Phe Gln Ser Gly Leu Asn Ala Leu Ala Glu Val Met Arg Phe
                405                 410                 415

Gly Asp Arg Ala Phe Tyr Asp Asp Trp Trp Asn Ser Lys Ser Val Gly
            420                 425                 430

Glu Tyr Trp Arg Leu Trp Asn Lys Pro Val Thr Asn Tyr Phe Arg Arg
        435                 440                 445

His Ile Tyr Val Pro Leu Val Arg Arg Gly Trp Asn Ser Ala Thr Ala
    450                 455                 460

Ser Val Met Val Phe Phe Val Ser Ala Val Leu His Glu Leu Val Val
465                 470                 475                 480

Gly Val Pro Thr His Asn Val Ile Gly Val Ala Phe Ser Ser Met Ile
                485                 490                 495

Leu Gln Ile Pro Leu Ile Gln Val Thr Ala Pro Leu Glu Lys Met His
            500                 505                 510

Gly Pro Thr Ser Gly Ile Ile Gly Asn Cys Ile Phe Trp Phe Ser Phe
        515                 520                 525

Phe Ile Gly Gln Pro Leu Gly Val Leu Leu Tyr Tyr Phe Ala Trp Asn
    530                 535                 540

Val Ser Met Ser Lys Val Lys Met Val Glu Ser
545                 550                 555
```

<210> SEQ ID NO 34
<211> LENGTH: 1668
<212> TYPE: DNA
<213> ORGANISM: Lipomyces starkeyi

<400> SEQUENCE: 34

```
atgtcgaccg ctgcacaatc tgatacagac aacgaggata tatcgactgt cgatttggtt      60

gactctcgtg cagatactca cacatcttca aatgttatgt tgcaacagca aaaatcgcgt     120

cggagactaa tcgggaaaga cgccgagcca agaacacagc atccgtctgg aggcaaatcg     180

gagaaggagg agttgacgaa gccggatgac tcaaagggac ccataaaatt aagtcacata     240

tacccgatac atgccgttag ccgaggcagt attctgtcac gagagtcgac aactcctaca     300

ccgagttttg ttgggtttcg aaacttagcc atgatagtgc tagggaagtt acagtattca     360
```

```
ttattctttt ggtgcgatcg ggctaacatt ccgacagccg tcagcaatct tcgattggtg    420

attgaaaatt actcaaagta cggcgttctg atccgattcg cccgactcgg tatttcacaa    480

aaggacattc tgtattgcat attcttgacc gctaccatcc cgctgcacct atttattgct    540

attgtcattg aaagactagt tgcgattccg acggtaaact acgtcgcttc gctcagcgag    600

agcgaggata aaaaacgctc caaccccaaa atgggacgga aggggggcag tatatcgatt    660

ttgcgtccta agccaaaata tatgtggcgc ctgatcgtcc tattgcattc aataaacgca    720

atggcttgct tgtgggttac gactgttgtt gtttacaatt ctatttatca tccccttatt    780

gggacagctt gtgaatttca tgcagtgatt gtgtgtctta aggtcgcatc gtttgcgctt    840

accaatcgcg atcttcggga gtcgatgctg aactctcaac ctgtgccagc catatacaac    900

ttggcccctt atccaaaaaa cttaaccctc aagaacttgt catacttttg gtgggcgccg    960

actcttgttt atcaacctgt ctatccgcga tcgccttcat tccggccttt gtttttttgtc   1020

aagcggattc tggagatggt gggcctatca tttttaatat ggttcttgtc agctcaatat   1080

gctgtgccga cgctagaaaa tagtttggtg cattttcaca gtttgcaatt catgggaatt   1140

atggagcgac tcatgaagct tgctagcatt agcatggcta tttggcttgc tggtttttttc   1200

tgcatttttc agtctggact caatgcgctt gcggaggtaa tgcggtttgg tgacagagcc   1260

ttttacgacg actggtggaa cagcaaatct gtgggagagt attggcgtct gtggaataag   1320

ccggttacga attacttccg gcgtcatatt tacgtaccgc ttgtgcgccg cgggtggaat   1380

tctgcgacag ccagtgtcat ggtatttttc gtcagcgcgg tgttgcatga gctagttgtt   1440

ggagttccga cgcataacgt aattggagtt gcattctcgt cgatgattct acaaatccca   1500

ctcatacaag taaccgcgcc tctggagaag atgcatggac ctacatctgg aataataggg   1560

aactgtatct tttggtttag cttcttcatc ggtcagcctc tgggcgtgct actttactat   1620

tttgcgtgga acgttagtat gagcaaagta aagatggtcg agagctag                 1668
```

<210> SEQ ID NO 35
<211> LENGTH: 517
<212> TYPE: PRT
<213> ORGANISM: Aspergillus terreus

<400> SEQUENCE: 35

```
Met Val Met Asp Thr Gln Thr Thr Ala Ser Ala Thr Ser Thr Ala Leu
1               5                   10                  15

Thr Thr Asp His Thr Val Ala Ser Arg Thr Ser Arg Ser Glu Pro Asn
            20                  25                  30

Gly Gly Val His Asn Val Ser Ser Pro Pro Thr Ser Glu Pro Thr Gly
        35                  40                  45

Gly Asn Gly Gly Gly Arg Arg Arg Ser Lys Tyr Arg His Val Ala Ala
    50                  55                  60

Tyr His Ser Glu Val Arg His Ser Ser Leu Ser Arg Glu Ser Asn Thr
65                  70                  75                  80

Ser Pro Ser Phe Leu Gly Phe Arg Asn Leu Met Val Ile Val Leu Gly
                85                  90                  95

Glu Cys Pro Ser Ala Leu Leu Arg Phe Val Asn Pro Thr Glu Asn Ser
            100                 105                 110

Tyr Gly Ser Arg Leu Val Ala Met Asn Leu Arg Leu Val Ile Glu Asn
        115                 120                 125

Tyr Val Lys Tyr Gly Val Leu Ile Cys Ile Arg Cys His Asp Tyr Arg
    130                 135                 140
```

-continued

```
Lys Gln Asp Val Val Leu Gly Ser Met Leu Phe Ala Leu Val Pro Cys
145                 150                 155                 160

Gln Leu Phe Ile Ala Tyr Leu Leu Glu Leu Ala Ala Ala Gly Arg Ala
                165                 170                 175

Lys Gln Thr Val Gly Arg Lys Lys Lys Asp Gly Ser Ala Glu Glu Gly
            180                 185                 190

Glu Arg Glu Ala Arg Ala Phe Arg His Ile Trp Arg Phe Ala Leu Ser
        195                 200                 205

Phe His Ile Leu Asn Ile Val Leu Asn Leu Ala Val Thr Ser Phe Val
    210                 215                 220

Val Tyr Tyr Tyr Ile His His Pro Gly Ile Gly Thr Leu Cys Glu Val
225                 230                 235                 240

His Ala Ile Val Val Ala Leu Lys Asn Trp Ser Tyr Ala Phe Thr Asn
                245                 250                 255

Arg Asp Leu Arg Glu Ala Met Leu Asn Pro Ser Ala Glu Ser Ala Leu
            260                 265                 270

Pro Glu Ile Tyr Ser Ser Leu Pro Tyr Pro Lys Asn Ile Thr Leu Gly
        275                 280                 285

Asn Leu Thr Tyr Phe Trp Leu Ala Pro Thr Leu Leu Tyr Gln Pro Val
    290                 295                 300

Tyr Pro Arg Ser Pro Ser Ile Arg Trp Pro Phe Val Ala Lys Arg Leu
305                 310                 315                 320

Ser Glu Phe Ala Cys Leu Ser Val Phe Ile Trp Leu Leu Ser Ala Gln
                325                 330                 335

Tyr Ala Ala Pro Val Leu Arg Asn Ser Ile Asp Lys Ile Arg Asp Met
            340                 345                 350

Ala Tyr Ala Ser Ile Phe Glu Arg Val Met Lys Leu Ser Thr Ile Ser
        355                 360                 365

Leu Val Ile Trp Leu Ala Gly Phe Phe Ala Ile Phe Gln Ser Leu Leu
    370                 375                 380

Asn Ala Leu Ala Glu Ile Met Lys Phe Gly Asp Arg Glu Phe Tyr Thr
385                 390                 395                 400

Asp Trp Trp Asn Ser Pro Ser Leu Gly Val Tyr Trp Arg Ser Trp Asn
                405                 410                 415

Arg Pro Val Tyr Gln Phe Met Lys Arg His Val Tyr Ser Pro Leu Ile
            420                 425                 430

Gly Arg Gly Tyr Ser Pro Phe Val Ala Ser Thr Val Val Phe Thr Ile
        435                 440                 445

Ser Ala Leu Leu His Glu Leu Leu Val Gly Ile Pro Thr His Asn Met
    450                 455                 460

Ile Gly Val Ala Leu Val Gly Met Leu Phe Gln Leu Pro Leu Ile Ala
465                 470                 475                 480

Ile Thr Ala Pro Leu Glu Lys Met Lys Asp Pro Leu Gly Lys Pro Leu
                485                 490                 495

Gly Ala Leu Leu Tyr Phe Phe Ala Trp Gln Ala Lys Tyr Gly Ser Val
            500                 505                 510

Ser Arg Met Gly Asn
        515
```

<210> SEQ ID NO 36
<211> LENGTH: 1554
<212> TYPE: DNA
<213> ORGANISM: Aspergillus terreus

<400> SEQUENCE: 36

```
atggtgatgg acacacaaac cacagcatcc gccaccagca cggcgctcac gaccgaccac      60
actgttgcct ctcggacgtc ccgctctgag ccgaacggtg gtgtgcataa tgtatcgtca     120
cctccaacga gcgaaccgac tgggggaaat ggcggaggcc ggcgaaggag taaataccgg     180
catgtcgcag cgtaccattc cgaagtgcgc cattccagtc tcagtcggga atcgaatact     240
tctccgagtt tcctcggatt ccggaacctc atggtaatcg tattaggtga gtgccctagt     300
gctctcctac gttttgtgaa cccgacggag aactcatacg ggtcgcgact agttgctatg     360
aatcttcgat tggttatcga gaattacgtg aagtatgggg tcttgatctg catcagatgc     420
cacgattatc gaaagcagga cgttgtcctg ggctcaatgt tatttgctct cgtcccatgc     480
cagctattca tcgcctacct cctggaattg gccgcagcgg gtagggccaa acagactgtg     540
ggccgaaaga aaaaggacgg atcagccgag gagggcgaac gtgaagcacg tgcttttcga     600
cacatctggc ggtttgcatt gtcctttcac atcctcaaca ttgttctcaa tctcgccgtc     660
acgagcttcg ttgtgtatta ctacatccac catcccggca ttggtacgct ctgtgaagtg     720
catgcgatcg ttgtcgcgtt gaaaaactgg tcctatgcgt tcaccaatcg ggatctgcga     780
gaggcgatgc ttaatccctc ggcggagtcg gcgcttcccg agatctattc cagcctcccg     840
tacccgaaaa acatcacgtt aggaaatcta acgtacttct ggcttgcacc gacactgttg     900
tatcagccag tataccccag gtcgccttcc atccgatggc cattcgtggc caaacgcttg     960
tcggaatttg cgtgcttgtc ggtgttcatt tggctacttt cggcccaata cgctgcgcca    1020
gttttgcgca actccattga caagattcgt gatatggcat atgcatccat ttttgagcgc    1080
gttatgaagc tatccaccat ctctctcgtc atttggctgg ctgggttctt tgcgattttc    1140
caatcactct tgaatgcttt ggcggagatc atgaagtttg gcgatcggga attctacacc    1200
gattggtgga atagcccaag tctcggtgtt tactggcggt catggaatcg gccagtgtac    1260
cagttcatga agcggcacgt atattctccg ttgatagggc gggggtacag cccgtttgtg    1320
gcaagcactg tcgtattcac catctccgct ctccttcatg agctcctcgt ggggataccc    1380
acgcacaaca tgataggcgt cgcgcttgtt ggaatgctgt tccagctccc gttgatcgcc    1440
atcactgccc cattggaaaa gatgaaagat ccattgggta agcccctggg agcactgctg    1500
tatttctttg cctggcaggc aaaatatggc agtgtgagca ggatgggcaa ctga          1554
```

<210> SEQ ID NO 37
<211> LENGTH: 506
<212> TYPE: PRT
<213> ORGANISM: Claviceps purpurea

<400> SEQUENCE: 37

```
Met Ser Ala Thr Gly Val Asp Val Ala Asn Gly Arg Ser Gly Ala Arg
1               5                   10                  15

Arg Arg Asn Asp Thr Ala Val Asp Glu Thr Ile Ser Ala Val Thr Ala
            20                  25                  30

Glu Met Arg Ser Ser Ser His Pro Thr Tyr Arg His Val Ser Ala Val
        35                  40                  45

His Ser Thr Ser Arg Pro Ser Cys Leu Ser His Asp Ser Asp Ala Ala
    50                  55                  60

Pro Ser Phe Ile Gly Phe Arg Asn Leu Met Val Ile Val Leu Val Val
65                  70                  75                  80

Gly Asn Val Arg Leu Met Ile Glu Asn Leu Lys Lys Tyr Gly Val Leu
                85                  90                  95
```

-continued

```
Ile Cys Leu Arg Cys His Ser Tyr Lys Asn Glu Asp Ile Ile Ile Gly
            100                 105                 110

Gly Leu Leu Tyr Phe Leu Ile Pro Cys His Leu Leu Val Ala Tyr Gly
        115                 120                 125

Ile Glu Leu Ala Ala Ala Arg Gln Ala Arg Glu Ser Arg Thr Arg Pro
    130                 135                 140

Pro Gly Gln Ser Asp Thr Ala Ser Lys Ser Thr Glu Asp Asp Asn Lys
145                 150                 155                 160

His Phe His Ser Thr Trp Val Leu Ala Ala Trp Ala His Ile Ile Asn
                165                 170                 175

Met Thr Leu Ser Phe Ile Leu Thr Thr Phe Val Val Tyr Tyr Tyr Val
            180                 185                 190

His His Pro Leu Val Gly Thr Leu Thr Glu Met His Ala Val Ile Val
        195                 200                 205

Ser Leu Lys Thr Ala Ser Tyr Ala Phe Thr Asn Arg Asp Leu Arg His
    210                 215                 220

Ala Tyr Leu His Pro Asp Lys Arg Lys His Ile Pro Glu Leu Tyr Leu
225                 230                 235                 240

Glu Cys Pro Tyr Pro Gln Asn Leu Thr Phe Gly Asn Leu Val Tyr Phe
                245                 250                 255

Trp Trp Ala Pro Thr Leu Val Tyr Gln Pro Val Tyr Pro Arg Thr Asp
            260                 265                 270

Lys Ile Arg Trp Val Phe Val Phe Lys Arg Leu Gly Glu Val Cys Cys
        275                 280                 285

Leu Ser Ala Phe Ile Trp Phe Ala Ser Phe Gln Tyr Ala Ala Pro Val
    290                 295                 300

Leu Arg Asn Ser Leu Asp Lys Ile Ala Ser Leu Asp Phe Ile Met Ile
305                 310                 315                 320

Phe Glu Arg Leu Leu Lys Leu Ser Thr Ile Ser Leu Val Ile Trp Leu
                325                 330                 335

Ala Gly Phe Phe Ala Leu Phe Gln Ser Phe Leu Asn Ala Leu Ala Glu
            340                 345                 350

Val Leu Arg Phe Gly Asp Arg Cys Phe Tyr Asp Asp Trp Trp Asn Ser
        355                 360                 365

Glu Ser Leu Gly Ala Tyr Trp Arg Thr Trp Asn Arg Pro Val Tyr Thr
    370                 375                 380

Tyr Phe Lys Arg His Val Tyr Val Pro Met Ile Gly Arg Gly Trp Ser
385                 390                 395                 400

Pro Trp Thr Ala Ser Cys Thr Val Phe Phe Val Ser Ala Val Leu His
                405                 410                 415

Glu Val Leu Val Gly Val Pro Thr His Asn Ile Ile Gly Val Ala Phe
            420                 425                 430

Val Gly Met Phe Leu Gln Leu Pro Leu Ile Ala Leu Thr Ala Pro Met
        435                 440                 445

Glu Lys Lys Lys Trp Gly His Thr Gly Arg Val Met Gly Asn Val Ile
    450                 455                 460

Phe Trp Val Ser Phe Thr Ile Phe Gly Gln Pro Phe Ala Ala Leu Met
465                 470                 475                 480

Tyr Phe Tyr Ala Trp Gln Ala Lys Tyr Gly Ser Val Ser Arg Gln Ile
                485                 490                 495

Val Leu Val Asn Pro Val Glu Glu Ala Ser
            500                 505
```

<210> SEQ ID NO 38
<211> LENGTH: 1521
<212> TYPE: DNA
<213> ORGANISM: Claviceps purpurea

<400> SEQUENCE: 38

```
atgtccgcca cgggcgttga tgtggccaac ggccgcagcg gcgcgcgacg acgcaacgat     60
actgccgtcg acgagactat atccgccgtc acggccgaga tgcgttcctc gtcgcatcca    120
acataccgcc atgtgtctgc tgtgcactcc acgagccggc cctcgtgtct gagccatgat    180
tctgacgctg cgccgagctt cattggcttt cgaaatctca tggtcattgt tctggtcgtt    240
ggcaatgttc gattaatgat tgaaaatcta aaaaagtacg gcgtactgat atgcctccga    300
tgtcactcgt ataaaaacga agacatcatt atcggcggac tgctctactt cctgatcccc    360
tgccacttgc ttgtcgccta cggaatcgag ttagccgccg ccagacaagc acgcgaatct    420
cgaactcgtc caccaggcca gtccgacacg gcgtcgaaat caacagaaga tgacaacaag    480
cacttccact caacatgggt gctcgctgcc tgggcacaca tcatcaacat gacactttcc    540
ttcatcctca ccaccttcgt cgtctactac tacgtgcacc atcccctcgt cggcaccctg    600
accgagatgc acgccgtcat cgtctctctc aaaacagctt cctacgcatt caccaaccga    660
gatcttcgcc acgcatacct ccatcctgac aagcgcaagc acatccccga gctatatctc    720
gaatgtccct acccccagaa cctcaccttt ggcaatctcg tgtatttctg gtgggccccc    780
acgctggtat accagcccgt gtatccgcgc accgacaaga tcagatgggt ttttgttttt    840
aaaagactag gcgaagtctg ctgtctcagc gcattcatct ggttcgccag cttccagtac    900
gccgcgcccg tgttgcggaa ctccctggac aagattgcgt ctctcgactt catcatgatc    960
tttgagcgcc ttctcaagct atccaccatt tctctcgtca tctggctcgc cggcttcttc   1020
gccctgttcc agtctttcct gaatgccctg gctgaggtat tgcgctttgg ggaccggtgc   1080
ttctacgacg attggtggaa tagcgagagt ctgggggcgt attggaggac gtggaacagg   1140
cctgtgtata cctacttcaa gcgccatgtg tatgtgccca tgattgggag gggatggagt   1200
ccctggactg ctagttgtac tgtttttttt gtgtcggcgg tgctgcacga ggttcttgtt   1260
ggggtgccca cccacaatat cattggtgtc gcctttgtgg gcatgtttct gcagcttccc   1320
ctaatagccc tcaccgctcc catggaaaag aagaaatggg gccacaccgg ccgtgtgatg   1380
ggcaatgtta ttttctgggt gtcctttaca atctttgggc agccctttgc agcgctcatg   1440
tacttttatg cctggcaggc caagtacggg agcgtgagtc ggcaaattgt gctggtgaat   1500
ccggtggagg aggcgtcttg a                                              1521
```

<210> SEQ ID NO 39
<211> LENGTH: 551
<212> TYPE: PRT
<213> ORGANISM: Chaetomium globosum

<400> SEQUENCE: 39

```
Met Lys Ala Glu Thr Gly Thr Thr Met Ala Thr Ser Thr Ser Leu Glu
1               5                   10                  15

Thr Ser Gln Val Asn Gly Val Thr Asn Arg Ala Pro Val Gly Pro Ser
            20                  25                  30

His Asp Pro His Ala Thr Thr Pro Thr His Glu Thr Thr Thr Thr Ile
        35                  40                  45

Pro Ser Asp Val Leu Ala Asn Gly Ser Thr Asn Gly Thr Thr Asn Gly
    50                  55                  60
```

-continued

```
Thr Thr Asp Asp Ser Leu Asp Ile Ser Glu Leu Arg Lys Ala Phe Arg
65                  70                  75                  80

Asn Lys Tyr Arg His Val Glu Ala Val His Ser Glu Ser Lys Pro Ser
                85                  90                  95

Cys Leu Ser His Asp Ala Thr Glu Thr Pro Ser Phe Ile Gly Phe Arg
            100                 105                 110

Asn Leu Met Val Ile Val Leu Val Ala Ala Asn Leu Arg Leu Val Ile
        115                 120                 125

Glu Asn Ile Gln Lys Tyr Gly Val Leu Ile Cys Ile Lys Cys His Asp
    130                 135                 140

Phe Arg Pro Asn Asp Val Arg Leu Gly Leu Leu Leu Tyr Ile Leu Ile
145                 150                 155                 160

Pro Trp His Leu Met Leu Ala Tyr Leu Ile Glu Leu Val Ala Ala Ala
                165                 170                 175

Asn Ala Arg Asn Ser Arg Ala Lys Ala Lys Lys Arg Asp Gly Ser Thr
            180                 185                 190

Ser Pro Thr Glu Asp Glu Ser Lys Gln Phe Leu Gln Thr Trp Arg Met
        195                 200                 205

Leu Arg Ile Leu His Ala Val Asn Val Thr Ala Ala Leu Ala Val Thr
    210                 215                 220

Ser Tyr Val Val Tyr Tyr Tyr Ile His His Pro Leu Ile Gly Thr Leu
225                 230                 235                 240

Ser Glu Leu His Ala Ile Ile Val Trp Leu Lys Thr Ala Ser Tyr Ala
                245                 250                 255

Leu Thr Asn Arg Asp Leu Arg His Ala Tyr Leu His Pro Val Arg Gly
            260                 265                 270

Glu Arg Asp Ala Leu Pro Glu Ile Tyr Ala Gln Cys Pro Tyr Pro Ala
        275                 280                 285

Asn Val Thr Phe Ser Asn Leu Thr Tyr Phe Trp Trp Ala Pro Thr Leu
    290                 295                 300

Val Tyr Gln Pro Ala Tyr Pro Arg Thr Gln Arg Ile Arg Trp Val Phe
305                 310                 315                 320

Val Ala Lys Arg Leu Gly Glu Val Val Cys Leu Ser Ala Phe Ile Trp
                325                 330                 335

Phe Ala Ser Ala Gln Tyr Ala Thr Pro Val Leu Arg Asn Ser Leu Asp
            340                 345                 350

Lys Ile Ala Thr Leu Asp Tyr Met Ser Ile Val Glu Arg Leu Leu Lys
        355                 360                 365

Leu Ser Thr Ile Ser Leu Val Ile Trp Leu Ala Gly Phe Phe Ala Leu
    370                 375                 380

Phe Gln Ser Phe Leu Asn Ala Leu Ala Glu Val Met Arg Phe Gly Asp
385                 390                 395                 400

Arg Glu Phe Tyr Glu Ala Trp Trp Asn Ser Glu Ser Leu Gly Ala Tyr
                405                 410                 415

Trp Arg Thr Trp Asn Lys Pro Val Tyr Gln Phe Phe Arg Arg His Val
            420                 425                 430

Tyr Ser Pro Met Arg Ser Arg Gly Trp Ser His Leu Ser Ala Ser Leu
        435                 440                 445

Ala Val Phe Leu Leu Ser Ala Val Leu His Glu Leu Leu Val Gly Val
    450                 455                 460

Pro Thr His Asn Ile Ile Gly Val Ala Phe Leu Gly Met Phe Leu Gln
465                 470                 475                 480

Leu Pro Leu Ile Ala Met Thr Ala Arg Leu Gly Gly Arg Arg Gly Asn
```

-continued

```
                485                 490                 495

Thr Ala His Gly Arg Leu Leu Gly Asn Thr Ile Phe Trp Val Ser Phe
            500                 505                 510

Thr Ile Phe Gly Gln Pro Phe Ala Ala Leu Met Tyr Phe Tyr Ala Trp
        515                 520                 525

Gln Ala Lys Tyr Gly Ser Val Ser Lys Met Pro Leu Ala Gln Pro Gly
    530                 535                 540

Thr Cys Pro Ala Val Val Val
545                 550


<210> SEQ ID NO 40
<211> LENGTH: 1656
<212> TYPE: DNA
<213> ORGANISM: Chaetomium globosum

<400> SEQUENCE: 40

atgaaggcag aaacgggcac aacgatggca acgtcgacta gtctcgagac ttcccaagtc     60

aatggcgtca ccaaccgggc ccctgttggc cctagtcacg acccccacgc tacaactccg    120

actcatgaga cgacaaccac cataccgtcc gacgtcctcg ccaatggttc tacaaatggg    180

actacgaatg ggacgacaga tgattcattg gacatatccg aattgcgcaa agcgttccgc    240

aacaagtatc gccatgtcga ggctgtccac tccgaatcga aaccatcctg tctgagccat    300

gacgctacag agacacccag tttcatcggt tttaggaatc tcatggtgat tgtgttggtt    360

gctgccaatc ttcgcctggt catcgagaac attcaaaagt atggagttct gatctgcatc    420

aaatgccacg actttcgccc caacgatgta cgcctggggc tcctcctcta catcctgatc    480

ccatggcacc tcatgctcgc ctacctcatt gagctggtcg ccgccgccaa tgcccgcaac    540

tcccgggcca aggcgaagaa gcgggacggc agtaccagcc cgaccgaaga cgagtccaag    600

caattcctgc agacctggcg gatgctccgc attctccacg ccgtcaacgt cacggccgcc    660

ctggccgtca cctcctacgt ggtctactac tacattcacc acccgctgat cggcacgctc    720

tcggagctgc acgccatcat cgtgtggctc aagacggcgt cgtacgcgct caccaaccgc    780

gacctgcgcc acgcctacct acacccggtg cgcggcgagc gcgacgctct gcccgagatc    840

tacgcccagt gcccctaccc ggccaacgtg accttctcca acttgaccta cttctggtgg    900

gcgcccaccc tggtgtacca gccggcgtac ccgcgcactc agcgcatccg ctgggtcttt    960

gtggctaagc gcctcggcga ggtcgtctgc ttgagcgcct tcatctggtt cgccagcgcc   1020

cagtacgcta cccccgtgct gcgaaactcg ctcgacaaga tcgctaccct ggattacatg   1080

tccattgtcg agcgtctgtt gaagctgtcg accatctcgc tggtcatctg gctggcgggc   1140

ttctttgcgc tgtttcagag tttcctgaat gccttggccg aggtgatgcg gtttggagac   1200

cgcgagttct acgaagcatg gtggaacagc gaaagcctcg gcgcctactg gcgcacctgg   1260

aacaaacccg tgtaccaatt cttccggcgg cacgtctact cgccgatgcg gtcgcgcggg   1320

tggagccact tgtcggccag cctcgccgtg tttctgctct cggccgtgct acacgagctg   1380

ctggtggggg tgccgacgca caacatcatc ggcgtcgcct tcctgggcat gttcctgcag   1440

ctgccgctca tcgccatgac ggcgcgcctg ggcggccgcc gcgggaacac cgcccacggc   1500

cgcctgctcg gcaacactat cttttgggtg tcatttacca tttttggcca gccgtttgcc   1560

gcgctgatgt atttttatgc atggcaggcc aagtatggta gtgtgagcaa gatgccgctg   1620

gcgcagccgg ggacgtgtcc ggctgtggtt gtttga                             1656
```

```
<210> SEQ ID NO 41
<211> LENGTH: 759
<212> TYPE: PRT
<213> ORGANISM: Saccharomyces cerevisiae

<400> SEQUENCE: 41

Met Pro Ala Pro Lys Leu Thr Glu Lys Phe Ala Ser Ser Lys Ser Thr
1               5                   10                  15

Gln Lys Thr Thr Asn Tyr Ser Ser Ile Glu Ala Lys Ser Val Lys Thr
            20                  25                  30

Ser Ala Asp Gln Ala Tyr Ile Tyr Gln Glu Pro Ser Ala Thr Lys Lys
        35                  40                  45

Ile Leu Tyr Ser Ile Ala Thr Trp Leu Leu Tyr Asn Ile Phe His Cys
    50                  55                  60

Phe Phe Arg Glu Ile Arg Gly Arg Gly Ser Phe Lys Val Pro Gln Gln
65                  70                  75                  80

Gly Pro Val Ile Phe Val Ala Ala Pro His Ala Asn Gln Phe Val Asp
                85                  90                  95

Pro Val Ile Leu Met Gly Glu Val Lys Lys Ser Val Asn Arg Arg Val
            100                 105                 110

Ser Phe Leu Ile Ala Glu Ser Ser Leu Lys Gln Pro Pro Ile Gly Phe
        115                 120                 125

Leu Ala Ser Phe Phe Met Ala Ile Gly Val Val Arg Pro Gln Asp Asn
    130                 135                 140

Leu Lys Pro Ala Glu Gly Thr Ile Arg Val Asp Pro Thr Asp Tyr Lys
145                 150                 155                 160

Arg Val Ile Gly His Asp Thr His Phe Leu Thr Asp Cys Met Pro Lys
                165                 170                 175

Gly Leu Ile Gly Leu Pro Lys Ser Met Gly Phe Gly Glu Ile Gln Ser
            180                 185                 190

Ile Glu Ser Asp Thr Ser Leu Thr Leu Arg Lys Glu Phe Lys Met Ala
        195                 200                 205

Lys Pro Glu Ile Lys Thr Ala Leu Leu Thr Gly Thr Thr Tyr Lys Tyr
    210                 215                 220

Ala Ala Lys Val Asp Gln Ser Cys Val Tyr His Arg Val Phe Glu His
225                 230                 235                 240

Leu Ala His Asn Asn Cys Ile Gly Ile Phe Pro Glu Gly Gly Ser His
                245                 250                 255

Asp Arg Thr Asn Leu Leu Pro Leu Lys Ala Gly Val Ala Ile Met Ala
            260                 265                 270

Leu Gly Cys Met Asp Lys His Pro Asp Val Asn Val Lys Ile Val Pro
        275                 280                 285

Cys Gly Met Asn Tyr Phe His Pro His Lys Phe Arg Ser Arg Ala Val
    290                 295                 300

Val Glu Phe Gly Asp Pro Ile Glu Ile Pro Lys Glu Leu Val Ala Lys
305                 310                 315                 320

Tyr His Asn Pro Glu Thr Asn Arg Asp Ala Val Lys Glu Leu Leu Asp
                325                 330                 335

Thr Ile Ser Lys Gly Leu Gln Ser Val Thr Val Thr Cys Ser Asp Tyr
            340                 345                 350

Glu Thr Leu Met Val Val Gln Thr Ile Arg Arg Leu Tyr Met Thr Gln
        355                 360                 365

Phe Ser Thr Lys Leu Pro Leu Pro Leu Ile Val Glu Met Asn Arg Arg
    370                 375                 380
```

-continued

```
Met Val Lys Gly Tyr Glu Phe Tyr Arg Asn Asp Pro Lys Ile Ala Asp
385                 390                 395                 400

Leu Thr Lys Asp Ile Met Ala Tyr Asn Ala Ala Leu Arg His Tyr Asn
                405                 410                 415

Leu Pro Asp His Leu Val Glu Glu Ala Lys Val Asn Phe Ala Lys Asn
            420                 425                 430

Leu Gly Leu Val Phe Phe Arg Ser Ile Gly Leu Cys Ile Leu Phe Ser
        435                 440                 445

Leu Ala Met Pro Gly Ile Ile Met Phe Ser Pro Val Phe Ile Leu Ala
    450                 455                 460

Lys Arg Ile Ser Gln Glu Lys Ala Arg Thr Ala Leu Ser Lys Ser Thr
465                 470                 475                 480

Val Lys Ile Lys Ala Asn Asp Val Ile Ala Thr Trp Lys Ile Leu Ile
                485                 490                 495

Gly Met Gly Phe Ala Pro Leu Leu Tyr Ile Phe Trp Ser Val Leu Ile
            500                 505                 510

Thr Tyr Tyr Leu Arg His Lys Pro Trp Asn Lys Ile Tyr Val Phe Ser
        515                 520                 525

Gly Ser Tyr Ile Ser Cys Val Ile Val Thr Tyr Ser Ala Leu Ile Val
    530                 535                 540

Gly Asp Ile Gly Met Asp Gly Phe Lys Ser Leu Arg Pro Leu Val Leu
545                 550                 555                 560

Ser Leu Thr Ser Pro Lys Gly Leu Gln Lys Leu Gln Lys Asp Arg Arg
                565                 570                 575

Asn Leu Ala Glu Arg Ile Ile Glu Val Val Asn Asn Phe Gly Ser Glu
            580                 585                 590

Leu Phe Pro Asp Phe Asp Ser Ala Ala Leu Arg Glu Glu Phe Asp Val
        595                 600                 605

Ile Asp Glu Glu Glu Glu Asp Arg Lys Thr Ser Glu Leu Asn Arg Arg
    610                 615                 620

Lys Met Leu Arg Lys Gln Lys Ile Lys Arg Gln Glu Lys Asp Ser Ser
625                 630                 635                 640

Ser Pro Ile Ile Ser Gln Arg Asp Asn His Asp Ala Tyr Glu His His
                645                 650                 655

Asn Gln Asp Ser Asp Gly Val Ser Leu Val Asn Ser Asp Asn Ser Leu
            660                 665                 670

Ser Asn Ile Pro Leu Phe Ser Ser Thr Phe His Arg Lys Ser Glu Ser
        675                 680                 685

Ser Leu Ala Ser Thr Ser Val Ala Pro Ser Ser Ser Ser Glu Phe Glu
    690                 695                 700

Val Glu Asn Glu Ile Leu Glu Glu Lys Asn Gly Leu Ala Ser Lys Ile
705                 710                 715                 720

Ala Gln Ala Val Leu Asn Lys Arg Ile Gly Glu Asn Thr Ala Arg Glu
                725                 730                 735

Glu Glu Glu Glu Glu Glu Glu Glu Glu Glu Glu Glu Glu Glu Glu Glu
            740                 745                 750

Glu Gly Lys Glu Gly Asp Ala
        755
```

<210> SEQ ID NO 42
<211> LENGTH: 2280
<212> TYPE: DNA
<213> ORGANISM: Saccharomyces cerevisiae

<400> SEQUENCE: 42

-continued

```
atgcctgcac caaaactcac ggagaaattt gcctcttcca agagcacaca gaaaactacg     60
aattacagtt ccatcgaggc caaaagcgtc aagacgtcgg ctgatcaggc atacatctac    120
caagagccta gcgctaccaa gaagatactt tactccatcg ccacatggct gttgtacaac    180
atcttccact gcttctttag agaaatcaga ggccggggca gtttcaaggt accgcaacag    240
ggaccggtga tctttgttgc ggctccgcat gctaaccagt tcgtcgaccc tgtaatcctt    300
atgggcgagg tgaagaaatc tgtcaacaga cgtgtgtcct tcttgattgc ggagagctca    360
ttaaagcaac cccccatagg gtttttggct agtttcttca tggccatagg cgtggtaagg    420
ccgcaggata atttgaaacc ggcagaaggt actatccgcg tagatccaac agactacaag    480
agagttatcg gccacgacac gcatttcttg actgattgta tgccaaaggg tctcatcggg    540
ttacccaaat caatgggatt tggagaaatc cagtccatag aaagtgacac gagtttgacc    600
ctaagaaaag agttcaaaat ggccaaacca gagattaaaa ctgctttact caccggcact    660
acttataaat atgccgctaa agtcgaccaa tcttgcgttt accatagagt ttttgagcat    720
ttggcccata acaactgcat tgggatcttt cctgaaggtg ggtcccacga cagaacaaac    780
ttgttgcccc tgaaagcagg tgtggcgatt atggctcttg gttgcatgga taagcatcct    840
gacgtcaatg ttaagattgt tccctgcggt atgaattatt tccatccaca taagttcagg    900
tcgagagcgg ttgttgaatt cggtgacccc attgaaatac cgaaggaact agtcgccaag    960
taccacaacc cggaaacgaa cagagatgca gtgaaagaat tattagatac catatcgaag   1020
ggtttacaat ccgttaccgt tacatgttct gattatgaaa ctttgatggt ggttcaaacg   1080
ataagaagac tatatatgac acaatttagc accaagttac cgttgccctt gattgtggaa   1140
atgaacagaa gaatggtcaa aggttacgaa ttctatagaa acgatcctaa aatagcggac   1200
ttgaccaaag atataatggc atataatgcc gccttgagac actataatct tcctgatcac   1260
cttgtggagg aggcaaaggt aaatttcgca aaaaacctcg gacttgtttt ttttagatcc   1320
atcgggctct gcatcctctt ttcgttagcc atgccaggta tcattatgtt ctcacctgtc   1380
ttcatattag ccaagagaat ttctcaagaa aaggcccgta ccgctttgtc caagtctaca   1440
gttaaaataa aggctaacga tgtcattgcc acgtggaaaa tcttgattgg gatgggattt   1500
gcgcccttgc tttacatctt ttggtccgtt ttaatcactt attacctcag acataaacca   1560
tggaataaaa tatatgtttt ttccgggtct tacatctcgt gtgttatagt cacgtattcc   1620
gccttaatcg tgggtgatat tggtatggat ggtttcaaat ctttgagacc actggtttta   1680
tctcttacat ctccaaaggg cttgcaaaag ctacaaaagg atcgtagaaa tctggcagaa   1740
agaataatcg aagttgtaaa taactttgga agcgaattat tccccgattt cgatagtgcc   1800
gccctacgtg aagaattcga cgtcatcgat gaagaggaag aagatcgaaa aacctcagaa   1860
ttgaatcgca ggaaaatgct aagaaaacag aaaataaaaa gacaagaaaa agattcgtca   1920
tcacctatca tcagccaacg tgacaaccac gatgcctatg aacaccataa ccaagattcc   1980
gatggcgtct cattggtcaa tagtgacaat tccctctcta acattccatt attctcttct   2040
acttttcatc gtaagtcaga gtcttcctta gcttcgacat ccgttgcacc ttcttcttcc   2100
tccgaatttg aggtagaaaa cgaaatcttg gaggaaaaaa atggattagc aagtaaaatc   2160
gcacaggccg tcttaaacaa gagaattggt gaaaatactg ccagggaaga ggaagaggaa   2220
gaagaagagg aagaagaaga agaggaagaa gaagaagaag ggaaagaagg agatgcgtag   2280
```

<210> SEQ ID NO 43

```
<211> LENGTH: 710
<212> TYPE: PRT
<213> ORGANISM: Arxula adeninivorans

<400> SEQUENCE: 43

Met Thr Ser Glu Ser Ile Asp Thr Gly Leu Asn Phe Lys Thr Trp Leu
1               5                   10                  15

Tyr Asp Leu Val Leu Trp Ile Phe Gln Val Thr Phe Asn Ile Phe Phe
            20                  25                  30

Arg Glu Ile Leu Ser Arg Gly Ala Phe Arg Ile Pro Lys Ser Gly Pro
        35                  40                  45

Val Ile Phe Val Gly Ala Pro His Ala Asn Gln Phe Val Asp Pro Met
    50                  55                  60

Leu Leu Met Gln Gln Ala Lys Gly Val Ala Gly Arg Arg Leu Ser Phe
65                  70                  75                  80

Leu Ile Ala Glu Thr Ser Leu Arg Arg Lys Phe Ile Gly Ala Ile Ala
                85                  90                  95

Arg Ala Thr Gln Ser Ile Gly Val Val Arg Ala Gln Asp Asn Leu Lys
            100                 105                 110

Pro Gly Ser Gly Lys Ile Ser Val Asp Ala Asp Asn Gly Thr Arg Ile
        115                 120                 125

Ile Gly Glu Gly Thr Lys Phe Thr Thr Glu Cys Met Val Lys Gly Ile
    130                 135                 140

Ile Gly Leu Pro Gln Gln Ala Gly Ser Ala Glu Ile Ala Glu Ile Val
145                 150                 155                 160

Ser Asp Thr Glu Leu Ile Leu Arg Lys Glu Phe Lys Gly Ala Lys Ala
                165                 170                 175

Ala Ser Leu Leu Lys Arg Gly Thr Ser Tyr Lys Arg Ala Asp His Val
            180                 185                 190

Asp Gln Ser Lys Met Tyr Arg Gln Val Phe Asp His Leu His Lys Gly
        195                 200                 205

Gly Cys Leu Gly Ile Phe Pro Glu Gly Gly Ser His Asp Arg Thr Asp
    210                 215                 220

Leu Leu Pro Leu Lys Ala Gly Val Ala Ile Met Ala Leu Gly Ala Ile
225                 230                 235                 240

Met Glu Tyr Pro Asp Leu Asp Val Lys Ile Val Pro Cys Gly Met Asn
                245                 250                 255

Tyr Phe His Pro Asn Lys Phe Arg Ser Arg Ala Val Ile Glu Phe Gly
            260                 265                 270

Ser Pro Met Thr Ile Pro Arg Glu Leu Val Glu Met Tyr Lys Gln Gly
        275                 280                 285

Gly Glu Gln Lys Arg Asp Ala Val Lys Gln Leu Leu Asp Gln Val Ala
    290                 295                 300

Asp Gly Leu Arg Thr Val Thr Val Thr Thr Pro Asp Tyr Glu Thr Leu
305                 310                 315                 320

Met Val Val Gln Ala Ala Arg Arg Leu Tyr Arg Pro Pro Asn Lys Lys
                325                 330                 335

Leu Pro Leu Pro Val Val Val Glu Leu Asn Arg Arg Leu Ile Arg Gly
            340                 345                 350

Tyr Glu Lys Tyr Lys Asp Asp Pro Lys Ile Val His Leu Arg Asn Ala
        355                 360                 365

Val Leu Ser Tyr Asn Lys Lys Leu Lys Gly Leu Gly Leu Lys Asp His
    370                 375                 380

Gln Val Glu Thr Ala Thr Leu Ser Pro His Lys Val Val Phe Lys Phe
```

```
385                 390                 395                 400

Leu Tyr Arg Leu Ser Lys Leu Leu Val Leu Ala Pro Leu Ala Met Pro
                405                 410                 415

Gly Ala Ile Met Phe Ser Pro Val Phe Val Ala Thr Lys Leu Ile Ser
            420                 425                 430

Arg Lys Arg Ala Lys Gln Ala Leu Ala Lys Ser Thr Val Lys Val Gln
        435                 440                 445

Ala Arg Asp Val Val Ala Thr Trp Lys Val Leu Val Ala Met Gly Leu
    450                 455                 460

Ala Pro Cys Leu Tyr Thr Val Tyr Ala Leu Val Ala Thr Tyr Ile Cys
465                 470                 475                 480

Tyr Lys Lys Gln Trp Val Ser Ser Glu Leu Trp Ser Leu Ala Lys Val
                485                 490                 495

Met Ile Ala Ser Tyr Ile Val Phe Pro Ala Ile Thr Trp Ser Ala Leu
            500                 505                 510

Val Ile Gly Glu Thr Gly Met Asp Ile Phe Lys Ser Leu Arg Pro Leu
        515                 520                 525

Ala Leu Ala Leu Asn Pro Phe His Lys Asn Ala Ile Glu Glu Leu Arg
    530                 535                 540

Glu Thr Arg Arg Asn Leu Val Met Glu Val Ser Glu Val Val Asn Ser
545                 550                 555                 560

Leu Gly Pro Glu Leu Tyr Pro Asp Phe Gly Lys Tyr Ser Phe Arg Tyr
                565                 570                 575

Asn Glu Tyr Gln Tyr Lys Glu Glu Lys Leu Ala Asn Gly Lys Val Glu
            580                 585                 590

Glu Ala Glu Glu Thr Glu Glu Ala Lys Glu Ala Lys Glu Asp Glu Glu
        595                 600                 605

Glu Asn Val Val Val Ala Lys Arg Arg Thr Ser Ser Ala Ser Thr Asp
    610                 615                 620

Thr Asn Val Ser Ser Asp Ser Asn Ser Ile Ser Arg Val Asn Ser Glu
625                 630                 635                 640

Ser Gly Leu Ala Asn Ile Pro Leu Phe Ser Ser Ala Asp Pro Val Ser
                645                 650                 655

Asn His Ser Arg Ala Ser Ser Gly Ser Ser Ala Leu Ser Met Glu Val
            660                 665                 670

Pro Asp Thr Thr Thr Ala Thr Gly Gln Lys Val Phe Gln Ser Glu Val
        675                 680                 685

Ser Lys Arg Ile Arg Gly Ala Met Glu Glu Arg Ile Arg Ala Arg Met
    690                 695                 700

Glu Glu Ser Asp Glu Glu
705                 710
```

<210> SEQ ID NO 44
<211> LENGTH: 2133
<212> TYPE: DNA
<213> ORGANISM: Arxula adeninivorans

<400> SEQUENCE: 44

```
atgactagcg aaagcataga cacaggacta aatttcaaga catggctcta cgatctagtg     60

ctatggatct ttcaggtgac atttaacatc ttcttccgag agattctttc tcgaggagca    120

ttcaggatcc caaagtccgg ccccgtcatc tttgtaggag cacctcatgc taaccagttt    180

gtagatccaa tgctgctgat gcagcaggcc aagggagttg cgggccgtcg tctttcgttt    240

ttgattgctg aaacgtcgtt gcgacgcaag tttattggcg caattgcccg ggccacccag    300
```

```
tcaattggag tggtacgtgc tcaggacaat ttgaagcctg ggtctggtaa gatttcagta    360
gatgccgaca atgggacccg tatcattggt gagggaacaa agttcaccac tgagtgtatg    420
gtcaagggta taattggatt gcctcagcaa gcgggcagcg cagagattgc tgaaattgtc    480
agcgacactg agctgattct gcgaaaggag tttaagggcg caaaggctgc ttctctgctt    540
aagcgaggaa cttcatacaa gagagcagac catgtggatc agtcgaaaat gtaccgtcaa    600
gtgtttgacc atcttcacaa gggtggatgc cttggtatct ttcccgaagg aggatctcat    660
gaccgtactg acctgttgcc tttgaaagct ggtgtagcga ttatggctct gggggccatt    720
atggagtatc ctgacctgga tgtgaaaatt gttccctgtg gtatgaacta tttccatcct    780
aacaagttta gatcccgagc agtcattgag tttggaagtc ccatgaccat tccccgggag    840
ttagtagaaa tgtacaaaca aggaggtgaa cagaaacgag atgcagttaa gcaattgctt    900
gaccaggttg ctgatgggct gagaacagtt actgtaacca ctcctgatta cgagactctg    960
atggttgttc aagcagcccg acgattgtac cgccctccta acaagaagct gccgttgcca   1020
gtggttgtgg aactgaaccg ccgactgatt cgtggatatg aaaagtacaa ggacgacccc   1080
aagattgttc atctcaggaa tgcagtcttg tcgtacaaca aaaaactcaa gggactgggc   1140
ctcaaggatc accaagtaga aactgccacc ctctctcctc acaaggttgt attcaagttt   1200
ttgtatcgac tttcaaagct gctggttctg gcccctctgg ctatgcctgg tgccatcatg   1260
ttctctcccg tgtttgtggc taccaagctg atctctagga agcgggccaa acaggcactt   1320
gccaagtcta ctgtcaaagt gcaggctcgc gatgtggtag ccacctggaa ggtacttgtt   1380
gccatgggat tagcaccatg cttgtatacc gtttacgctc tagtggccac ttacatttgc   1440
tacaagaagc aatgggtatc ctcagagctg tggtcgttgg ctaaggtaat gattgcttcg   1500
tacattgttt tccctgctat tacctggtct gctttggtga ttggtgagac cggtatggac   1560
attttcaagt ccctgcgccc tctggcgttg gcgctcaacc cattccacaa gaatgctatt   1620
gaagagctcc gagaaactcg acgcaatttg gtcatggaag tttctgaagt tgtcaattcc   1680
ctcgggcctg agctgtaccc agactttggc aagtactctt tccgatacaa cgaatatcag   1740
tacaaggagg agaaactggc caacggcaaa gtcgaagagg ccgaagagac cgaagaggcc   1800
aaagaggcca aagaggacga agaagaaaat gtggttgtgg ccaaacgacg cacgagcagt   1860
gcgtctacag atactaacgt ttcatcggat tccaattcca tctctcgagt caactcggag   1920
tctggcctgg ccaatattcc tctgttttcc agcgctgatc cagtaagcaa ccactctcga   1980
gccagttccg gttcgtctgc gttgagcatg gaagtgccag ataccaccac tgccactgga   2040
cagaaggtgt tccagtctga ggtatccaag cgaattcggg gtgccatgga ggagagaatc   2100
cgagctcgaa tggaagagag cgatgaggag tag                                2133
```

<210> SEQ ID NO 45
<211> LENGTH: 906
<212> TYPE: PRT
<213> ORGANISM: Rhodotorula glutinis

<400> SEQUENCE: 45

```
Met Pro Ala Ser Pro Asp Pro Ser Ser Ser Ser Asn Asp Val Asp Ser
1               5                   10                  15

Ala Pro Pro Asp Ser Gln Pro Pro Leu Pro Ser Ser Gly Ser Ala Leu
            20                  25                  30

Gly Leu Ser Phe Ala Pro Glu Asp Ser Pro Ala Pro Ala Pro Thr Pro
        35                  40                  45
```

```
Ala Gln Ala Pro Gly Ala Pro Leu Pro Glu Leu Ser Pro Ile Pro Ala
    50                  55                  60

Asp Pro Ala Pro Arg Leu Ala Lys Gln Ala His Phe Ser Asp Leu Thr
65                  70                  75                  80

Gln Ile Arg Thr Ile Ser Pro Val Pro Gln Arg Arg Gln Ser Tyr Arg
                85                  90                  95

Gln Pro Ser Thr Pro Ala Glu Pro Ala Pro Ala Pro Pro Pro Gly Asp
            100                 105                 110

Ser Leu Pro Arg Arg Pro Ser Leu Thr Gln Thr His Ser Asp Leu Arg
        115                 120                 125

Thr Leu Leu Lys Asn Phe Leu Leu Leu Val Pro Pro Ala Leu Arg Arg
    130                 135                 140

Leu Arg Phe Leu Val Pro Ser Pro Leu Arg Val Ile Ala Arg Phe Val
145                 150                 155                 160

Ile Arg Tyr Val Ala Met Phe Leu His Ala Arg Gly Ala Leu Gly Ser
                165                 170                 175

Asn Leu Val Tyr Asp Val Val Ala His Met Trp Arg Val Val Ile Thr
            180                 185                 190

Ile Phe Phe Arg Glu Ile Arg Ser Arg Gly Ala Trp Lys Ile Pro Arg
        195                 200                 205

Ser Ser Glu Gly Ala Val Ile Phe Val Val Gly Pro His His Asn Gln
    210                 215                 220

Phe Leu Asp Pro Leu Leu Leu Met Ser Glu Val Lys Arg Glu Ser Gly
225                 230                 235                 240

Arg Arg Ile Ser Phe Leu Ala Ala Ala Lys Ser Met Asp Arg Ala Phe
                245                 250                 255

Val Gly Leu Ala Ser Arg Leu Met Gln Ser Ile Pro Val Ala Arg Ala
            260                 265                 270

Gln Asp Tyr Ala Phe Ala Gly Gln Gly Thr Ile Ser Leu Ser Pro Ser
        275                 280                 285

Asp Pro Leu Thr Ile Leu Gly Thr Gly Thr Asn Phe Thr Lys Asp Phe
    290                 295                 300

Ser Lys Pro Arg Ser Gln Leu Leu Leu Pro Arg Asn Leu Gly Ser Ser
305                 310                 315                 320

Thr Ala Glu Val Val Glu Val Val Ser Asp Thr Glu Leu Lys Leu Lys
                325                 330                 335

Lys Glu Phe Ser Lys Lys Ala Leu Asp Ala Leu Lys Glu Arg Glu Asp
            340                 345                 350

Gly Val Ala Phe Lys Val Leu Pro His Val Asp Gln Ser Ser Met Tyr
        355                 360                 365

Ser Ala Val Tyr Gln Lys Leu Ile Asp Gly Gly Cys Ile Gly Ile Phe
    370                 375                 380

Pro Glu Gly Gly Ser His Asp Arg Thr Asp Leu Leu Pro Leu Lys Ala
385                 390                 395                 400

Gly Val Ser Ile Met Ala Leu Gly Ala Lys Ser Ala His Pro Asp Leu
                405                 410                 415

Lys Leu Gln Ile Val Pro Val Gly Leu Ser Tyr Phe His Pro His Lys
            420                 425                 430

Phe Arg Ser Arg Ala Val Val Glu Phe Gly Ser Pro Ile Glu Ile Pro
        435                 440                 445

Gln Asp Tyr Val Ser Glu Phe Glu Lys Gly Gly Glu Asn Lys Lys Lys
    450                 455                 460
```

-continued

```
Ala Ile Gly Glu Val Met Glu Leu Ile Val Asp Gly Leu Lys Ser Val
465                 470                 475                 480

Thr Ile Arg Ala Pro Asp Tyr Glu Thr Leu Met Leu Ile Gln Ala Ala
                485                 490                 495

Arg Arg Leu Tyr Arg Pro Pro Gly Thr Asn Leu Thr Ile Gly Gln Val
            500                 505                 510

Val Glu Leu Asn Lys Arg Phe Ile Val Gly Tyr Glu Val Tyr Lys Asp
        515                 520                 525

Asp Pro Arg Ile Lys Glu Leu Glu Arg Gly Val Arg Glu Tyr Asn Thr
    530                 535                 540

Leu Leu Arg Tyr Met Gly Leu Lys Asp His Gln Val Glu Ser Val Gly
545                 550                 555                 560

Arg Pro Arg Trp Arg Ser Phe Phe Leu Leu Cys Tyr Arg Leu Gly Leu
                565                 570                 575

Leu Ser Val Trp Gly Val Leu Ala Leu Pro Gly Val Val Leu Asn Ala
            580                 585                 590

Pro Ile Phe Ile Ala Ala Lys Leu Ile Ser Arg Ala Lys Ala Lys Glu
        595                 600                 605

Ala Leu Ala Ala Ser Thr Val Lys Ile Ala Gly Arg Asp Val Leu Ala
    610                 615                 620

Thr Trp Lys Val Leu Val Ala Leu Ala Gly Ala Pro Ser Leu Tyr Thr
625                 630                 635                 640

Ile Tyr Ala Ile Asn Ala Val Val Leu Ala His Lys Leu Gly Leu Pro
                645                 650                 655

Tyr Lys Tyr Lys Leu Ala Ala Pro Phe Ala Thr Phe Ala Gly Leu Pro
            660                 665                 670

Phe Ile Gly Val Ala Ala Leu Lys Phe Gly Glu Val Gly Met Asp Val
        675                 680                 685

Tyr Lys Ser Met Arg Pro Leu Leu Leu Ser Leu Ile Pro Gly Lys Glu
    690                 695                 700

Pro Glu Leu Lys Arg Leu Arg His Met Arg Glu Thr Leu Ala Ser Glu
705                 710                 715                 720

Leu Asn Glu Leu Val Asp Glu Leu Ala Pro Thr Val Phe Glu Asp Phe
                725                 730                 735

Asp Ser Arg Arg Ile Ile Pro Ser Thr Asp Val Gly Val Arg Arg Glu
            740                 745                 750

Ser Ala Gln Gly Lys Phe Leu Gln His Pro Leu Asn Trp Val Asp Glu
        755                 760                 765

Leu Leu Phe Gly Ser Gly Trp Ser Gln Ser Met Ala His Pro Ala Asp
    770                 775                 780

Arg Lys Val Lys Ser Met Leu Pro Glu Thr Ser Gly Met Glu Ser Asp
785                 790                 795                 800

Met Asp Gly Gly Phe Thr Asp Gly Gln Gly Gly Gly Ser Gly Tyr Ala
                805                 810                 815

Ser Gly Tyr Thr Thr Glu Asp Ala Pro Asp Tyr Asp Glu Val Ile His
            820                 825                 830

Ile Leu Asn Arg Glu Gln Gly Arg Pro Asp Ser Pro Leu Pro Ser Pro
        835                 840                 845

Arg Pro Gly Leu Tyr Arg Arg Ala Ser Arg Gln Arg Ser Arg Ser Gln
    850                 855                 860

Leu Asn Leu Ala Gly Met Ser Pro Val Thr Pro Thr Thr Pro Leu Ala
865                 870                 875                 880

Ala Ser Thr Ser Leu Gln Asp Gly Gly Glu Gly Thr Ala Arg Arg Arg
```

885 890 895

Thr Arg Gln Gly Ser Gly Asp Ala Gln Glu
900 905

<210> SEQ ID NO 46
<211> LENGTH: 2721
<212> TYPE: DNA
<213> ORGANISM: Rhodotorula glutinis

<400> SEQUENCE: 46
atgcccgcct cgcccgaccc ctcctcctca tccaacgacg tcgacagcgc tcctcccgac 60
tcgcaaccgc ctctcccctc gtctggatct gcgctcgggc tctcgttcgc gccagaagac 120
tcgcctgcac ccgcgccaac tcccgcacag gctccaggcg cgccgttgcc agagctctcc 180
cccatccctg ccgatcctgc tcctcgactt gcgaaacagg cgcacttcag cgacttgacg 240
cagatacgca ccatcagccc agtcccacag cgcaggcagt cctaccgcca gccgtccacg 300
cccgcagagc cagcgcccgc accaccgccc ggcgactctc tccctcgacg gccgtcgctc 360
acgcagacgc actcggacct gcgcaccttg ctcaagaact tcctcctcct cgtcccgccc 420
gcactccgcc gcctgcgctt cctcgtcccc tccccgctcc gcgtcatcgc ccgcttcgtc 480
attcgatacg tcgcaatgtt cctccacgcc cgcggcgcac tcggcagcaa cctcgtctac 540
gatgtcgtcg cgcacatgtg gcgagtcgtc atcaccatct tcttccgcga gatccgttct 600
cgcggcgcgt ggaagatccc gaggtcgtcg gagggcgccg tcatcttcgt tgttgggcct 660
caccacaacc agttcctcga ccccctcctg cttatgagtg aggtcaagcg cgagagcgga 720
cggcggatca gcttcctggc ggcggcaaag agcatggaca gggcattcgt cggcttggcg 780
tcgcggttga tgcagagcat ccccgtcgcc cgcgctcaag actacgcctt tgcaggccaa 840
ggcacaatct ccctctcccc ctccgaccca ctcaccatcc tcggcaccgg taccaacttc 900
accaaagact tctcgaaacc tcgaagccag ctccttctcc ctcgcaacct tggaagcagc 960
acggccgagg tcgtcgaagt cgttagcgat acggagttga agctcaagaa ggagttttcg 1020
aagaaggcgc ttgatgcctt gaaggagagg gaggacggcg tcgcgttcaa ggtcctcccg 1080
cacgtcgacc agtcgagcat gtacagcgcc gtttaccaga agctcatcga cggcggctgc 1140
atcggcatct tccccgaagg cggctctcac gaccgtaccg acctcctccc cctcaaagcc 1200
ggcgtctcga tcatggcgct cggcgcaaag tcggcccacc cagacctcaa gctccagatt 1260
gtccccgtcg gattgagcta cttccaccct cacaagttcc gctcgcgcgc tgtcgtcgag 1320
tttggaagcc cgattgagat cccgcaggac tatgtcagcg agtttgagaa gggcggcgag 1380
aacaagaaga aggccattgg ggaggtgatg gagttgattg tcgacgggct caagagcgtc 1440
acgattcgcg cgcccgacta cgagacgttg atgctcatcc aagccgcccg tcgcctgtac 1500
cgccctcccg gtacgaacct cacgatcggc caagtcgtcg agctcaacaa gcgcttcatc 1560
gtcggctacg aagtgtacaa ggacgacccg cgaatcaagg agctcgagcg cggcgtgcgc 1620
gagtacaaca cgttgttgcg gtacatgggc ctcaaggatc accaggttga aagcgtggga 1680
aggccgaggt ggaggtcgtt cttcctcctc tgctacaggc ttgggttgtt gagcgtctgg 1740
ggcgtcctcg ccctgccggg agtcgtcctc aacgccccga tcttcatcgc cgccaagctc 1800
atctcgcggg cgaaggccaa agaggctctc gccgcctcga cagtcaagat cgccggccgc 1860
gacgtcctcg caacctggaa ggtcctcgtc gcgctcgccg gcgcaccctc gctctacaca 1920
atctacgcca tcaacgccgt cgtcctcgcg cacaagctcg gcttgccgta caagtacaag 1980

```
cttgcggcgc cgtttgcgac gtttgcggga ttgccgttca tcggtgttgc ggcgctcaag   2040

ttcggcgagg tcggcatgga cgtctacaag tcaatgcgcc cgctcctcct ctctctgatc   2100

cccggcaagg agcccgagct gaagcgcctg cgacacatgc gcgagacgct cgcctcggag   2160

ctgaacgagc tcgtcgacga gctcgcgcca accgtcttcg aagacttcga ctctcgccgc   2220

atcatcccct cgacggacgt cggcgtccgc cgcgagtcgg cgcagggcaa gttcctccag   2280

cacccgctca actgggtcga cgagttgttg tttggatcgg ggtggagcca gtcgatggcg   2340

catccggcgg acaggaaggt caagagcatg ctgcccgaga ccagcgggat ggagagcgat   2400

atggacggcg ggttcaccga tggtcagggc ggcggcagcg ggtacgcctc gggctatacg   2460

accgaggatg cgcccgacta cgacgaggtc atccacatcc tcaatcgcga gcaaggccgt   2520

cccgactcgc ctctcccttc ccctcgtcca ggtttgtacc gccgagcatc ccgccagcgc   2580

tcgcgctcgc agctcaacct cgcgggcatg agccccgtca cgccgacgac tcctttggcg   2640

gcttcgacga gcttgcagga cgggggcgag ggcacggcga ggcggaggac gaggcagggt   2700

tcgggtgatg cgcaggagtg a                                              2721
```

<210> SEQ ID NO 47
<211> LENGTH: 907
<212> TYPE: PRT
<213> ORGANISM: Rhodosporidium toruloides

<400> SEQUENCE: 47

```
Met Pro Ala Ser Pro Asp Ser Ser Ser Ser Ser Ser Asn Asp Val Asp
1               5                   10                  15

Thr Ala Pro Pro Asp Ser Arg Pro Pro Leu Pro Pro Pro Gly Ser Ala
            20                  25                  30

Leu Gly Leu Ser Phe Ala Pro Glu Asp Ser Pro Val Ser Ala Gln Thr
        35                  40                  45

Pro Ala Gln Ala Pro Gly Ala Pro Val Pro Glu Leu Ser Pro Ile Pro
    50                  55                  60

Ala Asp Pro Ala Pro Arg Leu Ala Lys Gln Ala His Phe Ser Asp Leu
65                  70                  75                  80

Thr Gln Ile Arg Thr Ile Ser Pro Val Pro Gln Arg Arg Gln Ser Tyr
                85                  90                  95

Arg Gln Pro Ser Thr Pro Ala Glu Pro Ala Pro Ala Pro Pro Pro Arg
            100                 105                 110

Asp Ser Pro Pro Arg Arg Pro Ser Leu Thr Gln Thr His Ser Asp Leu
        115                 120                 125

Arg Thr Leu Leu Lys Ser Phe Leu Leu Leu Val Pro Pro Ala Leu Arg
    130                 135                 140

Arg Leu Arg Phe Leu Val Pro Ser Pro Leu Arg Val Ile Ala Arg Phe
145                 150                 155                 160

Val Ile Arg Tyr Val Ala Met Phe Leu His Ala Arg Gly Ala Leu Gly
                165                 170                 175

Ser Asn Leu Val Tyr Asp Val Val Ala His Met Trp Arg Val Val Ile
            180                 185                 190

Thr Ile Phe Phe Arg Glu Ile Arg Ser Arg Gly Ala Trp Lys Ile Pro
        195                 200                 205

Arg Ser Ser Glu Gly Ala Val Ile Phe Val Val Gly Pro His His Asn
    210                 215                 220

Gln Phe Leu Asp Pro Leu Leu Leu Met Ser Glu Val Lys Arg Glu Ser
225                 230                 235                 240
```

-continued

```
Gly Arg Arg Ile Ser Phe Leu Ala Ala Ala Lys Ser Met Asp Arg Ala
                245                 250                 255

Phe Val Gly Leu Ala Ser Arg Leu Met Gln Ser Ile Pro Val Ala Arg
            260                 265                 270

Ala Gln Asp Tyr Ala Phe Ala Gly Gln Gly Thr Ile Ser Leu Ser Pro
        275                 280                 285

Ser Asp Pro Leu Thr Ile Leu Gly Thr Gly Thr Asn Phe Thr Lys Asp
    290                 295                 300

Phe Ser Lys Pro Arg Ser Gln Leu Leu Leu Pro Arg Asn Leu Gly Ser
305                 310                 315                 320

Ser Thr Ala Glu Val Ile Glu Val Val Ser Asp Thr Glu Leu Lys Leu
                325                 330                 335

Lys Lys Glu Phe Ser Lys Lys Ala Leu Asp Ala Leu Lys Glu Arg Glu
            340                 345                 350

Asp Gly Val Ala Phe Lys Val Leu Pro His Val Asp Gln Ser Ser Met
        355                 360                 365

Tyr Ser Ala Val Tyr Gln Lys Leu Ile Asp Gly Gly Cys Ile Gly Ile
    370                 375                 380

Phe Pro Glu Gly Gly Ser His Asp Arg Thr Asp Leu Leu Pro Leu Lys
385                 390                 395                 400

Ala Gly Val Ser Ile Met Ala Leu Gly Ala Lys Ser Ala His Leu Asp
                405                 410                 415

Leu Lys Leu Gln Ile Val Pro Val Gly Leu Ser Tyr Phe His Pro His
            420                 425                 430

Lys Phe Arg Ser Arg Ala Val Val Glu Phe Gly Ser Pro Ile Glu Ile
        435                 440                 445

Pro Gln Glu Tyr Val Ser Glu Phe Glu Lys Gly Gly Glu Asn Lys Lys
    450                 455                 460

Lys Ala Ile Gly Glu Val Met Glu Leu Ile Val Asp Gly Leu Lys Ser
465                 470                 475                 480

Val Thr Val Arg Ala Pro Asp Tyr Asp Thr Leu Met Leu Ile Gln Ala
                485                 490                 495

Ala Arg Arg Leu Tyr Arg Pro Pro Gly Thr Asn Leu Thr Ile Gly Gln
            500                 505                 510

Val Val Glu Leu Asn Lys Arg Phe Ile Val Gly Tyr Glu Val Tyr Lys
        515                 520                 525

Asp Asp Pro Arg Ile Lys Glu Leu Glu Arg Gly Val Arg Glu Tyr Asn
    530                 535                 540

Thr Leu Leu Arg Tyr Met Gly Leu Lys Asp His Gln Val Glu Ser Val
545                 550                 555                 560

Gly Arg Pro Arg Trp Arg Ser Phe Phe Leu Leu Cys Tyr Arg Leu Gly
                565                 570                 575

Leu Leu Ser Val Trp Gly Val Leu Ala Leu Pro Gly Val Val Leu Asn
            580                 585                 590

Ala Pro Ile Phe Ile Ala Ala Lys Leu Ile Ser Arg Ala Lys Ala Lys
        595                 600                 605

Glu Ala Leu Ala Ala Ser Thr Val Lys Ile Ala Gly Arg Asp Val Leu
    610                 615                 620

Ala Thr Trp Lys Val Leu Val Ala Leu Ala Gly Ala Pro Ser Leu Tyr
625                 630                 635                 640

Thr Ile Tyr Ala Ile Asn Ala Val Val Leu Ala His Lys Leu Gly Leu
                645                 650                 655

Pro Tyr Lys Tyr Lys Leu Ala Ala Pro Phe Ala Thr Phe Ala Gly Leu
```

```
            660                 665                 670

Pro Val Ile Gly Val Ala Ala Leu Lys Phe Gly Glu Val Gly Met Asp
        675                 680                 685

Val Tyr Lys Ser Met Arg Pro Leu Leu Leu Ser Leu Ile Pro Gly Lys
    690                 695                 700

Glu Pro Glu Leu Lys Arg Leu Arg His Met Arg Glu Thr Leu Ala Ser
705                 710                 715                 720

Glu Leu Asn Glu Leu Val Asp Glu Leu Ala Pro Thr Val Phe Glu Asp
                725                 730                 735

Phe Asp Ser Arg Arg Ile Ile Pro Ser Thr Asp Val Gly Val Arg Arg
            740                 745                 750

Glu Ser Ala Gln Gly Lys Phe Leu Gln His Pro Leu Asn Trp Val Asp
        755                 760                 765

Glu Leu Leu Phe Gly Ser Gly Trp Ser Gln Ser Met Ala His Pro Ala
    770                 775                 780

Asp Arg Lys Val Lys Ser Met Leu Pro Glu Thr Ser Gly Met Glu Ser
785                 790                 795                 800

Asp Met Asp Gly Gly Phe Thr Asp Gly Gln Gly Gly Gly Ser Gly Tyr
                805                 810                 815

Ala Ser Gly Tyr Thr Thr Glu Asp Ala Pro Asp Tyr Asp Glu Val Ile
            820                 825                 830

His Ile Leu Asn Arg Glu Gln Gly Arg Pro Asp Ser Pro Leu Pro Ser
        835                 840                 845

Pro Arg Pro Gly Leu Tyr Arg Arg Val Ser Arg Gln Arg Ser Arg Ser
    850                 855                 860

Gln Leu Asn Leu Ala Gly Met Ser Pro Val Thr Pro Thr Thr Pro Leu
865                 870                 875                 880

Ala Ala Ser Thr Ser Leu Gln Asp Gly Gly Glu Gly Thr Ala Arg Arg
                885                 890                 895

Arg Thr Arg Gln Gly Ser Gly Asp Ala Gln Glu
            900                 905
```

<210> SEQ ID NO 48
<211> LENGTH: 2724
<212> TYPE: DNA
<213> ORGANISM: Rhodosporidium toruloides

<400> SEQUENCE: 48

```
atgcccgcct cgcccgactc gtcctcctcc tcatccaacg acgtcgacac cgctcctccc      60

gactcgcgac cgcctctccc tccgcctggc tctgcgttgg ggctctcctt tgcgccagaa     120

gactcgcctg tatccgcgca aactcccgca caggctccgg gcgcgccggt gccagagctc     180

tcccccatcc ctgccgatcc cgctcctcga cttgcgaaac aggcgcactt cagcgacctg     240

acgcagattc gcaccatcag cccagtacca cagcgcaggc agtcctaccg ccaaccgtcc     300

acgcccgcag agccagcgcc cgccccgccg ccccgcgact ctccccctcg acgaccgtcg     360

ctcacgcaga cgcactcgga cctgcgcacg ctgctcaaga gtttcctcct cctcgtcccg     420

cccgcactcc gccgcctgcg cttcctcgtc ccctctccgc tccgcgtcat cgcccgcttc     480

gtcattcgat acgtcgcaat gttcctccac gctcgcggcg cgctcggcag caacctcgtc     540

tacgatgtcg tcgcgcacat gtggcgagtc gtcatcacca tcttcttccg cgagatccgc     600

tcccgcggcg cgtggaagat cccgaggtcg tcggagggag ccgtcatctt cgttgttggg     660

cctcaccaca accagttcct cgaccctctc ctgcttatga gcgaggtcaa gcgcgagagc     720
```

-continued

```
ggacgacgga tcagcttcct ggccgcggca aagagcatgg acagggcgtt cgttggcttg    780

gcgtcgcgct tgatgcaaag cattcccgtc gcccgcgcgc aagactacgc ctttgcaggt    840

caaggcacca tctcgctctc cccctcagac ccactcacca tcctcggcac cggcaccaac    900

ttcaccaaag acttctcgaa accccgaagc cagctcctcc tccctcgcaa cctcggcagc    960

agcacggccg aggtcatcga ggtcgtcagt gatacggagt tgaagctcaa aaaggagttt   1020

tcgaagaagg cgcttgatgc gttgaaggag cgggaggacg gcgttgcgtt caaggtcctc   1080

ccgcacgtcg accagtcgag catgtacagc gccgtctacc aaaagctcat cgacggcggc   1140

tgcatcggca ttttccccga aggcggctct cacgaccgta ccgacctcct cccactcaaa   1200

gccggcgtct ccatcatggc gcttggcgcg aagtcggccc acctagacct caagctccag   1260

atcgtccccg tcggactgag ctacttccac cctcacaagt tccgctcgcg cgctgtcgtc   1320

gagtttggga gcccgattga gataccgcag gaatatgtca gcgagtttga gaagggcggc   1380

gagaacaaga agaaggccat tggggaggtg atggagctga ttgtcgacgg gctcaagagc   1440

gtcacggttc gcgcgcctga ctacgatacg ttgatgctca tccaagccgc tcgccgcctg   1500

taccgccctc ccggcacgaa cctcacgatt ggccaagtcg tcgagctcaa caagcgcttc   1560

atcgtcgggt acgaagtgta caaggacgac ccgcgaatca aggagctcga gcggggcgtg   1620

cgcgagtaca acacgctgtt gcggtacatg ggcctcaagg atcaccaggt tgagagcgtg   1680

ggaaggccca ggtggagatc gttcttcctc ctttgctaca ggcttgggtt gttgagcgtc   1740

tggggcgtcc tggcgctgcc cggagtcgtc cttaacgcgc cgatcttcat cgccgccaag   1800

ctcatctcgc gggcaaaggc caaggaggct ctcgccgcct cgaccgtcaa gatcgccggc   1860

cgcgacgtcc tcgcaacctg gaaggtcctc gtcgcgctcg ctggcgcacc atcgctctac   1920

acgatctacg ccatcaacgc cgtcgtcctc gcgcacaaac ttggcttgcc gtacaagtac   1980

aagcttgcgg cgccctttgc gacgtttgcg gggttgccgg tcatcggtgt tgcggcgctc   2040

aagtttggcg aggtcggcat ggacgtctac aagtcaatgc gcccgctcct cctctcgctc   2100

atccccggca aggagcccga gctgaagcgc ctgcgacaca tgcgcgagac gctcgcctcg   2160

gagctgaacg agctcgtcga cgagctcgcg ccgaccgtct tcgaagactt cgactctcgc   2220

cgcatcattc cctcgacgga cgtcggcgtc cgccgcgagt cggcgcaggg caagttcctc   2280

cagcacccgc tcaactgggt cgacgagttg ttgttcggat cggggtggag ccagtcgatg   2340

gcgcacccgg cggaccggaa ggtcaagagc atgctgcccg agacgagcgg gatggagagc   2400

gatatggacg gcgggttcac cgatggtcag ggtggcggca gcgggtacgc ctcgggctac   2460

acgaccgagg atgcgcccga ctacgacgaa gtcatccaca tcctcaaccg cgagcaaggt   2520

cgtcccgact ctcctctccc ttcacctcgc cccggcttgt accgccgcgt ctcccggcag   2580

cgttcgcgct cgcagctcaa cctggcgggg atgagccccg tcacgccgac aactcccttg   2640

gcggcttcga cgagcttgca ggacggcggt gagggtacgg cgaggcggag gacgagacaa   2700

ggctcgggcg acgcgcagga gtga                                          2724
```

<210> SEQ ID NO 49
<211> LENGTH: 413
<212> TYPE: PRT
<213> ORGANISM: Arxula adeninivorans

<400> SEQUENCE: 49

```
Met Ser Val Thr Leu Thr Gln Arg Arg Pro Ser Met Thr Ala Pro Lys
1               5                   10                  15
```

```
Glu Glu Pro Lys Lys Ala Leu Asp Thr Phe Gly Asn Glu Phe Val Val
            20                  25                  30

Pro Ser Tyr Ser Ile Lys Asp Ile Leu Asp Ala Ile Pro Ala His Cys
        35                  40                  45

Tyr Lys Arg Ser Ala Val Arg Ser Leu Ser Tyr Val Ala Arg Asp Val
    50                  55                  60

Phe Phe Ile Gly Leu Phe Gly Tyr Leu Ala Ala Ser Tyr Ile His Leu
65                  70                  75                  80

Ile Pro Trp Met Ser Gly Arg Val Val Ala Trp Phe Leu Tyr Ala Phe
                85                  90                  95

Val Gln Gly Leu Phe Gly Thr Gly Cys Trp Val Leu Ala His Glu Cys
            100                 105                 110

Gly His Arg Ala Phe Ser Glu Ser Asn Ala Ile Asn Asp Ser Val Gly
        115                 120                 125

Trp Val Leu His Ser Ala Leu Leu Val Pro Tyr His Ser Trp Arg Leu
    130                 135                 140

Ser His Ser Lys His His Lys Ala Thr Gly His Met Thr Arg Asp Met
145                 150                 155                 160

Val Phe Val Pro Lys Thr Arg Asp Glu Phe Leu Glu Arg Arg Gly Val
                165                 170                 175

Glu Pro Gly Thr Lys Ile Thr Asp Asn Leu Glu Asp Ala Pro Ile Val
            180                 185                 190

Thr Leu Tyr Tyr Val Val Leu Gln Gln Leu Phe Gly Trp Ile Met Tyr
        195                 200                 205

Leu Phe Thr Asn Val Thr Gly Gln Lys Tyr Pro Asn Arg Ser Lys Trp
    210                 215                 220

Val Thr Asn His Phe Val Pro Thr Ser Pro Leu Tyr Asp Lys Lys Asp
225                 230                 235                 240

Phe Ile Asn Ile Val Ile Ser Asp Ile Gly Ile Ile Ala Thr Leu Thr
                245                 250                 255

Cys Leu Tyr Leu Ala Ser Gln Lys Trp Gly Phe Ser Thr Val Ala Leu
            260                 265                 270

Met Tyr Val Phe Pro Tyr Leu Trp Val Asn His Trp Leu Val His Ile
        275                 280                 285

Thr Phe Leu Gln His Thr Asp Pro Arg Leu Pro His Tyr Asn Ala Asp
    290                 295                 300

Glu Trp Thr Phe Ala Lys Gly Ala Ser Ala Thr Ile Asp Arg Asp Phe
305                 310                 315                 320

Gly Phe Ile Gly Arg His Ile Phe His Asp Ile Ile Glu Thr His Val
                325                 330                 335

Leu His His Phe Val Ser Arg Ile Pro Phe Tyr Asn Gly Arg Glu Ala
            340                 345                 350

Thr Glu Ala Ile Arg Lys Val Met Gly Thr His Tyr Gln Arg Asp Asp
        355                 360                 365

Ser Asn Phe Val Thr Ser Leu Tyr Arg Val Ala Arg Thr Cys Gln Phe
    370                 375                 380

Val Glu Gly Asp Asn Gly Val Ser Met Phe Arg Asn Val Asn Asn Ile
385                 390                 395                 400

Gly Val Arg Pro Asn Leu Asp Gln Gly Gln Lys Leu Gln
                405                 410
```

<210> SEQ ID NO 50
<211> LENGTH: 1242
<212> TYPE: DNA

<213> ORGANISM: Arxula adeninivorans

<400> SEQUENCE: 50

```
atgtctgtca cccttactca acgtcgtccg tctatgacgg ctcccaagga ggagcccaag      60
aaggccttgg acacgtttgg aaatgaattc gttgtgcctt cgtactctat caaggacatt     120
ttggatgcca ttcccgctca ctgctacaag cgatccgcgg tgcgatctct gagctacgtg     180
gctcgggatg tcttcttcat tggtctgttc ggataccttg ctgcttcgta catccacctc     240
attccctgga tgtccggacg agtggttgcc tggttcctgt acgctttcgt acagggtctg     300
tttggaactg gatgctgggt cttggcccac gagtgtggac accgtgcctt ttctgaatcc     360
aatgctatca atgactctgt aggatgggtc cttcactccg ccctgctggt cccttatcac     420
tcgtggcgtc ttagtcactc caagcaccac aaggccactg gacacatgac ccgagacatg     480
gtgtttgtac caaagacccg agatgagttc cttgagcgcc gaggagtcga gcctggcacc     540
aagattaccg acaacctgga ggatgccccc attgtgaccc tgtactacgt tgtgctccag     600
cagctgtttg gatggattat gtatctgttc accaacgtta cgggacaaaa gtaccctaac     660
cgatcaaagt gggtgaccaa tcactttgtg cctacttctc ctctgtacga caagaaggac     720
tttatcaaca ttgtcatctc tgacattggt atcattgcta ccctgacctg tctgtacctt     780
gcttcccaga aatggggttt ctccaccgtg gccctcatgt acgttttccc ttacttgtgg     840
gttaaccact ggctggttca catcaccttc cttcagcaca ctgatccccg actccctcac     900
tacaatgccg acgaatggac ctttgccaag ggtgccagtg ctaccattga ccgagacttt     960
ggattcattg gccgtcacat cttccacgac attattgaga ctcacgttct tcaccacttt    1020
gtgtcgcgaa ttcctttcta caatggacga gaggccaccg aggcaatcag gaaggttatg    1080
ggcacgcact accagcgcga tgactccaac tttgttactt ccttgtaccg tgtcgctcga    1140
acttgtcaat ttgtggaagg agacaatggt gttagcatgt tccgcaatgt taacaacatt    1200
ggagtccggc ccaatttgga ccaagggcag aagcttcaat ag                       1242
```

<210> SEQ ID NO 51
<211> LENGTH: 388
<212> TYPE: PRT
<213> ORGANISM: Arxula adeninivorans

<400> SEQUENCE: 51

```
Met Val Arg Phe Ala Pro Leu Asn Val Pro Leu His Arg Arg Leu Glu
1               5                   10                  15

Thr Phe Ala Leu Thr Tyr His Ile Leu Ser Ile Pro Val Trp Met Ser
            20                  25                  30

Phe Phe Leu Leu Cys Cys Ala Ile Pro Leu Met Trp Pro Leu Val Ile
        35                  40                  45

Ile Tyr Leu Leu Tyr Tyr Ala Ser Asp Asn Ser Ser Glu Asn Gly Gly
    50                  55                  60

Val Ala Ser Arg Tyr Ser Pro Lys Phe Arg Ser Val Pro Leu Trp Lys
65                  70                  75                  80

Tyr Phe Ala Asn Tyr Phe Pro Ile Thr Leu His Arg Thr Gln Glu Leu
                85                  90                  95

Pro Pro Ala Phe Val Tyr Gln Gly Glu Asp Leu Asp Pro Glu Thr Pro
            100                 105                 110

Asp Asp Ser Asp Asp Gly His Ala Lys Ser Lys Ser Ile Val Leu Lys
        115                 120                 125

Leu Trp Lys Val Ala Phe Trp Trp Tyr Tyr Leu Pro Lys His Phe Leu
```

```
    130                 135                 140

Arg Lys Pro Glu Val Arg Pro Thr Gly Arg Arg Tyr Ile Phe Gly Tyr
145                 150                 155                 160

His Pro His Gly Ile Ile Gly Met Gly Ala Ile Gly Ala Ile Ala Thr
                165                 170                 175

Glu Gly Ala Gly Trp Ser Lys Leu Phe Pro Gly Ile Pro Val Ser Leu
            180                 185                 190

Leu Thr Leu Ala Asn Asn Phe Arg Ile Pro Leu Tyr Arg Glu Tyr Leu
        195                 200                 205

Met Ser Leu Gly Ile Ala Ser Val Ser Arg Arg Ser Cys Glu Ala Leu
    210                 215                 220

Leu Lys Arg Gly Gln Ser Ile Cys Ile Val Ile Gly Gly Ala Gln Glu
225                 230                 235                 240

Ser Leu Leu Ala His Pro Gly His Met Asp Leu Val Leu Lys Arg Arg
                245                 250                 255

Lys Gly Phe Ile Lys Leu Ala Leu Glu Val Gly Asn Thr Asp Leu Val
            260                 265                 270

Pro Val Met Ala Phe Gly Glu Asn Asp Leu Tyr Gln Gln Val Asn Ser
        275                 280                 285

Ser Lys Ser Ser Arg Leu Tyr Lys Leu Gln Ser Leu Val Lys Asn Ala
    290                 295                 300

Leu Gly Phe Thr Leu Pro Leu Met His Ala Arg Gly Val Phe Asn Tyr
305                 310                 315                 320

Asp Val Gly Ile Ile Pro Tyr Arg Arg Pro Ile Asn Val Val Val Gly
                325                 330                 335

Lys Pro Ile Pro Ile Pro His Ile Pro Asn Pro Ser Ala Asp Gln Val
            340                 345                 350

Asn Arg Tyr Gln Ile Gln Tyr Met Thr Glu Leu Lys Glu Leu Tyr Asp
        355                 360                 365

Lys Tyr Lys Asp Lys Cys Ser Asn Lys Asp Leu Pro Val Pro Glu Leu
    370                 375                 380

Thr Phe Val Glu
385
```

<210> SEQ ID NO 52
<211> LENGTH: 1167
<212> TYPE: DNA
<213> ORGANISM: Arxula adeninivorans

<400> SEQUENCE: 52

```
atggttcggt tcgctccttt aaatgttcct cttcatcgga ggttagagac gttcgcgctc      60

acctaccata tcctgtcgat tccagtatgg atgtccttct ttttgctatg ctgtgccatt     120

cctttaatgt ggccgttggt tatcatctac ctgctgtact atgcttccga caacagctct     180

gagaatggag gggttgcgag caggtattcg ccaaagttca ggtccgtgcc tctttggaag     240

tactttgcaa actactttcc aatcaccctt caccgtactc aagagctacc gcccgcattc     300

gtgtaccaag gcgaagactt ggaccctgag acgcccgatg acagtgacga cgggcatgca     360

aagtcaaagt ctattgtatt aaagctgtgg aaagttgcat tctggtggta ctacttgccc     420

aagcattttc ttcgcaaacc agaggttcgt cctacgggtc gaagatacat ctttggatat     480

cacccccatg gaatcattgg catgggtgcc attggcgcaa ttgctactga aggtgcgggg     540

tggtccaagc tcttccccgg gatccctgtc agtttgctca ctctggcaaa caactttcga     600

atccccctgt accgggaata tctcatgtct ctgggcattg cctcggtatc tagacggtcc     660
```

```
tgtgaagctt tattaaaaag aggacagtca atttgcattg taattggagg cgctcaggaa    720

agtcttcttg cacatccagg gcacatggat ttggtgctca agcgacgcaa gggattcatt    780

aaactagctc ttgaagttgg caacaccgac ttggtgccag ttatggcatt tggagaaaac    840

gatctctacc agcaagtgaa cagtagcaaa tcctcccgtc tatacaagct ccagagccta    900

gttaagaatg ccttgggatt cacgcttccg ctgatgcacg ctcgaggagt gttcaattat    960

gacgtgggca taatacccta tcgaagacca attaacgttg tagtgggcaa gcccatcccc   1020

attccacaca ttccaaaccc atctgccgac caggtcaatc ggtaccagat ccagtacatg   1080

actgaactca aagaattgta cgacaagtac aaagacaagt gcagtaacaa ggatcttcca   1140

gttccggagc ttacatttgt agagtag                                       1167
```

<210> SEQ ID NO 53
<211> LENGTH: 862
<212> TYPE: PRT
<213> ORGANISM: Saccharomyces cerevisiae

<400> SEQUENCE: 53

```
Met Gln Tyr Val Gly Arg Ala Leu Gly Ser Val Ser Lys Thr Trp Ser
1               5                   10                  15

Ser Ile Asn Pro Ala Thr Leu Ser Gly Ala Ile Asp Val Ile Val Val
            20                  25                  30

Glu His Pro Asp Gly Arg Leu Ser Cys Ser Pro Phe His Val Arg Phe
        35                  40                  45

Gly Lys Phe Gln Ile Leu Lys Pro Ser Gln Lys Lys Val Gln Val Phe
    50                  55                  60

Ile Asn Glu Lys Leu Ser Asn Met Pro Met Lys Leu Ser Asp Ser Gly
65                  70                  75                  80

Glu Ala Tyr Phe Val Phe Glu Met Gly Asp Gln Val Thr Asp Val Pro
                85                  90                  95

Asp Glu Leu Leu Val Ser Pro Val Met Ser Ala Thr Ser Ser Pro Pro
            100                 105                 110

Gln Ser Pro Glu Thr Ser Ile Leu Glu Gly Gly Thr Glu Gly Glu Gly
        115                 120                 125

Glu Gly Glu Asn Glu Asn Lys Lys Lys Glu Lys Lys Val Leu Glu Glu
    130                 135                 140

Pro Asp Phe Leu Asp Ile Asn Asp Thr Gly Asp Ser Gly Ser Lys Asn
145                 150                 155                 160

Ser Glu Thr Thr Gly Ser Leu Ser Pro Thr Glu Ser Ser Thr Thr Thr
                165                 170                 175

Pro Pro Asp Ser Val Glu Glu Arg Lys Leu Val Glu Gln Arg Thr Lys
            180                 185                 190

Asn Phe Gln Gln Lys Leu Asn Lys Lys Leu Thr Glu Ile His Ile Pro
        195                 200                 205

Ser Lys Leu Asp Asn Asn Gly Asp Leu Leu Leu Asp Thr Glu Gly Tyr
    210                 215                 220

Lys Pro Asn Lys Asn Met Met His Asp Thr Asp Ile Gln Leu Lys Gln
225                 230                 235                 240

Leu Leu Lys Asp Glu Phe Gly Asn Asp Ser Asp Ile Ser Ser Phe Ile
                245                 250                 255

Lys Glu Asp Lys Asn Gly Asn Ile Lys Ile Val Asn Pro Tyr Glu His
            260                 265                 270

Leu Thr Asp Leu Ser Pro Pro Gly Thr Pro Pro Thr Met Ala Thr Ser
```

-continued

```
        275                 280                 285

Gly Ser Val Leu Gly Leu Asp Ala Met Glu Ser Gly Ser Thr Leu Asn
    290                 295                 300

Ser Leu Ser Ser Ser Pro Ser Gly Ser Asp Thr Glu Asp Glu Thr Ser
305                 310                 315                 320

Phe Ser Lys Glu Gln Ser Ser Lys Ser Glu Lys Thr Ser Lys Lys Gly
                325                 330                 335

Thr Ala Gly Ser Gly Glu Thr Glu Lys Arg Tyr Ile Arg Thr Ile Arg
            340                 345                 350

Leu Thr Asn Asp Gln Leu Lys Cys Leu Asn Leu Thr Tyr Gly Glu Asn
        355                 360                 365

Asp Leu Lys Phe Ser Val Asp His Gly Lys Ala Ile Val Thr Ser Lys
    370                 375                 380

Leu Phe Val Trp Arg Trp Asp Val Pro Ile Val Ile Ser Asp Ile Asp
385                 390                 395                 400

Gly Thr Ile Thr Lys Ser Asp Ala Leu Gly His Val Leu Ala Met Ile
                405                 410                 415

Gly Lys Asp Trp Thr His Leu Gly Val Ala Lys Leu Phe Ser Glu Ile
            420                 425                 430

Ser Arg Asn Gly Tyr Asn Ile Leu Tyr Leu Thr Ala Arg Ser Ala Gly
        435                 440                 445

Gln Ala Asp Ser Thr Arg Ser Tyr Leu Arg Ser Ile Glu Gln Asn Gly
    450                 455                 460

Ser Lys Leu Pro Asn Gly Pro Val Ile Leu Ser Pro Asp Arg Thr Met
465                 470                 475                 480

Ala Ala Leu Arg Arg Glu Val Ile Leu Lys Lys Pro Glu Val Phe Lys
                485                 490                 495

Ile Ala Cys Leu Asn Asp Ile Arg Ser Leu Tyr Phe Glu Asp Ser Asp
            500                 505                 510

Asn Glu Val Asp Thr Glu Glu Lys Ser Thr Pro Phe Phe Ala Gly Phe
        515                 520                 525

Gly Asn Arg Ile Thr Asp Ala Leu Ser Tyr Arg Thr Val Gly Ile Pro
    530                 535                 540

Ser Ser Arg Ile Phe Thr Ile Asn Thr Glu Gly Glu Val His Met Glu
545                 550                 555                 560

Leu Leu Glu Leu Ala Gly Tyr Arg Ser Ser Tyr Ile His Ile Asn Glu
                565                 570                 575

Leu Val Asp His Phe Phe Pro Pro Val Ser Leu Asp Ser Val Asp Leu
            580                 585                 590

Arg Thr Asn Thr Ser Met Val Pro Gly Ser Pro Pro Asn Arg Thr Leu
        595                 600                 605

Asp Asn Phe Asp Ser Glu Ile Thr Ser Gly Arg Lys Thr Leu Phe Arg
    610                 615                 620

Gly Asn Gln Glu Glu Lys Phe Thr Asp Val Asn Phe Trp Arg Asp Pro
625                 630                 635                 640

Leu Val Asp Ile Asp Asn Leu Ser Asp Ile Ser Asn Asp Asp Ser Asp
                645                 650                 655

Asn Ile Asp Glu Asp Thr Asp Val Ser Gln Gln Ser Asn Ile Ser Arg
            660                 665                 670

Asn Arg Ala Asn Ser Val Lys Thr Ala Lys Val Thr Lys Ala Pro Gln
        675                 680                 685

Arg Asn Val Ser Gly Ser Thr Asn Asn Asn Glu Val Leu Ala Ala Ser
    690                 695                 700
```

```
Ser Asp Val Glu Asn Ala Ser Asp Leu Val Ser Ser His Ser Ser Ser
705                 710                 715                 720

Gly Ser Thr Pro Asn Lys Ser Thr Met Ser Lys Gly Asp Ile Gly Lys
                725                 730                 735

Gln Ile Tyr Leu Glu Leu Gly Ser Pro Leu Ala Ser Pro Lys Leu Arg
            740                 745                 750

Tyr Leu Asp Asp Met Asp Asp Glu Asp Ser Asn Tyr Asn Arg Thr Lys
        755                 760                 765

Ser Arg Arg Ala Ser Ser Ala Ala Ala Thr Ser Ile Asp Lys Glu Phe
    770                 775                 780

Lys Lys Leu Ser Val Ser Lys Ala Gly Ala Pro Thr Arg Ile Val Ser
785                 790                 795                 800

Lys Ile Asn Val Ser Asn Asp Val His Ser Leu Gly Asn Ser Asp Thr
                805                 810                 815

Glu Ser Arg Arg Glu Gln Ser Val Asn Glu Thr Gly Arg Asn Gln Leu
            820                 825                 830

Pro His Asn Ser Met Asp Asp Lys Asp Leu Asp Ser Arg Val Ser Asp
        835                 840                 845

Glu Phe Asp Asp Asp Glu Phe Asp Glu Asp Glu Phe Glu Asp
    850                 855                 860
```

<210> SEQ ID NO 54
<211> LENGTH: 2589
<212> TYPE: DNA
<213> ORGANISM: Saccharomyces cerevisiae

<400> SEQUENCE: 54

```
atgcagtacg taggcagagc tcttgggtct gtgtctaaaa catggtcttc tatcaatccg     60

gctacgctat caggtgctat agatgtcatt gtagtggagc atccagacgg aaggctatca    120

tgttctccct ttcatgtgag gttcggcaaa tttcaaattc taaagccatc tcaaaagaaa    180

gtccaagtgt ttataaatga gaaactgagt aatatgccaa tgaaactgag tgattctgga    240

gaagcctatt tcgttttcga gatgggtgac caggtcactg atgtccctga cgaattgctt    300

gtgtcgcccg tgatgagcgc cacatcaagc ccccctcaat cacctgaaac atccatctta    360

gaaggaggaa ccgagggtga aggtgaaggt gaaaatgaaa ataagaagaa ggaaaagaaa    420

gtgctagagg aaccagattt tttagatatc aatgacactg gagattcagg cagtaaaaat    480

agtgaaacta cagggtcgct ttctcctact gaatcctcta caacgacacc accagattca    540

gttgaagaga ggaagcttgt tgagcagcgt acaaagaact ttcagcaaaa actaaacaaa    600

aaactcactg aaatccatat acccagtaaa cttgataaca atggcgactt actactagac    660

actgaaggtt acaagccaaa caagaatatg atgcatgaca cagacataca actgaagcag    720

ttgttaaagg acgaattcgg taatgattca gatatttcca gttttatcaa ggaggacaaa    780

aatggcaaca tcaagatcgt aaatccttac gagcacctta ctgatttatc tcctccaggt    840

acgcctccaa caatggccac aagcggatca gttttaggct tagatgcaat ggaatcagga    900

agtactttga attcgttatc ttcttcacct tctggttccg atactgagga cgaaacatca    960

tttagcaaag aacaaagcag taaaagtgaa aaaactagca agaaaggaac agcagggagc   1020

ggtgagaccg agaaaagata catacgaacg ataagattga ctaatgacca gttaaagtgc   1080

ctaaatttaa cttatggtga aaatgatctg aaattttccg tagatcacgg aaaagctatt   1140

gttacgtcaa aattattcgt ttggaggtgg gatgttccaa ttgttatcag tgatattgat   1200
```

```
ggcaccatca caaaatcgga cgctttaggc catgttctgg caatgatagg aaaagactgg   1260

acgcacttgg gtgtagccaa gttatttagc gagatctcca ggaatggcta taatatactc   1320

tatctaactg caagaagtgc tggacaagct gattccacga ggagttattt gcgatcaatt   1380

gaacagaatg gcagcaaact accaaatggg cctgtgattt tatcacccga tagaacgatg   1440

gctgcgttaa ggcgggaagt aatactaaaa aaacctgaag tctttaaaat cgcgtgtcta   1500

aacgacataa gatccttgta ttttgaagac agtgataacg aagtggatac agaggaaaaa   1560

tcaacaccat tttttgccgg ctttggtaat aggattactg atgctttatc ttacagaact   1620

gtggggatac ctagttcaag aattttcaca ataaatacag agggtgaggt tcatatggaa   1680

ttattggagt tagcaggtta cagaagctcc tatattcata tcaatgagct tgtcgatcat   1740

ttctttccac cagtcagcct tgatagtgtc gatctaagaa ctaatacttc catggttcct   1800

ggctcccccc ctaatagaac gttggataac tttgactcag aaattacttc aggtcgcaaa   1860

acgctattta gaggcaatca ggaagagaaa ttcacagacg taaatttttg gagagacccg   1920

ttagtcgaca tcgacaactt atcggatatt agcaatgatg attctgataa catcgatgaa   1980

gatactgacg tatcacaaca aagcaacatt agtagaaata gggcaaattc agtcaaaacc   2040

gccaaggtca ctaaagcccc gcaaagaaat gtgagcggca gcacaaataa caacgaagtt   2100

ttagccgctt cgtctgatgt agaaaatgcg tctgacctgg tgagttccca tagtagctca   2160

ggatccacgc ccaataaatc tacaatgtcc aaaggggaca ttggaaaaca aatatatttg   2220

gagctaggtt ctccacttgc atcgccaaaa ctaagatatt tagacgatat ggatgatgaa   2280

gactccaatt acaatagaac taaatcaagg agagcatctt ctgcagccgc gactagtatc   2340

gataaagagt tcaaaaagct ctctgtgtca aaggccggcg ctccaacaag aattgtttca   2400

aagatcaacg tttcaaatga cgtacattca cttgggaatt cagataccga atcacgaagg   2460

gagcaaagtg ttaatgaaac agggcgcaat cagctacccc acaactcaat ggacgataaa   2520

gatttggatt caagagtaag cgatgaattc gatgacgatg aattcgacga agatgaattc   2580

gaagattaa                                                           2589
```

```
<210> SEQ ID NO 55
<211> LENGTH: 742
<212> TYPE: PRT
<213> ORGANISM: Arxula adeninivorans

<400> SEQUENCE: 55

Met Gln Tyr Val Gly Arg Ala Ile Gly Ser Val Ser Lys Thr Trp Asn
1               5                   10                  15

Ser Ile Asn Pro Ala Thr Leu Ser Gly Ala Ile Asp Ile Met Val Val
            20                  25                  30

Glu Gln Pro Asp Gly Thr Leu Ser Cys Ser Pro Phe His Val Arg Phe
        35                  40                  45

Gly Lys Phe Ser Leu Leu Arg Pro Ser Gln Lys Lys Val Gln Phe Ser
    50                  55                  60

Val Asn Gly Glu Ala Thr Asp Leu Pro Met Lys Leu Gly Asp Gly Gly
65                  70                  75                  80

Glu Ala Phe Phe Val Phe Glu Thr Pro Asn Lys Val Pro Ser Asp Leu
                85                  90                  95

Leu Thr Ser Pro Val Val Ser Pro Ser Ser Ser Pro Glu Ser Ile Val
            100                 105                 110

Ala Asp Asp Glu Asp Ala Glu Gly Arg Pro Leu Gln Glu Pro Glu Phe
        115                 120                 125
```

-continued

```
Leu Asp Leu Ser Arg Thr Glu Pro Glu Arg Ala Arg Ser Glu Ser Pro
    130                 135                 140

Gln Arg Pro Pro Asn Lys Asp Gly Ser Leu Arg Ser Ala Asp Ser Phe
145                 150                 155                 160

Pro Pro Pro Pro Ala Asn Asn Ala Gln Trp Ser Glu Ser Ser Pro Ser
                165                 170                 175

Leu Thr Glu Ala Pro Pro Leu Ser Pro Gly Glu Pro Glu Pro Glu Arg
            180                 185                 190

Ala Ile Ser Lys Asp Arg Val His Ser Leu Thr Lys Arg Leu Thr Asp
        195                 200                 205

Ile Asn Ile Pro Ser Lys Ile Thr Asp Asn Gly Asp Ile Val Leu Asp
    210                 215                 220

Met Thr Gly Tyr Lys Ser Gly Ala Asp Glu Phe Arg Thr Ser Glu Ala
225                 230                 235                 240

Val Val Lys Lys Leu Leu Ala Glu Glu Leu Gly Leu Gly Pro Glu Leu
                245                 250                 255

Asp Phe Glu Ser Ile Met Gly Pro Asp Glu Glu Gly Asn Ile Arg Ile
            260                 265                 270

Tyr Ser Arg Asp Asp Leu Tyr Ala Ala Thr Ala Gly His Arg His Ser
        275                 280                 285

His Ser His His Pro Phe Pro Ser Ala Glu Asp Thr Ala Pro Val Thr
    290                 295                 300

Pro Ala Pro Glu Ser Ser Ser Ser Ser Ser Glu Pro Ala Ser Thr Glu
305                 310                 315                 320

Gly Thr Pro Thr Ala Gly Glu Pro Phe Tyr Ala Lys Thr Leu Arg Leu
                325                 330                 335

Thr Ser Asp Gln Leu Lys Lys Leu Asn Leu Lys Ser Gly Arg Asn Glu
            340                 345                 350

Val Gln Phe Lys Val Leu Gln Asn Lys Ala Val Ile Asn Ala His Leu
        355                 360                 365

Tyr Tyr Trp Lys Ser Asn Ala Pro Ile Val Ile Ser Asp Ile Asp Gly
    370                 375                 380

Thr Ile Thr Lys Ser Asp Ala Leu Gly His Val Leu Thr Met Leu Gly
385                 390                 395                 400

Arg Asp Trp Thr His Ser Gly Val Ala Lys Leu Tyr Val Asp Ile Ala
                405                 410                 415

Asn Asn Gly Tyr Asn Ile Val Tyr Leu Thr Ala Arg Ser Val Gly Gln
            420                 425                 430

Ala Asp Ala Thr Arg Tyr Tyr Leu Gln Gly Ile Glu Gln Glu Gly Tyr
        435                 440                 445

Arg Met Pro Pro Gly Pro Val Ile Leu Ser Pro Asp Arg Thr Met Ala
    450                 455                 460

Ala Leu Arg Arg Glu Val Ile Met Arg Lys Pro Glu Val Phe Lys Met
465                 470                 475                 480

Ala Ala Leu Arg Asp Ile Gln Ser Leu Tyr Asp Tyr Lys Glu Gly Thr
                485                 490                 495

Pro Phe Tyr Ala Gly Phe Gly Asn Arg Ile Thr Asp Ala Leu Ser Tyr
            500                 505                 510

Arg Ser Val Gly Ile Pro Ser Ser Lys Ile Phe Thr Ile Asn Thr Asn
        515                 520                 525

Ser Glu Val His Met Glu Leu Leu Glu Leu Ala Gly Tyr Arg Ser Ser
    530                 535                 540
```

-continued

```
Tyr Val His Ile Ala Asp Leu Val Asp His Phe Phe Pro Pro Val Val
545                 550                 555                 560

Ala Ser Gly Gly Lys Asp Val Glu Asn Lys Tyr Ser Asp Val Asn Phe
                565                 570                 575

Trp Arg Asp Pro Ile Pro Asp Ile Ser Asp Leu Glu Ser Leu Asp Gly
            580                 585                 590

Phe Glu Asp Glu Gly Pro Lys Ser Pro Lys Ser Pro Glu Gln Arg Ala
        595                 600                 605

Lys Ser Pro Ser Asp Met Leu Ser Ser Ser Gln Ser Pro Gln Lys Ala
    610                 615                 620

Asn Glu Lys Thr Ser Asp Lys Ser Gly Pro Met Asp Met Gly Pro Pro
625                 630                 635                 640

Val Met Ser Ser Glu Lys Lys Ser Asp Lys Gly Glu Glu Asp Glu Asp
                645                 650                 655

Asp Glu Asp Tyr Asp Glu Asp Tyr Glu Asp Asp Asn Tyr Glu Asp Glu
            660                 665                 670

Tyr Asp Asp Tyr Glu Tyr Asp Glu Asp Glu Tyr Asp Asp Tyr Asp Tyr
        675                 680                 685

Glu Asn Glu Asp Tyr Gln Asp Gly Glu Thr Pro Asp Glu Arg Gln Gly
    690                 695                 700

Arg Ser Arg Gln Arg Arg Ser Ile Val Tyr Thr His Phe Gly Ala Arg
705                 710                 715                 720

Glu Pro Ala His Leu Glu Gln Ala Arg Thr Leu Arg Glu Thr Leu Lys
                725                 730                 735

Asp Ile Asn Thr Asn Leu
            740
```

<210> SEQ ID NO 56
<211> LENGTH: 2229
<212> TYPE: DNA
<213> ORGANISM: Arxula adeninivorans

<400> SEQUENCE: 56

```
atgcagtacg taggacgagc gattggatct gtgtccaaga catggaactc catcaaccct      60

gctacgctgt cgggagcaat tgatatcatg gttgtggaac agcccgatgg gactctgtcg     120

tgctctccct ttcatgtccg gttcggcaag ttctcgttgc ttcgtccctc gcagaagaag     180

gtccagtttt ccgtaaatgg ggaggccact gacttgccaa tgaagttggg ggatggcggc     240

gaagcgttct ttgtgtttga gactcccaac aaggtcccca gtgacctgtt aacttcaccg     300

gtagtgtccc cgtcgtcttc accagaatcg atcgtagcgg atgatgagga tgccgaagga     360

cgccctttgc aagagccgga gtttttggat ctttcccgta ctgaacctga gagagctcgc     420

tctgaaagcc ctcagcggcc acccaacaag gacggatctc tacgaagcgc tgattcgttc     480

cctccgccac ctgccaacaa cgcccaatgg agcgagtcca gtcctagttt gaccgaggcg     540

ccgccgctgt ctccaggaga gcctgaacca gagcgggcca tttcaaagga ccgggttcat     600

agtctgacca agagattgac tgatatcaat atcccatcca agatcaccga caatggcgac     660

attgtgctgg acatgaccgg gtacaagagc ggtgcggatg agtttagaac ttcagaagca     720

gtagtaaaga agcttttggc tgaggagctt gggctgggtc ccgagctcga ttttgaatcc     780

atcatgggcc ccgacgagga gggcaatatt cgtatttatt cccgtgacga tttgtatgct     840

gccacggcag gccaccgcca tagtcactct catcatccct tccctagtgc tgaggacact     900

gcgccggtga cccctgcccc tgagtcctct tcgtcatcat ctgaacctgc atctaccgaa     960
```

```
ggcactccca ccgccggaga gcccttctat gcaaagacgt tgcgattgac ttcggatcag   1020

ctcaagaagc tcaatctcaa gtctgggcgg aatgaggtcc agtttaaggt gctccaaaac   1080

aaggccgtga tcaacgctca cctgtactac tggaaaagca acgccccaat cgtcatttct   1140

gatatcgatg gaaccattac aaagtcggat gccctgggcc atgtcttgac catgcttggg   1200

cgggactgga ctcactctgg ggtcgccaaa ttatatgtgg atattgctaa caatgggtac   1260

aatattgtat atttgaccgc acgatcagtt ggccaggcag atgctactcg atattatctt   1320

cagggaattg agcaagaagg gtatagaatg ccccctggtc cagttatttt gtctccagat   1380

aggacaatgg ctgccttgcg ccgagaggtt atcatgcgca aacccgaggt gttcaagatg   1440

gccgcccttc gggatatcca gtctctgtac gactataaag agggcacccc attttatgca   1500

gggtttggta atcgtatcac cgacgcgcta tcttatcgat cggtgggaat cccttcgtcg   1560

aagatcttca ccatcaatac caattctgaa gtccacatgg aactcctgga gttggcaggg   1620

taccgctcca gctacgtcca tattgccgac ctcgtggacc acttttccc tccagtggtg    1680

gccagtgggg gtaaggatgt ggaaaacaag tattccgatg tcaatttctg gcgagaccct   1740

atccctgata tttccgacct ggaatctcta gatggatttg aagatgaagg accaaagagt   1800

ccaaagagcc ctgagcagcg agccaaatca ccatctgata tgctttctag tagtcaatcc   1860

cctcagaaag ctaacgagaa gacctccgac aaatcagggc ccatggacat gggtcctcca   1920

gtcatgtcat ccgaaaagaa gagcgataag ggcgaagagg acgaggatga tgaggactac   1980

gatgaggact acgaagacga caattacgag gatgagtatg atgactacga gtatgacgag   2040

gatgaatatg atgactatga ttacgagaac gaggactatc aagacggaga gacccctgat   2100

gaaagacagg gtcgctctag gcaacggcga tcgattgtat acacccattt cggtgcccga   2160

gagcccgccc atttggagca ggcacgcact ctgagagaga ctctcaagga tatcaatact   2220

aacttgtaa                                                           2229
```

```
<210> SEQ ID NO 57
<211> LENGTH: 723
<212> TYPE: PRT
<213> ORGANISM: Yarrowia lipolytica

<400> SEQUENCE: 57

Met Lys Val Gly Asp Gly Gly Glu Val Phe Phe Val Phe Glu Thr Asp
1               5                   10                  15

Ala Asp Val Pro Glu Glu Leu Leu Thr Ser Pro Val Ile Ser Pro Ser
            20                  25                  30

Ser Ser Pro Ser Trp Gly Gln Glu Glu Gly Gly Asp Gly Glu Pro Asp
        35                  40                  45

Tyr Leu Ala Leu Asn Asp Ser Lys Gln Gly Gly Asp Ser Lys His Gly
    50                  55                  60

Arg Ser Pro Ser Glu Gly Pro Pro Phe Arg Ser Pro Ser Ala Asp His
65                  70                  75                  80

Leu His Glu Met Gly Ser Phe Asp Asp Glu Asn Asp Pro Glu Val Asn
                85                  90                  95

Arg Arg Gln Arg Ala Ser Thr Ala Ala Pro Glu Pro Val Pro Gly Ser
            100                 105                 110

Leu Lys His Pro Ala Thr Ile Ser Glu Gly Ile Ser Ser Ala Ser Phe
        115                 120                 125

Ser Asn Ser Asp Thr Asp Arg Thr Asp Thr Ser Gly Pro Thr Glu Thr
    130                 135                 140
```

```
Glu Pro Thr Glu Leu Thr Glu Pro Thr Glu Pro Thr Glu Pro Thr Glu
145                 150                 155                 160

Pro Leu Asp Leu Glu Gln Ser Leu His Arg Ala Ala Thr Ser Pro Ala
                165                 170                 175

Pro Ser Ser Glu Glu Ile Trp Glu Lys Ala Arg Ala Leu Ser Lys Lys
            180                 185                 190

Leu Thr Ser Glu Asn Ile Gln Ser Lys Ile Ser Asp Asn Gly Asp Ile
        195                 200                 205

Ile Leu Asp Met Thr Gly Tyr Lys Tyr Asp His Glu Asp Val Ser Arg
    210                 215                 220

Ser Glu Glu Leu Val Lys Lys Ile Leu Ala Glu Glu Leu Gly Glu Asp
225                 230                 235                 240

Arg Asp Leu Ser His Ile Leu Val Glu Asp Glu Glu Gly Asn Leu Val
                245                 250                 255

Ile Gln Ser Ala Gly Asp Ser His His His Glu His Met Ser Ser Pro
            260                 265                 270

Glu Ser Leu Ala His Ser Pro Gln Pro Leu Pro Ser Ser Asn Leu Pro
        275                 280                 285

Ser Gln Ala Ser Asp Asn Lys His Tyr Ala Lys Thr Ile Arg Leu Thr
    290                 295                 300

Ser Asp Gln Leu Lys Ser Leu Asp Leu Lys Pro Gly Lys Asn Glu Val
305                 310                 315                 320

Thr Phe Ala Val Asn Asn Gly Lys Thr Ser Cys Ser Ala Gln Leu Phe
                325                 330                 335

Tyr Trp Lys Tyr Asp Ile Pro Val Val Ile Ser Asp Ile Asp Gly Thr
            340                 345                 350

Ile Thr Lys Ser Asp Ala Leu Gly His Leu Leu Thr Met Met Gly Arg
        355                 360                 365

Asp Trp Thr His Thr Gly Val Ala Lys Leu Phe Ser Asp Ile Arg Ala
    370                 375                 380

Asn Gly Tyr Asn Ile Met Tyr Leu Thr Ala Arg Ser Val Gly Gln Ala
385                 390                 395                 400

Asp Ala Thr Arg Ala Tyr Leu Gly Gly Val Asp Gln Phe Gly Phe Lys
                405                 410                 415

Leu Pro Pro Gly Pro Val Ile Leu Ser Pro Asp Arg Thr Leu Ala Ala
            420                 425                 430

Leu Lys Arg Glu Val Ile Leu Lys Lys Pro Glu Val Phe Lys Met Ala
        435                 440                 445

Cys Leu Arg Asp Ile Lys Ser Leu Phe Gly Glu Thr Glu Asp Ala Thr
    450                 455                 460

Asn Pro Phe Tyr Ala Gly Phe Gly Asn Arg Ile Thr Asp Ala Leu Ser
465                 470                 475                 480

Tyr Arg Ser Val Gly Val Pro Ser Ser Arg Ile Phe Thr Ile Asn Ser
                485                 490                 495

Asn Ala Glu Val His Met Glu Leu Leu Glu Leu Ala Gly Tyr Lys Ser
            500                 505                 510

Ser Tyr Val His Ile Ala Asp Leu Val Asp His Phe Phe Pro Pro Glu
        515                 520                 525

Ser Glu Phe Thr Thr Ile Gln Glu Glu Lys Tyr Thr Asp Val Asn Tyr
    530                 535                 540

Trp Arg Asp Pro Ile Ile Asp Leu Ser Asp Leu Thr Asp Asp Glu Leu
545                 550                 555                 560

Thr Asp Asp Asp Glu Leu Ser Lys Ser Pro Lys Ser Pro Arg Ser Pro
```

-continued

```
                565                 570                 575

Arg Ser Pro Arg Ala Gly Ser Ala Gly Ser Ser Ala Ala Pro Ser Gly
            580                 585                 590

Ser Gly Ala Asp Pro Ala Gly Pro Ser Glu Pro Lys Asp Ser Ala Asn
        595                 600                 605

Pro Ser Lys Phe Ser Tyr Lys Lys Ala Pro Thr Asn Ser Arg Phe Gln
    610                 615                 620

Pro Val Ser Tyr Asp Leu Asp Leu Asp Asp Gly Tyr Glu Tyr Asp Asp
625                 630                 635                 640

Asp Asp Asp Tyr Asp Asp Asp Glu Glu Phe Val Asp Ala Glu Ser Asp
                645                 650                 655

Ala Leu Glu Glu Asp Asp Asp Asp Asp Asp Asp Val Asp Leu Asp Asn
            660                 665                 670

Asp Ser Asp His Ser Pro Val Lys Pro Pro Ser Gln Met Gln Arg Val
        675                 680                 685

Ile Asn Lys Thr Ile Glu Asp Asn Lys Gly Leu His Met Asp Glu Asp
    690                 695                 700

Asp Val Gln Lys Ala Met Lys Ala Leu Lys Met Glu Arg Ala Ser Ile
705                 710                 715                 720

Asn Pro Glu


<210> SEQ ID NO 58
<211> LENGTH: 2172
<212> TYPE: DNA
<213> ORGANISM: Yarrowia lipolytica

<400> SEQUENCE: 58

atgaaggtgg gcgatggagg agaagtcttc tttgtgttcg agaccgacgc agacgtgccc     60

gaagagctcc tgacatcccc cgtcatttct ccctcttcgt cgccatcctg ggccaggag    120

gaaggcgggg atggtgagcc ggactacctt gctctgaacg actctaaaca gggtggcgac    180

agcaagcacg gcagatcgcc ctcggagggc ccaccattca gatcaccttc ggcggatcac    240

ttacatgaga tgggcagctt cgatgatgag aatgaccctg aggtgaacag aagacaacgt    300

gcgagcacgg cagctccaga gcctgttcct ggttcgttga aacacccagc cactatctcg    360

gaaggcatct cttcggcctc gttttccaac agcgatactg atcgaacaga cacttctgga    420

cccacagaga cagaacccac agagctcaca gagcctacag agcccacaga gcccacagag    480

cctctggatc ttgagcagag tctccaccgg gctgccactt ctcccgcccc ttcgtccgag    540

gagatttggg agaaggcccg tgcactgtcc aagaaactca catcagaaaa cattcagagt    600

aaaatctccg acaacggaga cattattctg gatatgactg gttacaagta cgaccacgag    660

gacgtgagtc gatcagagga gctggtcaag aaaatcctcg ctgaggaact gggagaagac    720

agagacctgt cccacatcct ggttgaagac gaggagggta accttgtgat tcagagcgct    780

ggagacagcc accatcacga gcatatgagc tcgcccgagt ctctggccca ctcccctcag    840

cccctccctt cttctaacct tccgtctcag gcctcggaca acaagcacta cgccaagacc    900

atccgtttga cgtctgacca gctcaagtct ctggatctca agcccggcaa gaacgaggtc    960

acctttgctg tcaataacgg caagacgtcg tgttcggccc agctgttcta ctggaagtac   1020

gacattcctg ttgtcatttc cgacattgat ggcacgatca ccaagtccga tgctctgggc   1080

catctgctca ccatgatggg ccgagactgg acccacaccg gcgtggccaa gctcttttcc   1140

gatatcagag ccaacgggta taatatcatg tatctgacag cacgatcagt gggacaggca   1200
```

```
gatgcaacca gggcatatct aggcggtgtt gaccagtttg gcttcaagct gcctccagga   1260

cccgtcatct tgtcgcctga tagaaccctg gcggctctca agagagaggt gattcttaag   1320

aaacctgagg tattcaagat ggcgtgtctg cgggacatta agtcgctgtt tggcgagacc   1380

gaagacgcca ccaatccatt ctacgctgga tttggcaacc gaatcaccga cgcgttgtcg   1440

tatagatctg tcggtgtgcc gtcgtctaga atcttcacaa tcaactcgaa cgccgaggtc   1500

catatggagc tgcttgaact ggctggctac aagtcctcgt atgtccacat tgccgatctt   1560

gtcgaccact tttccctcc ggaaagcgag ttcacgacca ttcaggagga aaaatacacg   1620

gacgtcaact actggcgaga tcccattatt gacctgtctg atctgaccga cgacgagctg   1680

actgacgatg atgagctctc caagtcgccc aagtcgccca gatctcctag aagcccgcgg   1740

gccggttcgg caggctccag cgcggctccc tcaggctcgg gcgccgaccc tgccggaccc   1800

tccgagccga aggactccgc gaacccgtcg aagttcagct ataagaaggc tcctacgaac   1860

tctcgattcc agcccgtttc gtacgatctt gatcttgacg acggatacga gtacgacgat   1920

gacgatgact atgatgacga tgaggagttt gtggacgctg agagcgacgc gctggaggag   1980

gatgacgacg atgatgatga cgtcgaccta gacaacgact ctgaccactc ccctgtcaag   2040

ccgccctcgc agatgcagcg agtcatcaac aagactattg aggacaacaa gggcctgcac   2100

atggatgagg atgacgttca aaaagccatg aaggccctga agatggaacg agcaagcatc   2160

aatcctgagt aa                                                         2172
```

<210> SEQ ID NO 59
<211> LENGTH: 282
<212> TYPE: PRT
<213> ORGANISM: Yarrowia lipolytica

<400> SEQUENCE: 59

```
Met Ser Val Ala Ser Lys Leu Val Phe Tyr Val Arg Ala Ala Ile Ala
1               5                   10                  15

Val Val Ile Phe Ala Ala Cys Ala Thr Tyr Gly Val Leu Ala Ser Thr
            20                  25                  30

Ile Leu Thr Ala Ile Gly Lys Gln Gly Leu Ala Gln Trp Thr Val Ala
        35                  40                  45

Arg Ala Phe Tyr Tyr Ser Val Arg Ile Phe Leu Gly Ile Ser Ile Lys
    50                  55                  60

Leu Arg Ser Arg Gln Val Thr Gly Thr Ala Gly Leu Asp Ala Ser Lys
65                  70                  75                  80

Ile Gln Val Ala Asn Thr Thr Lys Pro Ile Asp Asp Ile Thr Lys His
                85                  90                  95

Leu Pro Arg Pro Cys Ile Leu Ile Ser Asn His Gln Asn Glu Met Asp
            100                 105                 110

Ile Leu Val Leu Gly Arg Ile Phe Pro Gln Tyr Cys Ser Val Thr Ala
        115                 120                 125

Lys Lys Ala Leu Lys Trp Tyr Pro Leu Leu Gly Gln Phe Met Ala Leu
    130                 135                 140

Ser Gly Thr Ile Phe Leu Asp Arg Lys Asp Arg Thr Lys Ser Val Gln
145                 150                 155                 160

Thr Leu Gly Gly Ala Val Lys Thr Ile Gln Ser Gly Asn Gly Gly Lys
                165                 170                 175

Gly Gln Ser Val Phe Met Phe Pro Glu Gly Thr Arg Ser Tyr Ser Lys
            180                 185                 190

Asp Val Gly Ile Met Pro Phe Lys Lys Gly Cys Phe His Leu Ala Val
```

```
        195                 200                 205

Gln Ser Gly Ala Pro Ile Val Pro Val Val Val Gln Asn Thr Ser Arg
    210                 215                 220

Met Phe Ser Phe Gly Arg Gly Lys Leu Asp Ala Gly Glu Ile Leu Val
225                 230                 235                 240

Asp Val Leu Ser Pro Ile Glu Thr Lys Gly Leu Asp Ala Ser Asn Val
                245                 250                 255

Asp Ala Leu Met Ala Thr Thr Tyr Lys Ala Met Cys Glu Thr Ala Asp
            260                 265                 270

Gln Ile Gly Tyr Ala Gly Gln Lys Thr Gln
        275                 280
```

<210> SEQ ID NO 60
<211> LENGTH: 849
<212> TYPE: DNA
<213> ORGANISM: Yarrowia lipolytica

<400> SEQUENCE: 60

```
atgtccgttg catccaagct cgtcttctac gtccgcgccg ccatcgccgt ggtcatcttt      60

gccgcctgtg ccacctacgg cgtgctggcg tccaccattc tcaccgccat cggcaagcag     120

ggcctggccc aatggaccgt tgccagagcc ttctactact cggtgcgcat cttcctgggt     180

atcagcatca agctgcgtag ccggcaggtg accggaaccg ccggtctgga tgcctccaag     240

atccaggtcg ccaacaccac caagcccatt gacgacatca ccaaacacct gccccgacca     300

tgcattctga tttccaacca ccagaacgaa atggacattc tggtgctcgg tcgcatcttc     360

ccccagtact gctccgtcac cgccaaaaag gccctcaagt ggtaccctct gctgggccag     420

ttcatggcgc tgtccggcac catcttcctg gaccgaaagg accgaaccaa gtccgtgcag     480

accctcggcg gcgccgtcaa gaccatccag agcggcaacg gaggcaaggg ccagagcgtc     540

ttcatgttcc ccgagggaac ccgatcctac tccaaggacg tcggcatcat gcccttcaag     600

aagggctgtt tccacctggc ggtccagtcg ggcgctccca ttgtccccgt ggtggtccag     660

aacacctccc gaatgttttc tttcggccga ggcaagctgg acgccggaga gatccttgtc     720

gacgtcctga gccccattga gaccaagggt ctggacgcca gcaacgtcga cgctctcatg     780

gccaccactt ataaggccat gtgcgagact gccgaccaga ttggctacgc tggccagaag     840

actcagtag                                                               849
```

<210> SEQ ID NO 61
<211> LENGTH: 281
<212> TYPE: PRT
<213> ORGANISM: Arxula adeninivorans

<400> SEQUENCE: 61

```
Met Ala Thr Val Val Lys Gln Leu Val Gln Tyr Leu Pro Lys Ala Val
1               5                   10                  15

Ala Gly Thr Val Val Leu Gly Tyr Phe Gly Ile Ile Lys Pro Leu Gln
            20                  25                  30

Phe Tyr Val Arg Leu Ala Val Tyr Ile Leu Ala Val Ala Phe Cys Ala
        35                  40                  45

Phe Asn Gly Ala Val Leu Ser Ala Val Leu Thr Leu Ile Gly Lys Gln
    50                  55                  60

Gly Leu Ser Gln Trp Cys Val Ala Arg Met Phe Leu Tyr Ile Ala Gly
65                  70                  75                  80

Thr Ile Leu Gly Ile Lys Val Val Ile Lys Asn Pro Glu Arg Leu Lys
```

```
                85                  90                  95

Thr Arg Pro Ala Val Phe Ile Ser Asn His Gln Ser Glu Leu Asp Ile
            100                 105                 110

Leu Ile Leu Gly Ala Thr Phe Pro Gln Tyr Cys Ser Val Thr Ala Lys
        115                 120                 125

Lys Ser Leu Lys Tyr Tyr Pro Phe Leu Gly Trp Phe Met Ala Leu Ser
    130                 135                 140

Gly Ser Val Phe Ile Asp Arg Ala Asn Arg Asp Asn Ala Leu Lys Ala
145                 150                 155                 160

Phe Glu Gly Ala Ala Lys Lys Val Asn Arg Asp Lys Gln Ser Val Phe
                165                 170                 175

Met Phe Pro Glu Gly Thr Arg Ser Tyr Tyr Gln Glu Pro Gly Leu Leu
            180                 185                 190

Pro Phe Lys Lys Gly Ala Phe His Phe Ala Val Gln Ala Gly Val Pro
        195                 200                 205

Ile Val Pro Phe Val Val Ser Asn Tyr Ser Lys Val Val Asn Phe Lys
    210                 215                 220

Lys Arg Ile Phe Glu Pro Gly Val Ile Glu Ile Glu Val Leu Glu Pro
225                 230                 235                 240

Ile Lys Val Thr Gly Lys Glu Thr Lys Glu Glu Ile Asn Gln Leu Val
                245                 250                 255

Glu Gly Thr Arg Glu Arg Met Leu Glu Ser Thr Gln Arg Leu Gly Tyr
            260                 265                 270

Gly Ser Glu Tyr Asn Lys Lys Ser Asn
        275                 280
```

<210> SEQ ID NO 62
<211> LENGTH: 846
<212> TYPE: DNA
<213> ORGANISM: Arxula adeninivorans

<400> SEQUENCE: 62

```
atggcgacgg ttgtaaagca gctggttcag tatctgccaa aggccgtggc aggaacggtt     60

gttctaggct attttggcat tatcaagccc ctacagtttt acgtgcggtt ggcggtttac    120

attctggcgg ttgccttttg cgcgttcaat ggagcggtgc tgtctgcggt gctgactttg    180

attggaaagc agggtctttc gcaatggtgt gtggccagaa tgttcctgta cattgcggga    240

acgattctgg gaatcaaggt tgtgattaag aaccccgagc gtctcaagac ccgacctgcg    300

gtgttcatct ccaaccacca gtccgagctg gacattctca tcttgggagc tactttccct    360

cagtactgta gtgtgacggc aaagaagagt ctcaagtact acccgttctt gggatggttc    420

atggctctga gtggatcggt gtttattgac cgagccaatc gagacaatgc tctcaaggct    480

tttgagggag cggccaagaa ggtgaaccgt gacaagcaga gcgtgttcat gttccccgag    540

ggcactcgat cgtactacca ggagcccggt ctattgccat ttaagaaggg agcgttccac    600

tttgccgtcc aggctggtgt tcccattgtg ccatttgtag tgagcaacta ctccaaggtg    660

gtgaacttta agaagcgaat ttcgagcct ggtgtgattg aaattgaggt gttggagccc     720

atcaaggtca ctggaaagga gaccaaggag gagattaacc aattggtcga aggtactagg    780

gagcgcatgc tggagagcac ccagcgattg ggctatggct ctgagtacaa caagaagagc    840

aactaa                                                               846
```

<210> SEQ ID NO 63
<211> LENGTH: 579

<212> TYPE: PRT
<213> ORGANISM: Arxula adeninivorans

<400> SEQUENCE: 63

Met Ala Leu Gly Val Phe Ile Gln Leu Ala Glu Glu Gly Ser Arg Met
1               5                   10                  15

Thr Gly Ile Pro Pro Asp Leu Leu Arg Leu Ala Phe Cys Leu Val Phe
            20                  25                  30

Ser Tyr Pro Gly Cys Ala Ile Leu Lys Arg Leu Pro Asp Asn Asn Thr
        35                  40                  45

Leu Val Lys Glu Leu Phe Ile Met Ser Val Ser Leu Phe Tyr Leu Leu
    50                  55                  60

Gly Val Phe Ser Met Trp Gly Gly Val Arg Thr Leu Leu Ile Ser Thr
65                  70                  75                  80

Leu Ala Thr Tyr Tyr Ile Thr Lys Lys Trp Pro Ser Ser Pro Phe Met
                85                  90                  95

Pro Trp Ala Asn Phe Leu Phe Val Met Ala His Leu Phe Thr Asn His
            100                 105                 110

Ile Ala Asn Gln Ile Lys Glu Ala Gly Glu Leu Tyr Asp Pro Asn Val
        115                 120                 125

Ile Asp Ile Thr Gly Ala Gln Met Val Leu Cys Met Lys Leu Ser Ala
    130                 135                 140

Phe Gly Trp Asn Val Tyr Asp Gly Thr Gln Pro Gln Gly Ser Leu Ser
145                 150                 155                 160

Asp Phe Gln Lys Met Arg Ala Val Lys Lys His Pro Ser Leu Leu Asp
                165                 170                 175

Phe Val Thr Tyr Ala Phe Phe Phe Pro Ser Val Leu Thr Gly Pro Ser
            180                 185                 190

Phe Asp Tyr Glu Glu Phe Arg Gln Trp Ile Asp Leu Ser Met Phe Asp
        195                 200                 205

Val Thr Ala Asn Asp Pro Lys Arg Gly Arg Ala Val Asn Arg Lys Ile
    210                 215                 220

Pro Arg Ser Gly Arg Val Ala Thr Leu Lys Ala Leu Glu Gly Val Leu
225                 230                 235                 240

Trp Ile Val Val Trp Val Leu Val Thr Ser Tyr Phe Asn Leu Asp Tyr
                245                 250                 255

Ala Leu Ser Pro Lys Phe Thr Ser Glu Leu Asn Phe Val Leu Lys Met
            260                 265                 270

Leu Tyr Leu Tyr Val Leu Gly Phe Ser Tyr Arg Leu Lys Tyr Tyr Gly
        275                 280                 285

Ala Trp Ser Ile Ser Glu Gly Ser Cys Ile Leu Ala Gly Ile Gly Phe
    290                 295                 300

Asn Gly Lys Thr Lys Ser Gly Lys Tyr Lys Trp Asp Arg Val Lys Asn
305                 310                 315                 320

Ile Asp Pro Trp Lys Phe Glu Phe Gly Gln Asn Thr Phe Thr Leu Leu
                325                 330                 335

Glu Ala Trp Asn Met Asn Thr Asn Lys Trp Leu Lys Asn Tyr Val Tyr
            340                 345                 350

Leu Arg Val Thr Pro Lys Gly Lys Lys Pro Gly Phe Arg Ser Thr Leu
        355                 360                 365

Ala Thr Phe Phe Thr Ser Ala Phe Trp His Gly Thr Arg Pro Gly Tyr
    370                 375                 380

Tyr Leu Thr Phe Val Thr Gly Ala Phe Phe Gln Ala Leu Gly Lys Ile
385                 390                 395                 400

-continued

Phe Arg Arg Asn Leu Arg Pro Ile Phe Leu Glu Ala Asp Gly Val Thr
405 410 415

Pro Gly Pro Tyr Lys Lys Tyr Tyr Asp Ile Leu Thr Trp Val Thr Val
420 425 430

Gln Leu Gly Phe Gly Tyr Met Val Gln Pro Phe Met Ile Leu Glu Phe
435 440 445

Gly Pro Ser Leu Arg Leu Trp Ser Thr Val Tyr Phe Cys Val His Leu
450 455 460

Phe Ile Ala Leu Val Ile Leu Leu Phe Tyr Gly Pro Tyr Lys Arg Thr
465 470 475 480

Val Thr Gly Tyr Leu Asn Ser Leu Arg Pro Lys Glu Thr Thr Ile Lys
485 490 495

Pro Ala Asp Lys Leu Lys Met Asp Ala Glu Lys Leu Arg Gln Leu Gln
500 505 510

His Glu Leu Arg Val Leu Ser Ser Asn Glu Pro Ser Leu Gly Val Pro
515 520 525

Gln Pro Asp Phe Glu Asp Phe Asp Asp Asp Val Lys Glu Ala Ile Ala
530 535 540

Glu Phe Glu Ala Leu Lys Asn Glu Ile Ala Arg Asp Ile Asp Ala Leu
545 550 555 560

Arg Pro Lys Val Asp Lys Glu Pro Leu Lys Asn Ala Lys Pro Gln Ser
565 570 575

Lys Arg Gln

<210> SEQ ID NO 64
<211> LENGTH: 1740
<212> TYPE: DNA
<213> ORGANISM: Arxula adeninivorans

<400> SEQUENCE: 64
atggcgctcg gggtatttat tcagctggcc gaggaggggt ctcggatgac gggaattcct 60
cctgatttgc tgcggttggc gttttgtcta gtattctcct acccaggatg tgccattctt 120
aagcggttac ctgataacaa cactcttgtc aaagagctgt tcatcatgtc agtgtctctt 180
ttctacttgc ttggagtatt cagcatgtgg ggcggagtga gaacgctgct tatcagcaca 240
ttggcgacct attatatcac aaaaaagtgg ccgtcttccc cgtttatgcc ttgggctaac 300
ttccttttcg tcatggcaca cttgttcaca aaccacattg ccaatcagat taaagaggct 360
ggcgaattgt atgaccccaa tgtcattgac atcaccgggg cacagatggt gctttgtatg 420
aagctttcgg catttgggtg gaacgtgtac gacggcacac agccacaggg gtcgctgtcg 480
gatttccaaa agatgcgggc tgtcaagaag cacccatctc tattagattt tgtcacgtat 540 gctttttttct ttccttcagt gcttacgggc ccttcgtttg actacgaaga gtttaggcaa 600
tggattgacc tgtcaatgtt tgacgttact gctaatgatc ccaagcgagg acgggccgtc 660
aatcgtaaaa ttccccgtag tggaagagta gccaccctca aagcactgga gggagtgtta 720
tggattgtgg tgtgggttct agtcacgtcc tactttaatc tcgactatgc gctgtcgcca 780
aagtttacct ccgagctcaa tttcgtcttg aaaatgctat acctctatgt tctgggattc 840
tcgtacagac tcaagtatta tggtgcttgg tccatttccg agggctcgtg catcttggcc 900
ggcattgggt tcaacggaaa gacaaaatct ggaaagtaca aatgggatcg tgttaagaac 960
attgaccctt ggaagtttga gtttggccaa aacacgttta cccttctgga ggcttggaat 1020
atgaatacaa acaagtggct caagaattat gtctatttgc gagtcactcc aaagggtaaa 1080

-continued

```
aagccaggct tccgtagtac tctggccacc ttttttacgt cggccttttg gcatggtacc   1140

aggcctgggt attacttgac gtttgtgact ggtgcttttt tccaggccct aggtaaaata   1200

tttagacgca acctccgtcc aattttcctg gaagctgatg gagttacccc tggaccctat   1260

aaaaagtact acgatattct gacttgggtc acggtgcagc taggctttgg atacatggtt   1320

caaccgttta tgatcctaga gtttggaccc tctcttagac tttggtctac ggtctacttt   1380

tgcgtccacc ttttcatcgc tcttgtcatt cttctctttt atggaccgta caagcgtact   1440

gttaccggat acctcaattc tttacgaccg aaggagacca ccattaagcc cgccgacaag   1500

ctcaagatgg atgctgaaaa gcttcgccag ctccaacacg agctacgagt gttgtcttca   1560

aacgagcctt ctttgggagt tcctcagccc gattttgaag attttgacga cgacgtcaag   1620

gaagcaattg ccgaatttga agcgctcaag aatgaaattg ctcgggacat tgacgccctg   1680

cgaccaaagg tcgacaagga gcctctcaag aacgcaaagc cacagagcaa acgacagtaa   1740


<210> SEQ ID NO 65
<211> LENGTH: 512
<212> TYPE: PRT
<213> ORGANISM: Yarrowia lipolytica

<400> SEQUENCE: 65

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255
```

-continued

```
Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 66
<211> LENGTH: 1539
<212> TYPE: DNA
<213> ORGANISM: Yarrowia lipolytica

<400> SEQUENCE: 66

atggcctttc catgggcaga taagtgggca gccgatgcgt ctgcatctac agggctgcct      60

ccggacctcc tcaagattgc attcactctg gtcatgtctt atccgctgag ttctctcatg     120

aaacggctgc cagatgacgc caaaaacctc aagatcatct atatcatctc cgtgtccatc     180

ttctacatgg tgggtgtctt ctccctctat ggcggagctg ccactctgct cttctcctca     240

atgggtacct tcttcatcac ccaatggaag agcccttaca tgccctgggt caattttggt     300

tttgtcatga cccatctctt cgtcaatcac ctgcgttcgc agtttttccc cgaaacatac     360

gaccccaatg tcattgacat caccggagca cagatggttc tgtgtatgaa gctatcgtct     420

tttggatgga acgtctacga tggatggcag attgagaagg gtgagcagct cagcgagttc     480

cagactaaaa gggctgttct caagcacccc agtcttatgg acttcctagc ttttgtgttc     540

tacttccctt ccattctgac aggtccttct tacgactata tggagttcca taactggctc     600

gatctcagcc tgttcaagga gctggagaaa gataaggacc ccaagcgagc tgctcgacga     660

aagcgacaca agatccccccg atctggaatc gctgcttcca agaaactcgc cgctggtatc     720
```

```
ttctggatcg ttctgtggac ccaggtggac tctcgaatct ccaccgccta cgcttactca    780

gacgcattca ccaaggagca caacatcttt ggacgaattg tgtacctcta catgctcggt    840

ttcatgtacc gactcaagta ctacggagcc tggtccattt ccgagggagc ctgcatcttg    900

tctggcctcg gattccatgg cgtggacccc aaaactggca agtacaagtg ggaccgtgtc    960

cagaacgtgg acccgtgggg attcgaaact ggtcaaaaca caaaggctct gctggaggcc   1020

tggaaccaga acactaacaa gtggctacga aactatgtgt acctccgagt ggtgcccaaa   1080

ggccaaaagc ctggattccg agccactatc ttcacatttg tggtttccgc cttctggcat   1140

ggaactcgac ctggctacta tctcaccttt gtgaccgctg ccatgtacca gtctgttggt   1200

aagttcttcc gacgatacct gcgacccttc ttcatggagt ctgatggaaa gactgccggt   1260

ccctataaga tctactacga cattgtgtgt tggatcgttg tccaaaccgc atttggatac   1320

gctacccagt cctttatgat tctagacttc tggctgtcgc tcaagtgttg gaagaactcc   1380

tggttcctgt accacattgc tctgggcgcc atctttgcaa tttctagccc ctacaaggca   1440

tgggcgattc ccaagatcaa gaaaaagcag gctggagccg tcactgacaa gaaggacgcc   1500

aaggaggagg tgaagaagga caccatcaag accaagtaa                          1539
```

<210> SEQ ID NO 67
<211> LENGTH: 346
<212> TYPE: PRT
<213> ORGANISM: Rhodosporidium toruloides

<400> SEQUENCE: 67

```
Met Pro Ser Pro Leu Ser Arg Trp Leu Pro Val Ile Ala Phe Trp Thr
1               5                   10                  15

Phe Pro Leu Leu Ala Met Leu Ser Val Ser Pro Ser Leu Arg Thr Phe
            20                  25                  30

Leu Leu Ser Arg Pro Thr Leu Thr Tyr Ala Leu Ala Ser Val Leu Pro
        35                  40                  45

Thr Ile Met Leu Ser Arg Phe Val Ala Pro Ile Arg Tyr Tyr Leu Arg
    50                  55                  60

Leu Thr Thr Phe Leu Val Gly Leu Ala Ala Asn Ala Met Phe Gly Ala
65                  70                  75                  80

Ile Met Ala Leu Pro Met Ser Leu Val Gly Lys Gly Lys Asp Asn Gln
                85                  90                  95

Trp Leu Val Ala Arg Ser Phe Val Asn Thr Val Ala Pro Leu Val Gly
            100                 105                 110

Val Lys Phe Arg Val Glu Gly Arg Glu Asn Leu Asp Lys Ala Asn Pro
        115                 120                 125

Ala Val Leu Val Gly Asn His Gln Thr Met Val Asp Ile Leu Tyr Leu
    130                 135                 140

Gly Ala Val Phe Pro Lys Gly Thr Ser Val Met Ala Lys Arg Glu Leu
145                 150                 155                 160

Gln Trp Thr Pro Ile Leu Gly Gln Trp Met Thr Leu Ser Lys Ala Val
                165                 170                 175

Phe Val Asn Arg Ala Lys Arg Glu Asp Ala Val Lys Val Phe Ala Lys
            180                 185                 190

Val Ala Ala Lys Met Lys Lys Asn Ser Leu Ser Leu Trp Ile Phe Ala
        195                 200                 205

Glu Gly Thr Arg Ser Ala Ser Pro Thr Pro Ser Leu Leu Pro Phe Lys
    210                 215                 220
```

-continued

Lys Gly Ala Phe His Leu Ala Val Gln Ala Gly Leu Pro Val Val Pro
225 230 235 240

Ile Val Cys Glu Asn Tyr Ala His Val Tyr His Ala Lys Ala Arg Arg
245 250 255

Phe Asn Asp Gly Glu Ile Val Val Arg Val Leu Glu Pro Ile Ser Thr
260 265 270

Glu Gly Tyr Thr Ser Ser Ser Ala Asp Ile Ala His Leu Thr Glu Leu
275 280 285

Thr Arg Asp Arg Met Leu Glu Ala Ile Glu Asp Leu Gly Arg Lys Arg
290 295 300

Gln Glu Gln Leu Arg Leu Ala Gly His Gly Gln Gly Gln Gly Gln Gly
305 310 315 320

Glu Arg Glu Ala Leu Leu Ala Gly Arg Glu Ser Thr Ser Gly Glu Thr
325 330 335

Ala Ser Ala Arg Ile Glu Ala Pro Ser Glu
340 345

<210> SEQ ID NO 68
<211> LENGTH: 1041
<212> TYPE: DNA
<213> ORGANISM: Rhodosporidium toruloides

<400> SEQUENCE: 68
atgccctcgc ccttgtcccg gtggctcccc gtcatcgcat tctggacgtt ccccctcctc 60
gccatgctca gtgtctctcc ctcgctacgc acattcctcc tctcccgccc aacactcacc 120
tacgcgctcg cctcggtcct accaacaatc atgctgtccc gcttcgtcgc accgataagg 180
tattacctcc gcctgacgac tttcctcgtc ggactcgcgg caaacgccat gtttggcgcg 240
atcatggctc tcccgatgag tctcgtgggc aagggaaagg acaaccagtg gctcgtcgcg 300
aggagctttg tcaatactgt tgcgcccctc gtgggagtca agttccgcgt cgaggggagg 360
gagaatttgg acaaggcgaa cccggcggtg cttgtcggga accaccagac catggttgac 420
atcctctacc tcggcgccgt cttccccaag ggcacgtcag tcatggccaa gcgcgagttg 480
cagtggacgc caatcctcgg ccagtggatg acgctctcca aggcggtgtt tgtcaaccgc 540
gccaagcgcg aggacgcagt caaggtgttt gccaaggtcg ccgcaaagat gaagaagaac 600
agcctctcgc tctggatctt tgccgagggc acccgctcgg cctccccgac cccctcgctc 660
ctcccgttca aaaagggcgc gttccacctc gccgtccagg caggcttgcc cgtcgtgcca 720
atcgtgtgcg agaactatgc gcatgtgtat catgccaagg cgaggaggtt caacgacgga 780
gagattgtcg tccgggttct cgaacccatc tcgaccgagg gctacacctc gtcgtcggcc 840
gacatcgcgc acctgacaga gctcacgcgc gaccggatgc tcgaggcgat cgaagacctc 900
ggtcgcaagc ggcaggagca gttgcggctc gccggtcacg gccaaggcca agggcagggc 960
gagcgagagg cactcctcgc gggacgggag agtacgagcg gcgagacggc gagtgcgagg 1020
attgaggcgc cgtccgaata a 1041

<210> SEQ ID NO 69
<211> LENGTH: 326
<212> TYPE: PRT
<213> ORGANISM: Rhodotorula graminis

<400> SEQUENCE: 69

Met Leu Ser Pro Ser Ser Ser Ser Ala Leu Thr Ser Ser Pro Ala Thr
1 5 10 15

```
Leu Val Pro Thr Leu Ala Val Gly Ala Leu Leu Pro Ala Met Ile Leu
            20                  25                  30

Ala Arg Val Phe Ser Pro Val Arg Tyr Tyr Ala Lys Leu Val Thr Phe
        35                  40                  45

Leu Val Gly Ser Ala Ser Ala Ser Ala Phe Gly Val Ala Ser Ser Leu
    50                  55                  60

Val Met Ala Val Leu Gly Arg Arg Glu Asp Ile Gln Trp Leu Val Ala
65                  70                  75                  80

Arg Phe Leu Lys Tyr Thr Thr Ala Pro Leu Leu Gly Val Lys Phe Arg
                85                  90                  95

Val Glu Gly Ala Asp Lys Leu Glu Thr Thr His Pro Ala Val Leu Val
            100                 105                 110

Gly Asn His Gln Thr Met Leu Asp Leu Leu Tyr Leu Gly Ala Ile Phe
        115                 120                 125

Pro Pro Arg Thr Thr Ile Met Ala Lys Arg Glu Leu Gln Trp Val Pro
    130                 135                 140

Ile Leu Gly Gln Phe Met Thr Leu Ala Lys Ala Ile Phe Val Asn Arg
145                 150                 155                 160

Val Lys Arg Glu Asp Ala Ile Arg Val Phe Asp Gln Val Ala Lys Glu
                165                 170                 175

Met Lys Arg Arg Glu Leu Ser Leu Phe Ile Phe Pro Glu Gly Thr Arg
            180                 185                 190

Ser Ala Ser Ala Ala Pro Ser Leu Leu Pro Phe Lys Lys Gly Ala Phe
        195                 200                 205

His Leu Ala Val Gln Ala Gly Leu Pro Ile Val Pro Ile Val Cys Glu
    210                 215                 220

Asn Tyr Ala His Ile Tyr Tyr Ser Lys Ala Arg Arg Phe Asn Ala Gly
225                 230                 235                 240

Glu Ile Val Val Arg Val Leu Asp Pro Ile Ser Thr Glu Gly Val Thr
                245                 250                 255

Ser Ser His Glu Asp Ile Thr Ala Leu Ile Glu Arg Thr Arg Asn Ala
            260                 265                 270

Met Leu Asp Ala Ile His Gln Leu Gly Arg Glu Arg Arg Ala Gln Leu
        275                 280                 285

Gly Gly Pro Glu Gly Glu Arg Glu Ala Leu Leu Pro Pro Thr Pro Arg
    290                 295                 300

Ala Ser Ile Gly Gly Thr Glu Thr Glu Gly Glu Thr Ala Ser Ala Arg
305                 310                 315                 320

Leu Pro Glu Gly Thr Gln
                325
```

<210> SEQ ID NO 70
<211> LENGTH: 981
<212> TYPE: DNA
<213> ORGANISM: Rhodotorula graminis

<400> SEQUENCE: 70

```
atgctctcgc cctcctcgtc ctccgccctc acctcgtcgc ccgcgaccct cgtcccgacc      60

ctcgccgtcg gggccctcct gcccgccatg atcctcgccc gcgtcttctc gcccgtgcgg     120

tactacgcca agctcgtcac cttcctcgtc ggctcggcga gcgcctctgc gtttggcgtc     180

gcgtcgtccc ttgtcatggc cgtcctcggc cgccgcgagg acatccagtg gctcgtcgca     240

cggttcctca agtacacgac cgcgcccctc ctcggcgtca agttccgcgt cgagggcgcc     300

gacaagctcg agacgaccca cccggccgtc ctcgtcggca accaccagac catgctcgac     360
```

```
ctcctgtacc tcggcgccat cttcccgccc cggacgacca tcatggccaa gcgcgagctg    420

cagtgggtgc ccatcctcgg ccagttcatg acgctcgcaa aggccatctt tgtcaaccgc    480

gtcaagcgcg aggacgccat ccgcgtgttc gaccaggtcg caaaggagat gaagcggcgc    540

gagctgtcgc tcttcatctt ccccgagggc actcgctcgg cgtcggcggc gccgtcgctc    600

ctcccgttca agaagggcgc gttccacctc gccgtccagg ccggcctccc catcgtgccc    660

atcgtgtgcg agaactacgc ccacatctac tactcgaagg ccaggcgctt caacgcgggc    720

gagatcgtcg tgcgggtgct cgacccgatc tcgaccgagg gcgtcacgtc gtcgcacgaa    780

gacatcacgg ccctgatcga gcgcacgcgc aacgccatgc tcgacgccat tcaccagctc    840

gggcgcgagc gtcgcgcgca gctcggcggg cccgagggtg agcgcgaggc gctgctgccg    900

cctacgccga gggcatcgat tggcggtacc gagaccgagg gcgagacggc gagcgcgcgg    960

ttgccggaag ggacgcagta a                                              981


<210> SEQ ID NO 71
<211> LENGTH: 399
<212> TYPE: PRT
<213> ORGANISM: Phaeodactylum tricornutum

<400> SEQUENCE: 71

Met Arg His Leu Arg Gly Val Leu Ile Thr Leu Ile Leu Asp Trp Val
1               5                   10                  15

Ser Leu Ser Arg Ser Leu Thr Thr His Ala Pro Tyr Arg Arg Thr Thr
            20                  25                  30

Ala Thr Arg Ser Thr Cys Thr Ala Arg Gln Thr Arg Gly Ser Gln Leu
        35                  40                  45

Ala Ser Thr Thr Pro Phe Asp Arg Asp Gln Ser Glu Ser Phe Ile Val
    50                  55                  60

Pro Asn Glu Asp Val Asn Pro Ile Ile Arg Leu Gly Lys Asp Glu Gln
65                  70                  75                  80

Glu Lys Ile Val Asn Gly Phe Gly Leu Trp Cys Ala Ala Val Ser Val
                85                  90                  95

Phe Thr Gly Pro Leu Trp Val Ala Ala Met Ser Thr Leu Gln Ala Ile
            100                 105                 110

Tyr Lys Ile Asn Ala Asp Trp Asp Pro Asn Arg Ala Leu Tyr Asp Lys
        115                 120                 125

Thr Gly Lys Ile Trp Ser Lys Thr Trp Leu Thr Leu Thr Asp Ser Tyr
    130                 135                 140

Pro Thr Phe Ser Gly Asp Val Asp Arg Leu Lys Ser Ser Gln Gly Pro
145                 150                 155                 160

Cys Leu Tyr Val Ala Asn His Ala Ser Trp Leu Asp Ile Pro Val Ile
                165                 170                 175

Cys Thr Val Leu Asp Pro Val Phe Lys Phe Ile Ala Lys Gly Glu Leu
            180                 185                 190

Arg Lys Val Pro Cys Ile Gly Gln Gln Leu Glu Gly Gly Asn His Ile
        195                 200                 205

Leu Ile Asp Arg Glu Asp Arg Arg Ser Gln Leu Arg Thr Phe Lys Asp
    210                 215                 220

Gly Ile Gly Trp Leu Lys Lys Gly Val Pro Ile Met Ala Phe Pro Glu
225                 230                 235                 240

Gly Met Arg Ser Arg Asp Gly Lys Leu Met Asp Phe Lys Gly Gly Leu
                245                 250                 255
```

```
Phe Ser Met Ala Val Lys Thr Gln Val Pro Ile Val Pro Ile Thr Ile
            260                 265                 270

Ser His Thr His Ala Val Met Pro Ser Asn Ala Leu Phe Pro Val Gln
        275                 280                 285

Thr Gly Ala Gly Lys Leu His Val His Val His Asp Pro Ile Asp Thr
    290                 295                 300

Thr Gly Lys Thr Glu Ala Glu Leu Gly Ala Leu Val Arg Ala Ser Phe
305                 310                 315                 320

Leu Ser Thr Leu Pro Leu Gly Gln His Pro Lys Pro Val Val Pro Glu
                325                 330                 335

Ile Glu Gln Thr Ala Glu Lys Asp His Lys Thr Ile Pro Ile Thr Pro
            340                 345                 350

Lys Val Gln Asp Thr His His Leu His Gln Gln His Ile Thr Pro Ser
        355                 360                 365

Gln Thr Leu Ser His Tyr Thr Ala Ala Ser Ser Thr Ile Asn Ser Ser
    370                 375                 380

Gln Glu Val Thr Ser Lys Asn Arg Thr Glu Glu Thr Thr Val Pro
385                 390                 395
```

```
<210> SEQ ID NO 72
<211> LENGTH: 1200
<212> TYPE: DNA
<213> ORGANISM: Phaeodactylum tricornutum

<400> SEQUENCE: 72

atgaggcatt tgagaggcgt actaattaca ctgattctag attgggtttc tttatcgcga     60

tcgttgacga cacacgctcc gtacaggcgt accacagcta cacgttccac ctgtactgct    120

cggcaaaccc ggggatccca attggcatcc accacacctt tcgatcgcga tcagagtgaa    180

agctttattg ttcccaacga agacgttaac ccgattattc ggcttggaaa ggatgagcag    240

gaaaaaattg tgaacggatt tggcctttgg tgcgcagctg tttccgtctt tacggggccc    300

ttgtgggtcg ctgccatgag tacactacaa gctatttaca aaattaacgc cgactgggat    360

ccgaatcgag cactctacga caaaacgggc aaaatttggt ccaaaacctg gctcacactg    420

acagattcct atccgacctt ttccggcgat gtggaccgct taaaaagttc tcaaggccca    480

tgtctatacg tggcgaatca cgcatcttgg ctggacattc cggtgatctg caccgtttta    540

gatccagttt tcaagtttat tgccaaggga gaattgcgca aagtgccatg tattggacaa    600

caactagagg ggggaaatca cattctcatc gatcgagagg accgtcggtc gcaactgcgc    660

acattcaaag atggtattgg ttggctgaaa aagggcgtac caatcatggc ctttcccgaa    720

ggtatgcgct cccgcgatgg aaaactcatg gatttcaaag gagggctctt ttcgatggcg    780

gtaaaaacac aggtgcccat tgttccaatc acgatttcgc acacgcacgc cgtcatgccg    840

tccaacgcct tgtttcccgt gcaaacagga gccggcaaac ttcacgtaca tgttcacgat    900

cccatcgaca cgactggcaa gaccgaagcc gaactaggag cactggtacg ggcatccttt    960

ttgtccacct taccgttggg acagcatcca aagccagtag taccagaaat tgagcaaaca   1020

gccgaaaaag accataagac gattccgatt actcccaaag tgcaagatac acaccacctt   1080

catcaacagc atattacacc cagtcagacc ttatcgcact acacagcagc ctcttctaca   1140

ataaattcca gccaggaagt tacatcaaag aatcggacgg aggagactac tgtaccataa   1200

<210> SEQ ID NO 73
<211> LENGTH: 262
<212> TYPE: PRT
```

<213> ORGANISM: Rhodotorula minuta

<400> SEQUENCE: 73

```
Met Asn Ala Thr Leu Arg Tyr Tyr Tyr Arg Phe Thr Leu Tyr Cys Thr
1               5                   10                  15

Thr Leu Gly Leu Thr Ser Ala Trp Ala Val Leu Val Ser Ile Ala Leu
            20                  25                  30

Ser Ile Phe Gly Gln Asn His Ser Ile Gln His Tyr Val Ala Arg Ser
        35                  40                  45

Phe Tyr Tyr Phe Ala Ser Pro Ile Val Gly Trp Lys Ile Lys Val Glu
    50                  55                  60

Gly Glu Glu Tyr Leu Lys Asn Glu Gln Ser Thr Val Phe Val Gly Asn
65                  70                  75                  80

His Gln Ser Met Ile Asp Ile Leu Tyr Leu Gly Arg Met Phe Pro Lys
                85                  90                  95

Arg Cys Thr Val Thr Ala Lys Lys Glu Leu Lys Trp Thr Pro Phe Leu
            100                 105                 110

Gly Gln Phe Met Trp Leu Ser Asn Ala Ile Phe Ile Asn Arg Thr Asn
        115                 120                 125

Arg Ala Asp Ala Leu Lys Thr Phe Gln Lys Ala Ala Glu Asp Met Lys
    130                 135                 140

Arg Arg Ser Met Ser Ile Phe Ile Phe Ala Glu Gly Thr Arg Thr Asn
145                 150                 155                 160

Ser Ala Glu Ile Gly Met Leu Pro Phe Lys Lys Gly Ala Phe His Leu
                165                 170                 175

Ala Val Gln Gly Gly Phe Pro Ile Val Pro Met Val Cys Glu Asn Tyr
            180                 185                 190

Tyr Ser Leu Tyr Ala Ala Gly Ile Lys Arg Phe Glu Ala Gly Glu Leu
        195                 200                 205

Val Leu Lys Val Leu Pro Pro Val Ser Thr Glu Gly Tyr Thr Ser Ser
    210                 215                 220

Ser Glu Asp Ile Ala Lys Leu Ser Asp Lys Val Arg Thr Ala Met Leu
225                 230                 235                 240

Glu Ala Leu Glu Glu Leu Ala Glu Arg Arg Lys Ala Ser Thr Thr Gln
                245                 250                 255

Lys Arg Ile Asn Gln Gln
            260
```

<210> SEQ ID NO 74
<211> LENGTH: 789
<212> TYPE: DNA
<213> ORGANISM: Rhodotorula minuta

<400> SEQUENCE: 74

```
atgaatgcta ctctgcggta ctactaccgc tttacgctgt actgcaccac gctgggcctc      60

acttcagcct gggctgttct cgtgtcgata gccctgtcca tctttggcca aaatcactcc     120

atacagcact acgtagctag aagcttttat tactttgcaa gtccgatagt aggatggaag     180

atcaaggttg aaggggagga gtacttgaag aatgaacagt caacggtgtt tgttggcaat     240

catcagtcca tgatcgacat cttgtaccta ggacgcatgt tcccaaagag atgtacagtg     300

acggcaaaga aagagctgaa atggacgccc ttcttaggcc aattcatgtg gctgtcaaac     360

gcaatcttca tcaatcgcac aaaccgagcc gatgcattga agaccttcca aaaagcagca     420

gaggatatga agcgacgcag catgtcaatc ttcatctttg ccgagggtac acggacgaat     480
```

```
tcggccgaaa ttgggatgct gcctttcaag aagggagctt tccatctggc tgtgcagggt    540

ggattcccta ttgtacctat ggtctgcgag aactactata gcttatatgc agcgggtatt    600

aagaggtttg aggctggcga actcgttcta aaagtattac cgcccgtctc gacggagggc    660

tacacatcgt catctgaaga cattgcaaaa ctcagtgata aagtgagaac agccatgctt    720

gaagcgctag aagagctcgc agaacgtagg aaggcatcta cgacgcagaa aaggataaac    780

cagcagtag                                                            789


<210> SEQ ID NO 75
<211> LENGTH: 303
<212> TYPE: PRT
<213> ORGANISM: Saccharomyces cerevisiae

<400> SEQUENCE: 75

Met Ser Val Ile Gly Arg Phe Leu Tyr Tyr Leu Arg Ser Val Leu Val
1               5                   10                  15

Val Leu Ala Leu Ala Gly Cys Gly Phe Tyr Gly Val Ile Ala Ser Ile
            20                  25                  30

Leu Cys Thr Leu Ile Gly Lys Gln His Leu Ala Gln Trp Ile Thr Ala
        35                  40                  45

Arg Cys Phe Tyr His Val Met Lys Leu Met Leu Gly Leu Asp Val Lys
    50                  55                  60

Val Val Gly Glu Glu Asn Leu Ala Lys Lys Pro Tyr Ile Met Ile Ala
65                  70                  75                  80

Asn His Gln Ser Thr Leu Asp Ile Phe Met Leu Gly Arg Ile Phe Pro
                85                  90                  95

Pro Gly Cys Thr Val Thr Ala Lys Lys Ser Leu Lys Tyr Val Pro Phe
            100                 105                 110

Leu Gly Trp Phe Met Ala Leu Ser Gly Thr Tyr Phe Leu Asp Arg Ser
        115                 120                 125

Lys Arg Gln Glu Ala Ile Asp Thr Leu Asn Lys Gly Leu Glu Asn Val
    130                 135                 140

Lys Lys Asn Lys Arg Ala Leu Trp Val Phe Pro Glu Gly Thr Arg Ser
145                 150                 155                 160

Tyr Thr Ser Glu Leu Thr Met Leu Pro Phe Lys Lys Gly Ala Phe His
                165                 170                 175

Leu Ala Gln Gln Gly Lys Ile Pro Ile Val Pro Val Val Val Ser Asn
            180                 185                 190

Thr Ser Thr Leu Val Ser Pro Lys Tyr Gly Val Phe Asn Arg Gly Cys
        195                 200                 205

Met Ile Val Arg Ile Leu Lys Pro Ile Ser Thr Glu Asn Leu Thr Lys
    210                 215                 220

Asp Lys Ile Gly Glu Phe Ala Glu Lys Val Arg Asp Gln Met Val Asp
225                 230                 235                 240

Thr Leu Lys Glu Ile Gly Tyr Ser Pro Ala Ile Asn Asp Thr Thr Leu
                245                 250                 255

Pro Pro Gln Ala Ile Glu Tyr Ala Ala Leu Gln His Asp Lys Lys Val
            260                 265                 270

Asn Lys Lys Ile Lys Asn Glu Pro Val Pro Ser Val Ser Ile Ser Asn
        275                 280                 285

Asp Val Asn Thr His Asn Glu Gly Ser Ser Val Lys Lys Met His
    290                 295                 300


<210> SEQ ID NO 76
```

<211> LENGTH: 912
<212> TYPE: DNA
<213> ORGANISM: Saccharomyces cerevisiae

<400> SEQUENCE: 76
atgagtgtga taggtaggtt cttgtattac ttgaggtccg tgttggtcgt actggcgctt 60
gcaggctgtg gcttttacgg tgtaatcgcc tctatccttt gcacgttaat cggtaagcaa 120
catttggctc agtggattac tgcgcgttgt ttttaccatg tcatgaaatt gatgcttggc 180
cttgacgtca aggtcgttgg cgaggagaat ttggccaaga agccatatat tatgattgcc 240
aatcaccaat ccaccttgga tatcttcatg ttaggtagga ttttcccccc tggttgcaca 300
gttactgcca agaagtcttt gaaatacgtc ccctttctgg gttggttcat ggctttgagt 360
ggtacatatt tcttagacag atctaaaagg caagaagcca ttgacacctt gaataaaggt 420
ttagaaaatg ttaagaaaaa caagcgtgct ctatgggttt ttcctgaggg taccaggtct 480
tacacgagtg agctgacaat gttgcctttc aagaagggtg ctttccattt ggcacaacag 540
ggtaagatcc ccattgttcc agtggttgtt tccaatacca gtactttagt aagtcctaaa 600
tatggggtct tcaacagagg ctgtatgatt gttagaattt taaaacctat ttcaaccgag 660
aacttaacaa aggacaaaat tggtgaattt gctgaaaaag ttagagatca aatggttgac 720
actttgaagg agattggcta ctctcccgcc atcaacgata caaccctccc accacaagct 780
attgagtatg ccgctcttca acatgacaag aaagtgaaca agaaaatcaa gaatgagcct 840
gtgccttctg tcagcattag caacgatgtc aatacccata acgaaggttc atctgtaaaa 900
aagatgcatt aa 912

<210> SEQ ID NO 77
<211> LENGTH: 619
<212> TYPE: PRT
<213> ORGANISM: Saccharomyces cerevisiae

<400> SEQUENCE: 77

Met Tyr Asn Pro Val Asp Ala Val Leu Thr Lys Ile Ile Thr Asn Tyr
1 5 10 15

Gly Ile Asp Ser Phe Thr Leu Arg Tyr Ala Ile Cys Leu Leu Gly Ser
20 25 30

Phe Pro Leu Asn Ala Ile Leu Lys Arg Ile Pro Glu Lys Arg Ile Gly
35 40 45

Leu Lys Cys Cys Phe Ile Ile Ser Met Ser Met Phe Tyr Leu Phe Gly
50 55 60

Val Leu Asn Leu Val Ser Gly Phe Arg Thr Leu Phe Ile Ser Thr Met
65 70 75 80

Phe Thr Tyr Leu Ile Ser Arg Phe Tyr Arg Ser Lys Phe Met Pro His
85 90 95

Leu Asn Phe Met Phe Val Met Gly His Leu Ala Ile Asn His Ile His
100 105 110

Ala Gln Phe Leu Asn Glu Gln Thr Gln Thr Thr Val Asp Ile Thr Ser
115 120 125

Ser Gln Met Val Leu Ala Met Lys Leu Thr Ser Phe Ala Trp Ser Tyr
130 135 140

Tyr Asp Gly Ser Cys Thr Ser Glu Ser Asp Phe Lys Asp Leu Thr Glu
145 150 155 160

His Gln Lys Ser Arg Ala Val Arg Gly His Pro Pro Leu Leu Lys Phe
165 170 175

```
Leu Ala Tyr Ala Phe Phe Tyr Ser Thr Leu Leu Thr Gly Pro Ser Phe
            180                 185                 190

Asp Tyr Ala Asp Phe Asp Ser Trp Leu Asn Cys Glu Met Phe Arg Asp
        195                 200                 205

Leu Pro Glu Ser Lys Lys Pro Met Arg Arg His His Pro Gly Glu Arg
    210                 215                 220

Arg Gln Ile Pro Lys Asn Gly Lys Leu Ala Leu Trp Lys Val Val Gln
225                 230                 235                 240

Gly Leu Ala Trp Met Ile Leu Ser Thr Leu Gly Met Lys His Phe Pro
                245                 250                 255

Val Lys Tyr Val Leu Asp Lys Asp Gly Phe Pro Thr Arg Ser Phe Ile
            260                 265                 270

Phe Arg Ile His Tyr Leu Phe Leu Leu Gly Phe Ile His Arg Phe Lys
        275                 280                 285

Tyr Tyr Ala Ala Trp Thr Ile Ser Glu Gly Ser Cys Ile Leu Cys Gly
    290                 295                 300

Leu Gly Tyr Asn Gly Tyr Asp Ser Lys Thr Gln Lys Ile Arg Trp Asp
305                 310                 315                 320

Arg Val Arg Asn Ile Asp Ile Trp Thr Val Glu Thr Ala Gln Asn Thr
                325                 330                 335

Arg Glu Met Leu Glu Ala Trp Asn Met Asn Thr Asn Lys Trp Leu Lys
            340                 345                 350

Tyr Ser Val Tyr Leu Arg Val Thr Lys Lys Gly Lys Lys Pro Gly Phe
        355                 360                 365

Arg Ser Thr Leu Phe Thr Phe Leu Thr Ser Ala Phe Trp His Gly Thr
    370                 375                 380

Arg Pro Gly Tyr Tyr Leu Thr Phe Ala Thr Gly Ala Leu Tyr Gln Thr
385                 390                 395                 400

Cys Gly Lys Ile Tyr Arg Arg Asn Phe Arg Pro Ile Phe Leu Arg Glu
                405                 410                 415

Asp Gly Val Thr Pro Leu Pro Ser Lys Lys Ile Tyr Asp Leu Val Gly
            420                 425                 430

Ile Tyr Ala Ile Lys Leu Ala Phe Gly Tyr Met Val Gln Pro Phe Ile
        435                 440                 445

Ile Leu Asp Leu Lys Pro Ser Leu Met Val Trp Gly Ser Val Tyr Phe
    450                 455                 460

Tyr Val His Ile Ile Val Ala Phe Ser Phe Phe Leu Phe Arg Gly Pro
465                 470                 475                 480

Tyr Ala Lys Gln Val Thr Glu Phe Phe Lys Ser Lys Gln Pro Lys Glu
                485                 490                 495

Ile Phe Ile Arg Lys Gln Lys Lys Leu Glu Lys Asp Ile Ser Ala Ser
            500                 505                 510

Ser Pro Asn Leu Gly Gly Ile Leu Lys Ala Lys Ile Glu His Glu Lys
        515                 520                 525

Gly Lys Thr Ala Glu Glu Glu Glu Met Asn Leu Gly Ile Pro Pro Ile
    530                 535                 540

Glu Leu Glu Lys Trp Asp Asn Ala Lys Glu Asp Trp Glu Asp Phe Cys
545                 550                 555                 560

Lys Asp Tyr Lys Glu Trp Arg Asn Lys Asn Gly Leu Glu Ile Glu Glu
                565                 570                 575

Glu Asn Leu Ser Lys Ala Phe Glu Arg Phe Lys Gln Glu Phe Ser Asn
            580                 585                 590

Ala Ala Ser Gly Ser Gly Glu Arg Val Arg Lys Met Ser Phe Ser Gly
```

-continued 595 600 605

Tyr Ser Pro Lys Pro Ile Ser Lys Lys Glu Glu
610 615

<210> SEQ ID NO 78
<211> LENGTH: 1860
<212> TYPE: DNA
<213> ORGANISM: Saccharomyces cerevisiae

<400> SEQUENCE: 78
atgtacaatc ctgtggacgc tgttttaaca aagataatta ccaactatgg gattgatagt 60
tttacactgc gatatgctat ctgcttattg ggatcgttcc cactgaatgc tattttgaag 120
agaattcccg agaagcgtat aggtttaaaa tgttgtttta tcatttctat gtcgatgttt 180
tacttattcg gtgtgctgaa tctagtaagt ggattcagga ccctgtttat tagtaccatg 240
tttacttact tgatctcaag attttaccgt tccaagttta tgccacactt gaatttcatg 300
tttgttatgg gtcatttggc aataaatcat atacacgccc aattccttaa cgaacagact 360
caaactaccg ttgacattac aagttcacaa atggttttag ccatgaaact aacttctttt 420
gcatggtcgt actatgatgg ttcatgcact agcgaaagcg atttcaaaga tttgactgag 480
catcaaaaat ctcgtgctgt cagaggtcat ccacccttat taaagttcct ggcatatgca 540
tttttctatt caacgttgct aactggccca agtttcgatt atgccgattt tgacagctgg 600
ttgaattgtg agatgttccg tgacttgcct gaaagcaaaa agcctatgag aagacaccac 660
cctggtgaaa gaagacagat tccaaagaat ggtaaacttg cattatggaa agttgttcaa 720
ggtcttgctt ggatgatttt aagtacacta ggaatgaagc acttccccgt aaaatacgtt 780
ttggacaaag atggcttccc aacgagatct tttatattca gaatccatta cttattcttg 840
cttggtttca tccatagatt caagtactac gctgcctgga ctatttcgga aggatcttgt 900
attttgtgcg gtttgggtta taatggttat gattcaaaga cacaaaagat cagatgggat 960
cgtgtcagaa atattgacat ttggaccgta gaaacggcgc agaatacgcg tgaaatgttg 1020
gaagcatgga atatgaatac taacaagtgg ctaaaatact ctgtttattt acgtgtcaca 1080
aagaagggca aaaaacctgg tttccgctca actttgttta ctttcctaac ttccgcattt 1140
tggcatggta ccagacctgg gtactatctg acttttgcga caggggcttt gtaccaaaca 1200
tgtggtaaaa tctacagacg caattttaga ccaattttct tgcgagaaga tggtgtcact 1260
cctttgcctt ctaaaaaaat ctacgattta gttggcatat atgcaattaa actagcattt 1320
ggttacatgg tgcaaccatt tattatcctt gatttgaagc catctttaat ggtatggggc 1380
tctgtttatt tctatgttca tattattgtt gctttctcat tttcctattt cagaggacca 1440
tatgctaaac aagttactga attttttaaa tccaaacaac ctaaagaaat attcattaga 1500
aaacaaaaga agttggaaaa agatatttct gcaagctctc caaacttggg tggtatattg 1560
aaggcaaaga ttgaacatga aaagggaaag acagcagaag aagaagaaat gaacttaggt 1620
attccaccaa ttgagttaga aaagtgggac aatgctaagg aagattggga agatttctgc 1680
aaagattaca aagaatggag aaataaaaat ggtcttgaaa tagaagagga aaacctttct 1740
aaagcttttg aaagattcaa gcaggaattt tctaacgctg caagtggatc aggtgaacgt 1800
gtgagaaaaa tgagttttag tggttactca ccaaagccta tttcaaaaaa ggaagagtag 1860

<210> SEQ ID NO 79
<211> LENGTH: 300
<212> TYPE: PRT

<213> ORGANISM: Saccharomyces cerevisiae

<400> SEQUENCE: 79

Met Glu Lys Tyr Thr Asn Trp Arg Asp Asn Gly Thr Gly Ile Ala Pro
1 5 10 15

Phe Leu Pro Asn Thr Ile Arg Lys Pro Ser Lys Val Met Thr Ala Cys
20 25 30

Leu Leu Gly Ile Leu Gly Val Lys Thr Ile Ile Met Leu Pro Leu Ile
35 40 45

Met Leu Tyr Leu Leu Thr Gly Gln Asn Asn Leu Leu Gly Leu Ile Leu
50 55 60

Lys Phe Thr Phe Ser Trp Lys Glu Glu Ile Thr Val Gln Gly Ile Lys
65 70 75 80

Lys Arg Asp Val Arg Lys Ser Lys His Tyr Pro Gln Lys Gly Lys Leu
85 90 95

Tyr Ile Cys Asn Cys Thr Ser Pro Leu Asp Ala Phe Ser Val Val Leu
100 105 110

Leu Ala Gln Gly Pro Val Thr Leu Leu Val Pro Ser Asn Asp Ile Val
115 120 125

Tyr Lys Val Ser Ile Arg Glu Phe Ile Asn Phe Ile Leu Ala Gly Gly
130 135 140

Leu Asp Ile Lys Leu Tyr Gly His Glu Val Ala Glu Leu Ser Gln Leu
145 150 155 160

Gly Asn Thr Val Asn Phe Met Phe Ala Glu Gly Thr Ser Cys Asn Gly
165 170 175

Lys Ser Val Leu Pro Phe Ser Ile Thr Gly Lys Lys Leu Lys Glu Phe
180 185 190

Ile Asp Pro Ser Ile Thr Thr Met Asn Pro Ala Met Ala Lys Thr Lys
195 200 205

Lys Phe Glu Leu Gln Thr Ile Gln Ile Lys Thr Asn Lys Thr Ala Ile
210 215 220

Thr Thr Leu Pro Ile Ser Asn Met Glu Tyr Leu Ser Arg Phe Leu Asn
225 230 235 240

Lys Gly Ile Asn Val Lys Cys Lys Ile Asn Glu Pro Gln Val Leu Ser
245 250 255

Asp Asn Leu Glu Glu Leu Arg Val Ala Leu Asn Gly Gly Asp Lys Tyr
260 265 270

Lys Leu Val Ser Arg Lys Leu Asp Val Glu Ser Lys Arg Asn Phe Val
275 280 285

Lys Glu Tyr Ile Ser Asp Gln Arg Lys Lys Arg Lys
290 295 300

<210> SEQ ID NO 80
<211> LENGTH: 903
<212> TYPE: DNA
<213> ORGANISM: Saccharomyces cerevisiae

<400> SEQUENCE: 80
atggaaaagt acaccaattg gagagacaat ggtacgggaa tagctccatt tctaccaaac 60
acaatcagga aacctagtaa ggtgatgaca gcgtgtttgt tgggtatcct aggggtgaaa 120
accattataa tgctaccatt gattatgctg taccttctaa ctggccagaa caacttactg 180
ggtttgatat tgaagtttac attcagttgg aaagaggaaa ttaccgtgca aggaatcaag 240
aaacgtgacg taaggaaatc caagcattat ccacagaagg gcaagcttta tatttgcaat 300

-continued

```
tgtacctcac ctttagatgc tttttcagtg gtgttattag ctcaagggcc tgttacgttg    360

ttggtcccat ccaatgacat tgtatacaaa gtttccataa gagaattcat caacttcatc    420

ctcgccggtg ggttagatat aaaactctat ggccacgagg tagcagagct atctcaattg    480

ggcaataccg tgaattttat gtttgctgag ggtacctcat gtaatggtaa aagcgtctta    540

ccgtttagta taaccgggaa aaaacttaaa gaattcatag acccttcaat aaccacaatg    600

aaccccgcaa tggccaaaac taaaaaattt gaattgcaga ccatccaaat caaaactaat    660

aaaactgcca tcaccacatt gcccatctcc aatatggagt atttatctag atttctgaac    720

aagggcatta atgttaaatg caagatcaac gagccacaag tactctcgga taatttagag    780

gaattacgcg ttgcattaaa cggtggcgac aaatataaac tagtctcacg gaagttagat    840

gttgaatcta agaggaattt tgtgaaggaa tatatcagcg atcaacgtaa aaagaggaag    900

tag                                                                  903


<210> SEQ ID NO 81
<211> LENGTH: 280
<212> TYPE: PRT
<213> ORGANISM: Arxula adeninivorans

<400> SEQUENCE: 81

Met Glu Lys Phe Ser Asn Trp Arg Asp Gly Ala Thr Gly Val Ala Pro
1               5                   10                  15

Phe Leu Pro Leu Pro Lys Pro Glu Ser Ser Pro Ala Gly Thr Ala Cys
            20                  25                  30

Gly Leu Ile Leu Gly Leu Ile Arg Leu Pro Leu Val Ile Val Leu Thr
        35                  40                  45

Ile Phe His Phe Leu Leu Phe Gln Trp Leu Gly Pro Leu Asn Ala Val
    50                  55                  60

Ser Ile Arg Leu Ile Leu Met Val Leu Gly Val Tyr Arg Val Ser Thr
65                  70                  75                  80

Val Leu Glu Asn Lys Arg Ala Pro Thr Pro Gly Lys Gly Asp Ile Ile
                85                  90                  95

Val Ser Asn Phe Thr Ser Pro Leu Asp Pro Leu Ile Tyr Ser Val Leu
            100                 105                 110

Phe Asp Pro Leu Phe Val Ile Pro Asp Gly Asn Ala Arg Phe Leu Ala
        115                 120                 125

Leu Ser Met Pro Gly Ala Phe Arg Gln Ala Leu Ser Val Pro Thr Ile
    130                 135                 140

Gly Gln Gly Pro Ser Ala Gly His Asp Leu Ala Lys Leu Val Asp Arg
145                 150                 155                 160

Ala Arg Ala Ser Gly Lys Leu Leu Val Ile Phe Ala Glu Gly Thr Thr
                165                 170                 175

Thr Asn Gly Arg Gly Leu Leu Ala Ile Pro Asp Lys Gly Thr Pro Ile
            180                 185                 190

Ser Asn Thr Ala Thr Gly Arg Val Tyr Ala Ser Ala Val Arg Tyr Asn
        195                 200                 205

Pro Pro Arg Gly Cys Ser Pro Val Pro Gln Thr Ala Val Arg Trp Val
    210                 215                 220

Trp Gly Leu Val Ser Cys Thr Gly Val Asn Cys Thr Val Arg Met Ser
225                 230                 235                 240

Ala Pro Val Glu Gly Lys Gln Thr Val Ala Glu Ser Ile Cys Arg Val
                245                 250                 255

Gly Arg Leu Arg Gln Leu Gly Leu Ser Ala Asn Asp Lys Val Asp Phe
```

```
            260                 265                 270

Tyr Gln Ala Trp Lys Lys Tyr His
        275                 280


<210> SEQ ID NO 82
<211> LENGTH: 843
<212> TYPE: DNA
<213> ORGANISM: Arxula adeninivorans

<400> SEQUENCE: 82

atggagaagt tttccaactg gcgagacggc gctacgggcg tggcaccatt tttaccgttg      60

ccaaagccag aatcttcacc ggcaggcaca gcatgtggac tgattttggg cctgatccgg     120

ctacctctgg tgattgtttt gacgatattt cactttctcc tgtttcaatg gctggggcca     180

ttgaatgcgg tgtcaattcg attgatactc atggtcttag gagtatacag agtttcgaca     240

gtgctcgaga acaaacgtgc accaactcct ggcaaaggag acattatcgt atccaatttc     300

acgtccccat tggaccctct aatctattca gtattgtttg accccctgtt tgtcattcct     360

gatggaaatg cgagatttct ggccctgtca atgccgggtg cgttccgaca agcattaagc     420

gttccaacca tcggtcaggg accatctgca ggacacgacc tggctaagct agtcgatcgc     480

gccagggcat ccggaaagct cttggtgatc ttcgccgaag gcaccaccac gaacggccgg     540

ggcctcctgg caatcccaga caaaggcacc ccaatctcga acaccgcgac tggacgcgta     600

tatgcatcgg cggtacggta taatccccct cgaggatgct ctcctgtgcc ccagaccgcg     660

gtacgatggg tgtggggatt agtgtcttgc actggcgtca attgcaccgt ccggatgtct     720

gctccagtgg agggcaagca aaccgttgcc gagagtatct gtcgggttgg ccgcctccgt     780

cagctcggac tatctgcaaa cgacaaggta gatttttacc aagcttggaa aaagtaccac     840

taa                                                                   843


<210> SEQ ID NO 83
<211> LENGTH: 305
<212> TYPE: PRT
<213> ORGANISM: Yarrowia lipolytica

<400> SEQUENCE: 83

Met Glu Lys Phe Ser Gln Tyr Arg Asp Lys Gly Thr Gly Val Ala Pro
1               5                   10                  15

Tyr Leu Pro His Pro Arg Ser Lys Ala Asp Gly Ser Leu Pro Ser Thr
            20                  25                  30

Ile Phe Val Val Leu Gln Ala Pro Leu Ala Leu Val Glu Ser Val Ile
        35                  40                  45

Lys Ile Pro Leu Leu Leu Ala Leu Leu Ala Leu Tyr Ala Gly Ile Ile
    50                  55                  60

Gln Phe Ile Thr Ile Glu Pro Val Arg Lys Ala Tyr Phe Ser Thr Leu
65                  70                  75                  80

Leu Phe Val Ser Gly Phe Trp Phe Trp Asn Val Ser Ala Glu Ala Val
                85                  90                  95

Arg Arg Asn Lys Leu Thr Glu Ala Tyr Pro Lys Pro Gly Glu Val Val
            100                 105                 110

Val Ser Asn Tyr Leu Ser Pro Ile Asp Ala Phe Val Tyr Ser Ala Leu
        115                 120                 125

Phe Asp Pro Val Phe Ile Val Pro His Ala Ser Ser Arg Val Tyr Gln
    130                 135                 140

Glu Leu Gly Pro Phe Gly Val Phe Phe Lys Ala Leu Gly Ile Pro Glu
```

-continued

```
145                 150                 155                 160

Ile Val Pro Pro Thr His Gly Glu Ser Leu Ser Lys Ile Val Phe Asp
                165                 170                 175

Ala Thr Ser Lys Gly Arg Ala Val Val Val Phe Ala Glu Gly Thr Thr
            180                 185                 190

Ser Asn Gly Arg Gly Leu Leu Pro Leu Leu His Ile Asp Phe His Gln
        195                 200                 205

Leu Ser Gln Asn Thr Lys Val Ile Pro Ala Gly Leu Arg Leu Ala Pro
    210                 215                 220

Gln Tyr Ile Thr Thr Pro Leu Pro Val Thr Leu Pro Met Trp Val Phe
225                 230                 235                 240

Arg Leu Leu Ser Asn Pro Thr Gly Trp His Val Ser Leu Arg Phe Ala
                245                 250                 255

Glu Pro Cys Tyr Ala Lys Asp Thr Asn Val Asn Asn Thr Leu Val Glu
            260                 265                 270

Ser Ile Cys Arg Val Gly Arg Leu Lys Ser Ile Gly Pro Asp Leu Gly
        275                 280                 285

Val Glu Gly Lys Arg Asn Phe Trp Lys Val Tyr Asn Lys Lys Lys Asp
    290                 295                 300

Val
305
```

<210> SEQ ID NO 84
<211> LENGTH: 918
<212> TYPE: DNA
<213> ORGANISM: Yarrowia lipolytica

<400> SEQUENCE: 84

```
atggaaaagt tctcccagta ccgcgataag ggcacaggtg ttgctcccta cctgccgcat      60

ccgcgctcca aggctgacgg ttcgctcccc agcacgattt tcgtcgttct gcaggcgccc     120

ctggctcttg tggagagtgt gatcaagatc cccctcttgc tcgccctgct ggcgctgtat     180

gcgggcatca tccaattcat cacaatcgag ccggtacgaa aggcctactt ttcgacgctg     240

ctgtttgtca gtggcttctg gttctggaac gtgtccgccg aagcggtgag aagaaacaag     300

ctgaccgagg cctaccccaa gcccggagag gtcgtggtgt ccaactacct gtcgcccatt     360

gacgcctttg tgtactctgc acttttcgac cccgttttca tcgtccccca cgcctcttcc     420

cgagtctacc aggagctggg tccgtttgga gtcttcttca aggccctggg tatccccgaa     480

atcgtgcctc caacccatgg ggagtcgctg tccaagattg tgtttgacgc cacctccaag     540

ggacgagccg tggttgtgtt tgccgaggga acaacctcca acggacgagg tctgctgccc     600

ctgctacaca ttgacttcca ccagctctct caaaacacaa aggtgattcc ggcaggcctc     660

agactcgccc cccagtacat caccacccct ctgcccgtga cgctgcccat gtgggtcttc     720

cgactgctct caaaccccac tggatggcac gtgtctctac ggtttgccga accgtgctac     780

gcgaaggaca ccaacgtcaa caacacactg gtggagagca tttgtcgggt gggccgactc     840

aagagcatcg gtccagatct cggtgttgag ggaaagcgaa acttttggaa ggtctacaac     900

aagaagaagg acgtttga                                                   918
```

<210> SEQ ID NO 85
<211> LENGTH: 579
<212> TYPE: PRT
<213> ORGANISM: Arxula adeninivorans

<400> SEQUENCE: 85

-continued

```
Met Ile Arg Ala Ala Tyr Gly Ser Val Ser Arg Ala Arg Asp Ser Leu
1               5                   10                  15

Thr Leu Arg Ala Pro Ser Phe Pro Thr Thr Ala Val Glu Val Arg Asp
            20                  25                  30

Lys Ile Leu Trp Ile Leu Tyr Ala Trp Ile Glu Met Phe Thr Asp Val
        35                  40                  45

Phe Ser Phe Trp Thr Glu Lys Val Trp Gly Tyr Val Ser Thr Pro Thr
    50                  55                  60

Lys Glu Ser Ile Leu Arg Lys Gln Leu Asp Glu Ala Lys Ser Tyr His
65                  70                  75                  80

Glu Trp Glu Glu Leu Ser Tyr Lys Leu Asp Ser Ile Leu Gly Asn Asp
                85                  90                  95

Ile Trp Arg Gln Asn Pro Val Ser Arg Lys Tyr Asp Tyr Arg Leu Ile
            100                 105                 110

Ser Thr Arg Leu Lys Glu Leu Val Ala Ala Arg Asp Asn Arg Asn Ile
        115                 120                 125

Glu Leu Leu Met Asp Arg Leu Arg Ser Gly Leu Leu Arg Asn Ile Gly
    130                 135                 140

Ser Ile Ala Ser Thr His Leu Tyr Asn Arg Ala Tyr Ser Gly Thr Lys
145                 150                 155                 160

Leu Leu Ile Glu Asp Tyr Ile Asn Val Val Ile Gln Cys Leu Glu Tyr
                165                 170                 175

Val Glu Arg Gly Gly Arg Pro Leu Thr Ala Ser Ala Ser Lys Ile Pro
            180                 185                 190

Asn Gly Gly Glu Pro Pro Ser Pro Arg Thr Tyr His Lys Pro Met Ile
        195                 200                 205

Thr Arg Gln Arg Lys Leu Asn Phe Phe Asn Asp Thr Arg Gln Ser Phe
    210                 215                 220

Gly Ser Thr Ala Val Val Leu His Gly Gly Ser Leu Phe Gly Leu Cys
225                 230                 235                 240

His Ile Gly Met Ile Lys Thr Leu Phe Asn Gln Gly Leu Leu Pro Arg
                245                 250                 255

Ile Val Cys Gly Ser Thr Val Gly Ala Leu Val Ala Ser Leu Val Cys
            260                 265                 270

Ser Cys Val Asp Glu Glu Val Tyr Glu Thr Leu Asp Asn Val Ser Ser
        275                 280                 285

Glu Met Ser Pro Leu Arg Gln Gly Tyr Thr Asp Ile Lys Tyr His Ser
    290                 295                 300

Val Ala Glu Gly Val Ile Ser Ser Met Cys Pro Pro Glu Ile Leu Ile
305                 310                 315                 320

Phe Glu Gln Tyr Ile Arg Glu Lys Leu Gly Asp Leu Thr Phe Glu Glu
                325                 330                 335

Ala Tyr Gln Arg Thr Gly Arg Ile Leu Asn Ile Pro Val Thr Pro Lys
            340                 345                 350

Ala Lys Pro Gly Gln Val Ala Pro Pro Val Pro Thr Leu Leu Asn Tyr
        355                 360                 365

Leu Ser Ser Pro Asn Val Val Val Trp Ser Ala Ala Gln Cys Ser Ile
    370                 375                 380

Gly Thr Gly Ile Ile His Lys Lys Val Glu Leu Leu Val Lys Gly Leu
385                 390                 395                 400

Asp Gly Gln Leu Lys Pro Tyr Leu Asp Ala Asp Asp Ile Glu Tyr Thr
                405                 410                 415
```

-continued

```
Pro Ala Asn Gln Ala Val Tyr Ala Ala Asp Arg Glu Ser Pro Tyr Thr
            420                 425                 430

Arg Leu Ser Glu Leu Phe Asn Val Asn Asn Tyr Ile Val Ser Val Ala
        435                 440                 445

Arg Pro Tyr Phe Ala Pro Ile Leu Leu Ser Asp Phe Lys Tyr Arg Ala
    450                 455                 460

Ala Lys Ser Phe Lys Thr Arg Phe Leu Lys Leu Thr Arg Leu Glu Leu
465                 470                 475                 480

Gln Tyr Arg Leu Asn Gln Leu Ser Gln Leu Gly Leu Val Pro Pro Met
                485                 490                 495

Ile Gln Gln Trp Phe Val Asp Gly Asn Ile Pro Ala Gly Phe Gln Val
            500                 505                 510

Thr Val Val Pro Glu Leu Pro Ser Leu Ile Arg Asp Ile Gly Lys Val
        515                 520                 525

Phe Asp Ser Asp Asn Ile Lys Glu Lys Val Asp Tyr Trp Ile Lys Ile
    530                 535                 540

Gly Glu Arg Ser Val Trp Pro Val Leu Asn Ile Ile Trp Ala Arg Cys
545                 550                 555                 560

Ala Ile Glu Phe Val Leu Asp Asp Leu Tyr His Ser Arg Arg Lys Asp
                565                 570                 575

Glu Leu Asp


<210> SEQ ID NO 86
<211> LENGTH: 1740
<212> TYPE: DNA
<213> ORGANISM: Arxula adeninivorans

<400> SEQUENCE: 86

atgattaggg ctgcctacgg gtcagtgtcc agggcccgag attctttaac gttgagggct      60

ccatcttttc ctaccactgc tgtggaggtc cgtgacaaga ttctatggat tctgtatgcc     120

tggattgaaa tgttcacgga cgtctttagc ttctggacgg agaaggtgtg gggttatgtt     180

tctactccta ctaaagaaag cattcttaga aagcaactcg acgaggcaaa atcataccat     240

gaatgggagg agctcagcta caaactagac tcaattttag ggaacgatat ttggcgacag     300

aaccctgtta gccgaaagta tgactatcgc ctgatttcta cccgcctcaa ggaattggtt     360

gctgctaggg ataatcgcaa cattgaattg ctaatggatc ggctaaggtc aggcctgctt     420

cgtaatattg gatcgattgc aagtactcat ctctacaacc gagcgtattc gggcacaaaa     480

ctgttaattg aggattacat taatgtagtg attcaatgcc tggagtatgt tgaacggggc     540

ggcaggccat tgactgcttc agcatccaag attcccaatg gcggtgaacc cccttctcca     600

cgaacctacc ataagcccat gattaccaga cagcgcaagc tcaacttctt caatgataca     660

cgccagtcgt ttggaagtac agctgtggta cttcacggcg ggtccttgtt tggactttgc     720

catattggca tgattaaaac attgttcaac cagggtctac ttcctcgcat agtctgtggc     780

tccacagtgg gagcactagt agcgagtcta gtatgctcct gtgtggatga agaggtgtat     840

gagactttgg ataatgtgtc ttcggaaatg tctcctctcc gccaaggata cactgatata     900

aagtaccatt cggtagccga aggggtcatt tcatcaatgt gtccgccaga gattttgatt     960

tttgaacagt acatccgaga aaaactcgga gacctgacat ttgaagaagc atatcaacgc    1020

accggccgca ttcttaatat cccagtgaca ccaaaggcaa aaccaggtca ggtagcacca    1080

ccagtcccga cgctcctgaa ttatttgtcg agcccgaatg ttgtagtatg gtcagcagcg    1140

caatgcagca ttggaacggg gattattcac aagaaggttg aacttttagt aaaaggtctg    1200
```

```
gatggtcaat taaaacctta tttggatgcg gatgatattg aatacactcc tgcaaatcaa   1260

gctgtatacg ctgctgatcg cgagagtccc tatacaagat tgtctgagct gttcaatgtg   1320

aacaattaca ttgtatcagt agctcgcccc tactttgccc caattctgct ttcggatttc   1380

aagtaccgtg cagctaaaag cttcaagacc cggttcctca aactaacccg tctggagtta   1440

cagtatcgtc tcaatcagct gtctcaattg ggctggttc  cgcccatgat tcaacaatgg   1500

tttgtggacg gtaacattcc cgccgggttc caagttaccg tggtgcctga attaccctca   1560

cttattagag acatcggcaa ggttttcgat tcggataata taaaggagaa ggtcgactac   1620

tggattaaga tcggtgagcg cagtgtgtgg ccagtgctga atattatctg ggcaaggtgc   1680

gcaattgagt ttgtgctcga cgatctatat cacagccgac gtaaagacga actcgactag   1740
```

<210> SEQ ID NO 87
<211> LENGTH: 633
<212> TYPE: PRT
<213> ORGANISM: Arxula adeninivorans

<400> SEQUENCE: 87

```
Met Asn Pro Phe Asp Val Asp Tyr Thr Asn Arg Asp His Leu Val Asp
1               5                   10                  15

Phe Glu Arg Ala Leu His Glu Asp Glu Ala Ser His Ile Ile Ser Val
            20                  25                  30

Asn Asp Trp Ala Pro Val His Ala Pro Leu Lys Arg Arg Leu Arg Arg
        35                  40                  45

Lys Pro Thr Asp Ser Asp Pro Gly Thr Gly Leu Gly Tyr Thr Leu Leu
    50                  55                  60

Arg Trp Pro Ile Leu Val Ala Ile Ala Leu Trp Leu Ala Leu Leu Ala
65                  70                  75                  80

Phe Val Tyr Ala Ile Val Arg Phe Trp Val Ala Leu Phe Glu Tyr Phe
                85                  90                  95

Val Thr Trp Arg Gly Pro Arg Arg Asn Leu Arg Glu Lys Leu Arg Ser
            100                 105                 110

Ala Arg Ser Tyr Glu Glu Trp Ile Ser Ala Ala Lys Val Leu Asp Asp
        115                 120                 125

His Leu Gly Asn Thr Ser Trp Lys His Asn Pro Lys Phe Ser Arg Tyr
    130                 135                 140

Asp Tyr Arg Thr Ile Asp Arg Ile Thr Asn Ser Leu Arg Gln Leu Arg
145                 150                 155                 160

Asn Gln Asn Lys Ala Glu Glu Val Gly Ser Ile Leu Gln Gly Cys Val
                165                 170                 175

Lys His Asn Phe Ala Gly Thr Gln Gly Gln Pro Leu Tyr Ser Gln Cys
            180                 185                 190

Tyr Tyr Gly Thr Lys Asp Leu Val Glu Glu Phe Asn Ser Glu Ile Val
        195                 200                 205

Lys Ser Leu Asp Tyr Leu Ala Thr His Pro Asp Leu Ser Pro Gln Ser
    210                 215                 220

Arg Arg Leu Leu Phe Lys Met Phe Ser Lys Asn Phe Gly Lys Thr Ala
225                 230                 235                 240

Leu Cys Leu Ser Gly Gly Ala Thr Phe Ala Tyr Arg His Phe Gly Val
                245                 250                 255

Val Lys Ala Leu Leu Glu Gln Gly Leu Leu Pro Asn Ile Ile Ser Gly
            260                 265                 270

Thr Ser Gly Gly Gly Leu Val Ala Ala Leu Val Gly Thr Arg Thr Asn
```

-continued

```
        275                 280                 285

Ser Glu Leu Arg Glu Leu Leu Thr Pro Gln Leu Ala Asp Lys Ile Thr
    290                 295                 300

Ala Cys Trp Glu Lys Phe Pro Lys Trp Val Tyr Arg Phe Tyr Ser Thr
305                 310                 315                 320

Gly Ala Arg Phe Asp Ala Val Asp Trp Ala Glu Arg Ser Cys Trp Phe
                325                 330                 335

Thr Leu Gly Ser Leu Thr Phe Arg Glu Ala Tyr Asp Arg Thr Gly Lys
            340                 345                 350

Ile Leu Asn Ile Ser Thr Val Pro Ala Asp Pro Asn Ser Pro Ser Ile
        355                 360                 365

Leu Cys Asn Tyr Ile Thr Ser Pro Asp Cys Val Ile Trp Ser Ala Leu
    370                 375                 380

Leu Ala Ser Ala Ala Val Pro Gly Ile Leu Asn Pro Val Val Leu Met
385                 390                 395                 400

Met Lys Thr Lys Lys Gly Asn Leu Val Pro Tyr Ser Phe Gly Asn Lys
                405                 410                 415

Trp Lys Asp Gly Ser Leu Arg Thr Asp Ile Pro Val His Ala Leu Asn
            420                 425                 430

Val Tyr Phe Asn Val Asn Phe Thr Ile Val Ser Gln Val Asn Pro His
        435                 440                 445

Ile Ser Leu Phe Met Tyr Ala Pro Arg Gly Thr Val Gly Arg Pro Val
    450                 455                 460

Ser His Arg Gln Gly Lys Gly Trp Arg Gly Gly Phe Leu Gly Ser Ala
465                 470                 475                 480

Leu Glu Asp Met Leu Lys Leu Glu Ile Arg Lys Trp Leu Lys Leu Met
                485                 490                 495

Lys Asn Leu Ser Leu Met Pro Arg Phe Phe Asn Gln Asp Trp Ser Ser
            500                 505                 510

Val Trp Leu Gln Thr Phe Glu Gly Ser Val Thr Leu Trp Pro Arg Ile
        515                 520                 525

Arg Leu Lys Asp Phe Tyr Tyr Ile Leu Ser Asp Pro Thr Arg Glu Gln
    530                 535                 540

Met Glu Thr Met Ile Ile Ser Gly Gln Arg Cys Thr Phe Pro Lys Leu
545                 550                 555                 560

Leu Phe Ile Lys His Gln Val Asn Ile Glu Arg Ala Ile Asp Arg Gly
                565                 570                 575

Arg Lys His Asn Ala Lys Ala Arg Glu Glu Asn Gly Pro Gln Leu Arg
            580                 585                 590

Arg Val Asn Pro Phe Leu His Asp Leu Asp Asp Arg Val Tyr His Ser
        595                 600                 605

Ser Ser Ser Val Asp Pro Arg Glu Phe Gln Asp Asp His Asp Asp Glu
    610                 615                 620

Asp Asp Asp Ser Thr Asp Ser Ser Met
625                 630
```

<210> SEQ ID NO 88
<211> LENGTH: 1902
<212> TYPE: DNA
<213> ORGANISM: Arxula adeninivorans

<400> SEQUENCE: 88

```
atgaacccgt ttgatgtaga ttacacaaac agggaccatc tggtcgactt tgaacgagct      60

ttgcacgaag atgaggcttc ccatattata tcggtaaacg actgggctcc agtgcatgct     120
```

```
cctctcaagc gacggttgag acgcaagccg acagattcgg atcctgggac aggattagga    180

tacactttgc ttagatggcc tattctggtg gcaattgcgc tgtggctggc cctgttagca    240

tttgtgtacg ccatagtgag gttttgggtc gctctgtttg agtactttgt tacctggcga    300

ggaccccggc gcaatcttcg tgaaaagcta cgcagcgctc gtagttacga ggaatggatt    360

agtgctgcca aagttcttga tgaccatcta ggaaatactt cttggaagca caacccaaag    420

ttctctcgat acgactaccg tactattgat cgcatcacta actcactgcg gcaactgcga    480

aaccagaaca aggccgagga ggttggctct attctacaag gatgcgtcaa gcacaacttt    540

gctggaactc agggccaacc tttgtactct cagtgctact atggcacaaa ggacctggta    600

gaggagttca attctgaaat tgtgaaatcg ctcgattacc tggcaaccca tccagacctg    660

agtcctcaat ctagacgtct tttgttcaaa atgttttcca agaattttgg aaagacggca    720

ttgtgcctct ctggaggggc aacatttgcc tatagacatt tcggagttgt taaagcgctc    780

ttggaacagg gcttgctgcc taatattatt tctggtactt ctggcggagg attggtagct    840

gcgctagttg gtaccagaac aaatagtgaa ctccgtgagc ttctcactcc tcaactggcc    900

gacaagatca ccgcctgctg ggaaaagttc ccaaaatggg tttatagatt ctacagcacc    960

ggcgctcgat tcgatgccgt cgactgggct gaacggtctt gctggtttac actaggaagc   1020

ctgactttta gagaggccta cgatcgaact ggaaagatcc tcaacatttc cactgttcct   1080

gctgacccta attccccttc aatcctctgc aattacatta cttctcccga ctgtgtcatc   1140

tggtcggctt tacttgcttc tgctgcagta ccgggaattc tgaacccagt ggtgctcatg   1200

atgaagacga aaaagggcaa tctggtacct tacagctttg gtaacaagtg gaaggatggt   1260

tctctccgaa ctgatattcc tgtccacgca ctcaacgtgt actttaacgt caacttcacc   1320

atcgtgtccc aggtcaaccc tcacatttct ctgttcatgt atgccccgcg gggaactgtg   1380

ggtaggccag tatctcaccg tcagggtaaa ggctggcgag gtgggttcct aggctcagct   1440

ttggaagaca tgctgaagct ggaaattcgt aaatggctca aactcatgaa aaaccttagt   1500

cttatgccac ggtttttcaa tcaagattgg tcttcagtat ggcttcaaac gttcgaggga   1560

tccgtcacct tgtggccaag gatcaggcta aaggactttt attatattct gtctgatccc   1620

actcgggaac aaatggaaac catgatcatt agtggacagc gatgcacatt cccaaagctc   1680

ttgttcatca agcaccaagt caacatagag cgggcaattg accgtggaag aaagcacaat   1740

gcaaaagcca gggaggaaaa tggtccccag cttagacggg taaacccatt cctgcacgac   1800

ttggatgacc gtgtatacca ttccagctct agcgtggacc ctcgcgagtt tcaggatgat   1860

cacgatgatg aagacgacga cagcactgat tctagcatgt aa                      1902
```

<210> SEQ ID NO 89
<211> LENGTH: 662
<212> TYPE: PRT
<213> ORGANISM: Arxula adeninivorans

<400> SEQUENCE: 89

```
Met Gln Ser Leu Asp Leu Leu Asp Asp Arg Ser Trp Val Pro Asn Tyr
1               5                   10                  15

Ala Arg Val Gly Leu Lys Ser Leu Lys Glu Tyr Leu Val Ser His Arg
            20                  25                  30

Tyr Gln Ser Glu Glu Ala Arg Lys His Ala Glu Ala Leu Glu Arg Trp
        35                  40                  45

Thr Lys Ser Gln Ala Gln Ala Glu Thr Tyr Glu Gln Trp Leu Phe Ala
```

-continued

```
    50                  55                  60

Ser Glu Gln Leu Asp Lys Leu Ser Gly Asn Asp Lys Trp Lys Glu Asp
65                  70                  75                  80

Pro Val Ser Pro Tyr Tyr Asp Ser Val Leu Val Gln Gln Arg Leu Gln
                85                  90                  95

Gln Leu Arg Asp Ala Arg Val Asn Ser Asn Met Asp Glu Leu Leu Tyr
            100                 105                 110

Leu Val Arg Thr Ser Leu Gln Arg Asn Leu Gly Asn Met Gly Asp Pro
        115                 120                 125

Arg Leu Tyr Val Arg Thr His Thr Gly Ser Lys Thr Leu Ile Glu Gln
    130                 135                 140

Tyr Ile Ala Glu Val Glu Leu Ala Leu Asp Thr Leu Leu Ser Cys Gly
145                 150                 155                 160

Pro Gly Thr Phe Ser Pro Lys Val Leu Leu Ser Asn Leu Ile Gln Thr
                165                 170                 175

Arg Lys Ala Phe Gly Arg Thr Ala Leu Val Leu Ser Gly Gly Ser Thr
            180                 185                 190

Phe Gly Ile Leu His Ile Gly Val Met Arg Glu Leu His Arg Ala His
        195                 200                 205

Leu Leu Pro Gln Val Ile Ser Gly Ser Ser Ala Gly Ser Ile Phe Ala
    210                 215                 220

Ser Met Leu Cys Ile His Leu Glu Asp Glu Ile Glu Glu Leu Leu Gln
225                 230                 235                 240

Leu Pro Leu His Lys Glu Ser Phe Glu Ile Phe Glu Pro Ala Gly Glu
                245                 250                 255

Arg Glu Gly Leu Met Val Arg Leu Ala Arg Phe Leu Lys His Gly Thr
            260                 265                 270

Trp Phe Asp Asn Lys Tyr Leu Ser Thr Thr Met Arg Glu Leu Leu Gly
        275                 280                 285

Asp Leu Thr Phe Gln Glu Ala Tyr Tyr Arg Thr Gln Arg Ile Leu Asn
    290                 295                 300

Val Thr Val Ser Pro Ser Ser Met His Glu Met Pro Lys Ile Leu Asn
305                 310                 315                 320

Tyr Leu Thr Ala Pro Asn Val Leu Ile Trp Ser Ala Val Cys Ala Ser
                325                 330                 335

Cys Ser Val Pro Phe Val Phe Asp Ser His Asp Ile Leu Ala Lys Asn
            340                 345                 350

Pro Arg Thr Gly Glu Phe Tyr Ser Trp Asn Ala Ser Thr Phe Ile Asp
        355                 360                 365

Gly Ser Val Tyr Asn Asp Leu Pro Leu Ser Arg Leu Ala Glu Met Phe
    370                 375                 380

Asn Val Asn His Phe Ile Ala Cys Gln Val Asn Pro His Val Val Pro
385                 390                 395                 400

Phe Val Lys Phe Ala Glu Thr Met Ser Leu Val Glu Ala Arg Pro Thr
                405                 410                 415

Thr Thr Glu Pro Gly Ser Leu Thr Lys Leu Trp His Ser Thr Gln Leu
            420                 425                 430

Ala Leu Ser Ser Glu Ile Ser His Tyr Leu Asp Leu Ala Ala Glu Met
        435                 440                 445

Gly Leu Phe Lys Asn Ile Ser Ser Lys Leu Arg Ser Val Leu Asp Gln
    450                 455                 460

Gln Tyr Ser Gly Asp Ile Thr Ile Leu Pro Glu Leu Tyr Leu Ser Glu
465                 470                 475                 480
```

-continued

```
Phe Gly Gln Ile Phe Lys Asn Pro Ser Lys Glu Phe Phe Gln Lys Ala
                485                 490                 495

Glu Leu Arg Ala Ala Arg Ala Thr Trp Pro Lys Met Ser His Ile His
            500                 505                 510

Asn Arg Val Ala Ile Glu Leu Ala Leu Val Lys Ala Ile His Lys Leu
        515                 520                 525

Arg Ala Arg Ile Val Ser Gln Ser Val His Glu Pro Gly Ser Ser Leu
    530                 535                 540

Gln Val His Ala Ala Asn Asp Glu Gly Thr Leu Ala Pro Ile Arg Arg
545                 550                 555                 560

Arg His Ser Ser Thr Lys Leu His His Arg Arg Gln Arg Ser Asp Gly
                565                 570                 575

Met Ala Val Lys Tyr Leu Val Arg Arg His Ser Leu Gln Tyr Phe Gly
            580                 585                 590

Thr Glu Gly Pro Gly Pro Ala Ala Leu Ser Arg Lys Lys Ser Ser Ala
        595                 600                 605

Gly Leu Thr Gln Ala His Thr Pro Thr Pro Ser Leu Thr Asn Ser Val
    610                 615                 620

Ser Val Gly Gly Ser Pro Arg His Arg Arg Phe Thr Thr Ser Ser Arg
625                 630                 635                 640

Gln Ser Ser Gly Asp His Leu Glu Met Phe Ser Gln Asn His Pro Leu
                645                 650                 655

Glu Arg Ile Ser Thr Gly
            660


<210> SEQ ID NO 90
<211> LENGTH: 1989
<212> TYPE: DNA
<213> ORGANISM: Arxula adeninivorans

<400> SEQUENCE: 90

atgcaatccc tggacctatt agacgacagg tcctgggtcc ccaattatgc gcgtgtgggc     60

ctgaaatcgc taaaagaata cttggttagc catagatatc agtctgaaga agctcgaaag    120

catgccgaag cgttagaaag atggacaaag tctcaggctc aggcggagac atacgaacag    180

tggctatttg cttcggagca gctcgacaag ctgtctggga acgacaagtg gaaagaggac    240

ccggtgtccc catattatga cagtgtgcta gtacaacagc ggttacagca gctccgagat    300

gctagggtga atagtaacat ggacgagctg ctgtatttgg tccgcactag cttgcaaaga    360

aacttgggta acatgggtga tcctcgacta tacgtgagga cccatactgg ctctaagacg    420

ctcattgaac aatatattgc tgaggtagaa ctggcattag acactctgct gagctgcgga    480

ccggggacgt tttcacccaa agttctgtta tccaatctta ttcagacaag aaaggcgttt    540

ggacgaacag ccctggtgct ttctggaggt agtacgtttg gaattttaca tattggtgta    600

atgcgagagc ttcaccgagc ccatctgtta ccgcaggtca tttctggatc gtcggccgga    660

tccatctttg cgtccatgct atgtattcac ttagaagacg agattgaaga actactgcaa    720

ctgcctctac acaaggaaag ctttgaaatc ttcgaacctg ctggagaacg agaaggacta    780

atggttcggc tggcacggtt cctcaaacat ggcacttggt tcgacaacaa gtatcttagc    840

acaactatgc gagagcttct aggagacctc actttccagg aggcctacta ccgaacgcag    900

cgaattctaa atgtcactgt gtctccttcg agtatgcacg aaatgccgaa gattctcaac    960

tatctgaccg ctcctaacgt gctcatttgg tcggcagtgt gtgcatcgtg ctcagtacca   1020
```

-continued

```
tttgtgtttg attctcacga cattctggca aaaaaccctc gaactgggga gttttattca   1080

tggaacgctt ctactttcat cgacgggagt gtgtataatg atctgccatt gtctcgacta   1140

gcggaaatgt ttaacgtgaa ccattttatt gcgtgccagg taaacccgca tgtggttcca   1200

ttcgtcaaat ttgccgagac aatgtcattg gtggaagctc gtcccactac tactgaaccg   1260

ggatcgttga caaagctatg gcacagtact cagctcgcgc tttctagtga gatctcacac   1320

tatctggatt tggctgctga aatgggcttg ttcaagaaca ttagttccaa gctgcgatcg   1380

gtgctagatc aacaatattc cggcgacatt actattcttc ccgaattata cctgtctgag   1440

tttggtcaga ttttcaaaaa cccatcaaag gagttcttcc agaaggcaga gcttcgagct   1500

gccagagcga catggcccaa gatgtcccac attcacaacc gtgtggccat cgagttggct   1560

ttagtaaagg caattcacaa gcttcgtgcc cgtattgtat ctcagagcgt ccatgagcct   1620

ggcagttctc tacaagtaca tgctgctaat gacgaaggca ccctagcacc tattcgccgt   1680

cgccattctt cgaccaagct tcaccataga cgacaacggt ccgatggaat ggccgtgaaa   1740

tacttggtcc gcagacattc gctacagtac tttggcactg agggccctgg tcccgctgcg   1800

ctatctcgta aaaagagttc ggccgggctt acccaggctc atactcctac gccttcactg   1860

accaacagcg ttagtgtagg gggcagtcca aggcaccgtc gcttcactac tagctctaga   1920

cagtcctcag gagaccattt ggaaatgttc tctcaaaatc atccgctaga acgtatctct   1980

accggctga                                                           1989
```

<210> SEQ ID NO 91
<211> LENGTH: 666
<212> TYPE: PRT
<213> ORGANISM: Yarrowia lipolytica

<400> SEQUENCE: 91

```
Met Lys Ser Arg Val Ala Val Val Leu Ala Pro Val Leu Ala Pro Phe
1               5                   10                  15

Val Ala Ile Leu Lys Asn Leu Trp Val Phe Phe Thr Ala Leu Leu Glu
            20                  25                  30

Leu Leu Phe Asp Val Ser Trp His Trp Met Leu Gln Ser Trp His Trp
        35                  40                  45

Trp Cys Ser Thr Asp Gln Lys Thr Leu Leu Gln Leu Gln Leu Asp Gln
    50                  55                  60

Ala Asp Thr Tyr Glu Glu Trp Glu Ser Ile Ala Ser Glu Leu Asp Glu
65                  70                  75                  80

Leu Leu Gly Asn Asp Val Trp Arg Gln Thr Ala Ala Ser Lys Arg Tyr
                85                  90                  95

Asp Tyr Arg Leu Ile Ala Gly Arg Leu Arg Asp Phe Ile Glu Cys Arg
            100                 105                 110

Ala Val Gly Asp Ile Ala Thr Leu Ile Ser Arg Leu Arg Ser Gly Leu
        115                 120                 125

Leu Arg Asn Leu Gly Ser Ile Ser Ser Leu Gln Leu Tyr Thr Arg Ser
    130                 135                 140

Tyr Leu Gly Ser Lys Leu Leu Ile Glu Glu Tyr Ile Thr Glu Val Ile
145                 150                 155                 160

Asp Cys Leu Lys Tyr Ile Lys Asp Tyr Gly Thr Thr Gly Gly Leu Asp
                165                 170                 175

Thr Lys Gly Val His Phe Phe Pro Lys Ser Glu Gln Arg Gln Leu Asp
            180                 185                 190

Ser Glu Gln Leu Thr Arg Gln Lys Lys His Lys Leu Phe Tyr Asp Thr
```

```
        195                 200                 205

Arg Gln Ser Phe Gly Arg Thr Ala Leu Val Leu Gln Gly Gly Thr Ile
    210                 215                 220

Phe Gly Leu Thr His Leu Gly Thr Ile Lys Ala Leu Thr Leu Gln Gly
225                 230                 235                 240

Leu Leu Pro Gly Ile Val Thr Gly Phe Lys Glu Gly Ala Phe Ile Ala
                245                 250                 255

Ala Leu Thr Gly Ile Tyr Val Ser Asp Leu Glu Leu Leu Glu Thr Ile
            260                 265                 270

Asp Ser Leu Pro Asp Thr Leu Asn Asp Leu Tyr Gln Lys Tyr Lys Glu
        275                 280                 285

Arg Leu Ala Glu Glu Asn Lys His Lys Asp His Ser Phe Ser Asn Ser
    290                 295                 300

Asn Ser Asp Tyr Asp Phe Asp Tyr Ala Phe Asp Phe Glu Gln Phe Ala
305                 310                 315                 320

Asn Thr Tyr Asn Val Thr Phe Ser Ser Val Thr Asp Lys Val Leu Arg
                325                 330                 335

Ser Glu Tyr Pro Pro Glu Val Lys Met Tyr Glu Glu Phe Ile Glu Asn
            340                 345                 350

Gln Leu Gly Asp Leu Thr Phe Glu Glu Ala Phe Asn Lys Ser Asp Arg
        355                 360                 365

Val Leu Asn Ile Val Ala His Ser His Asp Ser Ser Phe Pro Thr Leu
    370                 375                 380

Met Asn Tyr Leu Thr Thr Pro Asn Val Leu Ile Arg Ser Ala Cys Arg
385                 390                 395                 400

Ala Ser Met Val Thr Ala His Asp Glu Pro Gln Thr Lys Lys Ala Cys
                405                 410                 415

Ala His Leu Leu Val Lys Asp Asp Asp Asn Ser Val Ile Pro Tyr Asp
            420                 425                 430

Ala Cys Lys Ser Arg Arg Gly Ser Ser Thr Asp Val Ile Leu Gly Pro
        435                 440                 445

Val Gln Glu Glu Val Asp Pro Leu Asp Ser Thr Ala Asn Gly Thr Asn
    450                 455                 460

Ser Ser Gly Pro Pro Lys Leu Glu Ile Thr Thr Asp Thr Trp Lys Arg
465                 470                 475                 480

Asn Asn Ala Asp Asp Glu Asp His Val Asp Thr Leu Pro Gly Arg Val
                485                 490                 495

Ser Ala Leu Pro Thr Pro Ser Tyr Ser Met Ile Asn Gln Gly Lys Ile
            500                 505                 510

Val Ser Pro Tyr Ala Arg Leu Ser Glu Leu Phe Asn Val Asn His Phe
        515                 520                 525

Ile Val Ser Leu Ser Arg Pro Tyr Leu Ala Pro Leu Leu Ala Ile Glu
    530                 535                 540

Gly Arg His Arg Gly Tyr His Gly Trp Arg Val Asn Leu Ile Arg Val
545                 550                 555                 560

Leu Lys Leu Glu Phe Glu His Arg Leu Ala Gln Phe Asp Tyr Ile Gly
                565                 570                 575

Leu Leu Pro Thr Ile Phe Arg Arg Phe Phe Ile Asp Asp Lys Ile Pro
            580                 585                 590

Gly Ile Gly Pro Asn Ala Glu Val Leu Ile Val Pro Glu Leu Ala Ala
        595                 600                 605

Gly Met Ile Ser Asp Phe Lys Lys Ala Phe Ser Asn His Asp Ile Pro
    610                 615                 620
```

-continued

Glu Lys Val Arg Tyr Trp Thr Thr Val Gly Glu Arg Ala Thr Trp Pro
625                 630                 635                 640

Leu Val Ala Ala Ile Trp Ala Arg Thr Ala Ile Glu Tyr Thr Leu Asn
                645                 650                 655

Asp Met Tyr Asn Gln Thr Lys Arg Gln Asn
            660                 665

<210> SEQ ID NO 92
<211> LENGTH: 2201
<212> TYPE: DNA
<213> ORGANISM: Yarrowia lipolytica

<400> SEQUENCE: 92
cttttacgag tgtgtatcat cacatgatta tgcagcaaga tcagtatcat ttcggctatc 60
cagctctctt cccccgttca gctccttttc taccgcgatt atgaaaagcc gcgtggccgt 120
tgtcttggcg ccggttctgg caccatttgt ggcgattttg aaaaacctgt gggtcttctt 180
cacagctcta ctggagctct tattcgacgt tagctggcac tggatgttac aatcatggca 240
ctggtggtgc tccaccgacc aaaaaacact gctacaactg cagctggacc aggcagacac 300
ctacgaggaa tgggaaagca ttgcatcgga gctggacgag ctgctgggca acgacgtgtg 360
gcgtcagacc gcagcctcga aacgatacga ctaccggctg attgcaggcc gtctgagaga 420
ctttatcgag tgccgggcgg tcggcgacat tgcgacgctg atttctcgtc tgcgaagcgg 480
actgctgcgg aatttgggct cgatttcgtc gctccagctg tacactcgct cgtacctcgg 540
ctctaaactg ctcatcgaag agtacatcac cgaggtcatt gactgtctca agtacatcaa 600
ggactatggg acgacgggcg gactggacac caagggagtg catttcttcc caaagtccga 660
acagcgacaa ctggacagtg aacagctgac tcgacaaaag aaacacaagt tattctacga 720
cacacgacaa tcttttggcc gaacggccct cgtgttgcag ggaggaacta ttttcggact 780
tactcatctc ggaacaatca aggctcttac tctccagggt ctgctaccgg gtattgtcac 840
cggtttcaag gagggggcgt ttattgccgc tctcacaggc atctacgtat ccgacctgga 900
gctgctcgaa accattgact ctttgccaga cactctcaat gacctgtacc aaaaatacaa 960
ggagcgactg gcggaggaaa acaaacacaa ggaccactcg ttcagtaact ccaattcgga 1020
ctacgacttt gactacgcat ttgactttga acagtttgca aacacctata atgtgacctt 1080
ctcgtctgtc actgacaaag tattgcgatc ggagtacccc ccggaagtca aaatgtacga 1140
ggagttcatc gagaatcaac tcggagacct cacgttcgaa gaggccttca acaaaagcga 1200
ccgcgtgctc aacattgtcg cccattccca tgactcttcc ttcccgacac tgatgaacta 1260
cctcaccact cccaatgtgc tcatcagaag cgcatgtaga gcttccatgg tgaccgccca 1320
cgacgagccc caaacgaaaa aggcatgtgc ccatctgctg gtcaaggatg acgacaacag 1380
cgtcattccc tatgacgcct gcaaatccag gcgaggaagc tcgaccgacg tgattctggg 1440
acctgtccag gaggaggtgg atccattaga ttcaacagct aacggtacta actcttctgg 1500
acctcccaaa ctcgaaatca caactgacac ctggaaacga aacaatgcag acgacgagga 1560
ccacgtggat actctcccgg gccgcgtgag tgctctacct acaccttcgt actccatgat 1620
taaccagggc aagattgtct ctccctacgc tcgcctttcc gaactcttta acgtcaacca 1680
cttcatcgtc tctctctcaa gaccctacct ggcgcctctt ctggccatcg aaggccgaca 1740
tagaggctac cacggctgga gagtgaacct gatccgagta ctgaaactag aattcgaaca 1800
cagactcgcc cagttcgact acataggcct gctgccgacc atcttccgtc ggttcttcat 1860

-continued

```
cgacgataag atccctggca tcggtcccaa cgccgaggtg ctcattgttc ctgagctagc   1920

ggctggcatg atctccgact tcaaaaaggc cttttcgaac cacgacattc ccgagaaggt   1980

ccgctactgg accactgtgg gcgaacgagc cacctggcct ctagtcgccg ccatctgggc   2040

cagaacagca atcgagtaca ccctcaacga catgtacaac cagaccaagc gacaaaacta   2100

gaccccgagc agagcacata actactaacg atgagactaa agtatgtact gtatgtacta   2160

aacatacgct cgtaaacagt tgtatttatt ctttttcagc a                       2201
```

<210> SEQ ID NO 93
<211> LENGTH: 526
<212> TYPE: PRT
<213> ORGANISM: Yarrowia lipolytica

<400> SEQUENCE: 93

```
Met Glu Val Arg Arg Arg Lys Ile Asp Val Leu Lys Ala Gln Lys Asn
1               5                   10                  15

Gly Tyr Glu Ser Gly Pro Pro Ser Arg Gln Ser Ser Gln Pro Ser Ser
            20                  25                  30

Arg Ala Ser Ser Arg Thr Arg Asn Lys His Ser Ser Ser Thr Leu Ser
        35                  40                  45

Leu Ser Gly Leu Thr Met Lys Val Gln Lys Lys Pro Ala Gly Pro Pro
    50                  55                  60

Ala Asn Ser Lys Thr Pro Phe Leu His Ile Lys Pro Val His Thr Cys
65                  70                  75                  80

Cys Ser Thr Ser Met Leu Ser Arg Asp Tyr Asp Gly Ser Asn Pro Ser
                85                  90                  95

Phe Lys Gly Phe Lys Asn Ile Gly Met Ile Ile Leu Ile Val Gly Asn
            100                 105                 110

Leu Arg Leu Ala Phe Glu Asn Tyr Leu Lys Tyr Gly Ile Ser Asn Pro
        115                 120                 125

Phe Phe Asp Pro Lys Ile Thr Pro Ser Glu Trp Gln Leu Ser Gly Leu
    130                 135                 140

Leu Ile Val Val Ala Tyr Ala His Ile Leu Met Ala Tyr Ala Ile Glu
145                 150                 155                 160

Ser Ala Ala Lys Leu Leu Phe Leu Ser Ser Lys His His Tyr Met Ala
                165                 170                 175

Val Gly Leu Leu His Thr Met Asn Thr Leu Ser Ser Ile Ser Leu Leu
            180                 185                 190

Ser Tyr Val Val Tyr Tyr Tyr Leu Pro Asn Pro Val Ala Gly Thr Ile
        195                 200                 205

Val Glu Phe Val Ala Val Ile Leu Ser Leu Lys Leu Ala Ser Tyr Ala
    210                 215                 220

Leu Thr Asn Ser Asp Leu Arg Lys Ala Ala Ile His Ala Gln Lys Leu
225                 230                 235                 240

Asp Lys Thr Gln Asp Asp Asn Glu Lys Glu Ser Thr Ser Ser Ser Ser
                245                 250                 255

Ser Ser Asp Asp Ala Glu Thr Leu Ala Asp Ile Asp Val Ile Pro Ala
            260                 265                 270

Tyr Tyr Ala Gln Leu Pro Tyr Pro Gln Asn Val Thr Leu Ser Asn Leu
        275                 280                 285

Leu Tyr Phe Trp Phe Ala Pro Thr Leu Val Tyr Gln Pro Val Tyr Pro
    290                 295                 300

Lys Thr Glu Arg Ile Arg Pro Lys His Val Ile Arg Asn Leu Phe Glu
```

```
305                 310                 315                 320

Leu Val Ser Leu Cys Met Leu Ile Gln Phe Leu Ile Phe Gln Tyr Ala
                325                 330                 335

Tyr Pro Ile Met Gln Ser Cys Leu Ala Leu Phe Phe Gln Pro Lys Leu
            340                 345                 350

Asp Tyr Ala Asn Ile Ser Glu Arg Leu Met Lys Leu Ala Ser Val Ser
        355                 360                 365

Met Met Val Trp Leu Ile Gly Phe Tyr Ala Phe Phe Gln Asn Gly Leu
    370                 375                 380

Asn Leu Ile Ala Glu Leu Thr Cys Phe Gly Asn Arg Thr Phe Tyr Gln
385                 390                 395                 400

Gln Trp Trp Asn Ser Arg Ser Ile Gly Gln Tyr Trp Thr Leu Trp Asn
                405                 410                 415

Lys Pro Val Asn Gln Tyr Phe Arg His His Val Tyr Val Pro Leu Leu
            420                 425                 430

Ala Arg Gly Met Ser Arg Phe Asn Ala Ser Val Val Val Phe Phe Phe
        435                 440                 445

Ser Ala Val Ile His Glu Leu Leu Val Gly Ile Pro Thr His Asn Ile
    450                 455                 460

Ile Gly Ala Ala Phe Phe Gly Met Met Ser Gln Val Pro Leu Ile Met
465                 470                 475                 480

Ala Thr Glu Asn Leu Gln His Ile Asn Ser Ser Leu Gly Pro Phe Leu
                485                 490                 495

Gly Asn Cys Ala Phe Trp Phe Thr Phe Phe Leu Gly Gln Pro Thr Cys
            500                 505                 510

Ala Phe Leu Tyr Tyr Leu Ala Tyr Asn Tyr Lys Gln Asn Gln
        515                 520                 525
```

<210> SEQ ID NO 94
<211> LENGTH: 1581
<212> TYPE: DNA
<213> ORGANISM: Yarrowia lipolytica

<400> SEQUENCE: 94

```
atggaagtcc gacgacgaaa aatcgacgtg ctcaaggccc agaaaaacgg ctacgaatcg     60

ggcccaccat ctcgacaatc gtcgcagccc tcctcaagag catcgtccag aacccgcaac    120

aaacactcct cgtccaccct gtcgctcagc ggactgacca tgaaagtcca gaagaaacct    180

gcgggacccc cggcgaactc caaaacgcca ttcctacaca tcaagcccgt gcacacgtgc    240

tgctccacat caatgctttc gcgcgattat gacggctcca accccagctt caagggcttc    300

aaaaacatcg gcatgatcat tctcattgtg ggaaatctac ggctcgcatt cgaaaactac    360

ctcaaatacg gcatttccaa cccgttcttc gaccccaaaa ttactccttc cgagtggcag    420

ctctcaggct tgctcatagt cgtggcctac gcacatatcc tcatggccta cgctattgag    480

agcgctgcca agctgctgtt cctctctagc aaacaccact acatggccgt ggggcttctg    540

cataccatga acactttgtc gtccatctcg ttgctgtcct acgtcgtcta ctactacctg    600

cccaaccccg tggcaggcac aatagtcgag tttgtggccg ttattctgtc tctcaaactc    660

gcctcatacg ccctcactaa ctcggatctc cgaaaagccg caattcatgc ccagaagctc    720

gacaagacgc aagacgataa cgaaaaggaa tccacctcgt cttcctcttc ttcagatgac    780

gcagagactt tggcagacat tgacgtcatt cctgcatact acgcacagct gccctacccc    840

cagaatgtga cgctgtcgaa cctgctgtac ttctggtttg ctcccacact ggtctaccag    900
```

```
cccgtgtacc ccaagacgga gcgtattcga cccaagcacg tgatccgaaa cctgtttgag     960

ctcgtctctc tgtgcatgct tattcagttt ctcatcttcc agtacgccta ccccatcatg    1020

cagtcgtgtc tggctctgtt cttccagccc aagctcgatt atgccaacat ctccgagcgc    1080

ctcatgaagt tggcctccgt gtctatgatg gtctggctca ttggattcta cgctttcttc    1140

cagaacggtc tcaatcttat tgccgagctc acctgttttg gaaacagaac cttctaccag    1200

cagtggtgga attcccgctc cattggccag tactggactc tatggaacaa gccagtcaac    1260

cagtacttta gacaccacgt ctacgtgcct cttctcgctc ggggcatgtc gcggttcaat    1320

gcgtcggtgg tggttttctt tttctccgcc gtcatccatg aactgcttgt cggcatcccc    1380

actcacaaca tcatcggagc cgccttcttc ggcatgatgt cgcaggtgcc tctgatcatg    1440

gctactgaga accttcagca tattaactcc tctctgggcc ccttccttgg caactgtgca    1500

ttctggttca cctttttcct gggacaaccc acttgtgcat tcctttatta tctggcttac    1560

aactacaagc agaaccagta g                                              1581
```

<210> SEQ ID NO 95
<211> LENGTH: 346
<212> TYPE: PRT
<213> ORGANISM: Rhodotorula graminis

<400> SEQUENCE: 95

```
Met Gly Ala Gln Glu Glu Val Asp Tyr Asp Gln Ser Asp His Thr Lys
1               5                   10                  15

Ile Lys Phe Val Pro Phe Val Val Pro Arg His Arg Arg Leu Gln Thr
            20                  25                  30

Phe Ser Val Phe Leu Trp Thr Thr Ala Leu Pro Ile Ser Leu Gly Ile
        35                  40                  45

Phe Cys Ile Leu Cys Ser Phe Pro Pro Leu Trp Pro Leu Val Ile Gly
    50                  55                  60

Tyr Leu Thr Trp Val Phe Leu Ile Asp Gln Ala Pro Met Arg Gly Gly
65                  70                  75                  80

Arg Pro Gln Ala Trp Leu Arg Lys Ser Arg Val Trp Glu Trp Phe Ala
                85                  90                  95

Gly Tyr Tyr Pro Val Ser Leu Ile Lys Ser Ala Asp Leu Pro Pro Asp
            100                 105                 110

Gln Arg Tyr Val Phe Gly Tyr His Pro His Gly Val Ile Gly Met Gly
        115                 120                 125

Ala Ile Ala Asn Phe Gly Thr Asp Ala Thr Gly Phe Ser Arg Leu Phe
    130                 135                 140

Pro Gly Ile Thr Pro His Leu Leu Thr Leu Ala Ser Asn Phe Lys Leu
145                 150                 155                 160

Pro Val Tyr Arg Glu Leu Leu Leu Ala Leu Gly Ile Ser Ser Val Ser
                165                 170                 175

Met Lys Ser Cys Gln Asn Ile Leu Arg Gln Gly Pro Gly Ser Ser Ile
            180                 185                 190

Thr Ile Val Val Gly Gly Ala Ala Glu Ser Leu Ser Ala His Pro Gly
        195                 200                 205

Thr Ala Asp Leu Thr Leu Lys Arg Arg Lys Gly Phe Ile Lys Leu Ala
    210                 215                 220

Ile Arg Thr Gly Ala Ser Leu Val Pro Val Phe Ser Phe Gly Glu Asn
225                 230                 235                 240

Asp Ile Phe Asn Gln Leu Ser Asn Glu Arg Gly Thr Arg Leu Tyr Lys
                245                 250                 255
```

Leu Gln Lys Arg Phe Gln Ala Val Phe Gly Phe Thr Leu Pro Ile Phe
260 265 270

Phe Gly Arg Gly Leu Phe Asn Tyr Asn Met Gly Leu Met Pro Tyr Arg
275 280 285

His Pro Ile Val Ser Val Val Gly Arg Pro Ile Lys Val Lys Gln Lys
290 295 300

Asp His Pro Ser Thr Ala Asp Leu Glu Glu Val Gln Glu Arg Tyr Ile
305 310 315 320

Ala Glu Leu Lys Arg Ile Trp Glu Asp Tyr Lys Glu Val Tyr Ala Lys
325 330 335

Ser Arg Thr Lys Glu Leu Thr Ile Ile Ala
340 345

<210> SEQ ID NO 96
<211> LENGTH: 1041
<212> TYPE: DNA
<213> ORGANISM: Rhodotorula graminis

<400> SEQUENCE: 96
atgggcgcac aagaagaggt cgactacgac cagtcggacc acaccaagat caagttcgtg 60
ccctttgtcg tcccgcggca ccgtcgcctc cagacgttct cggtcttcct gtggacgacg 120
gccctcccta tctcgctcgg catcttctgc atcctgtgct ccttccctcc tctttggccg 180
ctcgtcatcg ggtacctcac ctgggtcttc ctcattgacc aggcgccgat gcgcggcggg 240
aggccacaag cctggctgcg aaagtcgcgc gtgtgggagt ggttcgccgg ctactatccc 300
gtcagcctca tcaagagcgc cgacctcccg cccgaccagc gttacgtctt tggctaccac 360
cctcacggcg tcatcggcat gggcgccatc gccaactttg gcaccgacgc gaccgggttc 420
tcgcgcctgt tcccgggcat cacgccgcac ctcctcacgc tcgcgagcaa cttcaagctc 480
ccagtctacc gagagctcct cctcgccctc ggcatctcgt ccgtctcgat gaagagctgc 540
cagaacatcc tgcggcaagg tcccggctcg tccatcacga tcgtcgtcgg cggcgccgcc 600
gagagcctga gcgcgcaccc tggcacggcc gacctgacgc tcaagcgccg caagggcttc 660
atcaagctcg ccatccgcac cggcgcctcg ctcgtgcccg tcttttcctt tggcgagaac 720
gacatcttca accagctgtc gaacgagcga gggacgcgcc tgtacaagct gcagaagcgg 780
ttccaggccg tctttggctt cacattgccc atcttcttcg gccgaggcct gttcaactac 840
aacatgggct tgatgccgta ccgacacccg atcgtctcgg tcgtcggccg cccgatcaag 900
gtcaagcaga aggaccaccc gtcgactgcc gacctcgaag aagtccagga gcggtacatc 960
gccgagctca aaggatctgg ggaggactac aaggaggtgt acgccaagag tcgcaccaag 1020
gagctcacca tcatcgcctg a 1041

<210> SEQ ID NO 97
<211> LENGTH: 663
<212> TYPE: PRT
<213> ORGANISM: Rhodotorula graminis

<400> SEQUENCE: 97

Met Ser Thr Ala Asp Leu Pro Pro Gly Pro Ala Gln Leu Leu Glu Asp
1 5 10 15

Ala Leu Arg Gln Pro Asp Gly Pro Pro Leu Leu Ser Thr Ser Ala Ala
20 25 30

Asp Pro Ser Ser Pro Leu Gln Leu Asp His Asp His Arg Pro Gly Met
35 40 45

```
Ala Ala Asp Ala Ala Ser Ser Ala Ser Asp Ser Ser Ile Ser Thr Val
    50                  55                  60

Ser Ser Val Leu Arg Gly Gln Gln Ala Thr Thr Thr Val Thr Thr Asn
65                  70                  75                  80

Arg Gly Glu Gly Gly Arg Glu Thr Thr Glu Thr Phe Thr His Val Gly
                85                  90                  95

Ala Ala Asn Val Asp Ala Glu Tyr Ser Ser Ser Thr Gly His Ile Thr
            100                 105                 110

Leu Arg Pro Val Val Ala Lys Gly Gly Asp Pro Arg Arg Ile Arg Leu
        115                 120                 125

Val Arg Ser Arg Arg Thr His Phe Glu Pro Arg Ile Ser His Phe Asp
    130                 135                 140

Arg His Asn Lys Thr Ser Ala Glu Asp Thr Phe Arg Gly Phe Phe Ser
145                 150                 155                 160

Leu Phe Trp Ile Val Ile Ala Val Gly Gly Thr Arg Thr Ile Tyr Asn
                165                 170                 175

Arg Val Ala Glu Thr Gly Gly Leu Leu Gly Gly Trp Gln Phe Ala Ala
            180                 185                 190

Leu Ile Ser Glu Asp Ala Trp Ala Leu Ala Leu Ser Asp Ala Val Leu
        195                 200                 205

Val Gly Ser Thr Ile Leu Cys Val Pro Phe Val Lys Leu Ile Val Asn
    210                 215                 220

Gly Trp Val Arg Tyr Tyr Tyr Thr Gly Leu Val Leu Gln His Leu Ala
225                 230                 235                 240

Gln Thr Leu Tyr Leu Gly Ile Ala Val Arg Trp Thr Phe His Arg His
                245                 250                 255

Trp Pro Trp Val Gln Ser Gly Phe Met Thr Leu His Ala Leu Ser Met
            260                 265                 270

Leu Met Lys Ile His Ser Tyr Cys Ser Leu Asn Gly Glu Leu Ser Glu
        275                 280                 285

Arg Val Arg Gln Leu Glu Lys Asp Glu Arg Lys Leu His Glu Ala Val
    290                 295                 300

Glu Glu Leu Gly Gly Gln Asp Ala Leu Glu Arg Glu Gly Arg Val Ala
305                 310                 315                 320

Trp Glu Lys Ala Cys Ala Glu Ala Ala Glu Gln Lys Ala Ala Glu Glu
                325                 330                 335

Ala Ala Gly Gly Arg Gly Lys Ala Ser Ala Ser Ser Leu Ala Pro Pro
            340                 345                 350

Pro Ala Thr Gly Pro Gln Pro Ser Ser Asp Glu Glu Ala Val Ser Thr
        355                 360                 365

Thr Leu Arg Gln Arg Pro Ser Ala Ala Arg Arg Arg Ser Leu Ser Pro
    370                 375                 380

Ser Ala Ala Arg Thr His Val Thr Pro Pro Ser Arg Lys Ala Glu Pro
385                 390                 395                 400

His Asp Val Glu Thr Leu Thr Trp Ser Pro Asn Glu Arg Val Ser His
                405                 410                 415

Leu Ala Ile Ala Ile Cys Glu Ala Arg Glu Ala Leu Ser Ser Ser Gly
            420                 425                 430

Ala Ala Lys Val Ser Phe Pro Asp Asn Val Thr Val Leu Asn Phe Val
        435                 440                 445

Asp Tyr Leu Leu Val Pro Thr Leu Val Tyr Glu Leu Glu Tyr Pro Arg
    450                 455                 460
```

-continued

```
Thr Asp Ser Ile Arg Pro Leu Tyr Ile Leu Glu Lys Thr Leu Ala Thr
465                 470                 475                 480

Phe Gly Thr Phe Ser Val Leu Leu Leu Ile Val Glu His Phe Ile Tyr
                485                 490                 495

Pro Val Met Pro Gly Pro Asp Ser Ser Phe Ile Ser Ser Leu Leu Asp
            500                 505                 510

Leu Ala Leu Pro Phe Thr Ile Cys Tyr Leu Leu Ile Phe Tyr Ile Ile
        515                 520                 525

Phe Glu Cys Ile Cys Asn Ala Phe Ala Glu Ile Thr Arg Phe Ser Asp
    530                 535                 540

Arg Ala Phe Tyr Ser Asp Trp Trp Asn Ser Ile Ser Phe Asp Glu Phe
545                 550                 555                 560

Ser Arg Lys Trp Asn Arg Pro Val His Thr Phe Leu Leu Arg His Val
                565                 570                 575

Tyr Ala Thr Thr Ile Ser Thr Tyr Lys Leu Ser Lys Phe Ser Ala Ala
            580                 585                 590

Phe Val Thr Phe Leu Leu Ser Ala Leu Val His Glu Leu Val Met Val
        595                 600                 605

Val Val Thr His Lys Ile Arg Met Tyr Leu Phe Met Ala Gln Leu Pro
    610                 615                 620

Leu Ile Met Leu Gly Arg Ala Ser Ile Phe Lys Arg His Pro Ala Leu
625                 630                 635                 640

Gly Asn Leu Phe Phe Trp Phe Gly Leu Leu Ser Gly Phe Pro Leu Leu
                645                 650                 655

Ala Val Ala Tyr Leu Lys Phe
            660
```

<210> SEQ ID NO 98
<211> LENGTH: 1992
<212> TYPE: DNA
<213> ORGANISM: Rhodotorula graminis

<400> SEQUENCE: 98

```
atgagcaccg ccgatcttcc accaggtcct gcccagctgc tcgaagacgc cctgcgccag     60

ccagacggcc cccctctcct gtcgacctcc gccgccgatc cctcctcccc acttcaactc    120

gaccacgacc accgccccgg catggctgca gacgccgcca gctcagcttc agacagctct    180

atcagcacgg tgtccagtgt cctgcgcggt cagcaagcca cgacaacggt gacgaccaac    240

aggggagaag gcgggcgaga aacgaccgag accttcaccc acgtcggcgc cgccaatgtc    300

gacgccgagt actcgtcctc gaccggccac atcacgctcc gacccgtcgt ggcaaagggc    360

ggtgaccctc gccggatccg cctcgtccgc tcgcgccgca cccacttcga gccgcgcatc    420

tcgcacttcg accgccacaa caagacgtcg gccgaggaca cgttccgcgg cttcttctcg    480

ctcttctgga tcgtcatcgc cgtcggcggc acgaggacca tctacaaccg cgtcgccgag    540

acgggcggtc tcctcggcgg gtggcagttt gcggcgctca tctccgagga cgcatgggct    600

ctggcgctga gcgatgcggt cctcgtcggg tcgacgatac tctgcgtccc gttcgtcaag    660

ctcatcgtca acggctgggt ccggtactac tacacgggcc tcgtcctcca gcacctcgcc    720

cagacgctct acctcggcat cgccgtccga tggacgttcc accgtcactg gccctgggtc    780

cagagcggct tcatgacgct gcacgccctg agcatgctca tgaagatcca ctcgtactgc    840

tcgctcaacg gcgagctgtc cgagcgcgtg cggcagctcg agaaggacga gcgcaagctg    900

cacgaggcgg tcgaggagct tggcggccag gacgcgctcg agcgcgaggg gcgcgtggcg    960
```

```
tgggagaagg cgtgcgccga ggcggccgag cagaaggcgg ccgaggaggc ggcaggcggt   1020

cgcggcaaag cttcggcgtc ctcgctcgcc ccgccgccgg cgacagggcc gcagccctcg   1080

tccgacgagg aggccgtctc gacgacgctc cgacagcgac cgtcggccgc tcgccgccgc   1140

tcgctctcgc cgtcggccgc acggacccac gtcacgccgc cgtcgcgcaa ggccgagccg   1200

cacgacgtcg agacgctcac ctggtcgccc aacgagcgcg tgtcgcacct cgccatcgcc   1260

atctgcgagg cacgcgaggc cctgtcgtcg agcggcgccg ccaaggtctc gttcccggac   1320

aacgtcacgg tcctcaactt tgtcgactac cttctcgtcc cgacgctcgt gtacgagctt   1380

gagtacccga ggaccgactc tatccgaccc ttgtacatcc tcgagaagac cctcgccacg   1440

ttcggcacat tctcggtcct cctcctcatc gtcgagcact tcatctaccc ggtcatgccc   1500

gggcccgaca gctcgttcat ctcgtccctc ctcgacctcg ccctcccatt caccatctgc   1560

tacctcctca tcttctacat catcttcgag tgtatctgca acgccttcgc cgagatcacg   1620

cgcttctcgg accgggcctt ctacagcgac tggtggaact cgatctcgtt cgacgagttc   1680

tcgcgcaagt ggaaccggcc cgtgcacacg ttcctcctgc gccacgtgta cgcgacgacc   1740

atctcgacct acaagctcag caagttctcg gccgcctttg tcacgttcct cctgagcgcg   1800

ctcgtgcacg agctcgtcat ggtagtcgtg acgcacaaga tccgcatgta tctctttatg   1860

gcgcagctcc ccctcatcat gctcggccga gcaagcatct tcaagcgtca ccctgcgctc   1920

ggcaacctct tcttctggtt cggcctcttg agcggtttcc ctctgctagc tgtagcgtac   1980

ctcaagttct ag                                                       1992
```

<210> SEQ ID NO 99
<211> LENGTH: 635
<212> TYPE: PRT
<213> ORGANISM: Pichia guilliermondii

<400> SEQUENCE: 99

```
Met Thr Lys Glu Val Asp Glu Ser Thr Gly Gly Ala Ser Asp Ile Pro
1               5                   10                  15

Asn Met Val Glu Glu Ala Lys Ser Ser Ser Phe Asp Arg Glu Thr Glu
            20                  25                  30

Glu Asn Leu Leu Leu Glu Thr Thr Lys Pro Asp Glu Asn Leu Val Pro
        35                  40                  45

Glu Ser Thr Lys His Asp Glu Lys Leu Val Pro Glu Ile Thr Lys His
    50                  55                  60

Glu Asp Asn Pro Met Glu Asn Asp Gln Val Ser Gln Asn Thr Ala Thr
65                  70                  75                  80

Ser Pro Met Thr Gly Ala Gly Ser Glu Glu Thr Arg Asp Leu Ile Thr
                85                  90                  95

Glu Asn Ile Glu Lys Pro Asp Glu Gly Asp Leu Leu Ile Glu Leu Ile
            100                 105                 110

Ser Lys Asp Asn Asp Gly Asp Gly Asp Asp Gly Leu Lys Asn Arg Lys
        115                 120                 125

Gln Lys Arg Ser Ser Ser Glu Val Lys Arg Leu Arg Met Ser Ser Leu
    130                 135                 140

Ala Pro Lys Gly Pro Thr Pro Gln Lys His Glu Arg Pro Lys Tyr Ile
145                 150                 155                 160

Asn Val Ala Pro Leu Asn Ile Pro Ile Arg Arg Arg Leu Glu Met Val
                165                 170                 175

Gly Ile Ile Trp His Thr Ile Cys Ile Pro Thr Phe Val Ser Leu Phe
            180                 185                 190
```

-continued

```
Phe Leu Thr Leu Ser Leu Gly Pro Phe Ala Trp Val Gly Val Ile Leu
        195                 200                 205

Pro Tyr Phe Leu Trp Trp Tyr Leu Ile Asp Leu His Thr Pro Thr Asn
    210                 215                 220

Gly Lys Val Ala Tyr Arg Ser Arg Asp Trp Met Lys Asn Phe Ile Val
225                 230                 235                 240

Trp Asp Trp Phe Val Asp Tyr Phe Pro Ile Arg Val His Lys Ser Cys
                245                 250                 255

Glu Leu Glu Pro Thr Phe Ser Asp Val Ile Ile Glu Asp Asp Val Val
            260                 265                 270

Pro Asp Asp Glu Glu Asp Leu Ile Ser Glu Gln Ser Arg Thr Gly Val
        275                 280                 285

Asp Lys Leu Phe Lys Phe Leu Gly Leu Arg Lys Arg Leu Asn Asp Asp
    290                 295                 300

Ser Asp Ala Ser Ser Gln Cys Ser Leu Leu Gln Glu Ser Leu Ser Thr
305                 310                 315                 320

Arg Arg Lys Val Lys Arg Met Ser Thr Gly Pro Arg Tyr Ile Phe Gly
                325                 330                 335

Tyr His Pro His Gly Val Ile Ser Met Gly Val Phe Gly Thr Phe Ala
            340                 345                 350

Thr Asn Ala Leu Arg Asn Glu Pro Tyr Glu Pro Pro Leu Arg Leu Leu
        355                 360                 365

Lys Pro Phe Phe His Asp Ser Ser Lys Gly Glu Arg Leu Phe Pro Gly
    370                 375                 380

Ile Gly Thr Val Phe Pro Leu Thr Leu Thr Thr Gln Phe Ile Val Pro
385                 390                 395                 400

Tyr Tyr Arg Asp Tyr Ile Leu Gly Met Gly Leu Thr Ser Ala Ser Ala
                405                 410                 415

Lys Asn Ile Lys Ser Leu Ile Ser Asn Gly Asp Asn Ser Ile Cys Val
            420                 425                 430

Val Val Gly Gly Ala Gln Glu Ser Leu Leu Asn Asp Met Val Ala Ala
        435                 440                 445

Thr Thr Val Pro Gly Arg Tyr Gly Lys Ser Asn Leu Pro Asn Asp Ser
    450                 455                 460

Asp Thr Asp Ser Glu Phe Asp Pro Gln Arg Lys Ile Glu Glu Asn Lys
465                 470                 475                 480

Glu Glu Thr Gly Val Lys Lys Ile Glu Leu Val Leu Asn Lys Arg Lys
                485                 490                 495

Gly Phe Val Lys Ile Ala Ile Glu Leu Gly Asn Val Ser Leu Val Pro
            500                 505                 510

Thr Phe Gly Phe Gly Glu Ala Asp Ile Tyr Arg Ile Thr Lys Pro Lys
        515                 520                 525

Pro Gly Ser Phe Gly Glu Met Phe Gln Ser Trp Met Lys Arg Thr Phe
    530                 535                 540

Gln Phe Thr Val Pro Phe Phe Ser Ala Arg Gly Val Phe Ile Tyr Asp
545                 550                 555                 560

Phe Gly Phe Leu Pro Tyr Arg Asn Pro Ile Asn Val Cys Phe Gly Arg
                565                 570                 575

Pro Ile His Ile Pro Ala Gly Leu Leu Asp Gln Tyr Lys Glu Pro Glu
            580                 585                 590

Thr Glu Lys Asp Glu Lys Glu Lys Glu Lys Asn Val Phe Gln Phe Thr
        595                 600                 605
```

```
Gln Asp Lys Gln Ala Pro Ala Phe Asn Ile Gln Ser Ile Gln Val Phe
    610                 615                 620

Gln Gly Glu Ala Thr Ile Lys Glu Glu Thr Ser
625                 630                 635


<210> SEQ ID NO 100
<211> LENGTH: 1908
<212> TYPE: DNA
<213> ORGANISM: Pichia guilliermondii

<400> SEQUENCE: 100

atgaccaagg aggttgatga aagcactggg ggtgccagtg atataccaaa tatggttgaa      60

gaagcgaaat catcgagttt tgaccgtgaa actgaagaga atctgctact ggagaccact     120

aaacctgacg agaatctggt accggagagt actaaacatg acgagaaact tgtaccggag     180

atcactaaac atgaagacaa tcccatggaa aatgaccaag tttcccaaaa cacagccacc     240

agtcctatga caggagctgg ttccgaagaa acccgtgatt tgattacaga gaacattgag     300

aaaccagatg agggtgatct gctaattgag cttatttcca aagataacga tggtgatgga     360

gatgatgggt tgaaaaatag aaaacaaaaa cgatcttctt ctgaagtgaa aaggctgcgc     420

atgtcgtctc tggctcctaa aggtccaact cctcaaaagc atgaacgtcc caagtatata     480

aatgtggcac ctcttaatat ccccattcga cggcgcttgg agatggtggg gataatctgg     540

cacaccattt gtattcccac gtttgtcagt ttgtttttct tgactttgtc gttgggtccg     600

tttgcttggg taggggtgat attgccgtac tttttatggt ggtatcttat cgatttacat     660

actcctacaa acggtaaggt tgcgtatcgg tctcgcgact ggatgaagaa tttcattgtg     720

tgggattggt tcgttgacta ttttcctatc agggtccaca agtcttgtga gttggagcct     780

acctttagcg atgttattat tgaagacgat gtggtgcccg atgatgaaga agaccttatc     840

tcagagcaat cacgaactgg agtcgataaa cttttcaaat ttttggggct tcgaaaacgc     900

ttaaatgacg actcggatgc ttcgtcgcag tgctcactgc tgcaagagtc tttaagcaca     960

agacgtaaag tgaaacgtat gtctactggt cctcgctaca tctttggata ccatccccat    1020

ggagtaattt cgatgggtgt ttttggaact ttcgctacca atgcgttgcg taacgagccg    1080

tacgaacctc ccttgcgttt gctaaagcca tttttccacg actcttccaa gggagaacgg    1140

ttgtttcccg gtattggcac cgtctttcca ttgacattga caacccaatt tattgtgccg    1200

tactaccgtg actatatctt gggcatggga ctcaccagtg cttcggctaa aaacatcaag    1260

agccttataa gcaacggaga caactcgata tgtgtcgttg ttggaggtgc tcaggaatcg    1320

ctcctaaacg atatggtagc cgcaaccaca gttcccggtc gttacggaaa gagcaatttg    1380

cccaatgaca gtgataccga tagcgagttt gatcctcagc gtaagattga agaaaacaag    1440

gaagaaaccg gcgtaaagaa aattgaactt gtacttaata agagaaaggg tttcgtcaag    1500

atagcgattg agttgggcaa cgtttcactc gtgcctacgt ttggttttgg agaagctgac    1560

atctacagaa tcaccaaacc caaaccaggt tcatttggag aaatgttcca atcttggatg    1620

aaacgcacat ttcaattcac ggttccattt ttcagcgcta gaggtgtgtt catttacgac    1680

tttgggtttc ttccttacag aaatcccatc aatgtctgct ttggacggcc cattcatatt    1740

ccagccggct tattggatca atacaaagag cccgaaactg agaaagatga aaaagaaaag    1800

gaaaaaaacg tcttccagtt cactcaagac aaacaagcgc cagccttcaa tatccaatct    1860

attcaagttt tccaagggga agcaaccatc aaagaggaaa cgagttag                 1908
```

-continued

<210> SEQ ID NO 101
<211> LENGTH: 597
<212> TYPE: PRT
<213> ORGANISM: Pichia guilliermondii

<400> SEQUENCE: 101

```
Met Ser Lys Glu Asn Leu Leu Lys Ile Ser Gln Tyr Asn Thr Glu Arg
1               5                   10                  15

Arg Pro Ser Leu Ala Thr Asp Val Asp Tyr Ser Ser Thr Asp Leu Ser
            20                  25                  30

Ser Arg Leu Asp Ser Ala Asn Thr Thr Asn Gly Thr Pro Thr Val Thr
        35                  40                  45

Leu His Lys Arg Gln Ser Ser Thr Glu Leu Leu Ser Glu Ser Pro Glu
    50                  55                  60

Gln Lys Arg Phe Leu Lys Thr Ile Asp Thr Leu Asn Arg Thr Thr Asn
65                  70                  75                  80

Ser Arg Leu Arg Gln Arg Leu Asn Arg Glu Gly Asp Lys His Lys Lys
                85                  90                  95

Glu His Lys Glu His Glu Lys His Lys Asp Asp His Ser Lys Tyr Lys
            100                 105                 110

Ser Arg Phe Gly Asp Ile His Phe Tyr Ser Asn Met Thr Thr Ile Phe
        115                 120                 125

Asp Ala Asp Tyr Phe Lys Glu Ser Gln Phe Phe Gly Val Tyr Ile Leu
    130                 135                 140

Phe Trp Leu Gly Thr Ala Phe Leu Ile Leu Asn Asn Leu Val His Thr
145                 150                 155                 160

Phe Leu Glu Asn Gly Asp Asn Leu Leu Asp Gly Pro Val Val Arg Thr
                165                 170                 175

Phe Lys Lys Asp Leu Leu Lys Ile Ala Leu Thr Asp Leu Gly Met Tyr
            180                 185                 190

Leu Thr Met Tyr Val Ser Val Phe Ile Gln Leu Gly Ile Arg Lys Gly
        195                 200                 205

Trp Tyr Ser Trp Ser Ser Thr Gly Ala Thr Leu Gln Asn Ile Tyr Ser
    210                 215                 220

Phe Val Tyr Phe Phe Ala Trp Ser Tyr Phe Ala Ser Pro Lys Tyr Met
225                 230                 235                 240

Asp Tyr Pro Trp Ile Gly Lys Val Phe Leu Ala Leu His Ser Leu Val
                245                 250                 255

Phe Leu Met Lys Met His Ser Tyr Ala Thr Tyr Asn Gly Tyr Leu Trp
            260                 265                 270

Asn Ile Phe Asn Glu Leu Gln Val Ser Arg Lys Tyr Leu Lys Ile Leu
        275                 280                 285

Asp Glu Thr Asp Glu Ser Met Ile Glu Gly Lys Ser Val Ser Asp Leu
    290                 295                 300

Arg Lys Ala Leu Val Asp Ser Ile Gly Phe Cys Ser Tyr Glu Leu Glu
305                 310                 315                 320

Tyr Gln Ser Lys Ser Thr Ser Val Asn Thr Asp Val Glu Ile Thr Gly
                325                 330                 335

Asp Lys Asn Lys Leu Asn Thr Thr Lys Ser Thr Ser Ser Leu Asp Asp
            340                 345                 350

Asp Tyr Val Ser Phe Pro Asn Asn Ile Thr Phe Phe Asp Phe Phe Arg
        355                 360                 365

Tyr Ser Met Phe Pro Thr Val Val Tyr Ser Leu Lys Phe Pro Arg Thr
    370                 375                 380
```

-continued

```
Lys Arg Ile Arg Trp Gly Tyr Val Met Glu Lys Ser Phe Ala Val Phe
385                 390                 395                 400

Gly Ile Ile Phe Leu Met Ile Thr Val Ala Gln Asn Trp Met Tyr Pro
                405                 410                 415

Ile Val Val Arg Ala Gln Glu Ala Ser Lys Leu Pro Met Ser Arg Glu
            420                 425                 430

Lys Val Leu Gln Tyr Cys Leu Val Leu Leu Asp Met Ile Pro Pro Phe
        435                 440                 445

Leu Met Glu Tyr Leu Phe Thr Phe Phe Leu Ile Trp Asp Val Ile Leu
    450                 455                 460

Asn Ala Ile Ala Glu Leu Ser Arg Phe Ala Asp Arg Asp Phe Tyr Gly
465                 470                 475                 480

Pro Trp Trp Ser Cys Thr Asp Trp Ser Glu Phe Ala Arg Ile Trp Asn
                485                 490                 495

Arg Pro Val His Lys Phe Leu Leu Arg His Val Tyr Gln Ser Thr Ile
            500                 505                 510

Ser Thr Phe Lys Leu Asn Lys Asn Gln Ala Ser Leu Val Thr Phe Ile
        515                 520                 525

Ile Leu Ser Phe Val His Glu Phe Val Met Phe Val Ile Phe Arg Lys
    530                 535                 540

Val Arg Phe Tyr Met Leu Ala Leu Gln Met Ser Gln Leu Pro Leu Ile
545                 550                 555                 560

Met Ile Ser Arg Thr Lys Phe Met Arg Asp Lys Lys Val Leu Gly Asn
                565                 570                 575

Val Ile Cys Trp Val Gly Phe Ile Ser Gly Pro Ser Met Ile Cys Thr
            580                 585                 590

Leu Tyr Leu Val Phe
        595
```

<210> SEQ ID NO 102
<211> LENGTH: 1794
<212> TYPE: DNA
<213> ORGANISM: Pichia guilliermondii

<400> SEQUENCE: 102

```
atgtccaagg aaaacttact taagatcagc cagtataata ctgagagaag accgtcgttg      60

gccacagacg ttgactactc ttccaccgat ttatccagtc gtctggattc ggccaacacg     120

acaaacggaa caccgaccgt aactcttcac aagaggcaat cgtctacaga gctcttgtct     180

gagtcacctg aacagaaaag gttcttgaaa acgatagaca ctttgaatcg aaccacaaat     240

tctagattac gccagaggtt aaaccgtgag ggcgataagc ataaaaagga acacaaagaa     300

catgaaaaac ataaagatga ccattctaaa tacaagtctc ggtttggaga tatccatttc     360

tactcaaaca tgacaaccat cttcgatgct gattacttta aggaatcgca gttctttgga     420

gtttacattc tcttttggct cggaacggca ttcttaattc tcaacaactt ggtccataca     480

tttttggaga acggagacaa tcttctcgat ggaccagttg tcagaacgtt taaaaaggac     540

ttacttaaaa ttgctcttac agacttggga atgtacttga cgatgtacgt ctctgtcttt     600

attcaattgg gcatccgcaa aggatggtat agctggagct caacaggagc caccttgcaa     660

aacatatact cattcgtgta cttctttgcc tggagttact ttgcgtcgcc aaagtacatg     720

gactaccctt ggattggaaa ggtgtttctt gcacttcaca gcttggtgtt tctcatgaaa     780

atgcattctt atgccacata caacggctat ctttggaaca tcttcaacga gcttcaagtg     840

tcacgaaagt acttgaagat attggacgag accgatgaat ccatgattga gggtaagagt     900
```

```
gtttccgatt tgcgaaaggc tttggtagac agcattggtt tctgctcata cgagttggag    960
taccagtcca aatcaacgag cgtgaacacg gatgtcgaaa tcaccggcga caagaacaaa   1020
ttgaacacaa ccaagtctac cagttcactc gatgacgact atgtgagttt ccccaataac   1080
attacgtttt tcgatttttt caggtattca atgtttccaa cagtggtgta ttctctcaag   1140
ttcccacgta caaagcgtat tagatggggt tacgtcatgg aaaagtcatt tgcagtgttt   1200
ggcatcatct tcttgatgat caccgtcgct caaaactgga tgtatcctat cgttgtacga   1260
gcacaagagg ctagcaaact cccaatgtca agagaaaagg tattgcagta ctgtttggtt   1320
ttactagaca tgattccacc atttctcatg gaatatcttt tcaccttttt cttgatttgg   1380
gacgtgatcc taaatgcgat agccgaattg agtaggtttg cagatcggga cttttatggt   1440
ccttggtggt cttgtaccga ttggtcggaa tttgcaagaa tttggaatcg tcctgttcac   1500
aaatttttgc ttcgtcatgt gtaccagtca actatcagta ctttcaaact caataaaaac   1560
caagcgtcgt tggtgacgtt tatcattctg agttttgttc atgagtttgt catgtttgtc   1620
atttttagaa aggtgagatt ctacatgttg gcgctccaga tgtctcagct tccattgata   1680
atgattagtc gaacaaaatt catgagagac aaaaaagtgt tgggaaatgt tatctgctgg   1740
gtaggattca tttctggacc atcgatgatc tgtactttgt atttagtatt ttaa         1794
```

<210> SEQ ID NO 103
<211> LENGTH: 515
<212> TYPE: PRT
<213> ORGANISM: Arxula adeninivorans

<400> SEQUENCE: 103

```
Met Ala Thr Ala Thr Ala Ile Ala Thr Val Thr Glu Gly Leu Gly Leu
1               5                   10                  15

Asp Lys Val Leu Ser Lys Glu Gln Pro Gly Leu Ser Lys Leu Ala Pro
            20                  25                  30

Arg Ala Asn Thr Asn Val Gln Pro Thr Gln Leu Gln Ser Pro Ser Pro
        35                  40                  45

Pro Gln Ser Arg Ser Ser Ser Pro Ile Ser Ala Ser Ser Ser Ser Glu
    50                  55                  60

Ser Leu Glu Leu Lys Val Pro Lys Ala Lys Ser Pro Ser Ser Ser Lys
65                  70                  75                  80

His Lys Pro His Tyr Arg Pro Val His Val Arg Ser Thr Ala Ser Ile
                85                  90                  95

Leu Ser Arg Asp Pro Ala Ala Arg Thr Glu Pro Pro Ser Tyr Ser Gly
            100                 105                 110

Phe Arg Asn Leu Ala Met Ile Ala Leu Ala Val Ser Asn Met Arg Leu
        115                 120                 125

Leu Leu Glu Asp Tyr Gln Asn Tyr Gly Val Phe His Thr Leu Asn Ile
    130                 135                 140

Met Gly Leu Ser Ala His Asp Val Arg Leu Thr Leu Ala Leu Thr Ala
145                 150                 155                 160

Ser Val Pro Phe His Leu Phe Val Ala Leu Ala Ile Glu Arg Ile Ala
                165                 170                 175

Val Leu Thr Met Pro Ser Lys Ser Thr Ala His Asn His Arg Ser Lys
            180                 185                 190

His Leu Trp Gly Leu Phe Ala Val Leu His Ala Leu Asn Ala Ala Ala
        195                 200                 205

Val Leu Ala Ile Ser Ser Tyr Thr Val Tyr Ser Arg Met Trp Ser Pro
```

```
    210                 215                 220

Ala Val Gly Thr Leu Cys Glu Cys His Ala Ile Val Val Cys Phe Lys
225                 230                 235                 240

Val Ala Ser Tyr Ala Leu Thr Asn Arg Asp Leu Arg Asp Ala Ala Ile
                245                 250                 255

Asp Gly Leu Glu Thr Thr Asp Pro Leu Leu Ser Lys Leu Pro Tyr Pro
            260                 265                 270

Ser Asn Leu Thr Leu Ser Asn Leu Val Tyr Phe Trp Trp Ala Pro Thr
        275                 280                 285

Leu Val Tyr Gln Pro Ile Tyr Pro Arg Trp Pro Leu His Arg Arg Trp
    290                 295                 300

Gly Phe Ile Phe Ser Arg Leu Leu Glu Ile Met Gly Ser Met Val Leu
305                 310                 315                 320

Ile Trp Phe Ile Ser Thr Gln Tyr Ala Asn Pro Ile Leu Glu Ser Ser
                325                 330                 335

Leu Gly His Phe Glu Gln Phe Asn Val Val Lys Ile Ser Glu Cys Leu
            340                 345                 350

Leu Lys Leu Ala Ser Val Ser Met Ala Ile Trp Leu Leu Gly Phe Phe
        355                 360                 365

Cys Leu Phe Gln Ser Phe Leu Asn Leu Leu Ala Glu Leu Val Arg Phe
    370                 375                 380

Gly Asp Arg Glu Phe Tyr Gln Asp Trp Trp Asn Ala Gly Ser Val Gly
385                 390                 395                 400

Thr Tyr Trp Arg Lys Trp Asn Arg Pro Val His Asn Tyr Phe Leu Arg
                405                 410                 415

His Phe Tyr Ile Pro Met Leu Lys Arg Gly Tyr Ser Gln Arg Thr Ala
            420                 425                 430

Ser Val Ile Val Phe Phe Leu Ser Ala Ile Leu His Glu Val Ala Val
        435                 440                 445

Gly Val Pro Thr Gln Ser Leu Ile Gly Val Ala Phe Val Gly Met Gly
    450                 455                 460

Ala Gln Ile Pro Leu Val Leu Ala Thr Ser Pro Leu Glu Lys Met Gly
465                 470                 475                 480

Glu Thr Gly Ala Thr Ile Gly Asn Cys Ile Phe Trp Leu Ser Phe Phe
                485                 490                 495

Leu Gly Gln Pro Met Gly Val Leu Leu Tyr Tyr Phe Ala Trp Asn Met
            500                 505                 510

Lys His Gln
        515
```

<210> SEQ ID NO 104
<211> LENGTH: 1548
<212> TYPE: DNA
<213> ORGANISM: Arxula adeninivorans

<400> SEQUENCE: 104

```
atggccaccg ctactgctat cgctacggtc acggagggcc tgggactaga taaggtgcta      60

tccaaggagc agccaggctt gtcgaagcta gctcctcgag cgaatacaaa tgtacaaccg     120

acccagttgc agtccccgtc tccaccacaa tctcgatctt cgtctccaat ttcggcctcc     180

tcatcatcag agtccctgga gctcaaggtg cccaaggcca aatcgccatc atcttccaaa     240

cacaaaccac actaccgccc cgtgcatgtg cggtcaacag catccatcct gtccagagac     300

ccggccgcca gaaccgagcc tccctcttac tctgggttca ggaacctagc catgattgca     360
```

```
ttggcggttt ctaatatgcg cctccttctc gaggactatc aaaactatgg cgtgttccac    420

actctcaaca ttatgggctt gagcgcacac gacgttcgcc tcacactggc attgacagct    480

tcggttccgt tccatctgtt tgtggccctg gccattgagc gcatcgcagt cctcactatg    540

ccctccaaat ctacagcaca caaccaccgc tcaaagcatc tctggggctt gtttgcagtt    600

ctgcatgctc tcaacgccgc tgctgtgcta gcaatcagct catacaccgt atacagtcgc    660

atgtggagtc ctgctgtggg aacattgtgc gaatgccacg caatcgtggt atgctttaag    720

gtggcatcgt atgcgcttac caaccgagac ttacgagatg ctgccattga tgggctagag    780

acaactgacc ctctgttgtc caagttgccc tacccatcca accttacctt gtcaaatctc    840

gtgtatttct ggtgggcccc aaccctagtg tatcagccaa tttaccctcg atggcccctg    900

catcgacgat ggggcttcat cttttctcgc ctgctcgaga ttatgggatc tatggtacta    960

atctggttca tttccaccca atacgccaac cccattttgg aatcatcctt ggggcacttt   1020

gaacagttta acgtggttaa aatctcagaa tgtctcctca aattagcatc ggtctccatg   1080

gccatctggc ttttgggttt cttttgtctc tttcaatcgt tttgaactt gctggcagaa   1140

ttggttcgtt ttggcgaccg cgagttctac caagactggt ggaacgccgg ctcagtaggt   1200

acctactggc gcaaatggaa ccgaccagtg cacaactatt tcttgcgcca tttctacatc   1260

ccaatgctca agcgaggtta ttcacagcgc actgcctcgg tcattgtatt ctttttatct   1320

gccattctcc atgaagttgc tgttggcgtg cctactcagt ccttgattgg agttgcgttt   1380

gtaggcatgg gtgcccagat tcctctagtg ctggccacta gtcctttgga aaagatgggc   1440

gaaactggcg caactattgg caactgcatc ttttggctct ctttcttcct gggccagcca   1500

atgggggtac tgctttacta ctttgcgtgg aatatgaagc accagtag                1548
```

```
<210> SEQ ID NO 105
<211> LENGTH: 687
<212> TYPE: PRT
<213> ORGANISM: Arxula adeninivorans

<400> SEQUENCE: 105

Met Ala Val Lys Arg Arg Ser Asn Leu Pro Gln Gln Glu Val Asp Ser
1               5                   10                  15

Asp Ser Ser Ser Asp Ser Ser Ser Val Ser Ser Ser Ala Ala Ser Ser
            20                  25                  30

Ser Val Asp Leu Ala Thr Gly Ser Ser Ser Gln Ile Glu Asp Arg Phe
        35                  40                  45

Pro Lys Lys Thr Ala Ser Ala Thr Lys Arg Ser Ser His His Arg Lys
    50                  55                  60

Ser Lys Lys Asp Gly Gly His Leu Ser Tyr Lys Trp Arg Leu Ala Tyr
65                  70                  75                  80

Ser Lys Arg Leu Val Phe Ile Ile Gly Ile Ile Phe Gly Leu Gly Ile
                85                  90                  95

Ala Trp Tyr Ser Ala Pro Lys Glu Phe Val Ser Leu Asp Arg Leu Ser
            100                 105                 110

Glu Leu Ser Leu Asp Gly Leu Leu Asp Glu Phe Arg Asp Met Leu Pro
        115                 120                 125

Lys Gly Ile Met Arg Glu Ala His Asp Ile Asp Lys Lys Ser Tyr Thr
    130                 135                 140

Leu Ser Asp Ser Phe Ala Val Gly Asn Tyr Leu Arg Glu Glu Gly Tyr
145                 150                 155                 160

Gly Val Lys His Pro Val Ile Leu Ile Pro Gly Val Ile Ser Thr Gly
```

-continued

```
                165                 170                 175

Leu Glu Ser Trp Gly Leu Glu Gly Thr Glu Glu Cys Pro Ser Gln Pro
            180                 185                 190

His Phe Arg Lys Arg Leu Trp Gly Ser Leu Tyr Met Leu Arg Thr Met
        195                 200                 205

Leu Leu Asp Lys His Cys Trp Leu Lys His Ile Met Leu Asp Pro Ser
    210                 215                 220

Thr Gly Leu Asp Pro Pro Gly Tyr Lys Ile Arg Ala Ala Leu Gly Met
225                 230                 235                 240

Glu Ser Ala Asp Phe Phe Val Pro Gly Tyr Trp Leu Trp Asn Lys Ile
                245                 250                 255

Leu Glu Asn Leu Ala Ala Met Gly Tyr Asp Ser Asn Asn Met Leu Val
            260                 265                 270

Ala Ser Tyr Asp Trp Arg Leu Ser Tyr Pro Asp Leu Glu Arg Arg Asp
        275                 280                 285

Ser Tyr Phe Ser Arg Leu Lys Ser Ala Ile Glu His Ser Val His Ser
    290                 295                 300

Thr Gly Glu Lys Val Ala Leu Val Gly His Ser Met Gly Thr Gln Val
305                 310                 315                 320

Ile Phe Tyr Phe Leu Lys Trp Ala Glu Ala Lys Gly Tyr Gly Asp Gly
                325                 330                 335

Gly Asp Gln Trp Val Asn Asp His Ile Ala Ser Leu Val Asp Ile Ser
            340                 345                 350

Gly Ser Thr Leu Gly Thr Pro Lys Ala Ile Val Ala Leu Leu Ser Gly
        355                 360                 365

Glu Met Lys Asp Thr Val Gln Leu Asn Ala Leu Ala Val Tyr Gly Leu
    370                 375                 380

Glu Lys Phe Phe Ser Arg Arg Glu Arg Ala Asp Met Leu Arg Ser Phe
385                 390                 395                 400

Gly Gly Ile Ala Ser Met Leu Pro Lys Gly Gly Glu Ala Val Trp Gly
                405                 410                 415

Asn Leu Thr Phe Ala Pro Asp Asp Pro Pro Ile Thr Pro Ala Asp Ala
            420                 425                 430

Gln Glu Gly Gln Glu Glu Ser Lys Glu Glu Gly Lys Glu Asp Leu Val
        435                 440                 445

Glu Ser Glu Ser Lys Pro Glu Pro Thr Pro Glu Pro Glu Pro Glu Arg
    450                 455                 460

Leu Ser Phe Gly Asn Phe Ile Arg Phe Arg Asn Pro Leu Ser His Leu
465                 470                 475                 480

Ser Ser Lys Asn Leu Thr Ile Pro Ala Ser Ile Asp Tyr Leu Phe Glu
                485                 490                 495

Gln Ala Pro Glu Trp Phe Lys Asn Arg Thr Leu Asn His Tyr Ser Tyr
            500                 505                 510

Gly Leu Ala Arg Thr Arg Lys Glu Val Lys Ala Asn Asn Asp Asp Pro
        515                 520                 525

Ser Lys Trp Ser Asn Pro Leu Glu Val Ala Leu Pro Asn Ala Pro Asp
    530                 535                 540

Met Glu Ile Tyr Cys Phe Tyr Gly Val Gly Lys Pro Thr Glu Arg Ser
545                 550                 555                 560

Tyr Tyr Tyr Gln Glu Glu Val Asp Lys Asp Leu Val Asn Leu Asn Ile
                565                 570                 575

Ser Ile Ala His Asn Asp Pro Glu Ala Val Ile Met Gly Glu Gly Asp
            580                 585                 590
```

```
Gly Thr Ile Ser Leu Asn Thr His Thr Met Cys His Arg Trp Lys Asp
        595                 600                 605

Pro Asn Ser Lys Phe Asn Pro Gly Gly Ser Lys Val Lys Val Val Glu
    610                 615                 620

Met Leu His Gln Pro Ala Thr Leu Asp Ile Arg Gly Gly Ala Lys Thr
625                 630                 635                 640

Ala Glu His Val Asp Ile Leu Gly Arg Thr Glu Leu Asn Glu Leu Val
                645                 650                 655

Leu Arg Val Ala Ala Gly Arg Gly Asp Glu Val Glu Glu Arg Ile Val
            660                 665                 670

Ser Asn Ile Asp Ser Trp Val Trp Asp Ile Asp Leu Gly Ser Asp
        675                 680                 685


<210> SEQ ID NO 106
<211> LENGTH: 2064
<212> TYPE: DNA
<213> ORGANISM: Arxula adeninivorans

<400> SEQUENCE: 106

atggctgtga agcgtcggag caacctcccg cagcaggagg ttgatagcga ttcatcgagt      60

gatagctcgt cggtgtcgag ctctgctgcc agcagctcgg tagatctggc gacgggttcg     120

tcatcgcaaa tcgaagatag gttccctaaa aagactgcaa gcgcgacaaa gcgaagctct     180

caccatcgca agagtaagaa agatggtgga cacttgagct acaagtggcg tttggcatat     240

tccaagcgat tggtgttcat tatcggaatc atttttgggc tgggaattgc gtggtactcg     300

gctccgaagg agtttgtgtc attagatagg ctgtcggagc tgtcgttaga cgggctgtta     360

gacgagttta gagatatgct gcccaagggg atcatgagag aggcccacga tattgataaa     420

aagtcgtata cgctgtccga ttcgtttgct gtgggcaatt acctgcggga agaagggtac     480

ggggtgaagc atcctgtgat cttgatccca ggagtgattt ccactgggct ggagtcatgg     540

ggtctggagg ggactgaaga gtgtccctca caaccccatt tccgtaaaag actatggggg     600

tcattgtata tgctgcgaac aatgcttctg gataagcatt gttggctcaa gcacattatg     660

ctggaccctt ctactgggct agatcctccc gggtataaga tacgtgctgc tttgggaatg     720

gaatcagccg atttctttgt cccggggtac tggttgtgga acaagatttt ggaaaacctg     780

gccgccatgg ggtacgattc caataacatg cttgtagctt cttacgactg gcgtctgtcg     840

taccctgatt tggagcgccg tgatagctat tttagtcgcc tcaagagtgc aattgagcat     900

tctgtacata gtactggcga aaaagtcgct ctggtaggcc attccatggg tactcaggtg     960

attttctact ttttaaagtg ggcagaagct aaaggctacg gtgatggagg agatcaatgg    1020

gtcaatgacc atattgcttc tctggttgat atttccggat ctaccttggg tactcccaag    1080

gccattgtgg ccctgctttc tggtgaaatg aaggatactg tccagcttaa tgcgctggct    1140

gtgtatggat tggaaaagtt cttttcccgc cgcgaacgag ctgatatgct gcggtcattt    1200

ggtggaattg cttctatgct tccaaagggt ggagaggcag tttggggtaa cttgacgttt    1260

gctccagatg accctcccat tactcctgcc gacgctcaag agggccaaga agagagcaaa    1320

gaagagggca aagaggacct cgttgagagt gagagtaagc ctgaacctac gcctgaacct    1380

gaacctgaaa gactttcttt tggaaatttc attcgattcc gcaaccctct gagccacttg    1440

tcaagtaaga acctgaccat tcccgcgtca attgactact tgtttgagca ggctcctgag    1500

tggttcaaaa atcgaactct gaaccattat tcatacgggc ttgctcgcac ccgaaaagag    1560
```

```
gtaaaggcca acaatgacga cccttctaaa tggtccaatc ctttggaagt tgcattgcca   1620

aacgctccag acatggaaat ctattgcttc tacggagtgg gcaaacctac tgaacgcagc   1680

tactactacc aagaagaagt cgacaaggat ttggtcaacc tcaatatcag tattgctcat   1740

aatgatcccg aggctgtgat aatgggtgag ggtgatggaa caatctccct caacacccac   1800

acaatgtgcc accgctggaa ggacccaaac tcaaagttca accccggagg cagcaaagta   1860

aaagtagtgg agatgctcca tcagcctgcc actctagata ttcgtggagg cgcaaagacc   1920

gcggagcacg tggatatctt gggccgtacc gagctcaacg agctggtcct tcgggtcgct   1980

gctggtcgag gtgatgaagt cgaagagcgc atcgtgagca acattgacag ctgggtgtgg   2040

gacatcgacc ttggtagtga ttaa                                          2064
```

```
<210> SEQ ID NO 107
<211> LENGTH: 331
<212> TYPE: PRT
<213> ORGANISM: Arxula adeninivorans

<400> SEQUENCE: 107

Met Thr Lys Leu Ser Tyr Val Gly Arg Pro Pro Thr Asp Ile Phe Gln
1               5                   10                  15

Trp Pro Val Gly Leu Ala Met Pro Ser Gly Pro Phe Gly Ser Trp Phe
            20                  25                  30

Glu Thr Met Met Asp Val Arg Val Pro Leu Thr Val Ala Ser Val Tyr
        35                  40                  45

Ala Thr Thr Val His Val Leu Asn His Phe Arg Lys Thr Asn Lys Glu
    50                  55                  60

Pro Ile Gly Leu Ala Lys Thr Arg Leu Phe Gln Trp Leu Val Val Ala
65                  70                  75                  80

His Asn Met Gly Leu Cys Val Tyr Ser Ala Trp Thr Cys Tyr Gly Met
                85                  90                  95

Ser Ala Ala Ile Tyr Gln Ser Val Phe Glu Val Thr Lys Val Ala Val
            100                 105                 110

Gly Asn Thr Glu Arg Gly Thr Val Asp Ala Tyr Leu Arg Gly Glu Gly
        115                 120                 125

Ser Leu Val Asp Gly Thr Ser Gly Asn Ala Thr Ala Gly Phe Trp Arg
    130                 135                 140

Ala Leu Cys Asp Val Asp Val Gly Ile Trp Asp His Gly Leu Ser Tyr
145                 150                 155                 160

Tyr Gly Phe Phe Phe Tyr Leu Ser Lys Phe Tyr Glu Val Val Asp Thr
                165                 170                 175

Leu Ile Ile Leu Ala Lys Gly Lys Gln Ser Ser Leu Leu Gln Thr Tyr
            180                 185                 190

His His Ala Gly Ala Met Leu Ser Met Trp Ala Gly Ile Arg Phe Ala
        195                 200                 205

Ser Pro Pro Ile Trp Ile Phe Val Val Phe Asn Ser Leu Ile His Thr
    210                 215                 220

Ile Met Tyr Phe Tyr Tyr Thr Leu Thr Thr Leu Lys Leu Arg Val Pro
225                 230                 235                 240

Thr Val Val Lys Arg Ser Leu Thr Thr Ala Gln Ile Cys Gln Phe Val
                245                 250                 255

Phe Gly Gly Ser Phe Ala Leu Leu His Met Phe Val Tyr Tyr Phe Asp
            260                 265                 270

Pro Asn Thr Gln Ser Tyr Ser Ser Cys Leu Ser Asp Pro Gly Gln Gly
        275                 280                 285
```

```
Phe Ala Leu Met Phe Asn Val Ala Tyr Leu Ala Pro Leu Thr Tyr Leu
    290                 295                 300

Phe Val Asn Phe Trp Ile Asp Ser Tyr Val Arg Ser Lys Gln Arg Ala
305                 310                 315                 320

Ala Asp Arg Lys Ala Ala Ala Lys Ala Lys Gln
                325                 330


<210> SEQ ID NO 108
<211> LENGTH: 996
<212> TYPE: DNA
<213> ORGANISM: Arxula adeninivorans

<400> SEQUENCE: 108

atgaccaagc tgtcgtacgt gggacgcccg ccaactgaca tttttcaatg gccagtaggc      60

ctggcaatgc catccggtcc gtttggatct tggttcgaga ctatgatgga tgtacgagtg     120

ccgttgacgg ttgcctctgt gtacgctaca actgttcatg tgctgaacca tttccgaaag     180

accaacaagg agcccattgg cctggcaaag actcgattgt tccagtggtt ggtcgtggcc     240

cacaacatgg gcctgtgtgt ttactctgcc tggacttgtt atggtatgtc tgcagcaatt     300

taccagtctg tgtttgaggt gaccaaggta gcagtcggaa acactgagcg tggtactgtt     360

gatgcgtacc tgcgtggaga gggtagtctg gtcgatggaa ccagcggtaa cgctactgcc     420

ggattctggc gagccttgtg cgatgtcgat gttggtatct gggaccacgg actgtcctac     480

tatggatttt tcttctatct ttcaaagttt tacgaggtgg tcgacactct gatcattctg     540

gccaagggta agcagtcgtc tcttcttcag acttatcacc acgccggtgc tatgttgtcc     600

atgtgggctg gaattcgatt cgcttcccct cccatttgga tctttgtggt gttcaattct     660

ctcattcaca ccatcatgta tttctactac accttgacca cccttaagct gcgcgttcct     720

accgtggtga agcgcagttt gaccaccgcc cagatttgcc aattcgtctt cggtggttcg     780

tttgcactgc tgcacatgtt tgtgtactat tttgatccca acacccaatc gtactcatcc     840

tgtctgtccg atccgggcca aggatttgcc ctcatgttca atgtagccta tctggcccca     900

ttgacttatc tattcgtcaa cttttggatt gacagttacg tgcgaagcaa gcagcgggcc     960

gccgaccgca aagctgcggc aaaggcaaag cagtaa                               996


<210> SEQ ID NO 109
<211> LENGTH: 648
<212> TYPE: PRT
<213> ORGANISM: Yarrowia lipolytica

<400> SEQUENCE: 109

Met Thr Gln Pro Val Asn Arg Lys Ala Thr Val Glu Arg Val Glu Pro
1               5                   10                  15

Ala Val Glu Val Ala Asp Ser Glu Ser Glu Ala Lys Thr Asp Val His
            20                  25                  30

Val His His His His His His His Lys Arg Lys Ser Val Lys Gly Lys
        35                  40                  45

Ile Leu Asn Phe Phe Thr Arg Ser Arg Arg Ile Thr Phe Val Leu Gly
    50                  55                  60

Ala Val Val Gly Val Ile Ala Ala Gly Tyr Tyr Ala Ala Pro Pro Glu
65                  70                  75                  80

Leu Ser Ile Asp Ile Asp Ala Leu Leu Gly Asp Leu Pro Ser Phe Asp
                85                  90                  95

Phe Asp Ala Leu Ser Leu Asp Asn Leu Ser Met Asp Ser Val Ser Asp
```

-continued

```
            100                 105                 110

Phe Val Gln Asp Met Lys Ser Arg Phe Pro Thr Lys Ile Leu Gln Glu
        115                 120                 125

Ala Ala Lys Ile Glu Lys His Gln Lys Ser Glu Gln Lys Ala Ala Pro
    130                 135                 140

Phe Ala Val Gly Lys Ala Met Lys Ser Glu Gly Leu Asn Ala Lys Tyr
145                 150                 155                 160

Pro Val Val Leu Val Pro Gly Val Ile Ser Thr Gly Leu Glu Ser Trp
                165                 170                 175

Ser Leu Glu Gly Thr Glu Glu Cys Pro Thr Glu Ser His Phe Arg Lys
            180                 185                 190

Arg Met Trp Gly Ser Trp Tyr Met Ile Arg Val Met Leu Leu Asp Lys
        195                 200                 205

Tyr Cys Trp Leu Gln Asn Leu Met Leu Asp Thr Glu Thr Gly Leu Asp
    210                 215                 220

Pro Pro His Phe Lys Leu Arg Ala Ala Gln Gly Phe Ala Ser Ala Asp
225                 230                 235                 240

Phe Phe Met Ala Gly Tyr Trp Leu Trp Asn Lys Leu Leu Glu Asn Leu
                245                 250                 255

Ala Val Ile Gly Tyr Asp Thr Asp Thr Met Ser Ala Ala Ala Tyr Asp
            260                 265                 270

Trp Arg Leu Ser Tyr Pro Asp Leu Glu His Arg Asp Gly Tyr Phe Ser
        275                 280                 285

Lys Leu Lys Ala Ser Ile Glu Glu Thr Lys Arg Met Thr Gly Glu Lys
    290                 295                 300

Thr Val Leu Thr Gly His Ser Met Gly Ser Gln Val Ile Phe Tyr Phe
305                 310                 315                 320

Met Lys Trp Ala Glu Ala Glu Gly Tyr Gly Gly Gly Gly Pro Asn Trp
                325                 330                 335

Val Asn Asp His Ile Glu Ser Phe Val Asp Ile Ser Gly Ser Met Leu
            340                 345                 350

Gly Thr Pro Lys Thr Leu Val Ala Leu Leu Ser Gly Glu Met Lys Asp
        355                 360                 365

Thr Val Gln Leu Asn Ala Met Ala Val Tyr Gly Leu Glu Gln Phe Phe
    370                 375                 380

Ser Arg Arg Glu Arg Ala Asp Leu Leu Arg Thr Trp Gly Gly Ile Ala
385                 390                 395                 400

Ser Met Ile Pro Lys Gly Gly Lys Ala Ile Trp Gly Asp His Ser Gly
                405                 410                 415

Ala Pro Asp Asp Glu Pro Gly Gln Asn Val Thr Phe Gly Asn Phe Ile
            420                 425                 430

Lys Phe Lys Glu Ser Leu Thr Glu Tyr Ser Ala Lys Asn Leu Thr Met
        435                 440                 445

Asp Glu Thr Val Asp Phe Leu Tyr Ser Gln Ser Pro Glu Trp Phe Val
    450                 455                 460

Asn Arg Thr Glu Gly Ala Tyr Ser Phe Gly Ile Ala Lys Thr Arg Lys
465                 470                 475                 480

Gln Val Glu Gln Asn Glu Lys Arg Pro Ser Thr Trp Ser Asn Pro Leu
                485                 490                 495

Glu Ala Ala Leu Pro Asn Ala Pro Asp Leu Lys Ile Tyr Cys Phe Tyr
            500                 505                 510

Gly Val Gly Lys Asp Thr Glu Arg Ala Tyr Tyr Tyr Gln Asp Glu Pro
        515                 520                 525
```

```
Asn Pro Glu Gln Thr Asn Leu Asn Val Ser Ile Ala Gly Asn Asp Pro
    530                 535                 540

Asp Gly Val Leu Met Gly Gln Gly Asp Gly Thr Val Ser Leu Val Thr
545                 550                 555                 560

His Thr Met Cys His Arg Trp Lys Asp Glu Asn Ser Lys Phe Asn Pro
                565                 570                 575

Gly Asn Ala Gln Val Lys Val Val Glu Met Leu His Gln Pro Asp Arg
            580                 585                 590

Leu Asp Ile Arg Gly Gly Ala Gln Thr Ala Glu His Val Asp Ile Leu
        595                 600                 605

Gly Arg Ser Glu Leu Asn Glu Met Val Leu Lys Val Ala Ser Gly Lys
    610                 615                 620

Gly Asn Glu Ile Glu Glu Arg Val Ile Ser Asn Ile Asp Glu Trp Val
625                 630                 635                 640

Trp Lys Ile Asp Leu Gly Ser Asn
                645


<210> SEQ ID NO 110
<211> LENGTH: 1947
<212> TYPE: DNA
<213> ORGANISM: Yarrowia lipolytica

<400> SEQUENCE: 110

atgacacaac ctgtgaatcg gaaggcgact gtcgagcggg tcgagccagc agtggaggtg     60

gctgactccg agtccgaggc caagaccgac gtccacgttc accaccatca tcaccaccac    120

aagcgaaaat ccgtcaaggg caagattctc aacttcttca cccgaagtcg acgtatcacc    180

ttcgtcctcg gcgccgtggt cggtgtgata gccgcgggat actacgctgc gccaccggag    240

ctcagcattg atatcgatgc tcttctcggc gacttgccct cgttcgactt tgacgctcta    300

tctctcgaca acttgtccat ggacagtgtg tcggactttg tacaagacat gaaatcgcgg    360

tttccgacca agattctgca ggaggcggcc aagatcgaga agcaccagaa aagcgaacag    420

aaggctgccc cttttgctgt gggcaaggct atgaagagcg agggactcaa cgccaagtac    480

ccggtggtgc tggtgcccgg cgtcatctcc acgggactgg agagctggtc cctggaggga    540

accgaggagt gtcccaccga gtcgcacttc agaaagcgaa tgtggggctc ctggtacatg    600

atccgagtca tgctgctgga caagtactgc tggctgcaga acctgatgct ggacacagag    660

accggtctag accctcccca tttcaagctg cgagccgccc agggatttgc ctccgccgac    720

ttctttatgg caggctactg gctgtggaac aagctgctcg agaacctggc tgttattgga    780

tacgatacgg atacaatgtc tgctgcggcg tacgactgga gactgtccta ccctgatttg    840

gagcaccgag acggatactt ctccaagctc aaagcttcaa tcgaagagac taagcgtatg    900

acaggtgaga agacagttct gacgggccat tccatgggct cccaggtcat cttctacttc    960

atgaagtggg ctgaggccga gggatatgga ggaggaggtc ccaactgggt caatgaccat   1020

attgaatcct ttgtcgacat ttccggctcc atgctgggta ctcccaagac cctggttgct   1080

cttctgtctg gagaaatgaa ggataccgtg cagctgaacg cgatggctgt gtatggactg   1140

gagcagttct tctctcgacg agagcgagcc gatctgctgc gaacatgggg aggaattgct   1200

tccatgattc ccaagggtgg taaggctatc tggggtgatc attctggagc ccctgatgac   1260

gagcctggcc agaatgtcac ctttggcaac ttcatcaagt tcaaggagtc cttgaccgag   1320

tactctgcta agaacctcac catggatgaa accgttgact tcctgtattc tcagtctccc   1380
```

gagtggtttg tgaaccgaac cgagggtgct tactcctttg gaattgccaa gactcgaaag 1440
caggttgagc agaatgagaa gcgaccttct acctggagca accctctgga agctgctctc 1500
cccaatgccc ccgatctcaa gatctactgc ttctatggag tcggtaagga taccgagcga 1560
gcctactact accaggatga gcccaatccc gagcagacca acttgaacgt cagtatcgct 1620
ggaaacgacc ctgatggtgt gcttatgggc cagggcgatg gaaccgtctc ccttgtgacc 1680
cataccatgt gtcaccgatg gaaggacgag aattccaagt tcaaccctgg taacgcccag 1740
gtcaaggttg tggagatgtt gcaccagcct gatcgacttg atattcgagg cggtgctcag 1800
actgccgagc atgtggacat tctggggcgt tctgagttga acgagatggt tctgaaggtg 1860
gccagtggaa agggaaatga gattgaagag agagtcatct ccaacattga tgagtgggtg 1920
tggaagattg atctcggcag caattag 1947

<210> SEQ ID NO 111
<211> LENGTH: 533
<212> TYPE: PRT
<213> ORGANISM: Rhodotorula glutinis

<400> SEQUENCE: 111

Met Thr Ala Ser Ser Ala Leu Glu Thr Ser Leu Pro His Ser Val Gly
1 5 10 15

Pro Glu Ser Ala Thr Thr Thr Ala Lys Pro Pro Arg Ala Pro Leu Arg
20 25 30

Met Arg His Pro Asp Tyr Thr Gln Thr Asp Val Leu Glu Ser Ser Asp
35 40 45

Ser Asp Ala Ala Ser Asp Ser Glu Gly Glu Thr Thr Ala Val Asp Asp
50 55 60

Gly Thr Tyr Glu Asp Asp Asn Tyr Val Arg Lys Val Leu Ser Lys Glu
65 70 75 80

Lys Pro Leu Pro Pro Ile Thr Trp Lys Asn Ile His Arg Asn Ile Gln
85 90 95

Trp Ile Ser Thr Leu Ala Leu Thr Ile Val Pro Leu Leu Ser Ile Tyr
100 105 110

Gly Ala Phe Thr Thr Pro Leu Lys Trp Gln Thr Ala Val Trp Ser Val
115 120 125

Val Tyr Tyr Tyr Phe Thr Gly Leu Gly Ser Tyr Thr Ala Ser Leu Pro
130 135 140

Leu Gln Tyr Phe Leu Ala Leu Gly Gly Ser Gly Ala Val Glu Gly Ser
145 150 155 160

Val Lys Trp Trp Ala Arg Gly His Arg Ala His His Arg Tyr Thr Asp
165 170 175

Thr Asp Leu Asp Pro Tyr Ser Ala Gln Lys Gly Phe Trp Trp Ala His
180 185 190

Leu Gly Trp Met Ile Val Lys Pro Arg Arg Arg Pro Gly Val Ala Asp
195 200 205

Val Ser Asp Leu Asn Asn Asn Pro Val Val Lys Trp Gln His Arg Phe
210 215 220

Tyr Leu Pro Leu Ile Leu Gly Met Gly Phe Ile Phe Pro Thr Ile Val
225 230 235 240

Ala Gly Leu Gly Trp Gly Asp Phe Arg Gly Gly Phe Phe Phe Ala Gly
245 250 255

Ala Ala Arg Leu Leu Phe Val His His Ser Thr Phe Cys Val Asn Ser
260 265 270

```
Leu Ala His Trp Leu Gly Glu Thr Pro Phe Asp Asp Lys His Thr Pro
        275                 280                 285

Lys Asp His Trp Leu Thr Ala Leu Ala Thr Val Gly Glu Gly Tyr His
    290                 295                 300

Asn Phe His His Glu Phe Pro Ser Asp Tyr Arg Asn Ala Leu Arg Trp
305                 310                 315                 320

Trp Gln Tyr Asp Pro Thr Lys Cys Phe Ile Tyr Ala Met Ser Lys Leu
                325                 330                 335

Gly Leu Ala Ser Gln Leu Lys Thr Phe Pro Asp Asn Glu Ile Lys Lys
            340                 345                 350

Gly Gln Tyr Ala Met Thr Leu Lys Ala Val Ala Arg Glu Ala Glu Asn
        355                 360                 365

Ile Glu Trp Pro Lys Ser Ser Asn His Leu Pro Val Leu Thr Trp Asp
    370                 375                 380

Glu Phe Gln Glu Ala Cys Lys Thr Arg Gln Leu Leu Val Val Ala Gly
385                 390                 395                 400

Phe Ile His Asp Val Ser Thr Phe Ile Asp Gln His Pro Gly Gly Ala
                405                 410                 415

Gly Leu Ile Lys Thr Arg Leu Gly Arg Asp Ala Thr Thr Ala Phe Tyr
            420                 425                 430

Gly Gly Tyr Tyr Asp His Ser Asn Gly Ala Ala Asn Leu Leu Ala Gln
        435                 440                 445

Tyr Arg Val Gly Val Ile Glu Gly Gly Tyr Glu Val Glu His Met Lys
    450                 455                 460

Lys Tyr Ser Glu Val Val Glu Asn Leu Lys Lys His Gly Ala Asp Gly
465                 470                 475                 480

Val Ala Gly Lys Ser Ala Asp Leu Ala Lys Gly Pro Lys Gln Met Ser
                485                 490                 495

Val Ile Lys Gly Asp Pro Gln Leu Lys Gly Ala Pro Leu Glu Thr Leu
            500                 505                 510

Ala Lys Pro Pro Thr Phe Ser Glu Thr Asn Leu Leu Gly Gly Leu Ser
        515                 520                 525

Leu Thr Val Lys Ala
    530
```

<210> SEQ ID NO 112
<211> LENGTH: 1602
<212> TYPE: DNA
<213> ORGANISM: Rhodotorula glutinis

<400> SEQUENCE: 112

```
atgactgcct cgtcggcact cgagacctcg ctcccgcact ctgtcgggcc cgagtctgcg      60

actaccaccg caaagccgcc ccgtgcgccg ctcaggatgc gtcaccccga ctacacccag     120

accgacgtcc tcgagtcgtc agactcggac gcagcgtcgg attccgaggg cgagacgacg     180

gctgtcgacg acgggaccta cgaggacgat aactacgtcc gcaaggtcct cagcaaggag     240

aagccgctcc cgcccatcac ctggaagaac atccaccgca acatccagtg gatctcgacc     300

ctcgccctca ccatcgtgcc cctcctctcg atctacggag cgttcacgac gcccctgaag     360

tggcagacgg cggtctggag tgtcgtctac tactacttca ccggtctcgg gtcctacact     420

gcctccctgc ctctccagta cttcctggca cttggcggaa gcggcgcagt ggagggttct     480

gtgaaatggt gggcccgagg acaccgcgca caccaccgct acaccgacac ggacctcgac     540

ccgtactcag cgcagaaggg cttctggtgg gcacacctcg gctggatgat tgtcaagccg     600
```

-continued

```
cgccgtcgtc ccggtgtcgc cgatgtctcc gacctcaaca acaacccagt cgtcaagtgg    660

cagcaccgct tctacctccc gctcatcctc ggcatgggct tcatcttccc taccatcgtc    720

gctggactcg gctggggcga cttccgcggc ggatttttct tcgccggcgc tgctcgcctc    780

ctctttgtcc accactcgac gttctgcgtc aactcgctcg cacactggct cggcgagacg    840

ccgtttgacg acaagcacac gccgaaggac cactggctca ccgcgctcgc gacggtcggc    900

gagggctacc acaacttcca ccacgagttc ccctccgact accgcaacgc gctcagatgg    960

tggcagtatg atccgactaa gtgtttcatt tacgcgatgt cgaaactcgg attggcgtcg   1020

cagctcaaga cgttccccga caacgagatc aagaagggtc agtacgccat gacgctcaag   1080

gctgtcgcgc gcgaggcgga gaacatcgag tggcccaagt cgtcgaacca cttgcctgtg   1140

ctcacctggg atgagttcca ggaggcctgc aagactcgcc agctcctcgt tgtcgccggt   1200

ttcatccacg atgtcagcac cttcatcgac cagcaccctg gcggtgccgg cttgatcaag   1260

acccgtctcg gccgcgatgc gacgaccgcc ttctacggtg gctactacga ccactcgaac   1320

ggcgcagcca acttgctcgc ccagtaccgt gtcggcgtca tcgagggcgg ctacgaggtc   1380

gagcacatga agaagtactc tgaggtcgtc gagaacctca agaagcacgg cgccgacggc   1440

gtggccggca agagcgccga cctcgccaag ggtccgaagc agatgtcggt catcaagggc   1500

gaccctcagc tcaagggcgc gccgctcgag acgctcgcca agccgcctac cttcagcgag   1560

accaaccttt tgggcggtct cagcctgacg gtcaaggcgt aa                      1602
```

```
<210> SEQ ID NO 113
<211> LENGTH: 579
<212> TYPE: PRT
<213> ORGANISM: Rhodotorula graminis

<400> SEQUENCE: 113

Met Arg His Pro Asp Tyr Ser Gln Gly Asp Val Val Glu Ser Ser Asp
1               5                   10                  15

Ser Asp Arg Glu Ala Ser Asp Ser Glu Gly Glu Thr Thr Ala Val Asp
            20                  25                  30

Asp Gly Thr Tyr Gln Asp Asp Asn Phe Val Arg Lys Val Leu Ala Lys
        35                  40                  45

Glu Arg Pro Leu Pro Pro Ile Thr Leu Lys Thr Leu Pro Gln Asn Ile
    50                  55                  60

Asn Val Ile Ser Thr Leu Ala Leu Thr Val Val Pro Ala Leu Ala Ile
65                  70                  75                  80

Tyr Gly Ala Phe Thr Thr Gln Ile Lys Trp Gln Thr Ala Leu Trp Ser
                85                  90                  95

Val Ile Tyr Tyr Phe Tyr Thr Gly Leu Gly Ile Thr Ala Gly Tyr His
            100                 105                 110

Arg Leu Trp Ala His Arg Ser Tyr Thr Ala Ser Leu Pro Leu Gln Tyr
        115                 120                 125

Phe Leu Ala Leu Gly Gly Ser Gly Ala Val Glu Gly Ser Ile Lys Trp
    130                 135                 140

Trp Ser Arg Gly His Arg Ala His His Arg Tyr Thr Asp Thr Asp Leu
145                 150                 155                 160

Asp Pro Tyr Ser Ala Gln Lys Gly Phe Trp Trp Ser His Ile Gly Trp
                165                 170                 175

Met Val Val Lys Pro Arg Arg Thr Pro Gly Val Ala Asp Val Ser Asp
            180                 185                 190

Leu Ser Val Asn Glu Val Val Lys Trp Gln His Arg Trp Tyr Val Tyr
```

```
        195                 200                 205

Leu Ile Val Gly Met Gly Phe Val Phe Pro Thr Leu Val Ala Gly Leu
    210                 215                 220

Gly Trp Gly Asp Tyr Arg Gly Gly Phe Phe Phe Ala Gly Ala Ala Arg
225                 230                 235                 240

Leu Leu Phe Val His His Ser Thr Phe Cys Val Asn Ser Leu Ala His
                245                 250                 255

Trp Leu Gly Glu Thr Pro Phe Asp Asp Lys His Ser Pro Arg Asp His
            260                 265                 270

Trp Ile Thr Ala Leu Val Thr Val Gly Glu Gly Tyr His Asn Phe His
        275                 280                 285

His Glu Phe Pro Gln Asp Phe Arg Asn Ala Ile Gln Thr Phe Gln Tyr
    290                 295                 300

Asp Pro Thr Lys Trp Phe Ile Ile Val Met His Trp Leu Gly Leu Ala
305                 310                 315                 320

Ser Gln Leu Lys Thr Phe Pro Asp Asn Glu Ile Arg Arg Gly Gln Tyr
                325                 330                 335

Ala Met Lys Leu Lys Ala Val Ala Arg Glu Ala Asp Glu Ile Arg Trp
            340                 345                 350

Pro Lys Ser Ser Asn His Leu Pro Val Leu Thr Trp Asp Glu Phe Gln
        355                 360                 365

Glu Ala Cys Lys Thr Arg Gln Leu Met Val Ile Ser Gly Tyr Ile His
    370                 375                 380

Asp Val Ser Thr Phe Ile Asp Glu His Pro Gly Gly Arg Ala Leu Ile
385                 390                 395                 400

Lys Thr Arg Leu Gly Arg Asp Ala Thr Asn Ala Phe Tyr Gly Gly Tyr
                405                 410                 415

Tyr Asp His Ser Asn Gly Ala Asn Asn Val Leu Ala Gln Tyr Arg Val
            420                 425                 430

Gly Val Ile Glu Gly Gly Tyr Glu Val Glu His Leu Lys Arg Phe Ser
        435                 440                 445

Lys Leu Ile Glu Asp Leu Lys Asp Ser Ser Ala Thr Ser Pro Ala Pro
    450                 455                 460

Ser Ala Ser Thr Pro Ser Ser Thr Leu Ser Ser Ala Cys Thr Pro Ser
465                 470                 475                 480

Thr Ser Thr Cys Thr Ser Pro Thr Ser Arg Ser Thr Arg Ser Ser Pro
                485                 490                 495

Pro Ser Pro Ser Ala Pro Thr Pro Thr Ser Ser Ser Thr Leu Pro Arg
            500                 505                 510

Arg Ala Arg Cys Thr Ser Arg Arg Ser Arg Arg Ser Ser Ser Arg Arg
        515                 520                 525

Ser Arg Arg Ser Arg Ser Ser Pro Arg Ala Ser Pro Ser Ala Thr Arg
    530                 535                 540

Ala Arg Ser Ser Thr Pro Pro Ser Arg Arg Arg Ser Ser Ser Ser Ala
545                 550                 555                 560

Arg Arg Arg Ser Ala Ala Ser Ser Arg Ala Ala Ser Ala Ser Ala Thr
                565                 570                 575

Arg Ala Ala
```

<210> SEQ ID NO 114
<211> LENGTH: 1740
<212> TYPE: DNA
<213> ORGANISM: Rhodotorula graminis

<400> SEQUENCE: 114
atgcgccacc cggactactc gcagggcgac gttgtcgagt cgtccgactc ggaccgcgag 60
gcgagcgact cggagggcga gacgaccgcc gtcgacgacg gcacctacca ggacgacaac 120
tttgtccgca aggtgctcgc caaggagcgt cctctgccgc ccatcacgct caagacgctc 180
ccgcagaaca tcaacgtcat ctcgaccctc gccctcaccg tcgtccccgc cctcgccatc 240
tacggcgcgt tcacgacgca gatcaagtgg cagacggctt tgtggagcgt catctactac 300
ttctacactg gcctcggtat cacggccggg taccaccgcc tgtgggctca ccgcagctac 360
acggcgtctt tgccgctcca gtacttcctc gctctcggag gatctggcgc tgtcgagggc 420
tcgatcaagt ggtggagccg tggtcaccgt gcgcaccacc gctacaccga caccgacctc 480
gacccgtact cggcgcagaa gggcttctgg tggtcgcaca tcggctggat ggtcgtcaag 540
ccccgtcgca cgcccggtgt cgccgacgtc agcgacctgt cggtcaacga ggtcgtcaag 600
tggcagcacc ggtggtacgt gtacctcatc gtcggcatgg gcttcgtctt cccgaccctc 660
gtcgccggcc tcggctgggg cgactaccgc ggcggcttct tcttcgccgg cgccgctcgc 720
ctcctgttcg tccaccactc gaccttctgc gtcaactcgc tcgcccactg gctcggtgag 780
acgccgttcg acgacaagca ctcgccgcgc gaccactgga tcacggcgct cgtcaccgtc 840
ggcgagggct accacaactt ccaccacgag ttcccccagg acttccgcaa cgcgatccag 900
accttccagt acgacccgac caagtggttc atcatcgtca tgcactggct cggcctcgcg 960
tcgcagctca agacgttccc cgacaacgag attcgccgcg gccagtacgc catgaagctc 1020
aaggccgtcg ctcgcgaggc cgacgagatc cgctggccca agtcgtccaa ccacctcccc 1080
gtcctcacgt gggacgagtt ccaggaggcg tgcaagactc gccagctcat ggtcatctcg 1140
ggctacatcc acgacgtctc gaccttcatc gacgagcacc ctggcggccg tgcgctcatc 1200
aagacccgcc tcggccgtga cgcgaccaac gccttctacg gtggctacta cgaccactcg 1260
aacggcgcca acaacgtcct cgcgcagtac cgcgtcggcg tcatcgaggg cggctacgag 1320
gtcgagcacc tcaagcgctt ctccaagctc atcgaggacc tcaaggactc ctccgcgacg 1380
tcaccggcgc cgagcgcctc gacgccctcg tcgactttgt cgtccgcctg tacgccgtct 1440
acgtcgacct gcacttcgcc tacctcgaga tcaacccgct cgtcgccgcc gtcgccaagt 1500
gccccgacgc cgacgtcgtc gtcaactttg cctcgtcgcg ctcggtgtac cagtcgacgc 1560
tcgaggcgct cgagttctcg cagatcaagg cgatcgcgct catcgccgag ggcgtccccg 1620
agcgccacgc gcgcgagatc ctccacgccg ccgagcagaa gaaggtcatc atcatcggcc 1680
cggcgacggt cggcggcatc aagccgggct gcttccgcat cggcaacacg ggcggcatga 1740

<210> SEQ ID NO 115
<211> LENGTH: 750
<212> TYPE: PRT
<213> ORGANISM: Rhodotorula graminis

<400> SEQUENCE: 115

Met Phe Leu His Ala Arg Gly Ala Leu Gly Ser Asn Ile Val Tyr Asp
1 5 10 15

Val Val Ala Ser Met Trp Arg Ile Val Ile Thr Leu Phe Phe Arg Glu
20 25 30

Ile Arg Ser Arg Gly Ala Trp Lys Ile Pro Arg Ala Ala Glu Gly Pro
35 40 45

Val Ile Phe Val Val Gly Pro His His Asn Gln Phe Leu Asp Pro Leu
50 55 60

-continued

```
Leu Leu Met Ser Glu Val Lys Arg Glu Ser Gly Arg Arg Ile Ser Phe
65                  70                  75                  80

Leu Thr Ala Ala Lys Ser Met Asp Arg Ala Phe Val Gly Leu Ala Ser
                85                  90                  95

Arg Leu Met Gln Ser Ile Pro Val Ala Arg Ala Gln Asp Ser Ala Phe
            100                 105                 110

Ala Gly Lys Gly Thr Ile Lys Leu Ser Asp Ser Asp Pro Cys Ile Ile
        115                 120                 125

Ile Gly Glu Gly Thr Ser Phe Thr Lys Asp Phe Glu Lys Pro Arg Ser
    130                 135                 140

Gln Val Leu Leu Pro Arg Asn Leu Gly Ser Ser Thr Ala Glu Val Val
145                 150                 155                 160

Glu Val Ile Ser Asp Thr Glu Leu Arg Leu Lys Lys Glu Phe Asn Arg
                165                 170                 175

Lys Ala Thr Glu Gly Leu Lys Glu Lys Ser Glu Gly Ser Ser Phe Lys
            180                 185                 190

Val Leu Pro His Val Asp Gln Thr Ser Met Tyr Ser Ala Val Tyr Gln
        195                 200                 205

Arg Leu Thr Glu Gly Gly Cys Ile Gly Ile Phe Pro Glu Gly Gly Ser
    210                 215                 220

His Asp Arg Thr Asp Leu Leu Pro Leu Lys Ala Gly Val Ser Ile Met
225                 230                 235                 240

Ala Leu Gly Ala Ile Ser Ala His Pro Asp Leu His Leu Gln Ile Val
                245                 250                 255

Pro Val Gly Leu Ser Tyr Phe His Pro His Lys Phe Arg Ser Arg Ala
            260                 265                 270

Val Val Glu Phe Gly Ser Pro Ile Glu Ile Pro Thr Glu Leu Val Arg
        275                 280                 285

Asp Phe Glu Gln Gly Gly Asp Ser Lys Lys Lys Ala Ile Ser Thr Val
    290                 295                 300

Met Asp Tyr Val Val Asn Gly Leu Lys Ser Val Thr Ile Arg Ala Pro
305                 310                 315                 320

Asp Tyr Asp Thr Leu Met Leu Val Gln Ala Ala Arg Arg Leu Tyr Arg
                325                 330                 335

Pro Pro Gly Gln Asn Leu Thr Leu Gly Gln Val Val Glu Leu Asn Lys
            340                 345                 350

Arg Phe Ile Val Gly Tyr Asp Ala Tyr Lys Glu Asp Pro Arg Ile Lys
        355                 360                 365

Asn Leu Glu His Arg Val Arg Glu Tyr Asn Thr Leu Leu Arg Tyr Met
    370                 375                 380

Gly Leu Lys Asp His Gln Val Asp Arg Ile Gly Arg Pro Arg Trp Arg
385                 390                 395                 400

Ser Phe Ala Leu Leu Cys Tyr Arg Leu Gly Leu Leu Gly Val Trp Gly
                405                 410                 415

Val Leu Ala Leu Pro Gly Val Val Leu Asn Ser Pro Ile Phe Leu Ala
            420                 425                 430

Ala Lys Ile Ile Ser His Lys Lys Ala Lys Asp Ala Leu Ala Ala Ser
        435                 440                 445

Ser Val Lys Ile Ala Gly Arg Asp Val Leu Ala Thr Trp Lys Val Leu
    450                 455                 460

Val Ala Leu Gly Gly Ala Pro Ala Leu Tyr Ser Val Tyr Ala Val Asn
465                 470                 475                 480
```

-continued

```
Ala Val Val Leu Ala His Lys Leu Ala Leu Pro Ala Ser Tyr Arg Phe
                485                 490                 495

Trp Ala Pro Phe Ala Thr Phe Ala Gly Leu Pro Leu Ile Gly Val Ala
            500                 505                 510

Ala Leu Lys Phe Gly Glu Val Gly Met Asp Val Tyr Lys Ser Leu Arg
        515                 520                 525

Pro Leu Val Leu Ser Leu Val Pro Gly Lys Glu Pro Gln Leu Met Arg
    530                 535                 540

Val Gln Arg Met Arg Glu Glu Leu Ala Ser Glu Leu Asn Leu Leu Val
545                 550                 555                 560

Asp Glu Leu Ala Pro Ala Leu Phe Asp Asp Phe Ser Ala Ser Arg Ile
                565                 570                 575

Ile Pro Ser Thr Thr Pro Val Pro Gln Arg Arg Asp Ser Ala Gln Gly
            580                 585                 590

Lys Phe Phe Gln His Pro Leu Ser Trp Val Asp Glu Leu Phe Phe Gly
        595                 600                 605

Pro Ala Trp Ser Ser Ser Met Ala Tyr Pro Gln Asp Arg His Val Arg
    610                 615                 620

Pro Asn Gln Gly Glu Ser Leu His Ala Pro Ser Thr Gly Asn Gly Ala
625                 630                 635                 640

Glu Ser Asp Leu Asp Gly Ala Phe Thr Asp Gly Gln Gly Thr Gly Ser
                645                 650                 655

Gly Tyr Val Ser Gly Tyr Thr Thr Glu Glu Ala Pro Asp Tyr Asp Glu
            660                 665                 670

Val Ile His Ile Leu Asn Arg Glu Gln Gly His Pro Asp Ser Pro Ala
        675                 680                 685

Val Gly Ala Arg Pro Thr Ile Ser Arg Arg Ala Ser Arg Gln Arg Ser
    690                 695                 700

Arg Ser Gly Leu Asn Leu Ala Ala Met Ser Pro Val Ser Pro Ala Thr
705                 710                 715                 720

Pro Leu Ser Ser Ala Thr Ala Ser Gly Ala Gln Ala Gly Ser Ser Gly
                725                 730                 735

Ala Glu Ala Arg Arg Arg Gly Ala Ala Pro Gln Gln Asp Glu
            740                 745                 750
```

<210> SEQ ID NO 116
<211> LENGTH: 2253
<212> TYPE: DNA
<213> ORGANISM: Rhodotorula graminis

<400> SEQUENCE: 116

```
atgttcctcc atgctcgagg cgcgcttggc agcaacatcg tgtacgacgt cgtcgcgtcg      60

atgtggcgca tcgtcatcac gctcttcttc cgcgagatcc gctcgcgcgg cgcgtggaag     120

atcccgcgcg ccgccgaggg gcccgtcatc tttgtcgtcg gtcctcacca caaccagttc     180

ctcgacccgc tgctcctcat gagcgaggtc aagcgcgaga gcggtcggcg catcagcttt     240

ctcacggcgg ccaagagcat ggacagggcg ttcgtcgggc tcgcctcgag gctcatgcag     300

agcatccctg tcgcgcgcgc ccaggactcg gcatttgccg gcaagggcac gatcaagctc     360

tccgactcgg acccgtgcat catcatcggc gagggcacgt cgttcaccaa ggactttgag     420

aagccgcgct cccaggtcct cctgccgcgc aacctcggca gctcgacggc cgaggtcgtc     480

gaggtcatca gcgacaccga gctgcgcctc aagaaggagt tcaaccgcaa ggcgaccgag     540

ggcctcaagg agaagagcga gggctcgtct ttcaaggttc ttccgcatgt cgaccagacg     600
```

```
agcatgtact cggccgtgta ccagcgcctg accgagggcg ggtgcatcgg catcttcccc    660

gagggcggct cccacgaccg caccgacctc ctgccgctca aggccggcgt ctcgatcatg    720

gcgctcggcg ccatctcggc gcacccggac ctgcacctcc agatcgtccc cgtcggcctc    780

agctactttc acccgcacaa gttccgctcg cgcgccgtcg tcgagttcgg cagcccgatc    840

gagatcccga ccgagctcgt gcgcgacttt gagcagggcg gcgacagcaa gaagaaggcg    900

atcagcaccg tcatggatta cgtcgtcaac gggctcaaga gcgtcacgat ccgtgcgcct    960

gactacgaca cgctgatgct cgtccaagcc gcacgtcgcc tgtaccgccc gcccgggcag   1020

aacctgacgc tcggccaggt cgtcgagctc aacaagcggt tcatcgtcgg gtacgacgcg   1080

tacaaggagg acccgcgcat caagaacctc gagcaccgcg tgcgcgagta caacacgctc   1140

ctgcgctaca tgggcctcaa ggaccaccag gtcgaccgca tcggccggcc ccgctggcgc   1200

tcgttcgccc tcctgtgcta ccgcctcggc ctcctcggcg tgtggggcgt cctcgcgctc   1260

cccggcgtcg tcctcaactc gcccatcttc ctcgccgcca agatcatctc gcacaagaag   1320

gccaaggacg ccctcgccgc ctcgtcggtc aagatcgccg gtcgcgacgt cctcgcgacc   1380

tggaaggtcc tcgtcgcgct cggcggcgcg ccggccctgt actcggtcta cgccgtcaac   1440

gccgtcgtcc tcgcgcacaa gctcgccctg ccggccagct accggttctg ggcgccgttc   1500

gccacgttcg cgggcctgcc gctcatcggt gtcgccgcgc tcaagtttgg cgaggtcggc   1560

atggacgtct acaagtcgct ccgccctctc gtcctgtcgc tcgtccccgg caaggagccg   1620

cagctcatgc gtgtgcagcg catgcgcgag gagctcgcct cggagctcaa cctcctcgtc   1680

gacgagctcg cgcccgccct gttcgacgac ttttcggcgt cgcgcatcat cccgtcgacc   1740

acgcccgtcc ctcagcgtcg cgactcggcg cagggcaagt tcttccagca cccgctcagc   1800

tgggtcgacg agctcttctt cggcccggcg tggagctcga gcatggcgta cccgcaggac   1860

cgccacgtgc gcccgaacca gggcgagtcg ctccacgcgc cctcgacggg caacggcgcc   1920

gagagcgacc tcgacggcgc gttcaccgac ggccagggca ccggcagcgg ctacgtctcg   1980

ggctacacga ccgaggaggc gcccgactac gacgaggtca tccacatcct caaccgcgag   2040

cagggccacc cggactcgcc cgccgtcggt gcgcgcccga ccatctcgcg ccgtgcgtcg   2100

cggcagcgct cgcgttcggg cctcaacctc gccgccatga gccccgtctc gccggcgacg   2160

ccgctctcga gcgcgacggc ctcgggcgct caggccgggt cgagcggcgc cgaggcgagg   2220

cgcaggggtg cggcgccgca gcaggacgag tga                                2253
```

<210> SEQ ID NO 117
<211> LENGTH: 551
<212> TYPE: PRT
<213> ORGANISM: Phaeodactylum tricornutum

<400> SEQUENCE: 117

```
Met Ala Met Arg Ala Val Asn Gln Leu Ala Val Phe Phe Val Leu Leu
1               5                   10                  15

Leu Leu Thr Ile Asp Asp Tyr Leu Met Ala Glu Ala Ser Trp Arg Arg
            20                  25                  30

Arg Ile Val Gly Asp Ile Ala Trp Ala Met Asp Val Val Pro Val Lys
        35                  40                  45

Arg Ala Gln Asp Ser Ala Lys Arg Gly Asn Gly Met Val Ser Leu Ala
    50                  55                  60

Thr Leu Asp Arg Asp Thr Arg Thr Ile Leu Val Ile Gly Arg Asn Thr
65                  70                  75                  80
```

-continued

```
Phe Phe Val Ala Asp Leu Ser Pro Gly Asp Lys Ile Arg Ile Glu Gly
                85                  90                  95

Ser Ala Val Gly Leu Lys Val Leu Asn Ile Glu Gly Asp His Lys Met
            100                 105                 110

Thr Val Asp Gly Ile Asp Phe Pro Glu Gly Val Pro Leu Pro Asp Glu
        115                 120                 125

Asn Val Gly Tyr Asp Ile Leu Gly Arg Val Asp Thr Lys Val Val Phe
    130                 135                 140

Glu Lys Val Leu Asp Lys Leu Thr Ala Gly Gly Ala Val Gly Ile Phe
145                 150                 155                 160

Pro Glu Gly Gly Ser His Asp Arg Thr Glu Leu Leu Pro Leu Lys Ala
                165                 170                 175

Gly Val Ala Leu Ile Ala Tyr Ser Ala Phe Glu Lys Ile Gly Gln Ser
            180                 185                 190

Val Pro Ile Val Pro Val Gly Leu Asn Tyr Phe Arg Ala His Arg Trp
        195                 200                 205

Arg Gly Arg Ala Val Ile Glu Tyr Gly Gln Pro Ile Ser Leu Asn Pro
    210                 215                 220

Lys Thr Met Pro Asp Tyr Glu Ala Gly Gly Leu Arg Arg Arg Asn Val
225                 230                 235                 240

Cys Asn Gln Leu Leu Glu Asn Ile Glu Thr Ser Met Lys Ser Val Ile
                245                 250                 255

Val Ser Thr Pro Asp Phe Glu Thr Leu Glu Leu Ile His Thr Ala Arg
            260                 265                 270

Arg Leu Tyr Gln Arg Lys Thr Gly Pro Met Asn Ile Ser Glu Lys Gln
        275                 280                 285

Asp Leu Ser Arg Arg Phe Ala Glu Gly Tyr Lys Arg Leu Leu Leu Met
    290                 295                 300

Thr Asn Gly Lys Pro Pro Thr Glu Trp Leu Asp Leu Gln Ser Arg Val
305                 310                 315                 320

Val Glu Tyr Arg Asn Glu Leu Lys His Leu Gly Leu Lys Asp Tyr Gln
                325                 330                 335

Val Asn Ala Leu Val Gly Glu His Leu Asp Ala Thr Met Asn Val Lys
            340                 345                 350

Glu Val Asp Gly Asp Val Val Leu Ser Phe Leu Gln Leu Pro Tyr His
        355                 360                 365

Ile Val His Leu Leu Leu Leu Val Ala Leu Ala Ala Val Pro Val Met
    370                 375                 380

Leu Leu Asn Leu Pro Val Gly Val Leu Ala Gly Leu Tyr Ala Glu Gln
385                 390                 395                 400

Arg Arg Lys Arg Ala Leu Ala Lys Ser Lys Val Lys Ile His Gly Tyr
                405                 410                 415

Asp Val Met Leu Thr Glu Lys Val Met Phe Cys Ile Val Met Val Pro
            420                 425                 430

Leu Met Trp Met Phe Tyr Gly Phe Leu Leu Phe Phe Leu Thr Glu Leu
        435                 440                 445

Asp Arg Pro Thr Ile Ala Leu Gly Ile Leu Ser Met Pro Leu Phe Ser
    450                 455                 460

Tyr Thr Gly Ile Val Ala Ala Glu Ala Gly Met Val Asp Leu Met Asp
465                 470                 475                 480

Leu Arg Pro Phe Phe Met Arg Leu Phe Pro Ser Ala Arg Arg Arg Leu
                485                 490                 495

Ala Ala Leu Pro Glu Lys Arg Arg Ile Leu Gln Lys Asp Leu Arg Ala
```

```
            500                 505                 510

Phe Ile Arg Ser Ile Gly Pro Gly Leu Gly Glu Ile Tyr Phe Lys Pro
        515                 520                 525

Asp Ile Asn Trp Lys Glu Ile Ile Glu Ala Ser Lys Ser Ser Asp Gly
    530                 535                 540

Met Asp Pro Asn Lys Pro Lys
545                 550


<210> SEQ ID NO 118
<211> LENGTH: 1656
<212> TYPE: DNA
<213> ORGANISM: Phaeodactylum tricornutum

<400> SEQUENCE: 118

atggcgatgc gagccgtcaa tcagctggca gtctttttcg tcttgctttt gttgacaatc      60

gatgactacc ttatggcgga ggcctcatgg aggcgccgta ttgttggtga tatcgcgtgg     120

gcaatggatg ttgtgccggt caaacgtgcg caggactccg ctaagcgagg aaatgggatg     180

gtttcacttg ctactttgga tagagacaca aggacgattt tggtcattgg gagaaacaca     240

ttttttgtgg ccgacttatc cccgggagac aagattcgaa tcgaaggtag tgcggttggg     300

ctaaaagtct tgaatattga aggcgaccat aaaatgactg tggatggtat tgatttccct     360

gaaggtgtcc cacttcctga cgagaatgtt ggctatgaca ttttaggacg tgtcgatacc     420

aaggtagtct tcgaaaaggt gttggataag cttacagcag gaggggctgt cggaatcttt     480

ccggaaggag gtagccatga cagaacggag cttttacctt tgaaagcagg tgttgccctc     540

attgcttatt ctgcttttga gaagattgga cagagtgtcc ccattgttcc tgttggcttg     600

aactatttta gggcccatcg ctggcgcgga cgggcggtga ttgaatatgg ccaaccaatc     660

tctctcaacc cgaagacaat gccggattat gaagccggag gactacgaag acgcaacgtg     720

tgcaaccaac tgcttgaaaa tattgagacc tcaatgaaat ctgtaatcgt ttcgacacca     780

gactttgaga ctttagaact catccatacc gcaagacgtc tatatcaaag gaagacaggc     840

ccaatgaata tctcggagaa gcaagatctg agtcgccggt ttgcagaagg ttacaagaga     900

cttcttctca tgacaaacgg caagccaccg acagaatggt tagatcttca aagccgtgtc     960

gtcgagtata gaaacgagct aaagcatttg ggattgaaag actaccaagt gaatgccttg    1020

gtcggtgaac atctcgatgc gacaatgaac gtcaaggaag tcgacggtga tgtcgtactt    1080

tctttcttgc agcttccgta tcatatagtt cacctcctgc ttctcgtcgc tctagcagcc    1140

gtcccagtta tgcttttgaa tctcccagtc ggtgtactag ctggtttgta tgccgaacag    1200

cgccgaaagc gtgcccttgc caagtcaaaa gtcaaaattc atggatacga tgtgatgcta    1260

accgagaagg tcatgttttg tattgtcatg gtgcccttga tgtggatgtt ttacgggttt    1320

cttctctttt ttctaactga attggatcgg ccgacaattg ctttggggat tctttcgatg    1380

cctctgtttt catacacagg aatcgttgct gcagaggctg ggatggtgga cttgatggat    1440

ttgcgcccat tcttcatgcg cctgttcccg tctgctcgta gacgtcttgc ggcattgcct    1500

gaaaagcgcc gaattctaca gaaagattta cgagccttta tccgctcgat tggacctggt    1560

ctaggggaaa tctactttaa acctgacata aattggaagg aaattatcga agcatcaaaa    1620

agttctgatg gaatggatcc aaacaaaccc aagtga                              1656


<210> SEQ ID NO 119
<211> LENGTH: 743
<212> TYPE: PRT
```

<213> ORGANISM: Saccharomyces cerevisiae

<400> SEQUENCE: 119

```
Met Ser Ala Pro Ala Ala Asp His Asn Ala Ala Lys Pro Ile Pro His
1               5                   10                  15

Val Pro Gln Ala Ser Arg Arg Tyr Lys Asn Ser Tyr Asn Gly Phe Val
            20                  25                  30

Tyr Asn Ile His Thr Trp Leu Tyr Asp Val Ser Val Phe Leu Phe Asn
        35                  40                  45

Ile Leu Phe Thr Ile Phe Phe Arg Glu Ile Lys Val Arg Gly Ala Tyr
    50                  55                  60

Asn Val Pro Glu Val Gly Val Pro Thr Ile Leu Val Cys Ala Pro His
65                  70                  75                  80

Ala Asn Gln Phe Ile Asp Pro Ala Leu Val Met Ser Gln Thr Arg Leu
                85                  90                  95

Leu Lys Thr Ser Ala Gly Lys Ser Arg Ser Arg Met Pro Cys Phe Val
            100                 105                 110

Thr Ala Glu Ser Ser Phe Lys Lys Arg Phe Ile Ser Phe Phe Gly His
        115                 120                 125

Ala Met Gly Gly Ile Pro Val Pro Arg Ile Gln Asp Asn Leu Lys Pro
    130                 135                 140

Val Asp Glu Asn Leu Glu Ile Tyr Ala Pro Asp Leu Lys Asn His Pro
145                 150                 155                 160

Glu Ile Ile Lys Gly Arg Ser Lys Asn Pro Gln Thr Thr Pro Val Asn
                165                 170                 175

Phe Thr Lys Arg Phe Ser Ala Lys Ser Leu Leu Gly Leu Pro Asp Tyr
            180                 185                 190

Leu Ser Asn Ala Gln Ile Lys Glu Ile Pro Asp Asp Glu Thr Ile Ile
        195                 200                 205

Leu Ser Ser Pro Phe Arg Thr Ser Lys Ser Lys Val Val Glu Leu Leu
    210                 215                 220

Thr Asn Gly Thr Asn Phe Lys Tyr Ala Glu Lys Ile Asp Asn Thr Glu
225                 230                 235                 240

Thr Phe Gln Ser Val Phe Asp His Leu His Thr Lys Gly Cys Val Gly
                245                 250                 255

Ile Phe Pro Glu Gly Gly Ser His Asp Arg Pro Ser Leu Leu Pro Ile
            260                 265                 270

Lys Ala Gly Val Ala Ile Met Ala Leu Gly Ala Val Ala Ala Asp Pro
        275                 280                 285

Thr Met Lys Val Ala Val Val Pro Cys Gly Leu His Tyr Phe His Arg
    290                 295                 300

Asn Lys Phe Arg Ser Arg Ala Val Leu Glu Tyr Gly Glu Pro Ile Val
305                 310                 315                 320

Val Asp Gly Lys Tyr Gly Glu Met Tyr Lys Asp Ser Pro Arg Glu Thr
                325                 330                 335

Val Ser Lys Leu Leu Lys Lys Ile Thr Asn Ser Leu Phe Ser Val Thr
            340                 345                 350

Glu Asn Ala Pro Asp Tyr Asp Thr Leu Met Val Ile Gln Ala Ala Arg
        355                 360                 365

Arg Leu Tyr Gln Pro Val Lys Val Arg Leu Pro Leu Pro Ala Ile Val
    370                 375                 380

Glu Ile Asn Arg Arg Leu Leu Phe Gly Tyr Ser Lys Phe Lys Asp Asp
385                 390                 395                 400
```

```
Pro Arg Ile Ile His Leu Lys Lys Leu Val Tyr Asp Tyr Asn Arg Lys
                405                 410                 415

Leu Asp Ser Val Gly Leu Lys Asp His Gln Val Met Gln Leu Lys Thr
            420                 425                 430

Thr Lys Leu Glu Ala Leu Arg Cys Phe Val Thr Leu Ile Val Arg Leu
        435                 440                 445

Ile Lys Phe Ser Val Phe Ala Ile Leu Ser Leu Pro Gly Ser Ile Leu
    450                 455                 460

Phe Thr Pro Ile Phe Ile Ile Cys Arg Val Tyr Ser Glu Lys Lys Ala
465                 470                 475                 480

Lys Glu Gly Leu Lys Lys Ser Leu Val Lys Ile Lys Gly Thr Asp Leu
                485                 490                 495

Leu Ala Thr Trp Lys Leu Ile Val Ala Leu Ile Leu Ala Pro Ile Leu
            500                 505                 510

Tyr Val Thr Tyr Ser Ile Leu Leu Ile Ile Leu Ala Arg Lys Gln His
        515                 520                 525

Tyr Cys Arg Ile Trp Val Pro Ser Asn Asn Ala Phe Ile Gln Phe Val
    530                 535                 540

Tyr Phe Tyr Ala Leu Leu Val Phe Thr Thr Tyr Ser Ser Leu Lys Thr
545                 550                 555                 560

Gly Glu Ile Gly Val Asp Leu Phe Lys Ser Leu Arg Pro Leu Phe Val
                565                 570                 575

Ser Ile Val Tyr Pro Gly Lys Lys Ile Glu Glu Ile Gln Thr Thr Arg
            580                 585                 590

Lys Asn Leu Ser Leu Glu Leu Thr Ala Val Cys Asn Asp Leu Gly Pro
        595                 600                 605

Leu Val Phe Pro Asp Tyr Asp Lys Leu Ala Thr Glu Ile Phe Ser Lys
    610                 615                 620

Arg Asp Gly Tyr Asp Val Ser Ser Asp Ala Glu Ser Ser Ile Ser Arg
625                 630                 635                 640

Met Ser Val Gln Ser Arg Ser Arg Ser Ser Ser Ile His Ser Ile Gly
                645                 650                 655

Ser Leu Ala Ser Asn Ala Leu Ser Arg Val Asn Ser Arg Gly Ser Leu
            660                 665                 670

Thr Asp Ile Pro Ile Phe Ser Asp Ala Lys Gln Gly Gln Trp Lys Ser
        675                 680                 685

Glu Gly Glu Thr Ser Glu Asp Glu Asp Glu Phe Asp Glu Lys Asn Pro
    690                 695                 700

Ala Ile Val Gln Thr Ala Arg Ser Ser Asp Leu Asn Lys Glu Asn Ser
705                 710                 715                 720

Arg Asn Thr Asn Ile Ser Ser Lys Ile Ala Ser Leu Val Arg Gln Lys
                725                 730                 735

Arg Glu His Glu Lys Lys Glu
            740
```

<210> SEQ ID NO 120
<211> LENGTH: 2232
<212> TYPE: DNA
<213> ORGANISM: Saccharomyces cerevisiae

<400> SEQUENCE: 120

```
atgtctgctc ccgctgccga tcataacgct gccaaaccta ttcctcatgt acctcaagcg     60

tcccgacggt acaaaaattc atacaatgga ttcgtataca atatacatac atggctgtat    120

gatgtgtctg tatttctgtt taatattttg ttcactattt tcttcagaga aattaaggta    180
```

-continued

```
cgtggtgcat ataacgttcc cgaagttggg gtgccaacca tccttgtgtg tgcccctcat    240

gcaaatcagt tcatcgaccc ggctttggta atgtcgcaaa cccgtttgct gaagacatca    300

gcgggaaagt cccgatccag aatgccttgt tttgttactg ctgagtcgag ttttaagaaa    360

agatttatct ctttctttgg tcacgcaatg ggcggtattc ccgtgcctag aattcaggac    420

aacttgaagc cagtggatga gaatcttgag atttacgctc cggacttgaa gaaccacccg    480

gaaatcatca agggccgctc caagaaccca cagactacac cagtgaactt tacgaaaagg    540

ttttctgcca agtccttgct tggattgccc gactacttaa gtaatgctca aatcaaggaa    600

atcccggatg atgaaacgat aatcttgtcc tctccattca gaacatcgaa atcaaaagtg    660

gtggagctct tgactaatgg tactaatttt aaatatgcag agaaaatcga caatacggaa    720

actttccaga gtgtttttga tcacttgcat acgaagggct gtgtaggtat tttccccgag    780

ggtggttctc atgaccgtcc ttcgttacta cccatcaagg caggtgttgc cattatggct    840

ctgggcgcag tagccgctga tcctaccatg aaagttgctg ttgtaccctg tggtttgcat    900

tatttccaca gaaataaatt cagatctaga gctgttttag aatacggcga acctatagtg    960

gtggatggga aatatggcga aatgtataag gactccccac gtgagaccgt ttccaaacta   1020

ctaaaaaaga tcaccaattc tttgttttct gttaccgaaa atgctccaga ttacgatact   1080

ttgatggtca ttcaggctgc cagaagacta tatcaaccgg taaaagtcag gctacctttg   1140

cctgccattg tagaaatcaa cagaaggtta cttttcggtt attccaagtt taaagatgat   1200

ccaagaatta ttcacttaaa aaaactggta tatgactaca acaggaaatt agattcagtg   1260

ggtttaaaag accatcaggt gatgcaatta aaaactacca aattagaagc attgaggtgc   1320

tttgtaactt tgatcgttcg attgattaaa ttttctgtct ttgctatact atcgttaccg   1380

ggttctattc tcttcactcc aattttcatt atttgtcgcg tatactcaga aaagaaggcc   1440

aaagagggtt taaagaaatc attggttaaa attaagggta ccgatttgtt ggccacatgg   1500

aaacttatcg tggcgttaat attggcacca attttatacg ttacttactc gatcttgttg   1560

attattttgg caagaaaaca acactattgt cgcatctggg ttccttccaa taacgcattc   1620

atacaatttg tctattttta tgcgttattg gttttcacca cgtattcctc tttaaagacc   1680

ggtgaaatcg gtgttgacct tttcaaatct ttaagaccac tttttgtttc tattgtttac   1740

cccggtaaga agatcgaaga aatccaaaca acaagaaaga atttaagtct agagttgact   1800

gctgtttgta acgatttagg acctttggtt ttccctgatt acgataaatt agcgactgag   1860

atattctcta agagagacgg ttatgatgtc tcttctgatg cagagtcttc tataagtcgt   1920

atgagtgtac aatctagaag ccgctcttct tctatacatt ctattggctc gctagcttct   1980

aacgccctat caagagtgaa ttcaagaggc tcgttgaccg atattccaat tttttctgat   2040

gcaaagcaag gtcaatggaa aagtgaaggt gaaactagtg aggatgagga tgaatttgat   2100

gagaaaaatc ctgccatagt acaaaccgca cgaagttctg atctaaataa ggaaaacagt   2160

cgcaacacaa atatatcttc gaagattgct tcgctggtaa gacagaaaag agaacacgaa   2220

aagaaagaat ga                                                        2232
```

<210> SEQ ID NO 121
<211> LENGTH: 745
<212> TYPE: PRT
<213> ORGANISM: Naumovozyma dairenensis

<400> SEQUENCE: 121

-continued

```
Met Thr Met Lys Glu Lys Pro Val Glu Thr Ile Asp Val Asn Pro Lys
1               5                   10                  15

Pro Lys Ser Arg Ala His Ile Pro Lys Ile Ser Arg Gln Tyr Lys Asn
            20                  25                  30

Asp Tyr Thr Gly Leu Thr Tyr Asn Leu Lys Ser Phe Thr Tyr Asp Ile
        35                  40                  45

Val Val Phe Leu Phe Asn Ile Leu Phe Thr Ile Phe Phe Arg Glu Ile
    50                  55                  60

Lys Val Arg Gly Gly Tyr Asn Ile Pro Pro Asn Gly Thr Pro Thr Ile
65                  70                  75                  80

Leu Val Cys Ala Pro His Ala Asn Gln Phe Ile Asp Pro Ser Leu Val
                85                  90                  95

Met Thr Thr Thr Arg Lys Leu Ala Ala Thr His Gly Ser Ser Arg Gly
            100                 105                 110

Arg Gln Ala Cys Phe Val Thr Ala Ala Ser Ser Leu Lys Leu Lys Leu
        115                 120                 125

Val Gly Phe Phe Gly Arg Cys Met Gly Ser Val Pro Val Glu Arg Ala
    130                 135                 140

Gln Asp Asn Leu Lys Pro Val Ser Ser Asn Ile Glu Ile Tyr Ala Pro
145                 150                 155                 160

Asp Leu Ile Asn Asn Ser Thr Leu Ile Lys Gly Arg Cys Arg Thr Gly
                165                 170                 175

Glu Asn Ile Ser Pro Gln Phe Thr Lys Arg Phe Asn Ala Lys Gly Leu
            180                 185                 190

Leu Gly Leu Pro Asn Tyr Leu Ser Asn Ala Gln Ile Ala Lys Val Val
        195                 200                 205

Asp Asp Glu Thr Ile Ile Leu Ser Ser Pro Phe Lys Ser Ser Asn Pro
    210                 215                 220

Lys Val Arg Glu Tyr Leu Glu Glu Gly Thr Thr Phe Lys Tyr Ala Lys
225                 230                 235                 240

Pro Ile Asp Asn Thr Gln Val Phe Gln Asn Val Phe Asp His Leu His
                245                 250                 255

Thr Lys Gly Cys Val Gly Ile Phe Pro Glu Gly Gly Ser His Asp Arg
            260                 265                 270

Pro Ser Leu Leu Pro Ile Lys Ala Gly Val Ala Ile Met Ala Leu Gly
        275                 280                 285

Ala Val Ala Ala Asp Pro Ser Met Thr Val Ser Val Val Pro Val Gly
    290                 295                 300

Leu His Tyr Phe His Arg Asp Lys Phe Arg Ser Arg Ala Val Leu Glu
305                 310                 315                 320

Tyr Gly Glu Pro Ile Leu Val Asn Gly Glu Met Gly Lys Gln Tyr Ala
                325                 330                 335

Leu Asn Ser Arg Glu Thr Val Ser Lys Leu Leu Thr Lys Ile Thr Asp
            340                 345                 350

Ala Leu Phe Ser Val Thr Glu Asn Ala Pro Asp Phe Asp Thr Leu Met
        355                 360                 365

Thr Ile Gln Ala Ala Arg Arg Leu Tyr Gln Arg Ser Lys Leu Thr Leu
    370                 375                 380

Ser Leu Pro Val Ile Val Glu Ile Asn Arg Arg Leu Leu Val Gly Tyr
385                 390                 395                 400

Ser Lys Phe Lys Asp Asp Glu Arg Ile Ile Asn Leu Lys Lys Met Val
                405                 410                 415

His Glu Tyr Asn Asp Lys Leu Phe Ala Met Gly Leu Lys Asp His Gln
```

-continued

```
            420                 425                 430

Val Met Ser Leu His Thr Gly Pro Leu Glu Thr Ile Arg Cys Leu Phe
        435                 440                 445

Tyr Ile Val Ser Arg Val Ala Arg Leu Ser Val Phe Phe Ala Leu Ser
    450                 455                 460

Leu Pro Gly Ser Ile Leu Phe Thr Pro Ile Phe Val Gly Cys Ser Ile
465                 470                 475                 480

Tyr Ser Lys Lys Lys Ala Arg Glu Gly Leu Lys Lys Ser Leu Val Lys
                485                 490                 495

Ile Lys Gly Thr Asp Leu Leu Ala Thr Trp Lys Leu Ile Val Ala Leu
            500                 505                 510

Ile Met Ala Pro Ile Leu Tyr Val Thr Tyr Ser Leu Met Leu Val Ser
        515                 520                 525

Ile Ala Ser Lys Asn Glu Ile Ser Ile Trp Val Pro Ser Ser Ser Pro
    530                 535                 540

Ile Ile Gln Phe Phe Tyr Phe Tyr Ala Ile Leu Val Phe Ile Ser Tyr
545                 550                 555                 560

Ser Ser Leu Lys Thr Gly Glu Ile Gly Met Asp Leu Phe Lys Ser Leu
                565                 570                 575

Arg Pro Leu Phe Ile Thr Leu Phe Tyr Pro Lys Gln Lys Ile Glu Glu
            580                 585                 590

Ile Gln Thr Thr Arg Lys Lys Leu Ser Leu Glu Ile Thr Thr Ile Cys
        595                 600                 605

Asn Glu Leu Gly Pro His Val Phe Lys Asp Phe Asp Gln Phe Ala Thr
    610                 615                 620

Thr Asn Lys Leu Thr Asp Glu Ser Asp Ser Lys Leu Thr Val Arg Gly
625                 630                 635                 640

Arg His Gln Glu Gln Thr Pro Asp Phe Leu Lys Ile Gln His Asp Ser
                645                 650                 655

Ile Arg Gly Arg Ser Ser Asp Arg Asp Val Gly Ser Ser Arg Ser Ser
            660                 665                 670

Ser Val Gly Ser Val Val Ser Arg Ile Ser Ser Ala Leu Ser Arg Val
        675                 680                 685

Asn Ser Arg Gly Ser Leu Ser Asn Val Pro Ile Leu Ser Glu Gly Arg
    690                 695                 700

Ser Asn Tyr Arg Tyr Val Tyr Asp Ser Ser Ser Ser Asp Ser Asp Asn
705                 710                 715                 720

Glu Asp Ala Thr Gly Asn Ser Lys Ile Thr Ser Leu Ile Arg Glu Lys
                725                 730                 735

Trp Glu Ala Ser His Ala Lys Gly Glu
            740                 745
```

<210> SEQ ID NO 122
<211> LENGTH: 2238
<212> TYPE: DNA
<213> ORGANISM: Naumovozyma dairenensis

<400> SEQUENCE: 122

```
atgactatga aggagaaacc agtggaaacc atcgatgtta atcccaaacc taagtcaagg      60

gctcatattc ccaagatatc acgacagtac aagaatgatt ataccggtct aacatacaat     120

ttaaaatctt ttacttacga cattgtcgtt ttcctttta atatcctttt tacaattttc      180

tttagggaga ttaaagtccg tggtggttat aacataccac cgaacggtac accaacaatt     240

ttagtctgtg ctcctcatgc gaatcaattc attgatcctt ctctagtcat gaccactacg     300
```

-continued

```
aggaaactcg ctgctactca tggtagttca agaggtagac aagcttgctt tgtaactgcc    360
gcctccagtt tgaaattgaa attagtaggg tttttcggtc gttgtatggg gagtgtcccc    420
gtagagagag ctcaggataa tttaaaacct gtctcctcaa atattgaaat ttatgctcct    480
gacttaatta acaattcaac tttaattaaa ggtagatgtc gtacgggaga aaacatctca    540
cctcaattta caaagaggtt caatgcaaaa ggtttacttg gattaccaaa ttatttaagc    600
aatgctcaaa ttgcaaaagt ggttgatgat gaaactataa tcttatcatc tcctttcaaa    660
tcttccaatc cgaaagtgag agaatattta gaggaaggaa ccactttcaa atatgctaaa    720
ccaattgata atactcaagt gttccaaaac gtttttgatc atttacatac taagggttgc    780
gttggtattt ttccagaagg tgggtcacat gacagacctt ctttattacc aataaaagca    840
ggtgtcgcga ttatggcatt aggtgctgtt gccgcagatc catcaatgac agtttctgtc    900
gtaccagtcg gattacatta tttccataga gataaattta gatcaagagc tgtattggaa    960
tatggtgaac caattttagt taatggagaa atgggtaagc aatatgcatt gaattcaagg   1020
gaaactgttt ctaaattatt gacaaagatt actgatgcgc tattttctgt tacagagaat   1080
gctcctgatt tcgacacttt aatgactatt caagctgccc gtagattata tcaacgttcc   1140
aaattgacac taagtttacc tgtcattgtc gagattaata gaagattact tgttggttat   1200
tctaagttta aagatgacga aagaattatc aatttgaaaa aaatggttca tgaatataat   1260
gataaattat ttgcaatggg attaaaagat catcaagtta tgtcattaca tactggtcca   1320
ttagaaacaa taagatgttt attttatatt gtttcaagag tagcaagatt atctgtgttt   1380
tttgctctat cattaccggg atctatatta tttacaccaa ttttcgttgg ttgtagtatt   1440
tattccaaga aaaaagcaag agaaggttta aagaaatcct tagtaaaaat taaaggcaca   1500
gatttattag ctacttggaa acttatagtt gcattaatta tggccccaat tctttatgtc   1560
acgtattcgt taatgttagt ttccattgca tccaaaaatg aaatatcaat ttgggttccg   1620
tcatcaagtc caatcatcca attcttttat ttttatgcca tactagtctt catttcatat   1680
tcaagtttga aaactggtga aatcggaatg gatcttttca aatcattacg ccctttattt   1740
attacattat tctatcctaa gcaaaaaatt gaagagattc aaacaacgag aaagaaattg   1800
agtttagaaa ttacaactat ttgtaatgaa ttaggtccac atgtattcaa agattttgat   1860
caatttgcaa ctaccaataa attaactgat gaatctgata gtaaattgac agttagaggt   1920
cgtcaccaag aacaaactcc tgatttccta aagattcaac atgattcaat tcgtggacgt   1980
agtagtgata gagacgttgg ttctagtaga tcttcttctg tagggtctgt cgtttcaaga   2040
atatcaagtg cgttgtctag agtcaattct agaggttcat tgtctaatgt tccaatttta   2100
tcagagggga ggtcaaatta ccgatatgtt tatgattcct cttcaagtga tagtgataat   2160
gaagatgcta cgggaaattc gaagatcact tctttaatta gagaaaaatg ggaagcttct   2220
catgcaaagg gtgaataa                                                 2238
```

<210> SEQ ID NO 123
<211> LENGTH: 722
<212> TYPE: PRT
<213> ORGANISM: Torulaspora delbrueckii

<400> SEQUENCE: 123

```
Met Ala Glu Asp Ser Asn Pro Ser Ser Lys Lys Gln Ile Lys Ala His
1               5                   10                  15

Val Pro Asn Ala Lys Ile Glu Tyr Asp Asn Lys Tyr Asn Gly Tyr Gly
```

```
            20                  25                  30

Tyr Ser Ile Gln Ala Trp Leu Phe Asp Cys Val Leu Phe Leu Leu Asn
        35                  40                  45

Ile Val Phe Thr Ile Phe Phe Arg Glu Ile Lys Val Arg Gly Gly His
    50                  55                  60

Asn Val Pro Pro Ile Gly Thr Ala Thr Met Leu Val Cys Ala Pro His
65                  70                  75                  80

Ala Asn Gln Phe Ile Asp Pro Ser Leu Val Met Val Thr Thr Arg Lys
                85                  90                  95

Leu Ala Lys Glu Ser Arg Asn Arg Ser Arg Gln Val Cys Phe Val Thr
            100                 105                 110

Ala Glu Ser Ser Leu Lys Lys Lys Phe Val Ser Leu Phe Gly Ile Cys
        115                 120                 125

Thr Gly Ala Ile Pro Val Pro Arg Ala Gln Asp Asn Leu Lys Pro Val
    130                 135                 140

Asp Ser Asp Val Lys Ile Tyr Cys Pro Asp Leu Glu Asn Asn Ala Thr
145                 150                 155                 160

Met Val Lys Gly Arg Leu Asp Ser Gly Gly Ser Pro Lys Phe Thr Lys
                165                 170                 175

Arg Phe Thr Ala Lys Ser Leu Ile Gly Leu Pro Asn Tyr Leu Gly Asn
            180                 185                 190

Ala Gln Ile Ala Glu Val Lys Asp Asp Glu Thr Ile Ile Leu Lys Ala
        195                 200                 205

Pro Phe Lys Phe Lys Thr Asn Glu Lys Ile Arg Ser Leu Leu Thr Glu
    210                 215                 220

Gly Thr Thr Phe Lys Tyr Ala Pro His Ile Asp Asn Ser Lys Val Phe
225                 230                 235                 240

Gln Asn Val Phe Gly His Leu His Thr Lys Gly Thr Val Gly Ile Phe
                245                 250                 255

Pro Glu Gly Gly Ser His Asp Arg Pro Ser Leu Leu Pro Ile Lys Ala
            260                 265                 270

Gly Val Ala Ile Met Ala Leu Gly Ala Thr Ala Ala Asp Pro Ser Met
        275                 280                 285

Lys Val His Val Val Pro Cys Gly Leu His Tyr Phe His Arg Asp Lys
    290                 295                 300

Phe Arg Ser Arg Ala Val Leu Glu Tyr Gly Glu Pro Ile Ile Val Asp
305                 310                 315                 320

Gly Glu Met Gly Lys Arg Tyr Ala Lys Asn Pro Arg Glu Thr Val Gln
                325                 330                 335

Glu Leu Leu Lys Val Ile Thr Ser Ser Leu Tyr Ala Val Thr Glu Asn
            340                 345                 350

Ala Pro Asp Phe Asp Val Leu Met Thr Ile Gln Ala Ala Arg Arg Leu
        355                 360                 365

Tyr Gln Pro Thr Arg Gly Lys Ile Pro Leu Pro Thr Val Val Asp Ile
    370                 375                 380

Asn Arg Arg Leu Leu Leu Gly Tyr Ser Thr Tyr Lys Asp Asp Pro Arg
385                 390                 395                 400

Ile Ile His Leu Gln Lys Met Val Asn Arg Tyr Asn Asn Ala Leu Tyr
                405                 410                 415

Ser Leu Gly Leu Lys Asp His Gln Val Ala Glu Leu Lys Thr Lys Lys
            420                 425                 430

Arg Glu Val Leu Arg Ser Leu Phe Val Leu Val Glu Arg Met Ile Arg
        435                 440                 445
```

-continued

```
Leu Leu Ile Phe Phe Cys Leu Ser Leu Pro Gly Ser Ile Leu Phe Thr
    450                 455                 460

Pro Ile Phe Ile Ser Cys Ser Ile Tyr Ala Lys Lys Lys Ala Lys Glu
465                 470                 475                 480

Gly Leu Ser Lys Ser Leu Val Lys Ile Lys Gly Thr Asp Leu Ile Ala
                485                 490                 495

Thr Trp Lys Leu Met Phe Ala Leu Val Phe Ala Pro Leu Leu Tyr Val
            500                 505                 510

Thr Tyr Ser Leu Ile Leu Val Tyr Phe His Ala Arg His Tyr Glu Trp
        515                 520                 525

Ile Ser Lys Ile Tyr Val Pro Phe Asp Asn Lys Phe Leu Gln Phe Cys
    530                 535                 540

Tyr Tyr Tyr Gly Leu Leu Val Ala Ala Thr Tyr Ser Ser Leu Lys Thr
545                 550                 555                 560

Gly Glu Ile Gly Met Asp Leu Phe Lys Ser Leu Pro Pro Leu Phe Ile
                565                 570                 575

Thr Leu Ile Tyr Pro Gly Arg Lys Ile Gln Gln Leu Lys Ser Met Arg
            580                 585                 590

Glu Lys Leu Ser Gln Glu Ile Thr Ala Val Ile Asn Glu Leu Gly Pro
        595                 600                 605

Lys Leu Phe Pro Asn Phe Asp Lys Ile Ile Lys Ala His Phe Asp Ser
    610                 615                 620

His Val Glu Glu Val Ile Ser Glu Ala Glu Glu Glu Leu Thr Asp Asp
625                 630                 635                 640

Ser Ala Ala Val Phe Ser Asn Ser Arg Ser Arg Ser Gly Ser Val His
                645                 650                 655

Ser Ala Thr Ser Thr Ser Ser Asn Ala Leu Ser Lys Val Asn Ser Arg
            660                 665                 670

Gly Ser Leu Thr Asp Val Pro Ile Phe Ala Glu Gly Lys His Thr Leu
        675                 680                 685

His His Ser Asp Asp Glu Ile Glu Leu Ser Pro Glu Asp Lys Glu Asn
    690                 695                 700

Asp Ser Lys Ile Thr Ala Met Ile Arg Glu Lys Trp Glu Arg Glu Lys
705                 710                 715                 720

Lys Asp
```

<210> SEQ ID NO 124
<211> LENGTH: 2169
<212> TYPE: DNA
<213> ORGANISM: Torulaspora delbrueckii

<400> SEQUENCE: 124

```
atggcggaag attcaaaccc cagctcaaag aaacaaataa aggctcatgt gcctaatgct      60

aagatcgaat acgataacaa gtataatggg tatggatatt ctattcaagc atggttattc     120

gattgtgtat tgttcttgtt gaacattgtt ttcaccatat tctttcgaga aattaaagtt     180

cgtggtggtc acaacgtccc acccatcgga acagcgacaa tgttggtgtg tgcccctcat     240

gcaaatcaat tcatcgaccc ttctctagtg atggtaacca ctaggaaact tgccaaagaa     300

tctagaaata gatctagaca ggtttgcttt gtaactgcag aatctagtct caagaagaaa     360

ttcgtgtctc tctttggtat atgtacaggc gctatcccag tgccaagggc ccaggacaac     420

ttgaaaccag ttgattctga tgttaagata tactgtccgg atttagaaaa taatgctact     480

atggtgaagg gccgtttgga ctctggaggt tctccaaaat ttaccaagag attcacagcc     540
```

```
aaatctctaa ttggtttgcc caactatctc gggaatgccc aaattgcaga ggttaaggat    600

gatgaaacga ttatacttaa ggctccgttc aagtttaaga ccaacgaaaa gattagatca    660

ttattgaccg agggaacaac ttttaaatac gctccacaca tcgacaactc caaagttttt    720

caaaacgttt ttggccattt acatacgaaa ggtactgttg ggatctttcc agagggtggg    780

tcccacgata gaccttcatt gttaccgatt aaggctggtg tcgctattat ggctctcggt    840

gccacggcag cagatccaag catgaaagtt catgttgtac catgtgggct gcactacttt    900

cacagggaca aattcagatc aagagccgtc ttggagtatg gcgagcctat cattgtcgat    960

ggagaaatgg gaaaaagata tgcgaaaaat cctagagaaa ctgtacaaga attattgaaa   1020

gtcattacta gttccctgta tgctgtgacc gaaaatgcgc cggatttcga cgttttaatg   1080

actattcagg cggcaagaag actctatcaa ccaacaagag ggaagattcc tttacctaca   1140

gtggtcgata tcaacagaag attattgctc ggctactcaa cttataagga tgatcctcgt   1200

atcattcatt tgcaaaaaat ggtcaacagg tataacaacg ccttgtactc attgggactc   1260

aaggatcatc aagtcgcaga gttgaaaacg aagaagagag aagtacttag aagtttgttc   1320

gttttggttg aaagaatgat aaggcttctc attttctttt gtttgtctct accgggttcc   1380

atcctattca ctccaatttt tattagttgc agcatttacg ccaagaagaa ggcaaaggaa   1440

ggcttgtcga agtctttggt aaagataaaa ggtactgatt tgattgccac atggaagcta   1500

atgtttgcac tcgtatttgc ccctcttctt tatgtcactt attcgttgat tttggtatat   1560

tttcatgcac gtcattacga gtggatttcc aagatttatg ttccatttga caacaaattt   1620

ctgcagttct gctactatta tggtcttctt gtggctgcca catattcaag tttgaaaacc   1680

ggagaaatag gaatggattt gttcaagtca ttaccacctc tattcatcac tctcatatac   1740

ccaggcagga agattcaaca gttgaaaagc atgcgtgaaa aactgagcca agaaataaca   1800

gctgtgatta acgagcttgg tcctaaactt ttccccaatt ttgacaagat tatcaaagca   1860

catttcgata gccatgttga agaagtcata tctgaagctg aagaagagct aactgatgat   1920

agcgcggcgg tgttcagcaa ctcgcgcagt cggtcaggct ctgttcattc tgcaacttcc   1980

acgagctcaa atgctttgtc aaaggttaac tcaagaggtt ctttgaccga tgtgcctatc   2040

tttgccgagg gaaaacatac tttgcatcac agtgatgatg agatagagtt gtcacctgaa   2100

gacaaagaga acgattctaa gatcactgct atgattagag agaaatggga gcgtgagaag   2160

aaagattaa                                                           2169
```

<210> SEQ ID NO 125
<211> LENGTH: 733
<212> TYPE: PRT
<213> ORGANISM: Naumovozyma castellii

<400> SEQUENCE: 125

```
Met Pro Pro Lys Ser Asn Ala His Val Pro Glu Val Ser Arg Thr Tyr
1               5                   10                  15

Lys Asn Asn Phe Asn Gly Leu Val Tyr Asn Ile His Thr Trp Thr Tyr
            20                  25                  30

Asp Cys Ile Ile Phe Leu Phe Asn Ile Ile Phe Thr Ile Phe Phe Arg
        35                  40                  45

Glu Ile Lys Val Arg Gly Gly Tyr Asn Val Pro Pro Ala Gly Thr Pro
    50                  55                  60

Thr Ile Leu Val Cys Ala Pro His Ala Asn Gln Phe Ile Asp Pro Thr
65                  70                  75                  80
```

-continued

```
Leu Val Met Val Thr Thr Arg Lys Leu Gly Met Tyr Gly Ala Thr Ser
                85                  90                  95

Val Ser Arg Ser Arg Gln Ala Cys Phe Val Thr Ala Ala Ser Ser Leu
            100                 105                 110

Asn Met Lys Leu Val Gly Phe Phe Gly Arg Arg Met Gly Gly Ile Pro
        115                 120                 125

Val Ala Arg Ala Gln Asp Tyr Leu Lys Pro Val Asp Asp Asn Leu Glu
    130                 135                 140

Ile Tyr Ala Pro Asp Leu Glu Asn Asn Pro Lys Leu Ile Lys Gly Arg
145                 150                 155                 160

Cys Lys Asp Ser Lys Ser Pro Glu Phe Thr Lys Arg Phe Thr Ala Lys
                165                 170                 175

Ser Leu Leu Gly Leu Pro Asn Tyr Leu Ser Asn Ala Gln Ile Ala Gln
            180                 185                 190

Ile Gln Asp Asp Glu Thr Ile Ile Leu Ser Ser Pro Phe Lys Ile Ser
        195                 200                 205

Asp Pro Arg Val Arg Lys Leu Leu Asn Asn Gly Thr Thr Phe Lys Tyr
    210                 215                 220

Ala Asn Lys Val Asp Asn Ser Lys Val Phe Gln Ser Val Phe Asp His
225                 230                 235                 240

Leu His Thr Lys Gly Cys Val Gly Ile Phe Pro Glu Gly Gly Ser His
                245                 250                 255

Asp Arg Pro Ser Leu Leu Pro Ile Lys Ala Gly Val Ala Ile Met Ala
            260                 265                 270

Leu Gly Ala Ala Ala Ala Asp Ala Asn Ile Lys Val His Val Val Pro
        275                 280                 285

Val Gly Leu His Tyr Phe His Arg Asp Lys Phe Arg Ser Arg Ala Val
    290                 295                 300

Leu Glu Tyr Gly Glu Pro Ile Val Val Asp Gly Thr Met Gly Lys Glu
305                 310                 315                 320

Tyr Ala Gln Ala Pro Arg Glu Thr Val Ser Lys Leu Leu Ser Arg Ile
                325                 330                 335

Thr Asp Ala Leu Phe Ser Val Thr Glu Asn Ala Pro Asp Tyr Asp Thr
            340                 345                 350

Leu Met Thr Ile Gln Ala Ala Arg Arg Leu Tyr Gln Pro Ser Glu Lys
        355                 360                 365

Arg Leu Ser Leu Pro Val Val Val Glu Ile Asn Arg Arg Leu Leu Val
    370                 375                 380

Gly Tyr Ser Lys Phe Lys Ser Asp Glu Arg Val Ile His Leu Lys Lys
385                 390                 395                 400

Met Val Gln Glu Tyr Asn Glu Lys Leu Tyr Ser Met Gly Leu Lys Asp
                405                 410                 415

His Gln Val Arg Glu Leu Glu Ser His Thr Val Gln Asn Thr Ile Arg
            420                 425                 430

Thr Leu Val Thr Leu Val Thr Arg Val Ser Arg Leu Leu Leu Phe Phe
        435                 440                 445

Met Leu Ala Leu Pro Gly Ser Ile Leu Phe Thr Pro Ile Phe Ile Gly
    450                 455                 460

Ser Ser Ile Tyr Ser Lys Lys Lys Ala Arg Glu Gly Leu Lys Lys Ser
465                 470                 475                 480

Leu Val Lys Ile Lys Gly Thr Asp Leu Leu Ala Thr Trp Lys Leu Ile
                485                 490                 495
```

```
Leu Ala Leu Val Met Ala Pro Ile Ser Tyr Val Thr Tyr Ser Leu Ile
            500                 505                 510

Leu Ile Ser Leu His Ser Arg Lys Asn Gly Trp Val Gln Trp Ile Trp
        515                 520                 525

Val Pro Ser Glu Asn Val Phe Ile Gln Phe Pro Tyr Phe Tyr Met Gln
    530                 535                 540

Leu Val Leu Thr Thr Tyr Gly Ser Leu Lys Thr Gly Glu Ile Gly Met
545                 550                 555                 560

Asp Leu Phe Lys Ser Leu Arg Pro Leu Val Val Thr Leu Met Tyr Pro
                565                 570                 575

Gly Lys Lys Ile Arg Glu Ile Gln Ser Ile Arg Glu Gln Leu Ser Glu
            580                 585                 590

Glu Ile Thr Ser Val Cys Asn Glu Leu Gly Pro Ser Val Phe Lys Asp
        595                 600                 605

Phe Asp Gln Phe Ala Ile Asn Asn Glu Ile Glu Ser Glu Arg Gly Arg
    610                 615                 620

Gly Arg Tyr Glu Lys Glu Lys Thr Pro Asp Tyr Leu Lys Ile Gln Arg
625                 630                 635                 640

Asp Pro Ser Arg Ser Arg Ser Arg Gly Ala Arg Ser Arg Ser Ser Ser
                645                 650                 655

Ile Ser Ser Phe Thr Ser Arg Ile Ser Asn Ala Ile Ser Arg Val Asn
            660                 665                 670

Ser Arg Gly Ser Leu Ser Asp Ile Pro Ile Leu Ser Glu Ala Arg Tyr
        675                 680                 685

Ser Ser Asn Asn Val Ile Asn Asp Ser Asp Ser Ser Cys Ser Ser Ser
    690                 695                 700

Asp Glu Glu Asn Ile Lys Ala Gly Ser Thr Ser Lys Ile Ser Ser Leu
705                 710                 715                 720

Met Arg Ala Arg Trp Glu Lys Ser His Asp Lys Glu Glu
                725                 730
```

<210> SEQ ID NO 126
<211> LENGTH: 2202
<212> TYPE: DNA
<213> ORGANISM: Naumovozyma castellii

<400> SEQUENCE: 126

```
atgcccccta aatcaaacgc tcacgtccca gaggtttcac gaacgtacaa gaacaacttc      60

aatgggctgg tatacaatat tcacacatgg acttacgatt gcataatatt cctcttcaat     120

attatattca ctattttctt ccgtgaaatt aaagttcgtg gaggttacaa cgtacctccc     180

gctgggaccc ccacaatact cgtctgtgct cctcatgcca atcaattcat tgaccctaca     240

ttggtaatgg tgacaaccag aaaactaggt atgtatggtg ccacctctgt ctctcgttca     300

agacaggcat gtttcgttac agctgcttca agtttgaata tgaaacttgt tggatttttt     360

ggaagaagaa tgggtgggat tcctgttgct agagcacaag attacttaaa accagtagat     420

gacaacttgg aaatctacgc tcccgacttg gaaaataatc caaaattaat aaaaggtcgt     480

tgtaaggatt ctaaatcacc tgaattcaca aagagattca ctgcaaaatc ccttttgggg     540

ttgcctaatt atttaagtaa tgcccaaatt gctcagattc aagatgatga aactatcata     600

ttaagctctc cctttaagat ttctgatcca agagtgagga aactattaaa taacggtaca     660

actttcaaat atgctaacaa ggtggataat agtaaagtat tccagagtgt ttttgatcat     720

ctgcatacaa aaggttgtgt cgggattttc ccagaaggtg gatctcacga tagaccttct     780
```

-continued

```
ttattaccta ttaaagcagg tgttgccatt atggccttag gtgctgcagc agctgatgca    840

aatataaaag tacatgttgt gcccgttggg ttgcattact tccacagaga caaatttaga    900

tcaagagctg ttctcgagta cggtgaaccc atagtcgtgg atggaaccat gggaaaagaa    960

tatgcacagg ctccacgtga aacagtttct aaattgttgt caagaattac agatgcacta   1020

ttctctgtta cagaaaatgc ccctgattat gatactttga tgactatcca ggcagctaga   1080

agattgtacc aaccttctga gaaaagatta tctttgcccg ttgtcgttga aattaataga   1140

agattactcg tgggatattc aaaatttaaa agtgatgaaa gggtcattca tttgaagaaa   1200

atggttcaag aatacaatga aaaattatac tctatggggt taaaagatca tcaagttaga   1260

gaattagaat ctcatactgt gcaaaataca attagaactt tggttacctt agtgacaaga   1320

gtttctagat tattactatt cttcatgttg gctcttcccg ggtccattct tttcactcct   1380

atcttcatcg gttctagcat ctattcaaag aagaaggcaa gagaagggtt gaaaaaatca   1440

ttagtgaaaa ttaagggaac tgatttatta gccacttgga aacttatctt agcacttgtg   1500

atggctccaa tttcatatgt tacttattcc ctcattttaa tttccctgca ttctcgtaaa   1560

aatggatggg ttcaatggat ttgggtacct agtgaaaatg ttttcatcca attcccttat   1620

ttttacatgc agttggtact taccacatat ggttctttga agactggtga aattggaatg   1680

gatcttttta aatctttacg tcccccttgta gtcaccttga tgtatccagg taagaaaatc   1740

agagaaattc aatcaatccg tgaacaattg agtgaagaga tcacttcagt ttgtaacgag   1800

ttaggtcctt ccgttttcaa agactttgat caatttgcaa ttaataacga gatcgagagt   1860

gaaagaggca gaggtcgcta tgagaaagaa aagactcctg attatttgaa gattcaacgt   1920

gatcctagtc gtagccgtag tcgtggtgct agaagtcgtt catcatcgat tagttcattt   1980

acttcacgta tctctaatgc tatttctaga gtgaactcca gaggttccct ctctgatatt   2040

ccaattttat cagaagcaag atatagttcc aataatgtca tcaatgatag tgattcatcc   2100

tgttcctctt ctgatgaaga gaatataaaa gcaggttcta cttctaaaat ttcatcttta   2160

atgagagcta gatgggaaaa atcgcatgat aaggaggaat ag                      2202
```

<210> SEQ ID NO 127
<211> LENGTH: 370
<212> TYPE: PRT
<213> ORGANISM: Microbotryum violaceum

<400> SEQUENCE: 127

```
Met Thr Ser Leu Arg Asp Val Asn Pro Thr Ser Thr Gln Ala Ser Leu
1               5                   10                  15

Tyr Lys Asp Glu Gly Lys Asp Lys Glu Asp Val Ala Pro Gln Glu Lys
            20                  25                  30

Tyr Thr Gln Ser Leu Arg Thr Asn Ile Lys Phe Ala Pro Leu Ala Val
        35                  40                  45

Pro Arg His Arg Arg Leu Gln Thr Met Ala Val Leu Gly Trp Thr Thr
    50                  55                  60

Ala Leu Pro Leu Met Leu Gly Leu Phe Phe Leu Leu Cys Ser Ile Pro
65                  70                  75                  80

Leu Leu Trp Pro Ile Ile Val Pro Tyr Leu Phe Trp Ile His Leu Ile
                85                  90                  95

Asp Asn Ser Pro Thr Gln Gly Gly Arg Ala Ser Lys Trp Leu Arg Gln
            100                 105                 110

Ser Arg Phe Trp Val Trp Phe Thr Gly Tyr Tyr Pro Ile Ser Leu Val
        115                 120                 125
```

```
Lys Thr Val Asp Leu Pro Pro Asp Arg Lys Tyr Val Phe Gly Tyr His
    130                 135                 140

Pro His Gly Ile Ile Gly Met Gly Ala Ile Ala Asn Phe Gly Thr Asp
145                 150                 155                 160

Ala Thr Gly Phe Ser Glu Leu Phe Pro Gly Leu Asn Pro His Leu Leu
                165                 170                 175

Thr Leu Ala Ser Asn Phe Lys Leu Pro Ile Tyr Arg Asp Phe Leu Leu
            180                 185                 190

Ala Leu Gly Ile Cys Ser Val Ser Met Lys Ser Cys Gln Asn Ile Leu
        195                 200                 205

Lys Gln Gly Pro Gly Ser Ala Leu Thr Ile Val Val Gly Gly Ala Ala
    210                 215                 220

Glu Ser Leu Ser Ala His Pro Gly Thr Ala Asn Leu Thr Leu Arg Arg
225                 230                 235                 240

Arg Met Gly Phe Ile Lys Leu Ala Met Arg Gln Gly Ala Asp Leu Val
                245                 250                 255

Pro Val Phe Ser Phe Gly Glu Asn Asp Ile Phe Glu Gln Met Pro Asn
            260                 265                 270

Glu Arg Gly Thr Lys Leu Tyr Lys Met Gln Lys Lys Phe Gln Thr Ala
        275                 280                 285

Phe Gly Phe Thr Leu Pro Ile Phe His Gly Arg Gly Ile Phe Asn Tyr
    290                 295                 300

Asn Leu Gly Ile Leu Pro Tyr Arg His Pro Ile Val Ser Val Val Gly
305                 310                 315                 320

Arg Pro Ile Arg Val Ser Gln Arg Asp Asn Pro Thr Lys Glu Glu Leu
                325                 330                 335

Glu Glu Val Gln Glu Arg Tyr Ile Glu Glu Leu Lys Arg Ile Trp Asp
            340                 345                 350

Asp Tyr Lys Asn Gln His Ala Ile Lys Arg Lys Gly Glu Leu Arg Ile
        355                 360                 365

Ile Ala
    370
```

<210> SEQ ID NO 128
<211> LENGTH: 1113
<212> TYPE: DNA
<213> ORGANISM: Microbotryum violaceum

<400> SEQUENCE: 128

```
atgacgtcgc tgcgagacgt gaacccgacc tcgacccaag catcgttgta caaagacgag      60

ggcaaggaca aggaggatgt cgcaccgcag gagaaataca cgcagtcgct ccggaccaac     120

atcaaatttg cacctctagc tgtaccacgc catcgacgac tgcagaccat ggcagtgttg     180

ggatggacga ccgcactgcc actcatgctt ggtttgttct ttctattgtg ctcaatcccc     240

cttctatggc ccatcatcgt gccctatctc ttctggatcc acctcatcga caactcgccg     300

acgcagggag gacgagcgag caaatggctt cgccaaagtc ggttctgggt gtggttcaca     360

gggtactatc ctatcagtct cgtcaagacg gtcgatttac ctccagatcg gaaatacgtc     420

ttcggttacc acccccatgg cataattgga atgggtgcaa ttgccaattt tgggaccgac     480

gccactgggt tctctgagct cttcccagga ctcaaccctc atctcctcac acttgccagc     540

aacttcaaat tgccgatata tcgagacttc ttgcttgcgc tcggcatctg ctcagtcagt     600

atgaaatctt gccaaaacat cctcaaacag ggcccggggt ctgctttgac cattgtcgtc     660
```

-continued

```
ggaggagctg cggaatccct ttcggcgcat cctggcacag ccaacttgac actccgtcgc    720

cgaatgggct tcatcaagct ggcgatgcgt caaggcgcgg atcttgtacc cgtcttttca    780

ttcggagaga acgatatctt cgaacagatg ccgaacgaga gagggacgaa gctgtacaag    840

atgcaaaaga agtttcagac cgcttttgga ttcactctac cgatcttcca cggccgagga    900

atttttaact ataaccttgg catcttgccg taccgtcatc cgatcgtgtc ggtcgtcggt    960

cggcccatcc gcgtttcgca gcgtgacaac cctactaagg aggaactcga ggaggtgcag   1020

gaacgataca tcgaggagtt gaagagaatc tgggacgatt acaaaaatca acatgccatc   1080

aagcgaaagg gcgaacttcg tattattgcc tga                                1113
```

<210> SEQ ID NO 129
<211> LENGTH: 365
<212> TYPE: PRT
<213> ORGANISM: Puccinia graminis

<400> SEQUENCE: 129

```
Met Lys Asp Asp Ser Arg Ser Pro Ser Gly Ser Glu Pro Glu Gly Asp
1               5                   10                  15

Asn His Lys Lys Glu Lys Arg Pro Ile Trp Ala Pro Ile Arg Val Pro
            20                  25                  30

Pro Tyr Arg Arg Ile Gln Thr Ala Ala Val Leu Leu Trp Thr Ser Gln
        35                  40                  45

Leu Ser Leu Cys Ile Ser Leu Phe Phe Phe Leu Met Ser Tyr Pro Ile
    50                  55                  60

Thr Trp Pro Ile Leu Leu Pro Tyr Val Ile Trp Ile Leu Val Ile Asp
65                  70                  75                  80

Pro Ala Pro Glu Lys Gly Gly Arg Leu Asn Gln Ser Val Arg Thr Trp
                85                  90                  95

Lys Phe Trp Asn Leu Phe Ala Ser Tyr Phe Pro Ile Ser Leu Ile Lys
            100                 105                 110

Thr Val Asp Leu Pro Ser Asp Arg Lys Tyr Val Phe Gly Tyr His Pro
        115                 120                 125

His Gly Ile Ile Gly Met Gly Ala Val Ala Asn Phe Gly Thr Glu Ala
    130                 135                 140

Thr Gly Phe Ser Glu Lys Phe Pro Gly Leu Asn Pro His Leu Leu Thr
145                 150                 155                 160

Leu Ser Thr Asn Phe Ile Ile Pro Phe Tyr Arg Asp Leu Ile Leu Ser
                165                 170                 175

Leu Gly Ile Cys Ser Val Ser Ile Lys Ser Cys Ile Ser Ile Leu Lys
            180                 185                 190

Ser Lys Asn Lys Arg Ser Ala Asp Val Lys Asn Asn Lys Gly Glu Gly
        195                 200                 205

Asn Cys Leu Val Ile Val Val Gly Gly Ala Ala Glu Ser Leu Ser Ala
    210                 215                 220

His Pro Gly Thr Ala Asp Leu Thr Leu Lys Arg Arg Leu Gly Phe Ile
225                 230                 235                 240

Lys Leu Ala Ile Arg Glu Gly Ala Asp Leu Val Pro Val Phe Ser Phe
                245                 250                 255

Gly Glu Asn Asp Ile Tyr Ala Gln Leu Ser Asn Ser Lys Gly Thr Ala
            260                 265                 270

Leu Tyr Ser Leu Gln Lys Arg Phe Gln Ala Val Phe Gly Phe Thr Leu
        275                 280                 285

Pro Val Phe His Gly Arg Gly Ile Phe Asn Tyr Ser Leu Gly Leu Leu
```

-continued

```
    290                 295                 300

Pro Tyr Arg His Pro Ile Val Ser Val Val Gly Lys Pro Ile Arg Val
305                 310                 315                 320

Glu Gln Asn Lys Asn Pro Gly Leu Glu Glu Ile Glu Lys Val Gln Lys
                325                 330                 335

Glu Tyr Ile Ala Glu Leu Thr Ala Val Trp Asp Gln Tyr Lys Asp Leu
            340                 345                 350

Tyr Ala Arg Asn Arg Lys Ser Glu Leu Thr Leu Ile Ala
        355                 360                 365


<210> SEQ ID NO 130
<211> LENGTH: 1098
<212> TYPE: DNA
<213> ORGANISM: Puccinia graminis

<400> SEQUENCE: 130

atgaaggatg actccagaag cccgtctggg tccgaacccg agggcgataa tcacaagaag      60

gagaaaaggc caatctgggc tccgattcgt gtacctcctt acaggcgcat ccaaacggcc     120

gcagtactct tatggacttc tcaactctca ctatgcattt ccttattctt tttcttaatg     180

tcttacccga tcacctggcc gatcctcctt ccatacgtta tttggatctt ggtcatagat     240

cctgctcccg agaagggtgg ccggttgaat caatctgttc ggacctggaa gttttggaat     300

ctatttgcgt cgtatttccc aatcagttta atcaaaactg ttgatttgcc cagtgaccgc     360

aaatatgtct ttggttacca ccctcatggt atcatcggaa tgggcgcggt ggccaacttt     420

ggaacggaag cgacaggatt ttcggaaaaa ttccctggtc tcaatccaca tctactcaca     480

ttgagcacga actttatcat cccattctat cgagacctga tcctcagtct tggaatctgt     540

tcggtgtcga tcaaatcatg catctcgatc ctcaaatcca aaaacaaacg ctcagctgat     600

gtcaagaaca ataagggcga aggaaattgt ttggttatcg ttgtcggtgg ggctgcggaa     660

agtttgtctg ctcatcctgg aacagccgat ctcactctaa aacgacggct gggtttcatc     720

aaactggcca ttcgagaagg agccgatctc gtccctgtgt tctcctttgg agagaatgac     780

atttacgccc aattatcaaa ctcaaaaggc acggcactct actctcttca aaaacgattt     840

caagctgtat ttggctttac cttacctgtt ttccatggcc gaggtatctt caactactct     900

ctcggcttgc ttccctatcg acacccgatt gtttcagtag ttggtaaacc tattcgagtc     960

gagcaaaata aaaaccccgg gctcgaagaa atcgaaaagg ttcagaaaga atacattgct    1020

gaacttaccg cagtatggga tcagtataaa gatttatacg ctagaaatcg gaagagtgaa    1080

ttgactttga ttgcttag                                                  1098


<210> SEQ ID NO 131
<211> LENGTH: 373
<212> TYPE: PRT
<213> ORGANISM: Gloeophyllum trabeum

<400> SEQUENCE: 131

Met Asp Ala Gly Arg Ala Phe Ser Ser Ala Ser Arg Ser Leu Ser Ser
1               5                   10                  15

Ser Ser Leu Lys Asp Lys Leu Ser Lys Val Ser Lys Leu Ser Thr Thr
            20                  25                  30

Pro Leu Arg Pro Val Ala Ala His Val Lys Asn Ile Asp Phe Val Pro
        35                  40                  45

Ser Lys Ile Pro Arg Lys Arg Arg Leu Gln Met Leu Ala Val Ala Val
    50                  55                  60
```

```
Trp Ala Leu Leu Ile Pro Ile Thr Thr Phe Leu Phe Leu Ile Leu Cys
65                  70                  75                  80

Ser Phe Pro Pro Leu Trp Pro Phe Leu Ala Ala Tyr Leu Ile Trp Ile
                85                  90                  95

Arg Trp Ile Asp Arg Ser Pro Glu His Gly Gly Arg Ile Ser Pro Trp
            100                 105                 110

Phe Arg Ser Met Arg Phe Trp Arg Tyr Phe Ala Asp Tyr Tyr Pro Ala
        115                 120                 125

Ser Phe Leu Lys Glu Cys Asp Leu Pro Pro Asp Arg Pro Tyr Val Phe
    130                 135                 140

Gly Tyr His Pro His Gly Ile Ile Gly Met Gly Ala Met Ala Thr Phe
145                 150                 155                 160

Ala Thr Glu Ala Thr Gly Phe Ser Glu Gln Phe Pro Gly Leu Thr Pro
                165                 170                 175

His Leu Leu Thr Leu Ala Thr Asn Phe Thr Met Pro Ile Tyr Arg Asp
            180                 185                 190

Ile Ile Leu Ala Leu Gly Ile Cys Ser Val Ser Lys Gln Ser Cys Ser
        195                 200                 205

Asn Ile Leu Ser Ser Gly Pro Gly Gln Ala Ile Thr Ile Val Val Gly
    210                 215                 220

Gly Ala Ala Glu Ser Leu Ser Ala Arg Pro Gly Thr Ala Asp Leu Thr
225                 230                 235                 240

Leu Lys Arg Arg Leu Gly Phe Ile Lys Ile Ala Ile Gln His Gly Ala
                245                 250                 255

Ala Leu Val Pro Val Phe Ser Phe Gly Glu Asn Asp Ile Tyr Gln Gln
            260                 265                 270

Met Pro Asn Glu Lys Gly Thr Thr Ile Tyr Ala Leu Gln Lys Lys Phe
        275                 280                 285

Gln Ser Val Phe Gly Phe Thr Leu Pro Leu Phe His Gly Arg Gly Met
    290                 295                 300

Leu Asn Tyr Asn Leu Gly Leu Met Pro Tyr Arg Arg Arg Ile Val Ser
305                 310                 315                 320

Val Ile Gly Arg Pro Ile Leu Cys Glu Lys Cys Glu Lys Pro Ser Met
                325                 330                 335

Glu Glu Val Thr Arg Val Gln Gln Glu Tyr Ile Ala Glu Leu Leu Arg
            340                 345                 350

Ile Trp Asp Thr Tyr Lys Asp Gln Phe Ala Arg Ser Arg Lys Arg Glu
        355                 360                 365

Leu Ser Ile Ile Asp
    370
```

<210> SEQ ID NO 132
<211> LENGTH: 1122
<212> TYPE: DNA
<213> ORGANISM: Gloeophyllum trabeum

<400> SEQUENCE: 132

```
atggacgctg gtcgcgcctt ctcctctgca tcccgctcgt tatcgtcctc gtccctgaag      60

gacaagctgt caaaggtctc gaagctcagc accactcctc tgcgaccggt cgctgcccat     120

gtcaagaata tcgacttcgt cccgtccaag atccccccgga aacggaggct gcagatgctc     180

gctgttgcag tatgggcgct cctgataccc atcacgacgt ttttgttcct catactatgt     240

tcttttccac cgctgtggcc atttttagcg gcgtatctta tatggataag atggatagac     300
```

-continued

```
cggagtcctg agcatggcgg gaggataagt ccgtggttcc gctcgatgag gttctggaga    360

tactttgccg actactaccc tgcatcgttc ttgaaggaat gcgacctccc cccagaccga    420

ccttacgtct tcgggtatca ccctcatggc atcattggca tgggtgccat ggccactttc    480

gccaccgaag ccactggatt cagcgaacag ttccctgggc tcactcccca cctgctcacc    540

ctagccacaa atttcaccat gcccatatac agagacatca tcctcgccct gggcatatgc    600

tccgtcagca agcagtcctg ctcgaacatc ctcagcagcg gccccgggca ggctatcaca    660

atcgtagtag gaggcgcagc agagagtctt agcgctcggc cgggcacggc cgacctcacg    720

ctcaaacgga ggcttggctt catcaagatt gctatacaac acggagcggc actggtccct    780

gtattttctt tcggcgagaa tgatatttat caacaaatgc ccaacgaaaa gggaaccaca    840

atatatgccc tacagaagaa attccagagc gtcttcggct tcacgttgcc cttgttccac    900

ggtcggggca tgctaaatta taaccttggt ttgatgccgt atcgacggcg gatcgtgtct    960

gtcatcggtc ggcccatatt atgcgagaag tgcgagaagc caagcatgga ggaggttacg   1020

cgggtgcaac aggagtacat cgcagagctg ctcagaaatat gggacacgta caaagatcaa   1080

tttgctcggt cgcggaagag agaactgagt attattgatt ga                       1122
```

<210> SEQ ID NO 133
<211> LENGTH: 346
<212> TYPE: PRT
<213> ORGANISM: Rhodosporidium diobovatum

<400> SEQUENCE: 133

```
Met Gly Ala Leu Asp Ala Gly Asp His Glu Gly Thr Glu His Pro Lys
1               5                   10                  15

Ile Lys Phe Val Pro Phe Val Val Pro Arg His Arg Arg Leu Gln Thr
            20                  25                  30

Phe Ser Val Phe Leu Trp Thr Thr Ala Leu Pro Leu Ser Leu Gly Ile
        35                  40                  45

Phe Cys Ile Leu Cys Ser Phe Pro Pro Leu Trp Pro Leu Val Ile Gly
    50                  55                  60

Tyr Leu Thr Trp Val Phe Leu Ile Asp Gln Ala Pro Met Arg Gly Gly
65                  70                  75                  80

Arg Pro Gln Ala Trp Leu Arg Lys Ser Arg Val Trp Glu Trp Phe Ala
                85                  90                  95

Gly Tyr Tyr Pro Val Ser Leu Ile Lys Ser Ala Asp Leu Pro Pro Asp
            100                 105                 110

Gln Arg Tyr Val Phe Gly Tyr His Pro His Gly Val Ile Gly Met Gly
        115                 120                 125

Ala Ile Ala Asn Phe Gly Thr Asp Ala Thr Gly Phe Ser Arg Leu Phe
    130                 135                 140

Pro Gly Ile Lys Pro His Leu Leu Thr Leu Ala Ser Asn Phe Lys Leu
145                 150                 155                 160

Pro Leu Tyr Arg Glu Leu Leu Leu Ala Leu Gly Ile Ser Ser Val Ser
                165                 170                 175

Met Lys Ser Cys Gln Asn Ile Leu Arg Gln Gly Pro Gly Ser Ser Ile
            180                 185                 190

Thr Ile Val Val Gly Gly Ala Ala Glu Ser Leu Ser Ala His Pro Gly
        195                 200                 205

Thr Ala Asp Leu Thr Leu Lys Arg Arg Lys Gly Phe Ile Lys Leu Ala
    210                 215                 220

Ile Arg Ser Gly Ala Tyr Leu Val Pro Val Phe Ser Phe Gly Glu Asn
```

```
225                 230                 235                 240

Asp Ile Phe Asn Gln Leu Ser Asn Glu Arg Gly Thr Arg Leu Tyr Lys
                245                 250                 255

Leu Gln Lys Arg Phe Gln Ala Val Phe Gly Phe Thr Leu Pro Ile Phe
            260                 265                 270

Phe Gly Arg Gly Leu Phe Asn Tyr Asn Met Gly Leu Met Pro Tyr Arg
        275                 280                 285

His Pro Ile Val Ser Val Val Gly Arg Pro Ile Lys Val Thr Gln Lys
    290                 295                 300

Asp His Pro Ser Thr Ala Asp Leu Glu Glu Val Gln Asp Arg Tyr Ile
305                 310                 315                 320

Ala Glu Leu Lys Arg Ile Trp Glu Asp Tyr Lys Glu Val Tyr Ala Lys
                325                 330                 335

Ser Arg Thr Lys Glu Leu Thr Ile Ile Ala
            340                 345


<210> SEQ ID NO 134
<211> LENGTH: 1041
<212> TYPE: DNA
<213> ORGANISM: Rhodosporidium diobovatum

<400> SEQUENCE: 134

atgggagcac tagatgcggg cgaccacgag gggaccgaac accccaagat caagttcgtt     60

cctttcgttg tgccgcgaca ccgcaggctg cagacctttt cggtgtttct gtggacgacc    120

gcgctgcctc tgtcgctcgg catcttctgc attctctgct ccttcccccc actctggccc    180

ctcgtcatag ggtatctcac gtgggtattc ctcatcgacc aggcgcccat gcggggtggc    240

aggcctcagg cctggttgcg caagtcgcgt gtgtgggagt ggttcgccgg ctactaccct    300

gtcagcttga tcaagagcgc cgacctcccg cccgaccagc gctacgtctt tggctaccac    360

ccacacggcg tcattgggat gggcgccatc gccaactttg gtaccgacgc gaccggcttc    420

tcgcggctgt tccccggcat caagccgcac ctcctcacgc tcgccagcaa cttcaagctg    480

ccgctctacc gagaactgct cctcgccttg ggcatttcgt ccgtgtcgat gaagagctgc    540

cagaacatcc tgcgccaagg tcccggctcg tcgatcacga ttgtcgtcgg aggggcagca    600

gaaagcctca gcgcgcaccc gggaacggca gacctgacgc tcaagcggcg gaaggggttc    660

atcaagctcg cgatccgctc aggggcctac ctcgtcccgg tattttcctt tggcgagaat    720

gacatcttca accagctgtc gaatgagcgc ggcacccgac tctacaagct gcaaaagcgg    780

ttccaggccg tctttggctt caccttgccc atcttcttcg gtcgcggcct cttcaactac    840

aacatgggct tgatgccata tcgacacccg atcgtctcgg tcgtcggacg ccccatcaag    900

gtcacgcaga aggatcaccc gtcgacggcc gacctcgaag aggtacagga ccgctacatt    960

gccgagttga agaggatctg ggaggactac aaagaggtgt acgccaagag ccgcaccaag   1020

gagctcacca tcatcgcatg a                                             1041


<210> SEQ ID NO 135
<211> LENGTH: 359
<212> TYPE: PRT
<213> ORGANISM: Phaeodactylum tricornutum

<400> SEQUENCE: 135

Met Lys Glu Arg Arg Ser Gly Leu Asn Pro Ser Gly Ser Ser Val Tyr
1               5                   10                  15

Pro Leu His Pro Pro Asp Ser Arg Val Leu Val Arg Val Pro Ser Asp
```

```
            20                  25                  30

Ile Ser Phe Leu Asp Arg Leu Ile Val Ala Gly Ser Ser Ile Phe Ile
        35                  40                  45

Val Gly Ser Leu Val Trp Val Pro Leu Thr Ala Arg Trp Val Tyr Arg
    50                  55                  60

Arg Trp Lys Gln Ala Lys Asp Lys Arg Lys Arg Ala Met Tyr Ala Ser
65                  70                  75                  80

Leu Leu Val Ile Leu Ala Val Leu Val Ile Gly Gly Pro His Arg Ser
                85                  90                  95

Pro Arg Val Gly Lys Trp Leu Gln Val Arg Lys Trp Ser Leu Phe Gln
            100                 105                 110

Ala Trp Val Lys Phe Ile Ala Met Glu Val Ile Leu Asp Gln Pro Lys
        115                 120                 125

Gly Ile Thr Met Asp Val Gln Gln Asp Lys Ala Ile Phe Ala Phe Ala
    130                 135                 140

Pro His Gly Ile Phe Pro Phe Ala Phe Ala Phe Gly Val Leu Pro Asp
145                 150                 155                 160

Ile Ala Thr Gln Ser Phe Gly Tyr Val Arg Pro Val Val Ala Thr Ala
                165                 170                 175

Thr Arg Leu Phe Pro Val Val Arg Asp Phe Ile Ser Trp Ala Asn Pro
            180                 185                 190

Val Asp Ala Ser Lys Asp Ser Val Glu Arg Ala Leu Ala Leu Gly Asp
        195                 200                 205

Arg Ile Ala Val Ile Pro Gly Gly Ile Ala Glu Ile Phe Glu Gly Tyr
    210                 215                 220

Pro Lys Pro Asn Thr His Pro Asp Glu Glu Tyr Ala Ile Val Arg Ser
225                 230                 235                 240

Gly Phe Leu Arg Leu Ala Ile Lys His Gly Ile Pro Val Ile Pro Val
                245                 250                 255

Tyr Cys Phe Gly Ala Thr Lys Met Leu Lys Arg Leu Glu Leu Pro Gly
            260                 265                 270

Leu Glu Gln Leu Ser Leu Phe Leu Arg Val Ser Ile Cys Leu Phe Phe
        275                 280                 285

Gly Val Gly Gly Leu Pro Ile Pro Phe Arg Gln Arg Leu Ser Tyr Val
    290                 295                 300

Met Gly Gln Pro Ile Leu Pro Pro Val Arg Thr Thr Gly Ser Asp Ile
305                 310                 315                 320

Ser Asp Ala His Val Lys Glu Met Gln Asp Arg Phe Cys Ala Glu Val
                325                 330                 335

Gln Arg Leu Phe Asp Arg His Lys Glu Ala Tyr Gly Trp Ser Tyr Lys
            340                 345                 350

Thr Leu Lys Leu Leu Glu Gln
        355
```

<210> SEQ ID NO 136
<211> LENGTH: 1080
<212> TYPE: DNA
<213> ORGANISM: Phaeodactylum tricornutum

<400> SEQUENCE: 136

```
atgaaagaaa gaagatctgg cctaaatccg tcaggatcct ccgtgtatcc attgcaccct      60

cctgacagtc gcgttctcgt tcgagtcccc tccgatattt cctttcttga tcgtctcatc     120

gtcgctggca gcagtatctt tattgtcggt tcgctagtat gggttccatt gaccgcaaga     180
```

-continued

```
tgggtctaca ggcggtggaa gcaagctaaa gataaacgaa agcgggctat gtatgcctct    240

ctactcgtga ttctggcagt tctcgttatt ggcggacccc accgatctcc tcgtgtcggc    300

aaatggctcc aagtacgaaa gtggtccctc ttccaagcgt gggtaaagtt tattgccatg    360

gaagtgattt tggatcaacc gaaaggcatt actatggacg tccaacaaga caaggcgatt    420

tttgcattcg cgccacatgg aatctttccg tttgcgttcg cctttggagt gcttcccgat    480

attgccacac aatcgtttgg ctacgttcgt ccggtcgtgg caaccgccac aaggttgttt    540

cctgtagtcc gggatttcat ctcttgggcg aatccggtag acgcttccaa agattccgtt    600

gaacgtgctt tagcattggg cgatcgcatt gctgtaatac ctggaggaat tgcagaaatt    660

ttcgaaggat atccgaaacc gaacacgcat ccggatgaag agtacgctat cgtacggagt    720

ggatttttgc gtttggcaat aaaacacggt atcccagtga ttcccgtata ctgtttcggc    780

gctaccaaaa tgttgaagcg tctggagctt cccggcctgg agcaactgtc cctgtttcta    840

cgcgtgagca tttgcctctt ttttggagtc ggcgggttgc ccatcccttt ccgacaacga    900

ttgtcgtacg taatgggaca accaattttg ccacccgtaa ggacaacggg cagcgatatt    960

tcggacgcac acgtcaaaga aatgcaagat cgcttttgtg ctgaggtcca gcggctcttt   1020

gatcgacata aggaagctta tggttggtca tacaaaacgc tgaaactatt ggaacagtga   1080
```

```
<210> SEQ ID NO 137
<211> LENGTH: 329
<212> TYPE: PRT
<213> ORGANISM: Phaeodactylum tricornutum

<400> SEQUENCE: 137

Met Glu Arg Thr Lys Ile Gln Asp Glu His Lys Ser Pro Pro Asn Pro
1               5                   10                  15

Ser Thr Phe Arg Trp Phe Leu Gly Leu Leu Val Ala Ser Thr Phe Ser
            20                  25                  30

Met Val Tyr Phe Val Ala Pro Phe Tyr Met Leu Thr Val Val Phe Ala
        35                  40                  45

Leu Val Phe Lys Tyr Pro Ser Val Glu Ile Ala Trp Met Tyr Ala Ile
    50                  55                  60

Pro Met Ile Val Ser Ala Ile Leu Pro Pro Met Ala Ser Pro Leu Ala
65                  70                  75                  80

Leu Arg Leu Ile Ser Pro Leu Ile Asp Tyr Phe Asp Tyr Glu Glu Ile
                85                  90                  95

His Glu Thr Ser Pro Val Asp Val Gln Lys Glu Ile Leu Ser Asn Asn
            100                 105                 110

Lys Asn Tyr Leu Leu Val Phe Gln Pro His Gly Ala Leu Ser Phe Thr
        115                 120                 125

Gly Ile Thr Ser Met Val Thr Ala Pro Gln Ala Met Lys Gly Lys Leu
    130                 135                 140

Pro Thr Ala Val Ala Asp Ala Leu Leu Tyr Thr Pro Ile Leu Lys His
145                 150                 155                 160

Val Leu Gly Ile Phe Gly Leu Ile Ser Ala Ser Lys Ser Ser Met Ile
                165                 170                 175

Arg Thr Leu Lys Lys Lys Gly Val Glu Gly Thr Ile Val Leu Tyr Val
            180                 185                 190

Gly Gly Ile Ala Glu Leu Phe Leu Thr Asp Glu Thr Asp Glu Arg Leu
        195                 200                 205

Tyr Leu Arg Lys Arg Lys Gly Phe Ile Lys Leu Ala Leu Gln Gln Gly
    210                 215                 220
```

Val Asp Val Val Pro Val Tyr Leu Phe Gly Asn Thr Asn Ala Leu Ser
225 230 235 240

Val Leu Lys Thr Gly Phe Leu Ala Ala Ile Ser Arg Lys Leu Gln Ile
245 250 255

Ser Leu Thr Tyr Ile Trp Gly Lys Trp Tyr Leu Pro Ile Pro Arg Asp
260 265 270

Cys Lys Leu Leu Tyr Ala Ser Gly Gln Pro Leu Gly Met Pro His Ile
275 280 285

Leu Asp Pro Ser Gln Ala Asp Ile Asp Lys Trp His Glu Lys Tyr Cys
290 295 300

Ser Glu Val Met Arg Ile Phe Glu Lys Tyr Lys Glu Lys Val Pro Glu
305 310 315 320

Tyr Lys His Lys Lys Leu Glu Ile Ile
325

<210> SEQ ID NO 138
<211> LENGTH: 990
<212> TYPE: DNA
<213> ORGANISM: Phaeodactylum tricornutum

<400> SEQUENCE: 138
atggagagaa caaagataca agacgagcac aaaagtcccc ctaatccgtc gacatttcga 60
tggttcctcg gccttctagt ggcgtcgacg ttttccatgg tctattttgt ggctcccttt 120
tacatgctta cagtcgtgtt tgcactagtt ttcaaatatc cttcggtaga aattgcatgg 180
atgtacgcta ttccgatgat tgtctcggcc attttgccac caatggcttc tccactggcc 240
ttgcgactca tctccccgct cattgactac ttcgattacg aagagatcca cgaaacctca 300
ccggtggacg tccagaagga aatactaagc aacaacaaaa actatttgct agtctttcaa 360
ccgcatggag cactgtcgtt tacaggaatc acttcaatgg tgacagctcc acaagcaatg 420
aaaggcaaat tgccaacagc tgtggctgac gcactcttgt acacacctat actgaaacat 480
gtcttaggaa ttttcgggct gattagtgcc tccaaaagca gcatgatccg aactttaaaa 540
aagaagggtg tggaaggaac cattgttttg tacgttggtg ggattgccga gctctttttg 600
accgacgaga cggacgagcg cctctatctg cgaaagcgaa aagggtttat caaattagct 660
ctacaacagg gtgtcgatgt tgtacctgtg tatctatttg ggaacacaaa cgcgctgtcg 720
gtactaaaga cgggatttct cgcggcaatt tcgcgaaaat tacagatatc tctgacgtac 780
atttggggaa agtggtatct tccgattccc cgtgattgca aattgctgta tgcttccggt 840
cagccattag gaatgcctca tattttagac ccaagccaag ccgacattga taaatggcac 900
gaaaagtact gctccgaggt catgcggatc ttcgaaaaat acaaggaaaa ggttccggaa 960
tacaagcaca agaaattaga aattatttga 990

<210> SEQ ID NO 139
<211> LENGTH: 392
<212> TYPE: PRT
<213> ORGANISM: Phaeodactylum tricornutum

<400> SEQUENCE: 139

Met Arg Glu Arg Ser Cys Ala Asn Ala Ser Asp Asp Asp Ser Ile His
1 5 10 15

Lys Gln Ser Pro Glu Leu Glu Ala Glu Phe Leu His Thr Ser Lys Leu
20 25 30

Thr Leu Ala Asp Met Arg Arg Leu Ala His Asp Pro Lys Asp Arg Gly

```
        35                  40                  45

Leu Ala Thr Lys Pro Ala Ala Gln Ala Thr Lys Glu Asp Val Leu Thr
    50                  55                  60

Val Gln Pro Met Ser Phe Val Glu His Thr Ala Cys Cys Leu Phe Leu
65                  70                  75                  80

Ala Phe Gly Val Pro Asn Gly Ala Leu Thr Ile Pro Ile Ala Thr Trp
                85                  90                  95

Leu Ile Gly Lys Phe Val Leu Arg Asn Val Phe Leu Ala Phe Leu Leu
            100                 105                 110

Ala Gly Cys Ile Leu Leu Pro Leu Ala Ile Leu Pro Gln Glu Tyr Val
        115                 120                 125

Pro Ala Arg Leu Gln Ser Trp Leu Ala Leu Gln Ile Leu Lys Tyr Phe
    130                 135                 140

Ser Phe Ser Leu Val Met Glu Glu Arg Pro Pro Thr Met Cys Thr Gly
145                 150                 155                 160

Lys Gln Leu Ile Glu Gln Pro Ala Arg Pro Arg Ile Val Thr Ala Tyr
                165                 170                 175

Pro His Gly Val Phe Pro Tyr Gly Asn Ala Leu Thr Val Val Thr Trp
            180                 185                 190

Pro Leu Leu Thr Gly His His Ile Val Gly Leu Ala Ala Asn Ala Ala
        195                 200                 205

Leu Arg Thr Pro Ile Phe Lys Gln Ile Leu Arg Ser Ile Gly Val Lys
    210                 215                 220

Asp Ala Ser Arg Ala Ser Val Arg Asn Ala Leu Glu Thr Trp Pro Phe
225                 230                 235                 240

Thr Val Gly Ile Ser Pro Gly Gly Val Ala Glu Val Phe Glu Thr Asn
                245                 250                 255

His Phe Asn Glu His Ile Leu Leu Lys Glu Arg Ile Gly Val Ile Lys
            260                 265                 270

Met Ala Ile Arg Thr Gly Ala Asp Leu Val Pro Gly Tyr Met Tyr Gly
        275                 280                 285

Asn Thr Asn Leu Tyr Trp Cys Trp Thr Gly Glu Gly Ile Pro Gly Ala
    290                 295                 300

Arg Trp Leu Leu Glu Tyr Val Ser Arg Lys Ile Leu Gly Phe Ala Leu
305                 310                 315                 320

Val Pro Ile Ala Gly Arg Trp Arg Leu Pro Ile Pro Tyr Arg Thr Pro
                325                 330                 335

Ile Leu Cys Val Val Gly Lys Pro Ile Pro Thr Ile His Leu Gln Thr
            340                 345                 350

Glu Glu Pro Ser Met Glu Gln Ile Val Asp Ile Gln Glu Gln Leu Ser
        355                 360                 365

Thr Glu Leu Lys Ser Met Phe Asp Arg Tyr Lys His Leu Tyr Gly Trp
    370                 375                 380

Glu Asp Arg Met Leu Val Ile Thr
385                 390
```

<210> SEQ ID NO 140
<211> LENGTH: 1179
<212> TYPE: DNA
<213> ORGANISM: Phaeodactylum tricornutum

<400> SEQUENCE: 140

```
atgcgtgagc gaagctgcgc caacgcttct gacgatgaca gcattcacaa gcagtcgcca      60

gaattggagg ctgagtttct tcataccagc aagttgacct tagccgacat gcgacgattg     120
```

```
gcgcacgatc cgaaggatcg ggggttggca acaaaacctg cggcgcaagc tacgaaagaa    180

gacgtcttga cggtacaacc catgagtttc gtagaacaca ctgcttgctg tctgtttctc    240

gcgtttggag tgcccaatgg cgctctgacg attcccatag caacgtggct gatcggaaaa    300

ttcgtgttgc gcaacgtttt cttggcgttt ctgttagcag gctgtatact tctaccgctt    360

gcgatactgc cgcaagaata tgtgcccgcc cgattgcaat cgtggcttgc tttgcagata    420

ctgaaatatt tttctttctc tttggtcatg gaggaacgcc ctccgacaat gtgtactggc    480

aagcagctga tcgagcagcc cgctcggcca cgaatcgtca cagcctatcc gcacggagtt    540

ttcccatacg gaaacgcgtt gactgtagtc acatggccgt tgttgacggg acaccatatt    600

gtgggtttgg cagcaaatgc cgctttgcgg acaccgatct ttaaacaaat cttgcggagc    660

attggcgtca aggacgcctc tcgagcgtcg gtacggaatg cgctggaaac atggcctttc    720

accgtcggga tttcgccagg tggcgtggcg gaagtttttg aaacaaacca cttcaatgag    780

cacattctgt tgaaagaacg tattggtgtc atcaagatgg ccattcgcac cggtgcggat    840

cttgtaccag gctatatgta tggtaatact aatctgtact ggtgctggac aggggaaggt    900

attcctggag ctcggtggct attggagtat gtttcgcgta aaatcctagg ttttgccctc    960

gtgcctatag cgggtagatg gagactacca ataccgtaca ggactccgat attgtgtgtc   1020

gtgggcaagc caataccaac cattcatttg caaaccgaag aaccatcaat ggagcaaatc   1080

gtggacattc aggaacaatt gtcaacagaa ttgaaatcaa tgttcgaccg ctataagcac   1140

ctgtacggat gggaagatcg aatgctagtg atcacataa                          1179
```

<210> SEQ ID NO 141
<211> LENGTH: 320
<212> TYPE: PRT
<213> ORGANISM: Phaeodactylum tricornutum

<400> SEQUENCE: 141

```
Met Thr Arg Ser Lys Phe Ile Gly Ser Ala Gly Ala Ile Gly Leu Phe
1               5                   10                  15

Cys Leu Met Ile Ile Pro Asn Val Gly Ile Leu Ile Ala Thr Phe Leu
            20                  25                  30

Tyr Pro Lys Val Leu Gly Leu Tyr Phe Leu Ile Pro Tyr Tyr Ala Tyr
        35                  40                  45

Asn Leu Ser Ile Gly Lys His Glu Ala Arg Asp Gly Asn Gly Trp Asn
    50                  55                  60

Trp Phe Ser Glu Asn Phe Phe Val Phe Asn Ile Val Arg Gly Tyr Leu
65                  70                  75                  80

Asn Leu Lys Ile Glu Ala Asp Ser Glu Leu Lys Glu Ala Glu Ala Lys
                85                  90                  95

Glu Gly Ala Gln Phe Val Phe Ala Val Ser Pro His Gly Thr Asn Ala
            100                 105                 110

Asp Tyr Arg Val Phe Ile Asp Gly Met Leu His Glu Ala Leu Pro Gln
        115                 120                 125

Thr Ala Ser Lys Ile Arg Thr Leu Ala Ala Thr Val Leu Phe His Ile
    130                 135                 140

Pro Leu Val Arg Glu Ile Ala Leu Trp Thr Gly Cys Val Asp Ala Ser
145                 150                 155                 160

Arg Ala Val Ala Val Glu Arg Leu Lys Glu Glu Gly Gly Ser Leu Leu
                165                 170                 175

Val Ile Pro Gly Gly Gln Ala Glu Gln Met Tyr Thr Gln Tyr Gly Arg
```

```
            180                 185                 190

Glu Arg Val Tyr Leu Lys Arg Arg Lys Gly Phe Leu Lys Leu Cys Leu
        195                 200                 205

Lys Tyr Glu Ile Pro Val Val Pro Ala Tyr Val Phe Gly Val Ser Asp
    210                 215                 220

Tyr Tyr Phe Thr Ser Ala Lys Leu Phe Gly Leu Arg Met Trp Leu Val
225                 230                 235                 240

Gln Asn Leu Gly Ile Ala Leu Pro Leu Cys Trp Gly Arg Tyr Gly Leu
                245                 250                 255

Pro Ile Cys Pro Arg Pro Val Asp Thr Thr Leu Val Phe Asp Lys Pro
            260                 265                 270

Leu Tyr Leu Ser Cys Gln Asn Pro Ser Asn Pro Ser Glu Asp Glu Val
        275                 280                 285

Asp Lys Ala His Leu Gln Phe Cys Gln Ala Leu Glu Lys Leu Phe Asp
    290                 295                 300

Thr His Lys Glu Arg Leu Gly Tyr Gly Asp Arg Lys Leu Glu Ile Ile
305                 310                 315                 320


<210> SEQ ID NO 142
<211> LENGTH: 963
<212> TYPE: DNA
<213> ORGANISM: Phaeodactylum tricornutum

<400> SEQUENCE: 142

atgaccagat cgaagtttat aggaagtgct ggagctattg gcttattttg tttgatgatc     60

ataccgaatg tgggaattct gatcgcaaca tttctttatc ccaaagtact tgggctctac    120

tttctgattc cgtactacgc atacaacttg tccattggca aacacgaagc tcgagacggc    180

aacggctgga attggttcag cgagaatttc tttgtcttta acattgtgag ggatatcta    240

aatcttaaga ttgaagctga ctccgagctc aaggaagccg aagcgaaaga aggcgcccaa    300

tttgtgttcg ccgttagccc tcacggaacg aacgcagact atcgagtttt tattgacggt    360

atgctacatg aggcactccc acagactgca agcaagatca gaacactagc ggcgacagta    420

ctgttccaca ttcccttggt tcgtgaaatc gcactttgga caggatgtgt cgatgccagc    480

cgcgcagttg ctgtcgagag attaaaagaa gaaggtggtt cactgcttgt gattcccggt    540

ggccaagcag aacaaatgta cacccaatat ggacgtgaaa gagtatatct gaaacggcgc    600

aaaggatttt tgaagctttg cttgaagtac gagattccgg tcgtcccagc ttatgttttt    660

ggcgtatctg actattactt cacgtccgca aagctctttg gtctgcgaat gtggctcgtt    720

cagaatcttg gcattgctct tccactgtgc tggggaagat atggtctacc aatctgtcct    780

agaccagtcg ataccaccct tgtctttgac aaacctttat acctatcctg ccagaatccg    840

tcgaatccct cggaagacga ggttgacaag gctcatctgc aattttgcca agccctcgag    900

aagctgtttg atacacacaa agagaggctt gggtacggcg atcgaaagct ggaaataatt    960

tag                                                                  963


<210> SEQ ID NO 143
<211> LENGTH: 564
<212> TYPE: PRT
<213> ORGANISM: Phaeodactylum tricornutum

<400> SEQUENCE: 143

Met Asp Glu Thr Glu Ile Thr Pro Leu Leu Arg Phe Ser Thr Pro Ser
1               5                   10                  15
```

```
Arg Ala Glu His Ser Ser Trp Ile Lys Leu Ala Ser Glu Ser Cys Ala
            20                  25                  30

Tyr Ser Glu Thr Asp Glu Phe Leu Ala Asp Glu Ala Ala Arg Ala Thr
        35                  40                  45

Gln Arg Ala Leu Gln His Gln Glu Ala Leu Gln Met Ala Gln Ala Met
    50                  55                  60

Pro Gly Ala Lys Pro Gly Thr Leu Pro Pro Leu Tyr Phe Ala Pro Thr
65                  70                  75                  80

Ile Lys Arg Ser Arg Ser Phe Ala Lys Leu Gln Glu His His Gly Asp
                85                  90                  95

Gly Met Pro Arg Val Asn Met Arg Arg Thr Lys Ser Arg Asp Phe Asn
            100                 105                 110

Ala Asp Lys Leu Asp Ala Arg Ser Thr Lys Gly Tyr Pro Pro Ser Lys
        115                 120                 125

Pro Met His Arg Ala Ala Glu Pro Ser Tyr Leu Ser Ala Asp Ala Pro
    130                 135                 140

Ile Gln Asn Tyr Arg Gly Phe Leu Asn Leu Gly Val Ile Ile Leu Ile
145                 150                 155                 160

Val Ser Asn Phe Arg Leu Ile Leu Gly Thr Ile Arg Ser Asn Gly Phe
                165                 170                 175

Val Leu Thr Thr Ala Val Lys His Tyr Lys Asn Leu Asn His Leu Lys
            180                 185                 190

Glu Asp Pro Trp Gln Glu Phe Pro Phe Val Ser Gly Phe Leu Leu Gln
        195                 200                 205

Leu Val Phe Val Ser Ile Ala Phe Gly Ile Glu Trp Met Leu Cys Arg
    210                 215                 220

Lys Tyr Phe Asn Glu Asn Phe Gly Met Ile Leu His His Phe Asn Ala
225                 230                 235                 240

His Ser Ala Leu Leu Ile Pro Leu Gly Ile Val Trp Asn Leu Ile Asp
                245                 250                 255

Arg Pro Ala Val Gly Ala Ile Leu Leu Leu His Ala Thr Ile Thr Trp
            260                 265                 270

Met Lys Leu Ile Ser Tyr Met Leu Ala Asn Glu Asp Tyr Arg Leu Ser
        275                 280                 285

Ser Arg Arg Val Gly Gly Asn Pro His Leu Ala Thr Leu Ala Leu Val
    290                 295                 300

Glu Asn Leu Asp Ser Asp Glu Ala Asn Ile Asn Tyr Pro Gln Asn Val
305                 310                 315                 320

Thr Leu Arg Asn Ile Phe Tyr Phe Trp Cys Ala Pro Thr Leu Thr Tyr
                325                 330                 335

Gln Ile Ala Phe Pro Lys Ser Pro Arg Val Arg Tyr Trp Lys Ile Ala
            340                 345                 350

Asp Ile Leu Met Arg Met Thr Val Ser Ile Ala Leu Phe Thr Phe Leu
        355                 360                 365

Leu Ala Gln Ile Val Gln Pro Ala Leu Glu Glu Leu Val Ser Asp Leu
    370                 375                 380

Asp Glu Thr Asn Gly Ser Tyr Thr Ala Ala Ile Phe Ala Glu Tyr Trp
385                 390                 395                 400

Leu Lys Leu Ser Ile Ala Asn Thr Tyr Leu Trp Leu Leu Met Phe Tyr
                405                 410                 415

Thr Tyr Phe His Leu Tyr Leu Asn Leu Phe Ala Glu Leu Leu Arg Phe
            420                 425                 430

Gly Asp Arg Val Phe Tyr Lys Asp Trp Trp Asn Ser Ser Glu Val Ser
```

```
        435                 440                 445

Ala Tyr Trp Arg Leu Trp Asn Met Pro Val His Tyr Trp Leu Ile Arg
    450                 455                 460

His Val Tyr Phe Pro Cys Val Arg Leu Lys Met Pro Lys Val Ala Ala
465                 470                 475                 480

Thr Phe Val Val Phe Phe Leu Ser Ala Val Met His Glu Val Leu Val
                485                 490                 495

Ser Val Pro Phe His Ile Ile Arg Pro Trp Ser Phe Ile Gly Met Met
            500                 505                 510

Met Gln Ile Pro Leu Val Ala Phe Thr Lys Tyr Leu Tyr Arg Lys Phe
        515                 520                 525

Pro Gly Gly Ser Ile Gly Asn Val Leu Phe Trp Met Thr Phe Cys Val
    530                 535                 540

Ile Gly Gln Pro Met Ala Ile Leu Leu Tyr Tyr His Asp Ile Met Asn
545                 550                 555                 560

Arg Lys Gly Asn


<210> SEQ ID NO 144
<211> LENGTH: 1695
<212> TYPE: DNA
<213> ORGANISM: Phaeodactylum tricornutum

<400> SEQUENCE: 144

atggatgaga ccgaaattac acctttgttg cgtttttcga caccttcccg agccgaacac      60

tcgtcctgga taaagcttgc ctcggaatcc tgtgcttaca gcgaaacgga cgagtttctc     120

gctgacgagg ccgctcgcgc aacccagcgt gctttgcaac atcaagaagc gctgcaaatg     180

gcccaagcca tgcctggggc aaagccagga acgctgccgc cactctactt cgcgcctacc     240

ataaagcgtt cgcgttcctt tgctaagcta caagaacatc atggagatgg gatgcctcgg     300

gtaaatatgc gtcggaccaa atcgcgagat tttaacgcgg ataagttgga tgcgcgaagt     360

accaagggct atccccccttc caagccgatg catcgtgcgg cagagccctc atacctcagc     420

gcggatgctc ccattcaaaa ctaccgagga tttctgaatt taggcgttat tattttgatt     480

gtttctaact ttcggctgat cttgggcaca atccgtagca acggatttgt cttgacgact     540

gcagtgaagc actacaagaa cctaaatcac ctcaaggaag atccctggca ggaatttcct     600

tttgtatcag gatttcttct ccagctcgtc tttgtttcga ttgcgtttgg gatcgaatgg     660

atgttgtgcc ggaaatactt caacgaaaac ttcggcatga tccttcatca cttcaatgcc     720

cactcagcct tgctgatacc tttaggtatt gtttggaatc tcatcgatag acctgcggtt     780

ggtgcaattt tgcttttaca cgctacgata acatggatga aactcatttc ttacatgttg     840

gcgaacgaag attaccggct atcatcgcgt cgcgttgggg gcaacccaca cctagctacg     900

ctcgcattag tcgaaaatct agattcagat gaggcgaaca ttaactaccc ccaaaatgtt     960

actctccgca acatttttta tttttggtgt gctccgacgt tgacttacca gattgccttc    1020

ccgaagtccc cgcgagttcg ctattggaaa atcgcggata tcctgatgcg catgacggtg    1080

tccatcgcac tattcacctt tttgctggca caaattgttc agcctgcatt ggaagagcta    1140

gtgagcgacc tggacgagac caatggatcc tacaccgcag caatatttgc cgagtactgg    1200

ctgaaacttt cgattgctaa cacatattta tggcttctta tgttctatac atatttccat    1260

ttgtatctga acctctttgc tgagcttctg cgatttggag atcgtgtgtt ctacaaagat    1320

tggtggaatt cgtcggaagt atctgcatat tggaggcttt ggaatatgcc tgttcactat    1380
```

-continued

```
tggttgatcc gacatgtgta tttcccctgc gtgcgactga agatgccgaa ggtcgctgca   1440

acctttgtcg tttttttcct ctccgccgtt atgcacgagg tgcttgtcag cgtacccttt   1500

catattattc gtccgtggtc ttttatcggg atgatgatgc agattccttt ggttgcgttc   1560

acaaagtatc tctatcgcaa attcccgggc ggctcgattg gtaatgtcct gttctggatg   1620

acattttgcg tcattggcca gccaatggcg attctcttgt actatcatga tattatgaat   1680

cgaaaaggaa attga                                                    1695


<210> SEQ ID NO 145
<211> LENGTH: 503
<212> TYPE: PRT
<213> ORGANISM: Metarhizium acridum

<400> SEQUENCE: 145

Met Ser Thr Ala Thr Thr Thr Ser Val Ser Pro Ala Asn Gly Thr Val
1               5                   10                  15

Ser Lys Arg Asn Ala Thr Lys Arg Arg Asn Gly Asn Ala Ser Pro Gly
            20                  25                  30

Pro Val Glu Glu Glu Ser Glu Asp Ala Ala Ala Ala Glu Lys Pro Arg
        35                  40                  45

Ala Ser Val Ala Gln Lys Asn Tyr Arg His Val Ala Ala Val His Ser
    50                  55                  60

Lys Ser Arg Pro Ser Cys Leu Ser His Asp Ser Asp Ala Thr Pro Ser
65                  70                  75                  80

Phe Ile Gly Phe Arg Asn Leu Met Val Ile Val Leu Asp Val Leu Ile
                85                  90                  95

Gly Gly Leu Leu Tyr Phe Leu Ile Pro Cys His Leu Leu Val Ala Tyr
            100                 105                 110

Leu Ile Glu Leu Ala Ala Ala Lys Gln Ala Arg Gly Ser Arg Lys Arg
        115                 120                 125

Leu Lys Pro Gly Ser Thr Val Pro Ser Glu Gln Asp Asn Ser Lys Phe
    130                 135                 140

His Ser Thr Trp Val Leu Val Ala Trp Ala His Gly Ile Asn Met Thr
145                 150                 155                 160

Leu Ala Leu Ala Leu Thr Thr Phe Met Val Tyr Phe Tyr Ile His His
                165                 170                 175

Pro Leu Val Gly Thr Leu Thr Glu Met His Ala Val Ile Val Ser Leu
            180                 185                 190

Lys Thr Ala Ser Tyr Ala Phe Thr Asn Arg Asp Leu Arg His Ala Tyr
        195                 200                 205

Leu His Pro Val Lys Gly Glu Phe Ile Pro Glu Leu Tyr Ser Lys Cys
    210                 215                 220

Pro Tyr Pro Asn Asn Ile Thr Phe Gly Asn Leu Ala Tyr Phe Trp Trp
225                 230                 235                 240

Ala Pro Thr Leu Val Tyr Gln Pro Val Tyr Pro Arg Thr Asp Lys Ile
                245                 250                 255

Arg Trp Val Phe Val Phe Lys Arg Leu Gly Glu Val Cys Cys Leu Ser
            260                 265                 270

Ala Phe Ile Trp Phe Ala Ser Phe Gln Tyr Ala Ala Pro Val Leu Gln
        275                 280                 285

Asn Ser Leu Asp Lys Ile Ala Ser Leu Asp Leu Leu Met Ile Leu Glu
    290                 295                 300

Arg Leu Leu Lys Leu Ser Thr Ile Ser Leu Val Ile Trp Leu Ala Gly
305                 310                 315                 320
```

```
Phe Phe Ala Leu Phe Gln Ser Phe Leu Asn Ala Leu Ala Glu Val Leu
                325                 330                 335

Arg Phe Gly Asp Arg Ser Phe Tyr Asp Asp Trp Trp Asn Ser Glu Ser
            340                 345                 350

Leu Gly Ala Tyr Trp Arg Thr Trp Asn Arg Pro Val Tyr Thr Tyr Phe
        355                 360                 365

Lys Arg His Val Tyr Val Pro Met Ile Gly Arg Gly Trp Ser Pro Trp
    370                 375                 380

Ala Ala Ser Cys Ala Val Phe Phe Val Ser Ala Val Leu His Glu Val
385                 390                 395                 400

Leu Val Gly Val Pro Thr His Asn Ile Ile Gly Thr Leu Ser Ser Val
                405                 410                 415

Leu Ser Ile Val Leu Thr Leu Val Pro Asn Leu Tyr Ser Gly Val Ala
            420                 425                 430

Phe Leu Gly Met Phe Leu Gln Leu Pro Leu Ile Ala Ile Thr Ala Pro
        435                 440                 445

Leu Glu Lys Met Lys Trp Gly His Thr Gly Arg Val Met Gly Asn Val
    450                 455                 460

Ile Phe Trp Val Ser Phe Thr Ile Phe Gly Gln Pro Phe Ala Ala Leu
465                 470                 475                 480

Met Tyr Phe Tyr Ala Trp Gln Ala Lys Tyr Gly Ser Val Ser Lys Glu
                485                 490                 495

Pro Ile Leu Ala Leu Gln Thr
            500
```

<210> SEQ ID NO 146
<211> LENGTH: 1512
<212> TYPE: DNA
<213> ORGANISM: Metarhizium acridum

<400> SEQUENCE: 146

```
atgagcacgg ccaccaccac cagtgtcagc ccagcgaatg gcaccgtgag caagagaaat      60

gccaccaagc gtcgcaacgg caatgcatct cccggcccgg tggaagaaga atccgaagac     120

gcagccgcag ccgagaagcc cagagcctct gtcgcccaga agaactatcg ccacgtagca     180

gcagtgcatt ccaagagccg cccgtcgtgc ctaagccacg actccgatgc cacgccaagc     240

tttatcgggt ttcgaaatct catggtcatt gttttggatg tcctcatcgg cggacttctc     300

tactttctca ttccctgcca tctgttggtt gcctacttga tcgaattggc cgccgcaaaa     360

caggctcgag gatcccgaaa gcgcctcaaa ccaggctcta ctgtaccgtc ggaacaagac     420

aattccaagt tccattcaac atgggttctg gtggcctggg ctcatggtat caatatgacg     480

cttgctttag ccctcacaac ctttatggtt tacttttaca tccaccaccc gctcgttggg     540

accctgaccg agatgcatgc cgtcattgtg tcgttgaaga cagcctcgta cgcattcacc     600

aaccgagatc ttcgccacgc ttacctgcac cccgttaaag gagagtttat tcctgaactc     660

tactcgaaat gcccgtaccc gaataacatc acctttggca acctcgccta cttctggtgg     720

gcgccgacgc tggtctatca gcccgtatac ccgcgcaccg acaagatcag atgggtcttt     780

gtttttaaga ggctgggcga agtatgctgt ttgagcgcat tcatctggtt cgccagcttc     840

caatacgccg cgccggttct gcagaattcg ctcgacaaga ttgcttcgtt ggacttactc     900

atgatcctag agcggctgct gaagctgtca accatttctc tggttatttg gctggcagga     960

ttctttgccc tattccagtc cttcttaaac gcacttgccg aagtgctgcg gttcggcgac    1020
```

-continued

```
cgatcatttt acgacgactg gtggaacagc gagagtctcg gagcctactg gagaacgtgg   1080

aacaggcccg tatatacgta ctttaagcgc catgtgtatg tacccatgat tgggcgtgga   1140

tggagcccat gggctgcaag ttgcgccgtc ttttttgtgt ctgccgtgtt acacgaggtt   1200

cttgttggtg ttcccaccca caacattatc ggtacgctat cctccgtctt atccatcgtc   1260

ttgaccctcg ttcctaacct atattcaggc gttgcttttc taggcatgtt cttgcagctt   1320

cctctcatcg ccatcacggc ccctctagag aaaatgaaat gggggcatac cggcagagta   1380

atgggaaacg taatcttttg ggtgtccttt accatcttcg gtcagccatt tgcggcattg   1440

atgtactttt acgcatggca ggccaagtac ggtagcgtca gtaaagaacc gattcttgcg   1500

ttgcagacat ga                                                       1512
```

<210> SEQ ID NO 147
<211> LENGTH: 516
<212> TYPE: PRT
<213> ORGANISM: Ophiocordyceps sinensis

<400> SEQUENCE: 147

```
Met Ala Ala Thr Gly Thr Ser Val Glu Pro Ser Thr Gly Thr Ala Thr
1               5                   10                  15

Gln Arg His Ser Gly Lys Asp Gln Thr Gly Val Glu Pro Arg Thr Gly
            20                  25                  30

Thr Val Lys Thr Ser Gln Lys Lys Tyr Arg His Val Val Val Val His
        35                  40                  45

Ser Gln Val Arg Pro Ser Cys Leu Ser His Asp Ser Asp Ala Ala Pro
    50                  55                  60

Ser Phe Ile Gly Phe Arg Asn Leu Met Val Ile Val Leu Val Val Gly
65                  70                  75                  80

Asn Leu Arg Leu Met Ile Glu Asn Ile Gln Lys Ala Arg Ser Tyr Leu
                85                  90                  95

Ser Phe Ile Pro Gly Gln Cys Ala Pro Gly Tyr Gly Val Leu Ile Cys
            100                 105                 110

Ile Arg Cys His Ala Tyr Ser Arg Gln Asp Ile Leu Val Gly Gly Leu
        115                 120                 125

Leu Tyr Ile Leu Ile Pro Cys His Leu Leu Ala Ala Tyr Leu Ile Glu
    130                 135                 140

Leu Ala Ala Ala Gln Gln Ala Leu Gly Ser Arg Lys Arg Leu Lys Asp
145                 150                 155                 160

Gly Ala Ala Ser Pro Glu Glu Glu Asp Arg Asn Ser Asn Lys Phe His
                165                 170                 175

Ala Thr Trp Leu Ile Val Ala Trp Val His Ala Val Asn Ile Thr Leu
            180                 185                 190

Ala Leu Val Val Thr Ser Ala Val Val Tyr Phe Tyr Ile His His Pro
        195                 200                 205

Leu Ile Gly Thr Leu Thr Glu Met His Ala Ile Ile Val Trp Leu Lys
    210                 215                 220

Thr Ala Ser Tyr Ala Phe Thr Asn Arg Asp Leu Arg His Ala Tyr Leu
225                 230                 235                 240

His Pro Val Glu Gly Glu Leu Val Pro Asp Met Tyr Ala Lys Cys Pro
                245                 250                 255

Tyr Pro Gln Asn Ile Thr Phe Gly Asn Leu Val Tyr Phe Trp Trp Ala
            260                 265                 270

Pro Thr Leu Val Tyr Gln Pro Val Tyr Pro Arg Thr Asp Lys Ile Arg
        275                 280                 285
```

```
Trp Leu Phe Val Ala Lys Arg Leu Gly Glu Val Phe Cys Leu Ser Ala
    290                 295                 300

Phe Ile Trp Phe Ala Ser Phe Gln Tyr Ala Ala Pro Val Leu Arg Asn
305                 310                 315                 320

Ser Leu Asp Lys Ile Ala Ser Leu Asp Phe Ala Ser Ile Phe Glu Arg
                325                 330                 335

Leu Val Lys Leu Ser Thr Ile Ser Leu Val Ile Trp Leu Ala Gly Phe
            340                 345                 350

Phe Ala Leu Phe Gln Ser Phe Leu Asn Ala Leu Ala Glu Val Leu Arg
        355                 360                 365

Phe Gly Asp Arg Ala Phe Tyr Asp Asp Trp Trp Asn Ser Glu Ser Leu
    370                 375                 380

Gly Ala Tyr Trp Arg Thr Trp Asn Lys Pro Val Tyr Thr Tyr Phe Lys
385                 390                 395                 400

Arg His Val Tyr Met Pro Met Ile Gly Arg Gly Trp Ser Pro Arg Val
                405                 410                 415

Ala Ser Leu Val Val Phe Phe Ile Ser Ala Val Leu His Glu Ile Leu
            420                 425                 430

Val Gly Leu Pro Thr His Asn Val Ile Gly Val Ala Phe Leu Gly Met
        435                 440                 445

Phe Leu Gln Leu Pro Leu Ile Ala Ile Thr Ala Pro Met Glu Lys Met
    450                 455                 460

Arg Leu Gly Lys Gly Gly Lys Leu Val Gly Asn Val Ile Phe Trp Val
465                 470                 475                 480

Ser Phe Thr Ile Phe Gly Gln Pro Phe Ala Thr Leu Met Tyr Phe Tyr
                485                 490                 495

Ala Trp Gln Ala Lys Tyr Gly Ser Val Ser Arg Glu Met Gln Gln Ala
            500                 505                 510

Ala Ser Ile Lys
        515


<210> SEQ ID NO 148
<211> LENGTH: 1551
<212> TYPE: DNA
<213> ORGANISM: Ophiocordyceps sinensis

<400> SEQUENCE: 148

atggcggcta cggggaccag cgtcgagccc tcgactggta ccgcgacaca acgccactcc      60

ggcaaggatc agactggggt cgagccacgc accggcacgg tcaagacatc ccagaaaaag     120

tatcgccatg tcgttgtcgt ccactcccag gtccggccct cgtgcctcag ccacgattca     180

gatgccgccc ccagcttcat tggcttccgc aatctcatgg ttattgtcct ggtcgtcggc     240

aacttgcgat tgatgattga aaacatccaa aaggctcgtt catacctgtc gttcatacct     300

ggccaatgcg ccccccggcta cggagtcttg atctgcatcc gctgccacgc ctacagccgc     360

caagacattc tcgtcggcgg gctgctgtac atcctcattc cctgccatct cctggccgcc     420

tatctcatcg agctcgccgc cgcccagcag gcactggggt cgagaaagcg cctcaaggat     480

ggcgccgcca gcccggagga ggaggaccgc aacagcaaca agtttcacgc gacatggctc     540

atcgtcgcct gggtccatgc cgtcaacatc accctggccc tggtcgtgac ctcggccgtc     600

gtctactttt acatccacca cccactcatc ggcaccctca ccgaaatgca cgccatcatc     660

gtctggctca agacggcctc gtacgccttt actaaccgcg acctgcgcca cgcgtacctg     720

caccccgtcg agggcgagct cgtcccggac atgtacgcca agtgcccgta tccgcaaaac     780
```

atcacctttg gcaacctcgt ctacttctgg tgggccccga cgctcgtcta ccagcccgtc 840
tatccccgga ccgacaagat caggtggctc tttgtcgcca agcggctggg agaggtcttt 900
tgcttgagcg ccttcatctg gttcgccagc ttccagtatg ccgcgcccgt cctgcgcaac 960
tctctcgaca aaattgcttc gctcgacttt gcctccatct ttgagcggct ggtgaagctg 1020
tccaccatct ccctcgtcat ctggctcgcc ggcttcttcg ccctcttcca gtcctttctc 1080
aacgccctcg ccgaggtgct tcggttcggc gaccgggctt tctacgatga ctggtggaac 1140
agcgagagcc taggcgccta ctggcggacc tggaacaagc ccgtctacac ctacttcaag 1200
cgccacgtgt acatgcccat gatcgggcgt ggctggagtc ccagggtggc cagtctggtc 1260
gtcttcttca tctcagccgt cctccacgag atccttgtcg ggctacccac tcacaacgtc 1320
atcggcgtcg cctttctcgg catgtttctc cagctgcctc tcatcgccat cacggcgccc 1380
atggagaaga tgaggctcgg caaaggcggc aagctcgtag gcaacgtcat cttctgggtg 1440
tcgtttacca tctttggcca gccctttgcg acattgatgt acttttatgc ttggcaggcc 1500
aaatacggga gcgtgagcag ggagatgcag caagcggcaa gcatcaagta a 1551

<210> SEQ ID NO 149
<211> LENGTH: 510
<212> TYPE: PRT
<213> ORGANISM: Trichoderma virens

<400> SEQUENCE: 149

Met Ala Pro Pro Ala Glu Ser Ser Thr Thr Thr Ser Val Glu Ala Ser
1               5                   10                  15

Thr Gly Ser Val Ser Arg Arg His Ala Ser Gln Ser Glu Ala Asp Leu
            20                  25                  30

Thr Ser Val Glu Pro Val Asn Gly Thr Thr Lys Asn Arg Leu Ser Lys
        35                  40                  45

Thr Pro Pro Lys Lys Tyr Arg His Val Ala Ala Val His Ser Gln Thr
    50                  55                  60

Arg Pro Ser Cys Leu Ser His Asp Ser Pro Ala Ala Pro Ser Phe Leu
65                  70                  75                  80

Gly Phe Arg Asn Leu Met Val Ile Val Leu Val Val Gly Asn Leu Arg
                85                  90                  95

Leu Met Ile Glu Asn Ile Gln Lys Tyr Gly Val Leu Ile Cys Ile Arg
            100                 105                 110

Cys His Asp Tyr Arg Arg Gln Asp Val Leu Leu Gly Leu Leu Leu Tyr
        115                 120                 125

Phe Leu Ile Pro Cys His Leu Phe Ala Ala Tyr Leu Ile Glu Leu Val
    130                 135                 140

Ala Ala Lys Gln Ala Glu Gly Ser Arg Lys Arg Ile Lys Asp Asn Asn
145                 150                 155                 160

Ser Gly Pro Ser Glu Ala Glu Arg Lys Lys Phe His Ser Ile Trp Val
                165                 170                 175

Leu Ala Ala Leu Ala His Gly Ile Asn Ile Thr Leu Ala Leu Ala Ile
            180                 185                 190

Thr Thr Val Val Val Tyr Phe Tyr Val Tyr His Pro Leu Ile Gly Thr
        195                 200                 205

Leu Thr Glu Met His Ala Ile Ile Val Trp Leu Lys Thr Ala Ser Tyr
    210                 215                 220

Ala Phe Thr Asn Arg Asp Leu Arg His Ala Tyr Leu His Pro Val Glu
225                 230                 235                 240

```
Gly Glu Glu Val Pro Asp Leu Tyr Lys Ser Cys Pro Tyr Pro Gln Asn
                245                 250                 255

Val Thr Met Lys Asn Leu Val Tyr Phe Trp Trp Ala Pro Thr Leu Val
            260                 265                 270

Tyr Gln Pro Val Tyr Pro Arg Thr Asp Lys Ile Arg Trp Val Phe Val
        275                 280                 285

Phe Lys Arg Leu Gly Glu Ile Phe Cys Leu Ala Val Phe Ile Trp Val
    290                 295                 300

Ala Ser Ala Gln Tyr Ala Thr Pro Val Leu Arg Asn Ser Leu Asp Lys
305                 310                 315                 320

Ile Ala Ser Leu Asp Leu Pro Asn Ile Leu Glu Arg Leu Met Lys Leu
                325                 330                 335

Ser Thr Ile Ser Leu Val Ile Trp Leu Ala Gly Phe Phe Ala Leu Phe
            340                 345                 350

Gln Ser Phe Leu Asn Ala Leu Ala Glu Ile Met Arg Phe Gly Asp Arg
        355                 360                 365

Ser Phe Tyr Asp Asp Trp Trp Asn Ser Glu Ser Leu Gly Ala Tyr Trp
    370                 375                 380

Arg Thr Trp Asn Lys Pro Val Tyr Thr Tyr Phe Lys Arg His Val Tyr
385                 390                 395                 400

Met Pro Met Ile Gly Arg Gly Trp Ser Pro Ala Ala Ala Ser Phe Ala
                405                 410                 415

Val Phe Phe Val Ser Ala Val Leu His Glu Ile Leu Val Gly Val Pro
            420                 425                 430

Thr His Asn Ile Ile Gly Val Ala Phe Phe Gly Met Phe Leu Gln Leu
        435                 440                 445

Pro Leu Ile Ala Ile Thr Thr Pro Leu Glu Lys Met Lys Leu Gly His
    450                 455                 460

Gly Gly Arg Ile Leu Gly Asn Val Ile Phe Trp Val Ser Phe Thr Ile
465                 470                 475                 480

Phe Gly Gln Pro Phe Ala Ala Leu Met Tyr Phe Tyr Ala Trp Gln Ala
                485                 490                 495

Lys Tyr Gly Ser Val Ser Arg Leu Pro Gln Met Val His His
            500                 505                 510
```

<210> SEQ ID NO 150
<211> LENGTH: 1533
<212> TYPE: DNA
<213> ORGANISM: Trichoderma virens

<400> SEQUENCE: 150

```
atggcgcctc ctgcagagtc ctccacgacg acaagcgtcg aggcctctac cggctccgtg      60

tctcgccgcc acgcctcaca aagtgaagca gatctaacgt cggtggagcc cgtcaacggc     120

acgaccaaga accggctctc caagacaccg ccgaagaaat atcgccatgt cgctgcggtg     180

cattcccaga cgcggccgtc gtgcctgagc catgattccc ctgcggctcc cagctttctc     240

ggattccgca atctcatggt cattgtgctg gttgttggca atctccgatt gatgattgag     300

aatattcaaa agtacggcgt cttaatttgc atcaggtgtc acgactacag acgtcaagat     360

gtgctcttgg gtcttttgct ttattttctt atcccctgcc atttgtttgc agcatacctg     420

atagagctgg tcgctgccaa gcaggctgag ggatccagga agcgaatcaa ggacaacaac     480

tctggcccgt cagaggcaga gcgcaagaag ttccactcaa tctgggttct tgcggctttg     540

gcccatggaa tcaacatcac tcttgccctt gcaattacca ccgttgtggt ctacttttac     600
```

```
gtctatcatc cgctgattgg cactttgacc gagatgcatg ccatcattgt gtggctcaag    660

acggcatcat atgcattcac caaccgagat cttcgtcacg cctatctgca tccagttgag    720

ggagaggaag tgcctgattt gtacaaatcc tgcccctatc cacaaaacgt gacgatgaag    780

aacttggtat acttctggtg ggctccgact ctggtgtacc aacctgttta tccgcggacc    840

gacaagattc gatgggtgtt cgtgtttaag cgactaggag agatcttttg ccttgctgtg    900

ttcatttggg ttgccagtgc ccaatatgcc acccccgttt tgcgcaactc tctcgacaag    960

attgcctctc ttgatttgcc caacatcttg gagcggctta tgaaactctc gacaatctct   1020

ttggtcatct ggctggccgg cttctttgcg ctcttccaat ctttcttaaa cgcccttgcc   1080

gagataatga ggtttggcga taggtcattc tacgacgact ggtggaacag tgagagcttg   1140

ggcgcctact ggaggacgtg gaacaagcct gtttatactt acttcaagcg ccatgtctat   1200

atgcccatga tcggacgagg ctggagcccg gccgctgcca gtttcgcagt ctttttttgtt  1260

tctgccgttc ttcatgaaat tcttgttggt gttccaacac ataacattat cggcgtcgct   1320

ttcttcggca tgttccttca gcttcctctc atcgccatta ctactccgct ggagaagatg   1380

aaactcggtc atggtggccg cattcttgga aatgtcatat tttgggtttc gtttacaatc   1440

tttggacagc cattcgcggc cctgatgtat ttctacgctt ggcaggccaa gtatggcagc   1500

gtgagtaggt tacctcagat ggtgcaccac taa                                 1533
```

<210> SEQ ID NO 151
<211> LENGTH: 332
<212> TYPE: PRT
<213> ORGANISM: Ricinus communis

<400> SEQUENCE: 151

```
Met Glu Val Ser Gly Leu Gly Cys Phe Ser Ser Ala Ala Thr Pro Ser
1               5                   10                  15

Leu Cys Gly Ala Val Asp Ser Gly Gly Val Ser Ser Leu Arg Pro Arg
            20                  25                  30

Lys Ala Phe His Arg Val Ser Asp Ser Cys Leu Gly Phe Arg Asp Asn
        35                  40                  45

Gly His Leu Gln Tyr Tyr Cys Gln Gly Gly Phe Val Arg Cys Gly Gly
    50                  55                  60

Gly Asn Lys Lys Ser Ile Lys Lys Lys Leu Lys Leu Val Lys Ser Leu
65                  70                  75                  80

Ser Glu Asp Phe Ser Met Phe Pro His Asn Asn Ala Leu Leu His Gln
                85                  90                  95

Pro Gln Ser Ile Ser Leu Gln Glu Ala Ala Gln Gly Leu Met Lys Gln
            100                 105                 110

Leu Gln Glu Leu Arg Ala Lys Glu Lys Glu Leu Lys Arg Gln Lys Lys
        115                 120                 125

Gln Glu Lys Lys Ala Lys Leu Lys Ser Glu Ser Ser Ser Ser Ser Ser
    130                 135                 140

Ser Glu Ser Ser Ser Asp Ser Glu Arg Gly Glu Val Ile His Met Ser
145                 150                 155                 160

Arg Phe Arg Asp Glu Thr Ile Pro Ala Ala Leu Pro Gln Leu His Pro
                165                 170                 175

Leu Thr His His His Pro Thr Ser Thr Leu Pro Val Ser Pro Thr Gln
            180                 185                 190

Glu Cys Asn Pro Met Asp Tyr Thr Ser Thr His His Glu Lys Arg Cys
        195                 200                 205
```

```
Cys Val Gly Pro Ser Thr Gly Ala Asp Asn Ala Val Gly Asp Cys Cys
    210                 215                 220

Asn Asp Arg Asn Ser Ser Met Thr Glu Glu Leu Ser Ala Asn Arg Ile
225                 230                 235                 240

Glu Val Cys Met Gly Asn Lys Cys Lys Lys Ser Gly Gly Ala Ala Leu
                245                 250                 255

Leu Glu Glu Phe Gln Arg Val Leu Gly Val Glu Ala Ala Val Val Gly
            260                 265                 270

Cys Lys Cys Met Gly Asn Cys Arg Asp Gly Pro Asn Val Arg Val Arg
        275                 280                 285

Asn Ser Val Gln Asp Arg Asn Thr Asp Asp Ser Val Arg Thr Pro Ser
    290                 295                 300

Asn Pro Leu Cys Ile Gly Val Gly Leu Glu Asp Val Asp Val Ile Val
305                 310                 315                 320

Ala Asn Phe Phe Gly Leu Gly Leu Ala Pro Ala Ser
                325                 330


<210> SEQ ID NO 152
<211> LENGTH: 999
<212> TYPE: DNA
<213> ORGANISM: Ricinus communis

<400> SEQUENCE: 152

atggaagtct caggcctggg ctgcttctcc tcggctgcaa cgccatcttt gtgtggggcg      60

gtggattcag gcggagtatc ctctttgaga ccgaggaagg cattccatag ggtttctgat     120

tcttgtttag ggtttagaga taatggacat ctgcagtatt attgtcaagg aggatttgtc     180

aggtgcggag gagggaacaa gaaatctatc aagaaaaagt tgaaattagt gaagtccttg     240

tctgaggact tttccatgtt tcctcataac aatgctttgc tccatcaacc tcaatccatc     300

tccctccagg aagctgcaca aggattaatg aaacagctcc aagaattgcg agcaaaggag     360

aaggaattaa agaggcagaa gaaacaagag aaaaaagcca agctaaaatc tgaatcatcc     420

tcatcctcat cctctgaatc cagtagtgat agcgaacgtg gggaggttat tcacatgagc     480

cgcttcagag atgaaactat tcctgccgca ctacctcaat tgcacccact tactcatcac     540

cacccaactt ccaccctacc agtctcccca acccaagaat gcaacccgat ggattacact     600

tcaacacatc atgaaaaacg atgctgcgtt ggaccaagca ccggtgccga taacgcagtc     660

ggtgactgtt gcaatgatag gaatagctcg atgacagagg aattgtcagc aaacagaatt     720

gaggtgtgca tgggtaataa gtgcaagaag tcgggaggtg cagcgttatt ggaggaattt     780

cagagggttt tgggtgtaga ggctgcagtt gttgggtgca agtgcatggg gaactgcagg     840

gacggtccta atgtaagggt caggaattct gtccaagaca gaaacacaga tgactctgtt     900

cgaaccccct ccaatcctct ctgcattggt gttggtttgg aggatgtgga tgttattgtg     960

gccaatttct ttgggttggg tctggcccct gcatcttaa                            999


<210> SEQ ID NO 153
<211> LENGTH: 345
<212> TYPE: PRT
<213> ORGANISM: Arachis hypogaea

<400> SEQUENCE: 153

Met Glu Val Ser Gly Ala Val Leu Arg Asn Val Thr Cys Pro Ser Phe
1               5                   10                  15

Ser Val His Val Ser Ser Arg Arg Arg Gly Gly Asp Ser Cys Val Thr
```

```
            20                  25                  30

Val Pro Val Arg Met Arg Lys Lys Ala Val Val Arg Cys Cys Cys Gly
        35                  40                  45

Phe Ser Asp Ser Gly His Val Gln Tyr Tyr Gly Asp Glu Lys Lys Lys
    50                  55                  60

Glu Asn Gly Thr Ala Met Leu Ser Thr Lys Lys Lys Leu Lys Met Leu
65                  70                  75                  80

Lys Lys Arg Val Leu Phe Asp Asp Leu Gln Gly Asn Leu Thr Trp Asp
                85                  90                  95

Ala Ala Met Val Leu Met Lys Gln Leu Glu Gln Val Arg Ala Glu Glu
            100                 105                 110

Lys Glu Leu Lys Lys Lys Arg Lys Gln Glu Lys Lys Glu Ala Lys Leu
        115                 120                 125

Lys Ala Ser Lys Met Asn Thr Asn Pro Asp Cys Glu Ser Ser Ser Ser
    130                 135                 140

Ser Ser Ser Ser Glu Ser Glu Ser Glu Ser Ser Glu Ser Glu Cys Asp
145                 150                 155                 160

Asn Glu Val Val Asp Met Lys Lys Asn Ile Lys Val Gly Val Ala Val
                165                 170                 175

Ala Val Ala Asp Ser Pro Arg Lys Ala Glu Thr Met Ile Leu Tyr Thr
            180                 185                 190

Ser Leu Val Ala Arg Asp Val Ser Ala Asn His His His His Asn Ala
        195                 200                 205

Val Glu Leu Phe Ser Arg Asn Asn Asp Ile Ser Val Gly Ser Ile Asn
    210                 215                 220

Gly Gly Leu Lys Asn Glu Asn Thr Ala Val Ile Thr Thr Glu Ala Ile
225                 230                 235                 240

Pro Gln Lys Arg Ile Glu Val Cys Met Gly Asn Lys Cys Lys Lys Ser
                245                 250                 255

Gly Ser Ile Ala Leu Leu Gln Glu Phe Glu Arg Val Val Gly Ala Glu
            260                 265                 270

Gly Gly Ala Ala Ala Ala Val Val Gly Cys Lys Cys Met Gly Lys Cys
        275                 280                 285

Lys Ser Ala Pro Asn Val Arg Ile Gln Asn Ser Thr Ala Asp Lys Ile
    290                 295                 300

Ala Glu Gly Phe Asn Asp Ser Val Lys Val Pro Ala Asn Pro Leu Cys
305                 310                 315                 320

Ile Gly Val Ala Trp Arg Met Leu Lys Pro Leu Trp Leu Arg Phe Leu
                325                 330                 335

Gly Glu Asn Gln Glu Ser Thr Asn Glu
            340                 345
```

<210> SEQ ID NO 154
<211> LENGTH: 1038
<212> TYPE: DNA
<213> ORGANISM: Arachis hypogaea

<400> SEQUENCE: 154

```
atggaggttt caggcgccgt tctaaggaat gtcacgtgcc cttccttttc tgtgcacgtg      60

agttcccgtc gtcgtggtgg tgatagttgt gttacagtgc cggtgaggat gagaaaaaag     120

gcggtggtgc gttgttgctg cgggttcagt gattcggggc atgtgcagta ttacggggac     180

gagaagaaga aggagaatgg aaccgctatg ttgagcacca agaagaagct caagatgctg     240

aagaaacgtg tccttttcga tgatcttcaa ggaaacctga cttgggatgc tgctatggtt     300
```

-continued

```
ttgatgaagc agctagagca agtaagggca gaggagaagg aattgaagaa aaaaaggaag    360

caagagaaga aggaggcaaa actcaaagcc tctaagatga acaccaatcc tgattgcgaa    420

tcgtcatcgt catcgtcatc atctgaatct gaatctgaat caagtgagag tgaatgtgac    480

aatgaggtgg ttgacatgaa gaagaacatt aaggttggtg ttgccgttgc tgttgccgat    540

tccccacgaa aggcggaaac catgattcta tacacctccc ttgttgcccg agatgttagt    600

gctaatcatc atcatcataa tgccgtggaa ttattctcta gaaacaatga catatcagtt    660

ggaagcatta atggtggcct taagaatgag aatactgcgg ttattaccac tgaagctatt    720

cctcagaaga ggattgaggt atgcatggga aacaagtgca agaaatccgg atctattgca    780

ttgttgcaag aatttgagag agtggttggt gctgaaggag gtgctgctgc tgcagttgtt    840

ggatgcaagt gcatggggaa gtgcaagagt gcacctaatg tgaggattca gaactctact    900

gcagataaaa tagctgaggg gttcaatgat tcagttaagg ttccagctaa ccctctttgc    960

attggggttg catggaggat gttgaaacca ttgtggctta gattcttggg cgagaatcag   1020

gaaagtacta atgaataa                                                 1038
```

```
<210> SEQ ID NO 155
<211> LENGTH: 267
<212> TYPE: PRT
<213> ORGANISM: Rattus norvegicus

<400> SEQUENCE: 155

Met Asn Met Ser Val Leu Thr Leu Gln Glu Tyr Glu Phe Glu Lys Gln
1               5                   10                  15

Phe Asn Glu Asn Glu Ala Ile Gln Trp Met Gln Glu Asn Trp Lys Lys
            20                  25                  30

Ser Phe Leu Phe Ser Ala Leu Tyr Ala Ala Phe Ile Phe Gly Gly Arg
        35                  40                  45

His Leu Met Asn Lys Arg Ala Lys Phe Glu Leu Arg Lys Pro Leu Val
    50                  55                  60

Leu Trp Ser Leu Thr Leu Ala Val Phe Ser Ile Phe Gly Ala Leu Arg
65                  70                  75                  80

Thr Gly Ala Tyr Met Leu Tyr Ile Leu Met Thr Lys Gly Leu Lys Gln
                85                  90                  95

Ser Val Cys Asp Gln Ser Phe Tyr Asn Gly Pro Val Ser Lys Phe Trp
            100                 105                 110

Ala Tyr Ala Phe Val Leu Ser Lys Ala Pro Glu Leu Gly Asp Thr Ile
        115                 120                 125

Phe Ile Ile Leu Arg Lys Gln Lys Leu Ile Phe Leu His Trp Tyr His
    130                 135                 140

His Ile Thr Val Leu Leu Tyr Ser Trp Tyr Ser Tyr Lys Asp Met Val
145                 150                 155                 160

Ala Gly Gly Gly Trp Phe Met Thr Met Asn Tyr Gly Val His Ala Val
                165                 170                 175

Met Tyr Ser Tyr Tyr Ala Leu Arg Ala Ala Gly Phe Arg Val Ser Arg
            180                 185                 190

Lys Phe Ala Met Phe Ile Thr Leu Ser Gln Ile Thr Gln Met Leu Met
        195                 200                 205

Gly Cys Val Ile Asn Tyr Leu Val Phe Asn Trp Met Gln His Asp Asn
    210                 215                 220

Asp Gln Cys Tyr Ser His Phe Gln Asn Ile Phe Trp Ser Ser Leu Met
225                 230                 235                 240
```

```
Tyr Leu Ser Tyr Leu Leu Leu Phe Cys His Phe Phe Phe Glu Ala Tyr
                245                 250                 255

Ile Gly Lys Val Lys Lys Ala Thr Lys Ala Glu
            260                 265
```

<210> SEQ ID NO 156
<211> LENGTH: 804
<212> TYPE: DNA
<213> ORGANISM: Rattus norvegicus

<400> SEQUENCE: 156

```
atgaacatgt cagtgttgac tttacaagaa tatgaattcg agaagcagtt caacgagaat      60

gaagccatcc aatggatgca ggaaaactgg aagaaatctt tcctgttttc tgcgctgtac     120

gctgccttta tatttggtgg tcggcatctg atgaacaagc gggccaagtt tgaactgcgg     180

aagccgctcg tgctctggtc actgactctt gcggtcttca gtatattcgg tgctcttcga     240

actggtgctt acatgctgta cattttgatg accaaaggcc tgaagcagtc agtttgtgac     300

cagagttttt acaacggacc tgtcagcaaa ttctgggctt acgcgtttgt gctcagcaaa     360

gcacccgaac taggtgatac gatattcatc attctgagga agcagaagct gatcttcctg     420

cactggtacc accacatcac tgtgctcctg tactcttggt actcctacaa agacatggta     480

gctgggggtg gttggttcat gactatgaac tatggcgtac acgccgtcat gtactcttac     540

tacgccttgc gggctgcggg tttccgggtc tcccggaagt ttgccatgtt catcacgttg     600

tcccagatca ctcagatgct gatgggctgt gtcattaact acctggtctt caactggatg     660

cagcatgaca atgaccagtg ctactcccac tttcagaaca tcttctggtc ctcactcatg     720

tacctcagct accttctgct cttctgccat ttcttctttg aggcctacat cggcaaagtg     780

aagaaagcga cgaaggccga gtag                                            804
```

<210> SEQ ID NO 157
<211> LENGTH: 206
<212> TYPE: PRT
<213> ORGANISM: Saccharomyces cerevisiae

<400> SEQUENCE: 157

```
Met Val Ser Asp Trp Lys Asn Cys Lys Ala Ser Arg Arg Thr Asp Arg
1               5                   10                  15

Asn Tyr Trp Asp Tyr Asn Arg Ala Val Gly Trp Ala Thr Ala Gly Arg
            20                  25                  30

Lys Asp Thr Val Gly Lys Ser Arg Val Ala Met Tyr Tyr Val Val Gly
        35                  40                  45

Gly Arg Ser Val Lys Ser Cys Lys Lys Arg Ser Val His Asn Met Thr
    50                  55                  60

Ser Val Ser Trp Met Val Met Val Tyr Arg His Gly Tyr Ala Val Cys
65                  70                  75                  80

Asn Val Ser Trp Thr Met Thr Tyr Tyr Asn Tyr Met Thr Lys Val Ala
                85                  90                  95

Asp Thr Val Met Val Lys His Arg Lys Thr His Thr Tyr His His Gly
            100                 105                 110

Ala Thr Ala Cys Tyr Asn Val Gly Tyr Thr Ala Val Thr Trp Val Val
        115                 120                 125

Thr Asn Ala Val His Val Met Tyr Trp Tyr Tyr Ser Ala Ser Gly Arg
    130                 135                 140

Val Trp Trp Lys Ala Trp Val Thr Arg Val Met Asp Val Val Tyr Tyr
```

-continued

```
145                 150                 155                 160

Val Tyr Lys Val Ala Ala Tyr Lys Asn Ala Cys Thr Cys Asp Cys Gly
                165                 170                 175

Ser Met Thr Ala Ala Ala Gly Ala Ala Thr Ser Tyr Ser Tyr Val Tyr
            180                 185                 190

Lys Arg Gly Ser Ala Ser Gly Lys Lys Lys Asn Lys Asn Asn
        195                 200                 205


<210> SEQ ID NO 158
<211> LENGTH: 933
<212> TYPE: DNA
<213> ORGANISM: Saccharomyces cerevisiae

<400> SEQUENCE: 158

atggtaagtg attggaaaaa tttttgcctc gagaaagcct ctaggtttcg cccaacaata      60

gataggcctt tttttaatat ttatttgtgg gactatttca atcgtgcggt tgggtgggcc     120

actgcaggtc gcttccagcc aaaggatttt gagtttaccg ttgggaagca gcctttgagt     180

gaacctcgtc cggtactgct tttattgcc atgtattatg tggttatatt tggcgggagg     240

tccctggtaa agtcatgtaa acctctcaag ttgagattta tttctcaagt ccataacttg     300

atgttgactt ctgtttcctt tttatggttg attttgatgg tggaacagat gctacccata     360

gtgtatcgcc atgggctgta ttttgctgtt tgtaatgttg aatcgtggac gcaaccgatg     420

gagacattat attatctcaa ctatatgaca aagtttgtgg agttcgcaga cactgtcttg     480

atggtgttga aacatagaaa gttgactttc ctacatacat accatcatgg tgctacagct     540

ttactgtgct ataatcaatt ggttggttac acagcagtta catgggttcc tgtcacctta     600

aacttagctg ttcacgttct tatgtattgg tattatttcc tttctgctag cggaattcgt     660

gtttggtgga aagcctgggt tacaagacta caaattgtgc agttcatgct tgatctcatt     720

gtcgtttatt acgtgcttta tcagaagatt gttgctgcat atttcaaaaa tgcttgtact     780

ccacagtgtg aggattgctt aggttcaatg acggctattg ctgctggtgc agccattctt     840

acatcctact tgtttttgtt catctctttc tatattgagg tttacaaacg tggaagtgct     900

agtggtaaga agaagatcaa caaaaacaat taa                                  933


<210> SEQ ID NO 159
<211> LENGTH: 334
<212> TYPE: PRT
<213> ORGANISM: Arxula adeninivorans

<400> SEQUENCE: 159

Met Leu Glu Val Thr Phe Pro Pro Thr Leu Asp Arg Pro Phe Gly Val
1               5                   10                  15

Tyr Leu Tyr Gly Leu Phe Asp Ala Leu Thr Asn Gly Trp Ala Thr Arg
            20                  25                  30

Phe Gln Phe Ala Gln Asp Ser Gly Ile Pro Phe Ser Ser Arg Trp Glu
        35                  40                  45

Val Ala Ala Gly Ile Val Thr Tyr Tyr Val Val Ile Phe Gly Gly Arg
    50                  55                  60

Glu Val Leu Lys Asn Ala Pro Val Ile Arg Leu Asn Phe Val Phe Gln
65                  70                  75                  80

Ile His Asn Leu Ile Leu Thr Leu Leu Ser Leu Gly Leu Leu Leu Leu
                85                  90                  95

Leu Val Glu Gln Leu Ile Pro Ile Ile Val Arg His Gly Val Leu Tyr
            100                 105                 110
```

```
Ala Ile Cys Asn Ser Gly Ser Trp Thr Gln Pro Ile Val Thr Val Tyr
        115                 120                 125

Tyr Leu Asn Tyr Leu Thr Lys Tyr Tyr Glu Leu Phe Asp Thr Val Phe
    130                 135                 140

Leu Val Leu Arg Lys Lys Pro Leu Thr Phe Leu His Thr Tyr His His
145                 150                 155                 160

Gly Ala Thr Ala Leu Leu Cys Phe Thr Gln Leu Ile Gly His Thr Ser
                165                 170                 175

Val Ser Trp Val Pro Ile Val Leu Asn Leu Phe Val His Val Ile Met
            180                 185                 190

Tyr Tyr Tyr Tyr Phe Leu Ser Ala Leu Gly Val Arg Asn Ile Trp Trp
        195                 200                 205

Lys Glu Trp Val Thr Arg Thr Gln Ile Ile Gln Phe Val Val Asp Leu
    210                 215                 220

Val Phe Val Tyr Phe Ala Thr Tyr Thr Tyr Phe Thr Asn Lys Tyr Trp
225                 230                 235                 240

Pro Trp Leu Pro Asn Lys Gly Thr Cys Ala Gly Glu Glu Phe Ala Ala
                245                 250                 255

Ile Tyr Gly Cys Ala Leu Leu Thr Ser Tyr Leu Phe Leu Phe Ile Ala
            260                 265                 270

Phe Tyr Ile Arg Val Tyr Thr Lys Ala Lys Ala Lys Gly Arg Lys Arg
        275                 280                 285

Ala Ala Ser Ala Ala Ala Lys Ala Thr Thr Gly Val Val Thr Ala Asp
    290                 295                 300

Arg Pro Ser Thr Pro Ile Ala Thr Thr Asn Gly Ala Ala Thr Gly Ala
305                 310                 315                 320

Ala Gly Ala Thr Gly Ser Val Lys Ser Arg Ser Arg Lys Ala
                325                 330
```

<210> SEQ ID NO 160
<211> LENGTH: 1005
<212> TYPE: DNA
<213> ORGANISM: Arxula adeninivorans

<400> SEQUENCE: 160

```
atgctggaag tcaccttccc cccgaccctg gaccgcccct ttggcgtgta cttgtacggg      60

ctgtttgacg cgttgaccaa cggatgggca acccgattcc agtttgctca ggactctggc     120

atccccttta gctcccgctg ggaagtggcc gcgggcattg tcacctacta cgtggtcatc     180

tttggcggcc gcgaggtgct caagaatgcc ccggtgattc gtctcaactt tgtgttccag     240

attcacaacc ttattctgac cctgctgtcc ctgggtctgt tgctgctgct ggtggagcag     300

ttgattccta tcattgtgcg ccacggagtg ctgtacgcca tctgcaactc tggatcgtgg     360

actcagccta ttgtgaccgt gtactacctc aactacctga caaagtacta cgagctgttt     420

gacactgtgt tcttggtgct gcgaaagaag cctctgacct tcttgcacac ttaccaccac     480

ggagccaccg ctctgctgtg cttcacccag ctcattggcc acacctcggt gtcgtgggtg     540

cccattgtgc tcaacctgtt tgtccatgtt atcatgtact actactactt tttgagcgct     600

ctgggagttc gcaacatctg gtggaaggag tgggtcactc gaacccagat catccagttt     660

gtggtggacc tggtgtttgt gtactttgct acctacacct actttaccaa caagtactgg     720

ccctggctcc ctaacaaggg cacttgcgct ggtgaggagt ttgctgccat ctacggatgt     780

gccctgctca cttcgtacct gttcctgttc attgcctttt acattcgcgt gtacaccaag     840
```

-continued gcaaaggcca agggtcgcaa gagagctgcc agcgctgctg ccaaggccac cactggcgtt 900
gtcactgccg accgtccttc cactccaatt gctaccacca acggagctgc cactggcgct 960
gctggagcca ctggttcggt caagtctcga tcgcgcaagg cctaa 1005

<210> SEQ ID NO 161
<211> LENGTH: 341
<212> TYPE: PRT
<213> ORGANISM: Escherichia coli

<400> SEQUENCE: 161

Met Lys Lys Pro Glu Leu Thr Ala Thr Ser Val Glu Lys Phe Leu Ile
1 5 10 15

Glu Lys Phe Asp Ser Val Ser Asp Leu Met Gln Leu Ser Glu Gly Glu
20 25 30

Glu Ser Arg Ala Phe Ser Phe Asp Val Gly Gly Arg Gly Tyr Val Leu
35 40 45

Arg Val Asn Ser Cys Ala Asp Gly Phe Tyr Lys Asp Arg Tyr Val Tyr
50 55 60

Arg His Phe Ala Ser Ala Ala Leu Pro Ile Pro Glu Val Leu Asp Ile
65 70 75 80

Gly Glu Phe Ser Glu Ser Leu Thr Tyr Cys Ile Ser Arg Arg Ala Gln
85 90 95

Gly Val Thr Leu Gln Asp Leu Pro Glu Thr Glu Leu Pro Ala Val Leu
100 105 110

Gln Pro Val Ala Glu Ala Met Asp Ala Ile Ala Ala Ala Asp Leu Ser
115 120 125

Gln Thr Ser Gly Phe Gly Pro Phe Gly Pro Gln Gly Ile Gly Gln Tyr
130 135 140

Thr Thr Trp Arg Asp Phe Ile Cys Ala Ile Ala Asp Pro His Val Tyr
145 150 155 160

His Trp Gln Thr Val Met Asp Asp Thr Val Ser Ala Ser Val Ala Gln
165 170 175

Ala Leu Asp Glu Leu Met Leu Trp Ala Glu Asp Cys Pro Glu Val Arg
180 185 190

His Leu Val His Ala Asp Phe Gly Ser Asn Asn Val Leu Thr Asp Asn
195 200 205

Gly Arg Ile Thr Ala Val Ile Asp Trp Ser Glu Ala Met Phe Gly Asp
210 215 220

Ser Gln Tyr Glu Val Ala Asn Ile Phe Phe Trp Arg Pro Trp Leu Ala
225 230 235 240

Cys Met Glu Gln Gln Thr Arg Tyr Phe Glu Arg Arg His Pro Glu Leu
245 250 255

Ala Gly Ser Pro Arg Leu Arg Ala Tyr Met Leu Arg Ile Gly Leu Asp
260 265 270

Gln Leu Tyr Gln Ser Leu Val Asp Gly Asn Phe Asp Asp Ala Ala Trp
275 280 285

Ala Gln Gly Arg Cys Asp Ala Ile Val Arg Ser Gly Ala Gly Thr Val
290 295 300

Gly Arg Thr Gln Ile Ala Arg Arg Ser Ala Ala Val Trp Thr Asp Gly
305 310 315 320

Cys Val Glu Val Leu Ala Asp Ser Gly Asn Arg Arg Pro Ser Thr Arg
325 330 335

Pro Arg Ala Lys Glu
340

<210> SEQ ID NO 162
<211> LENGTH: 1026
<212> TYPE: DNA
<213> ORGANISM: Escherichia coli

<400> SEQUENCE: 162
atgaagaagc ccgagctgac cgctacctct gttgagaagt tcctgattga gaagtttgat 60
tccgtttccg acctgatgca gctgtccgag ggcgaggagt ctcgagcctt ctcctttgac 120
gtgggcggac gaggttacgt tctgcgagtg aactcgtgtg ccgacggctt ctacaaggat 180
cgatacgtct accgacactt tgcttctgcc gctctgccca tccctgaggt tctcgacatt 240
ggcgagttct ctgagtccct cacctactgc atctctcgac gagctcaggg agtcaccctg 300
caggacctcc ctgagactga gctgcctgct gtcctccagc ctgttgctga ggccatggac 360
gctatcgctg ctgctgatct gtcccagacc tcgggtttcg gccccttttgg acctcaggga 420 attggacagt acaccacttg gcgagacttc atctgtgcta ttgccgatcc tcacgtctac 480
cattggcaga ccgttatgga cgatactgtg tcggcttctg tcgctcaggc tctggacgag 540
ctgatgctct gggccgagga ttgccccgag gttcgacacc tggtgcatgc tgacttcggt 600
tccaacaacg ttctcaccga caacggccga atcactgccg tgattgactg gtccgaggct 660
atgtttggcg actcgcagta cgaggtggcc aacatcttct tttggcgacc ctggctggct 720
tgtatggagc agcagacccg atacttcgag cgacgacatc ctgagctcgc tggatcccct 780
cgactgcgag cttacatgct ccgaattggt ctggaccagc tctaccagtc gctggtggat 840
ggcaactttg acgatgctgc ctgggctcag ggacgatgtg acgccatcgt gcgatctggc 900
gctggaaccg tcggacgaac tcagattgcc cgacgatccg ctgctgtctg gaccgacgga 960
tgcgtggagg tcctggctga ttcgggtaac cgacgaccct ctactcgacc tcgagctaag 1020
gagtaa 1026

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 163
accacttggc gagacttcat ctgt 24

<210> SEQ ID NO 164
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 164
agcatcgtca aagttgccat ccac 24

<210> SEQ ID NO 165
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 165
cagctctctt cccccgttca gctccttttc taccgcgatt atgaagaagc ccgagctgac 60

<210> SEQ ID NO 166
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 166
tttagtctca tcgttagtag ttatgtgctc tgctcggggt tactccttag ctcgaggtcg 60

<210> SEQ ID NO 167
<211> LENGTH: 898
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 167
cagctctctt cccccgttca gctccttttc taccgcgatt atgaagaagc ccgagctgac 60
cgctacctct gttgagaagt tcctgattga gaagtttgat tccgtttccg acctgatgca 120
gctgtccgag ggcgaggagt ctcgagcctt ctcctttgac gtgggcggac gaggttacgt 180
tctgcgagtg aactcgtgtg ccgacggctt ctacaaggat cgatacgtct accgacactt 240
tgcttctgcc gctctgccca tccctgaggt tctcgacatt ggcgagttct ctgagtccct 300
cacctactgc atctctcgac gagctcaggg agtcaccctg caggacctcc ctgagactga 360
gctgcctgct gtcctccagc ctgttgctga ggccatggac gctatcgctg ctgctgatct 420
gtcccagacc tcgggtttcg gcccctttgg acctcaggga attggacagt acaccacttg 480
gcgagacttc atctgtgcta ttgccgatcc tcacgtctac cattggcaga ccgttatgga 540
cgatactgtg tcggcttctg tcgctcaggc tctggacgag ctgatgctct gggccgagga 600
ttgccccgag gttcgacacc tggtgcatgc tgacttcggt tccaacaacg ttctcaccga 660
caacggccga atcactgccg tgattgactg gtccgaggct atgtttggcg actcgcagta 720
cgaggtggcc aacatcttct tttggcgacc ctggctggct tgtatggagc agcagacccg 780
atacttcgag cgacgacatc ctgagctcgc tggatcccct cgactgcgag cttacatgct 840
ccgaattggt ctggaccagc tctaccagtc gctggtggat ggcaactttg acgatgct 898

<210> SEQ ID NO 168
<211> LENGTH: 633
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 168
accacttggc gagacttcat ctgtgctatt gccgatcctc acgtctacca ttggcagacc 60
gttatggacg atactgtgtc ggcttctgtc gctcaggctc tggacgagct gatgctctgg 120
gccgaggatt gccccgaggt tcgacacctg gtgcatgctg acttcggttc caacaacgtt 180
ctcaccgaca acggccgaat cactgccgtg attgactggt ccgaggctat gtttggcgac 240
tcgcagtacg aggtggccaa catcttcttt tggcgaccct ggctggcttg tatggagcag 300

-continued

```
cagacccgat acttcgagcg acgacatcct gagctcgctg gatcccctcg actgcgagct    360

tacatgctcc gaattggtct ggaccagctc taccagtcgc tggtggatgg caactttgac    420

gatgctgcct gggctcaggg acgatgtgac gccatcgtgc gatctggcgc tggaaccgtc    480

ggacgaactc agattgcccg acgatccgct gctgtctgga ccgacggatg cgtggaggtc    540

ctggctgatt cgggtaaccg acgaccctct actcgacctc gagctaagga gtaaccccga    600

gcagagcaca taactactaa cgatgagact aaa                                 633
```

OLEIC ACID PRODUCTION IN YEAST

RELATED APPLICATION

This Application is a national phase application under 35 U.S.C. § 371 of International Application No. PCT/US2015/064710, filed Dec. 9, 2015, which claims the benefit of priority to U.S. Provisional Patent Application Ser. No. 62/090,169 filed Dec. 10, 2014. The contents of PCT/US2015/064710 are incorporated herein in their entirety.

SEQUENCE LISTING

The instant application contains a Sequence Listing which has been submitted electronically in ASCII format and is hereby it by reference in its entirety Said ASCII copy, created on Dec. 8, 2015, is named NGX-03725_SL.txt and is 523,236 bytes in size.

BACKGROUND

Lipids are indispensable ingredients in the food and cosmetics industries, and they are important precursors in the biodiesel and biochemical industries. Many oleaginous microorganisms, including the well-characterized yeast *Yarrowia lipolytica*, produce lipids.

Microorganisms synthesize lipids with distinct carbon chain lengths and degrees of unsaturation. These fatty acids can be stored in organelles, termed lipid bodies or lipid droplets, as storage lipids, for example, as triacylglyeerides (TAG), The lipid profile of a cell, i.e., the relative amounts of fatty acid species that make up the total lipids in the cell, is determined by the activities and substrate specificities of various enzymes that synthesize fatty acids (fatty acid synthase, elongase, desaturase), various enzymes that stabilize fatty acids by incorporating them into storage lipids (acyltransferases), and various enzymes that degrade fatty acids and storage lipids (e.g., lipases).

The ability to tailor the lipid profile of a cell to increase the concentration of a particular fatty acid is desirable when targeting the lipid product to a specific market/application. Specifically, increasing the oleic acid content of an oleaginous yeast, like *Yarrowia lipolytica*, increases the value of the TAG produced in the organism.

The lipid yield of oleaginous organisms can be increased by the up-regulation, down-regulation, or deletion of genes implicated in a lipid pathway. The successful modulation of enzymes, however, is unpredictable, at best. For example, overexpressing in *Y. lipolytica* the DGA1 from *Mortierella alpine* has no significant effect on lipid content (U.S. Pat. No. 7,198,937; incorporated by reference) likewise, overexpressing DGA2 has no significant effect on the lipid content in the absence of other genetic modifications.

SUMMARY

In some aspects, the invention relates to a transformed cell, wherein the cell is selected from the group consisting of algae, bacteria, molds, fungi, plants, and yeasts. The cell may be a yeast. For example, the cell may be a yeast selected from the group consisting of *Arxula adeninivorans, Saccharomyces cerevisiae*, and *Yarrowia lipolytica*.

In some embodiments, the transformed cell comprises one or more genetic modifications that increase the activity of one or more proteins in the cell. For example, the transformed cell may comprise one or more genetic modifications that increase the activity of a Δ9 desaturase protein; an elongase protein; a type 1 diacylglycerol acyltransferase protein; a type 2 diacylglycerol acyltransferase protein; a type 3 diacylglycerol acyltransferase protein; a glycerol-3-phosphate acyltransferase protein; a sn-2 acylglycerol fatty acyltransferase protein; a lysophosphatidic acid acyltransferase protein; a phosphatidate phosphatase protein; a glycerol-3-phosphate/dihydroxyacetone phosphate sn-1 acyltransferase protein; and/or a phospholipid:diacylglycerol acyltransferase protein. The one or more genetic modifications may be transformation with one or more nucleic acids that encode a Δ9 desaturase protein; an elongase protein; a type 1 diacylglycerol acyltransferase protein; a type 2 diacylglycerol acyltransferase protein; a type 3 diacylglycerol acyltransferase protein; a glycerol-3-phosphate acyltransferase protein; a sn-2 acylglycerol fatty acyltransferase protein; a lysophosphatidic acid acyltransferase protein; a phosphatidate phosphatase protein; a glycerol-3-phosphate/dihydroxyacetone phosphate sn-1 acyltransferase protein; and/or a phospholipid:diacylglycerol acyltransferase protein.

In some embodiments, the transformed cell comprises one or more genetic modifications that decrease the activity of a native protein in the cell. For example, the transformed cell may comprise one or more genetic modifications that decrease the activity of a native Δ9 desaturase protein; a native Δ12 desaturase protein; a native diacylglycerol acyltransferase protein; a native triacylglycerol lipase protein; a native sn-2 acylglycerol fatty acyltransferase protein; a native lysophosphatidic acid acyltransferase protein; a native phosphatidate phosphatase protein; a native glycerol-3-phosphate acyltransferase protein; a native glycerol-3-phosphate/dihydroxyacetone phosphate sn-1 acyltransferase protein; and/or a native phospholipid:diacylglycerol acyltransferase protein. The one or more genetic modifications may be, for example, knockout mutations.

In some aspects, the invention relates to a product derived from a transformed cell of the invention. In some embodiments, the product comprises an oil, lipid, or triacylglycerol. The product may comprise stearic acid, oleic acid, or linoleic acid. For example, the product may be oleic acid.

In some aspects, the invention relates to methods of modifying the lipid content of a comprising transforming the cell. The cell may be selected from the group consisting of alae, bacteria, molds, fungi, plants, and yeasts, e.g., the cell may be a yeast. For example, the cell may be a yeast selected from the group consisting of *Arxula adeninivorans, Saccharomyces cerevisiae*, and *Yarrowia lipolytica*.

In some embodiments, the method comprises transforming the cell with one or more nucleic acids that increase the activity of one or more proteins in the cell. For example, the one or more nucleic acids may increase the activity of a Δ9 desaturase protein; an elongase protein; a type 1 diacylglycerol acyltransferase protein; a type 2 diacylglycerol acyltransferase protein; a type 3 diacylglycerol acyltransferase protein a glycerol-3-phosphate acyltransferase protein a sn-2 acylglycerol fatty acyltransferase protein; a lysophosphatidic acid acyltransferase protein; a phosphatidate phosphatase protein; a glycerol-3-phosphate/dihydroxyacetone phosphate sn-1 acyltransferase protein; and/or a phospholipid:diacylglycerol acyltransferase protein. The one or tore nucleic acids may encode a Δ9 desaturase, elongase, type 1 diacylglycerol acyltransferase, type 2 diacylglycerol acyltransferase, type 3 diacylglycerol acyltransferase, glycerol-3-phosphate acyltransferase, sn-2 acylglycerol fatty acyltransferase, lysophosphatidic acid acyltransferase, phosphatidate phosphatase, glycerol-3-phosphate/dihydroxyacetone phosphate sn-1 acyltransferase, and/or phospholipid:diacylglycerol acyltransferase genes.

In some embodiments, the method comprises transforming the cell with a nucleic acid that decreases the activity of a native protein in the cell. For example, the nucleic acid may decrease the activity of a native Δ9 desaturase protein; a native Δ12 desaturase protein; a native diacylglycerol acyltransferase protein; a native triacylglycerol lipase protein; a native sn-2 acylglycerol fatty acyltransferase protein; a native lysophosphatidic acid acyltransferase protein; a native phosphatidate phosphatase protein; a native glycerol-3-phosphate acyltransferase protein; a native glycerol-3-phosphate/dihydroxyacetone phosphate sn-1 acyltransferase protein; and/or a native phospholipid:diacylglycerol acyltransferase protein. The nucleic acid may decrease the activity of a native protein by knocking out the gene that encodes the protein, e.g., the nucleic, acid may recombine with the gene and/or a nucleotide sequence m the regulatory region attic gene, thereby disrupting the transcription or translation of the gene into a protein with the same level of activity as the native protein.

These and other features, aspects, and advantages of the present invention will become better understood with reference to the following description, drawings, and claims.

BRIEF DESCRIPTION OF THE FIGURES

FIG. 15 depicts the percentage of various fatty acids as a percentage of total C16 and C18 fatty acids for *A. adeninivorans* strain NS554 and *Y. lipolytica* strain NS276 comprising various elongase genes. *A. adeninivorans* strain NS554 comprises a Δ12 desaturase knockout mutation and *Y. lipolytica* strain NS276 comprises an ELO1 knockout mutation.

FIG. 16 depicts the percentage of C16 and C18 fatty acids that are either C16 or C18 fatty acids for an *Y. lipolytica* strain comprising an ELO1 knockout and the addition of various elongase genes. Each elongase gene was added to *Y.*

*lipolytica* strain NS276, which comprises an ELO1 desaturase knockout and is shown as a control.

Figure 17:
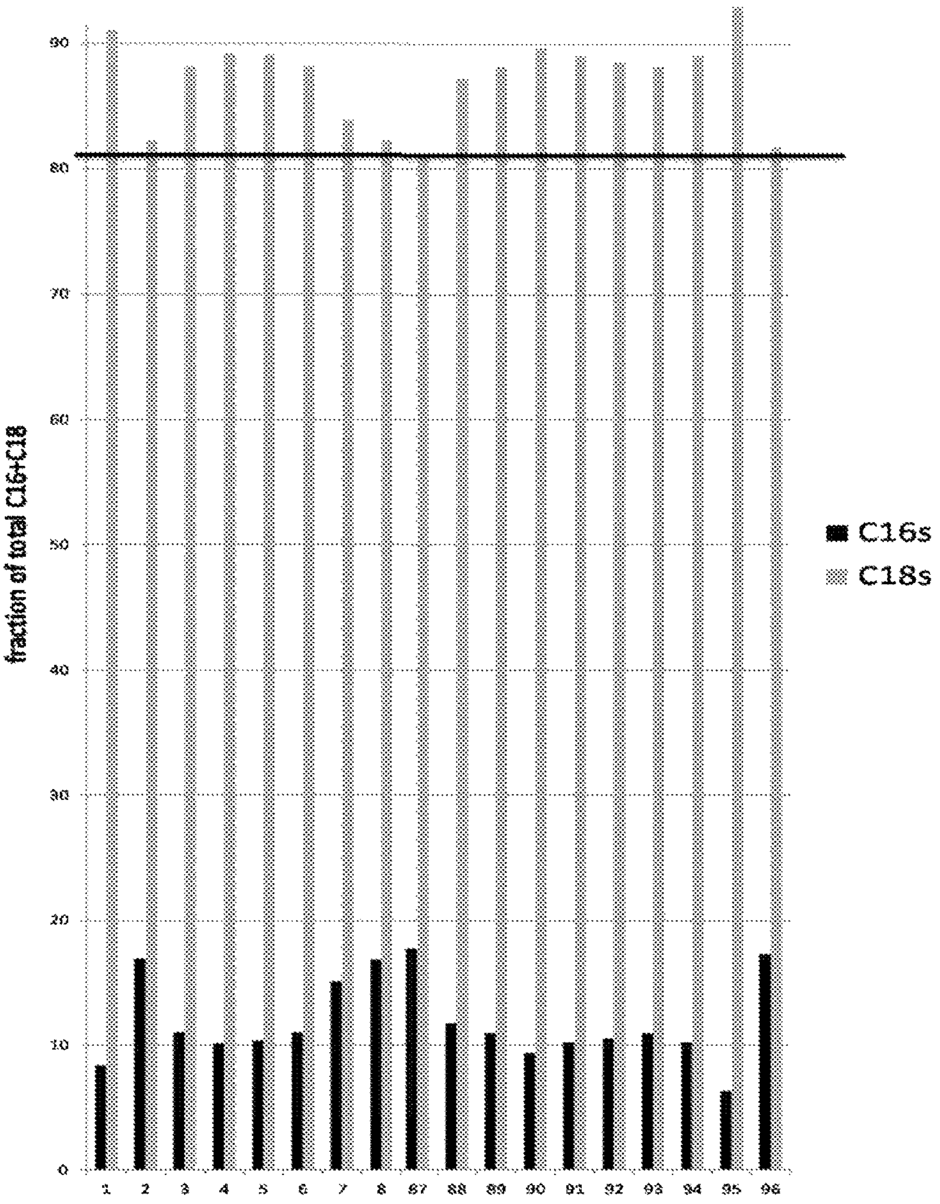

FIG. 17 depicts the percentage of C16 and C18 fatty acids that are either C16 or C18 fatty acids for *A. adeninivorans* strain NS557 further comprising an ELO1 gene from *Y. lipolytica*. The parent strain *A. adeninivorans* NS557 comprises a Δ12 desaturase knockout mutation and expresses *Y. lipolytica* DGA1. Strain NS557 was analyzed as a control, and the horizontal line marks the C18 percentage of this strain.

Figure 18:
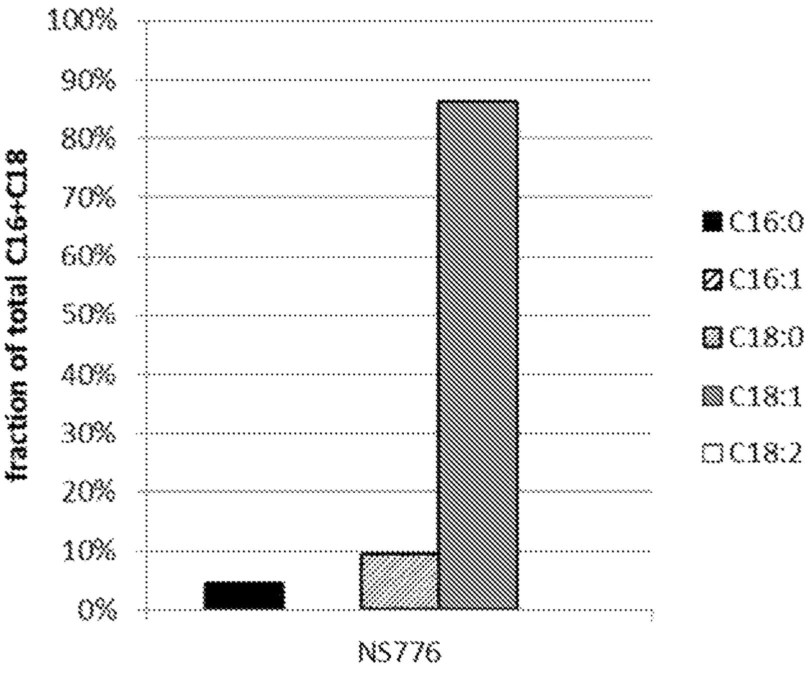

FIG. 18 depicts the percentage of C16 and C18 fatty acids for fatty acids comprising various chain lengths and saturation levels for *A. adeninivorans* strain NS776, described in Example 14.

Figure 19:
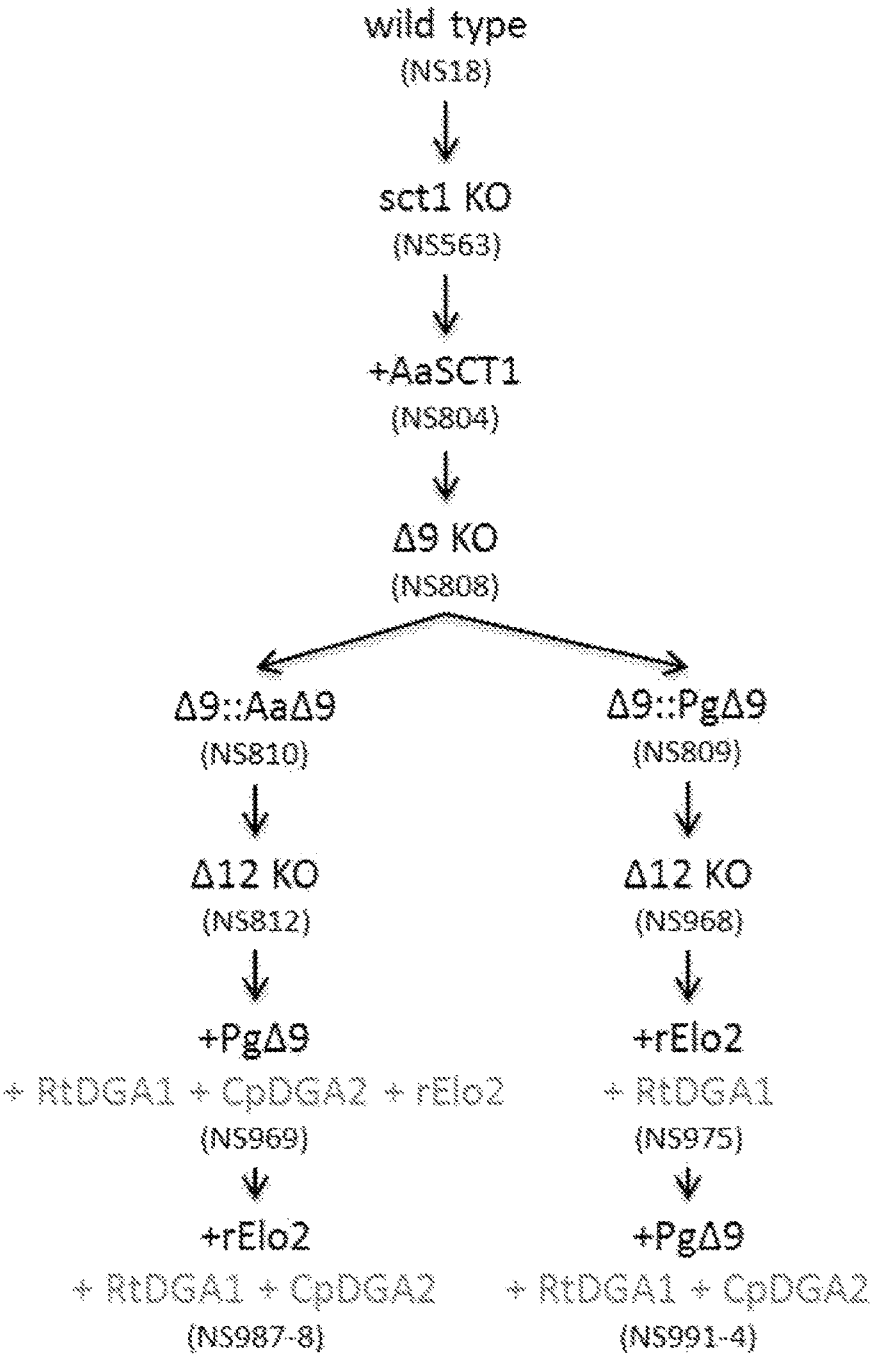

FIG. 19 is a flowchart that shows the order in which various genetic modifications were introduced into *Y. lipolytica* strain NS18, resulting in strains NS987, NS988, NS991, NS992, NS993, and NS994, which are described in Example 15.

Figure 20:
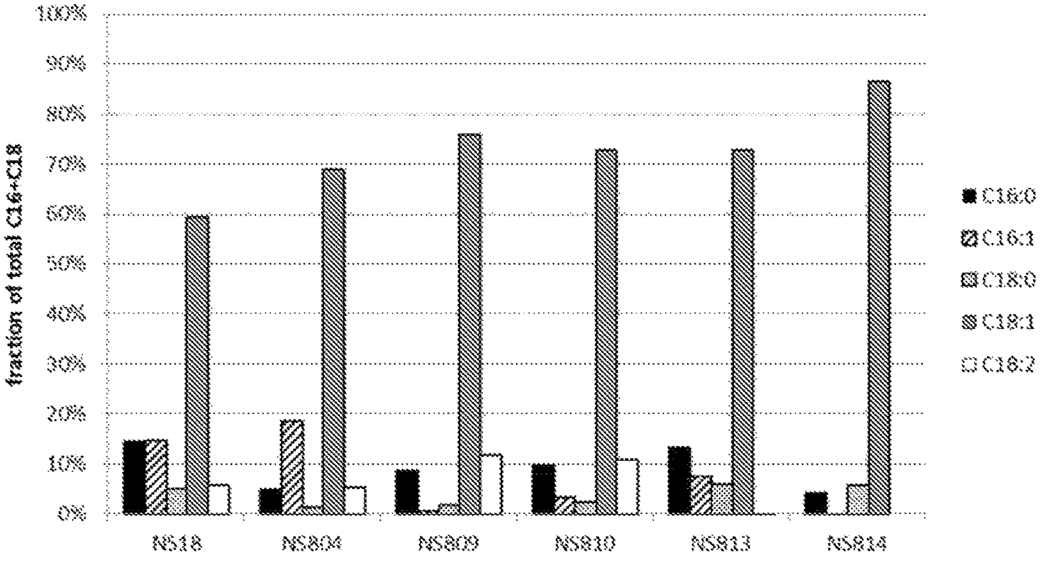

FIG. 20 depicts the percentage of C16 and C18 fatty acids that comprise various chain lengths and levels of saturation for various *Y. lipolytica* strains, which are described in Example 16.

Figure 21:
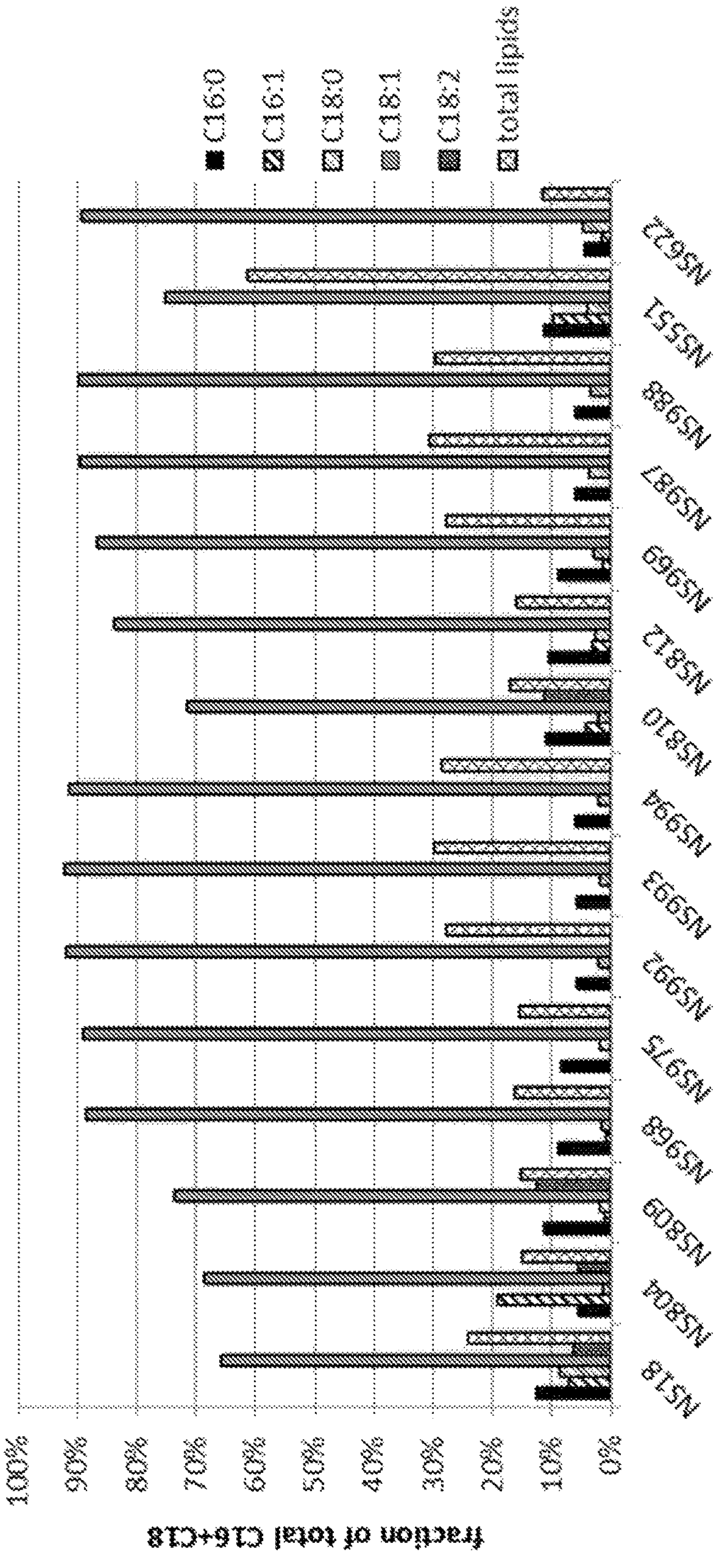

FIG. 21 depicts the percentage of C16 and C18 fatty acids that comprise various chain lengths and levels of saturation for various *Y. lipolytica* strains, which are described in Example 16. Additionally, the total lipid content of each strain is shown as % dry cell weight ("total lipids").

DETAILED DESCRIPTION

Definitions

The articles "a" and "an" are used herein to refer to one or to more than one (i.e., to at least one) of the grammatical object of the article. By way of example, an element" means one element or more than one element.

The term "activity" refers to the total capacity of a cell to perform a function. For example, a genetic modification that decreases the activity of an enzyme in a cell may reduce the amount of the enzyme in a cell, or reduce the efficiency of the enzyme. A knockout reduces the amount of a protein in the cell. Alternatively, a mutation to a gene may reduce the efficiency of its protein product with little effect on the amount of the protein in the cell. Mutations that reduce the efficiency of an enzyme may affect the active site, for example, by changing one or more active site residues; they may impair the enzyme's kinetics, for example, by sterically blocking substrates or products; they may affect protein folding or dynamics, for example, by reducing the proportion of properly-folded enzymes; they may affect protein localization, for example, by preventing the protein from localizing to lipid particles; or they may affect protein degradation, for example, by adding one or more protein cleavage sites or by adding one or more residues or amino acid sequences that target the protein for proteolysis. These mutations affect coding regions. Mutations that decrease the activity of a protein may instead affect the transcription or translation of the gene. For example, mutation of an enhancer or promoter can reduce the activity of a protein by reducing its expression. Mutating or deleting the non-coding portions of a gene, such as its introns, may also reduce transcription or translation. Additionally, mutations to the upstream regulators of a gene may affect the activity of its protein product; for example, the over-expression of one or more repressors may decrease the activity of a protein, and a knockout or mutation of one or more activators may similarly decrease the activity of a protein.

A genetic modification that increases the activity of a protein in a cell may increase the amount of the protein in the cell or increase the efficiency of the protein (e.g., the efficiency of an enzyme). For example, the genetic modification may simply insert an additional copy of the protein into the cell such that the additional copy is transcribed and translated into additional functional protein. The added gene can be native to the host organism or from a different organism. Alternatively, mutating or deleting the non-coding portions of a gene, such as its introns, may also increase translation. A native gene can be altered by adding a new promoter that causes more transcription. Similarly, enhancers may be added to the gene to increase transcription, or silencers may be mutated or deleted from the gene to increase transcription. Mutations to a native gene's coding region might also increase the activity of the protein, for example, by producing a protein variant that does not interact with inhibitory proteins or molecules. The over expression of one or more activators may increase the activity of a protein by increasing the expression of the protein, and a knockout or mutation of one or more repressors may similarly increase the activity of the protein.

The term "biologically-active portion" refers to an amino acid sequence that is less than a full-length amino acid sequence, but exhibits at least one activity of the full length sequence. For example, a biologically-active portion of a diacylglycerol acyltransferase may refer to one or more domains of DGA1 or DGA2 having biological activity for converting acyl-CoA and diacylglycerol to triacylglycerol. Biologically-active portions of a protein include peptides or polypeptides comprising amino acid sequences sufficiently identical to or derived from the amino acid sequence of the protein, e.g., the amino acid sequence set forth in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, or 159, which include fewer amino acids than the full length protein, and exhibit at least one activity of the protein. Similarly, biologically-active portions of a protein include peptides or polypeptides comprising amino acid sequences sufficiently identical to or derived from the amino acid sequence of the protein. e.g., the amino acid sequence set forth in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, or 159, which include fewer amino acids than the full length protein, and exhibit at least one activity of the protein. A biologically-active portion of a protein may comprise, for example, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 718, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 374, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 573, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 646, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700 or more amino acids. Typically, biologically-active portions comprise a domain or motif having a catalytic activity, such as catalytic activity for producing stearic acid, oleic acid, or linoleic acid. A biologically-active portion of a protein includes portions of the protein that have the same activity as the full-length peptide and every portion that has more activity than background. For example, a biologically-active portion of an enzyme may have 0.1%, 0.5%, 1%, 2%, 3%, 4%, 5%, 10%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, 100%, 100.1%, 100.2%, 100.3%, 100.4%, 100.5%, 100.6%, 100.7%, 100.8%, 100.9%, 101%, 105%, 110%, 115%. 120%, 125%, 1301, 135%, 140%. 145%, 150%, 160%, 170%, 180%, 190%, 200%, 220%, 240%, 260%, 280%, 300%, 320%, 340%, 360%, 380%, 400% or higher activity relative to the full-length enzyme. A biologically-active portion of a protein may include portions of a protein that lack a domain that targets the protein to a cellular compartment. A biologically active portion of a DGA1 protein can be a polypeptide which is, for example, 262 amino acids in length.

The term "DGAT1" refers to a gene that encodes a type 1 diacylglycerol acyltransferase protein, such as a gene that encodes a DGA2 protein.

The term "DGAT2" refers to a gene that encodes a type 2 diacylglycerol acyltransferase protein, such as a gene that encodes a DGA1 protein.

"Diacylglyceride," "diacylglycerol," and "diglyceride," are esters comprised of glycerol and two fatty acids.

The terms "diacylglycerol acyltransferase" and "DGA" refer to any protein that catalyzes the formation of triacylglycerides from diacylglycerol. Diacylglycerol acyltransferases include type 1 diacylglycerol acyltransferases (DGA2), type 2 diacylglycerol acyltransferases (DGA1), and type 3 diacylglycerol acyltransferases (DOA3) and all homologs that catalyze the above-mentioned reaction.

The terms "diacylglycerol acyltransferase, type 1" and "type 1 diacylglycerol acyltransferases" refer to DGA2 and DGA2 orthologs.

The terms "diacylglyceral acyltransferase, type 2" and "type 2 diacylglycerol acyltransferases" refer to DGA 1 and DGA1 orthologs.

The term "domain" refers to a part of the amino acid sequence of a protein that is able to fold into a stable three-dimensional structure independent of the rest of the protein.

The term "drug" refers to any molecule that inhibits cell growth or proliferation, thereby providing a selective advantage to cells that contain a gene that confers resistance to the drug. Drugs include antibiotics, antimicrobials, toxins, and pesticides.

"Dry weight" and "dry cell weight" mean weight determined in the relative absence of water. For example, reference to oleaginous cells as comprising a specified percentage of a particular component by dry weight means that the percentage is calculated based on the weight of the cell after substantially all water has been removed.

The term "encode" refers to nucleic acids that comprise a coding region, portion of a coding region, or compliments thereof. Both DNA and RNA may encode a gene. Both DNA and RNA may encode a protein.

The term "enzyme" as used herein refers to a protein that can catalyze a chemical reaction.

The term "exogenous" refers to anything that is introduced into a cell. An "exogenous nucleic acid" is a nucleic acid that entered a cell through the cell membrane. An exogenous nucleic acid may contain a nucleotide sequence that exists in the native genome of a cell and/or nucleotide sequences that did not previously exist in the cell's genome. Exogenous nucleic acids include exogenous genes. An "exogenous gene" is a nucleic acid that codes for the expression of an RNA and/or protein that has been introduced into a cell (e.g., by transformation/transfection), and is also referred to as a "transgene." A cell comprising an exogenous gene may be referred to as a recombinant cell into which additional exogenous gene(s) may be introduced. The exogenous gene may be from the same or different species relative to the cell being transformed. Thus, an exogenous gene can include a native gene that occupies a different location in the genome of the cell or is under different control, relative to the endogenous copy of the gene. An exogenous gene may be present in more than one copy in the cell. An exogenous gene may be maintained in a cell as an insertion into the genome (nuclear or plastid) or as an episomal molecule.

The term "expression" refers to the amount of a nucleic acid or amino acid sequence (e.g., peptide, polypeptide, or protein) in a cell. The increased expression of a gene refers to the increased transcription of that gene. The increased expression of an amino acid sequence, peptide, polypeptide, or protein refers to the increased translation of a nucleic acid encoding the amino acid sequence, peptide, polypeptide, or protein.

The term "gene," as used herein, may encompass genomic sequences that contain exons, particularly polynticleotide sequences encoding polypeptide sequences involved in a specific activity. The term further encompasses synthetic nucleic acids that did not derive from genomic sequence. In certain embodiments, the genes kick introns, as they are synthesized based on the known DNA sequence of cDNA and protein sequence. In other embodiments, the genes are synthesized, non-native cDNA wherein the codons have been optimized for expression in Y hpolynica based on codon usage. The term can further include nucleic acid molecules comprising upstream, downstream, and/or intron nucleotide sequences.

The term "genetic modification" refers to the result of a transformation. Every transformation causes a genetic modification by definition.

The term "homolog", as used herein, refers to (a) peptides, oligopeptides, polypeptides, proteins, and enzymes having amino acid substitutions, deletions and/or insertions relative to the unmodified protein in question and having similar biological and functional activity as the unmodified protein from which they are derived, and (b) nucleic acids which encode peptides, oligopeptides, polypeptides, proteins, and enzymes with the same characteristics described in (a).

"Inducible promoter" is a promoter that mediates the transcription of an operably linked gene in response to a particular stimulus.

The term "integrated" refers to a nucleic acid that is maintained in a cell as an insertion into the cell's genome, such as insertion into a chromosome, including insertions into a plastid genome.

"In operable linkage" refers to a functional linkage between two nucleic acid sequences, such at control sequence (typically an promoter) and the linked sequence (typically a sequence that encodes a protein, also called a coding sequence). A promoter is in operable linkage with a gene if it can mediate transcription of the gene.

The term "knockout mutation" or "knockout" refers to a genetic modification that prevents a native gene from being transcribed and translated into a functional protein.

The term "native" refers to the composition of a cell or parent cell prior to a transformation event. A "native gene" refers to a nucleotide sequence that encodes a protein that has not been introduced into a cell by a transformation event. A "native protein" refers to an amino acid sequence that is encoded by a native gene.

The terms "nucleic acid" refers to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

The acronym "ORF" stands for open reading frame.

The term "parent cell" refers to every cell from which a cell descended. The genome of a cell is comprised of the parent cell's gnome and any subsequent genetic modifications to parent the cell's genome.

As used herein, the term "plasmid" refers to a circular DNA molecule that is physically separate from an organism's genomic DNA. Plasmids may be linearized before being introduced into a host cell (referred to herein as a linearized plasmid). Linearized plasmids may not be sell-replicating, but may integrate into and be replicated with the genomic DNA of an organism.

The term "portion" refers to peptides, oligopeptides, polypeptides, protein domains, and proteins. A nucleotide sequence encoding a "portion of a protein" includes both nucleotide sequences that can be transcribed and/or translated and nucleotide sequences that must undergo one or more recombination events to be transcribed and/or translated. For example, a nucleic acid may comprise a nucleotide sequence encoding one or more amino acids of a selectable marker protein. This nucleic acid can be engineered to recombine with one or more different nucleotide sequences that encode the remaining portion of the protein. Such nucleic acids are useful for generating knockout mutations because only recombination with the target sequence is likely to reconstitute the full-length selectable marker gene whereas random-integration events are unlikely to result in a nucleotide sequence that can produce a functional marker protein.

A "promoter" is a nucleic acid control sequence that directs the transcription of a nucleic acid. As used herein, a promoter includes the necessary nucleic acid sequences near the start site of transcription. A promoter also optionally includes distal enhancer or repressor elements, which can be located as much as several thousand base pairs from Me start site of transcription.

The term "protein" refers to molecules that comprise an amino acid sequence, wherein the amino acids are linked by peptide bonds.

"Recombinant?" refers to a cell, nucleic acid, protein, or vector, which has been modified due to the introduction of an exogenous nucleic acid or the alteration of a native nucleic acid. Thus, recombinant cells can express genes that are not found within the native (non-recombinant) form of the cell or express native genes differently than those genes are expressed by a non-recombinant cell. Recombinant cells can, without limitation, include recombinant nucleic acids that encode for a gene product or for suppression elements such as mutations, knockouts, antisense, interfering RNA (RNAi), or dsRNA that reduce the levels of active acne product in a cell. A "recombinant nucleic acid" is a nucleic acid originally formed in vitro, in general, by the manipulation of nucleic acid, e.g., using polymerases, ligases, exonucleases, and endonucleases, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant-protein" is a protein made using recombinant techniques, i.e., through the expression of a recombinant nucleic acid.

The term "regulatory region" refers to nucleotide sequences that affect the transcription or translation of a gene but do not encode an amino acid sequence. Regulatory regions include promoters, operators, enhancers, and silencers.

The term "substantially identical" refers to a nucleotide or amino acid sequence that encodes a biologically-active portion of a protein, which has 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, $9^4$;%, 96%, 97%, 98%, 99%, 99.1%, 99.2%, 99.3%, 99.4%, 99.5%, 99.6%, 99.7%, 99.8%, 99.9% or more sequence identity with a reference sequence. For enzymes, a substantially identical sequence typically retains the enzymatic activity of the reference sequence. For example, a sequence is substantially identical to a reference sequence if it encodes an enzyme that: has between 10% and 1,000% of the enzymatic activity of the reference enzyme.

"Transformation" refers to the transfer of a nucleic acid into a host organism or the genome of a host organism, resulting in genetically stable inheritance. Host organisms containing the transformed nucleic acid fragments are referred to as "recombinant", "transgenic" or "transformed" organisms. Thus, isolated polytrucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encodina sequence in a given host cell. Typically, expression vectors include, for example, one or more cloned genes under the transcriptional control of 5' and 3' regulatory sequences and a selectable marker. Such vectors also ca contain a promoter regulatory region (eg., a regulatory region controlling inducible or constitutive, environmentally- or developmentally-regulated, or location-specific expression), a transcription initiation start site, a ribosome binding site, a transcription termination site, and/or a polyadenylation signal.

The term "transformed cell" refers to a cell that has undergone a transformation. Thus, a transformed cell comprises the parent's genome and an inheritable genetic modification.

The terms "triacylglyceride," "triacylglycerol," "triglyceride," and "TAG" are esters comprised of glycerol and three fatty acids.

The term "triacylglycerol lipase" refers to any protein that can catalyze the removal of a fatty acid chain from a triacylglycerol. Triacylglycerol lipases include TGL3, TGL4, and TGL3/4.

The term "vector" refers to the means by which a nucleic acid can be propagated and/or transferred between organisms, cells, or cellular components. Vectors include plasmids, linear DNA fragments, viruses, bacteriophage, proviruses, phagemids, transposons, and artificial chromosomes, and the like, that may or may not be able to replicate autonomously or integrate into a chromosome of a host cell.

Microbe Engineering

A. Overview

Figure 1:
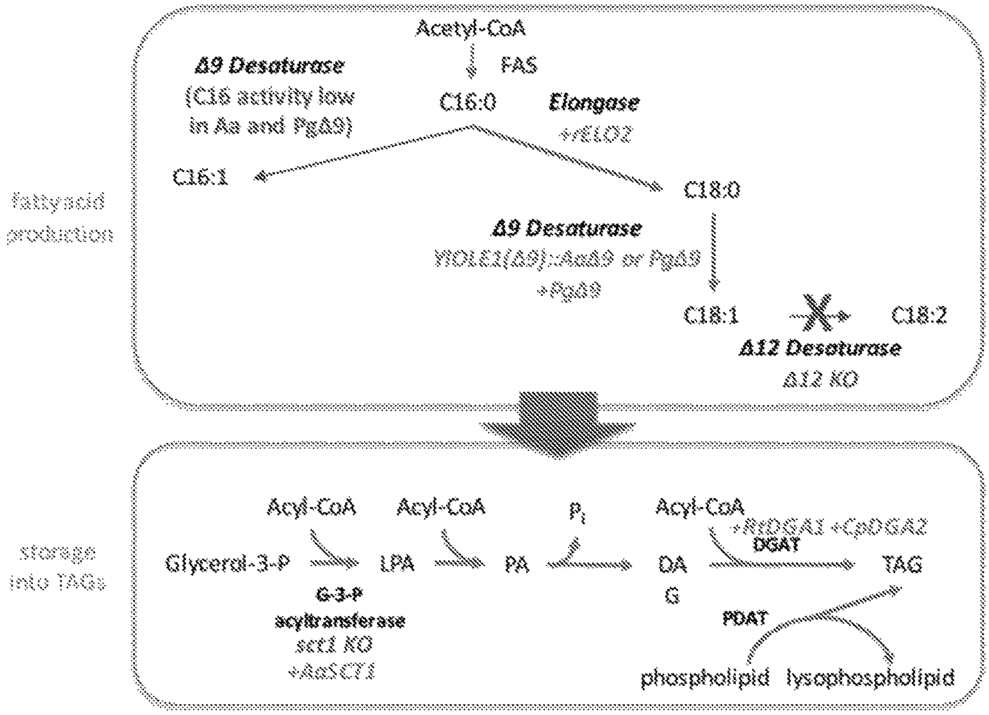
FIG. 1 depicts various biosynthetic pathways that may be manipulated to modify the lipid content or lipid composition of a cell.

In certain embodiments of the invention, a microorganism is genetically modified to change its lipid composition, e.g., to increase its oleic acid content (FIG. 1).

Genes and gene products may be introduced into microbial host cells. Suitable host cells for expression of the genes and nucleic acid molecules are microbial hosts that can be found broadly within the fungal or bacterial families. Examples of suitable host strains include but are not limited to fungal or yeast species, such as *Arxula, Aspergillus, Aurantiochytrium, Candida, Claviceps, Cryptococcus, Cunninghamella, Hansenula, Khuyveromyces, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Yarrowia*, or bacterial species, such as members of proteobacteria and actinomycetes, as well as the genera *Acinetobacter, Arthrobacter, Brevibacterium, Acidovorax, Bacillus, Clostridia, Streptomyces, Escherichia, Salmonella, Pseudomonas*, and *Cornyebacterium. Yarrowia lipolytica* and *Arxula adeninivorans* are suited for use as a host microorganism because they can accumulate a large percentage of their weight as triacylglycerols.

Microbial expression systems and expression vectors containing regulatory sequences that direct high level expression of foreign proteins are known to those skilled in the art. Any of these could be used to constrict chimeric, genes to produce any one of the gene products of the instant sequences. These chimeric genes could then be introduced into appropriate microorganisms via transformation techniques to provide high-level expression of the enzymes.

For example, a gene encoding an enzyme can be cloned in a suitable plasmid, and an aforementioned starting parent strain as a host can be transformed with the resulting plasmid. This approach can increase the copy number of each of the genes encoding the enzymes and, as a result, the activities of the enzymes can be increased. The plasmid is not particularly limited so long as it renders a desired genetic modification inheritable to the microorganism's progeny.

Vectors or cassettes useful for the transformation of suitable host cells are well known in the art. Typically the vector or cassette contains sequences that direct the transcription and translation of the relevant gene, a selectable marker, and sequences that allow autonomous replication or chromosomal integration. Suitable vectors comprise a region 5' of the gene harboring transcriptional initiation controls and a region 3' of the DNA fragment which controls transcriptional termination. In certain embodiments both control regions are derived from genes homologous to the transformed host cell, although it is to be understood that such control regions need not be derived from the genes native to the specific species chosen as a production host.

Promoters, cDNAs, and 3'UTRs, as well as other elements of the vectors, can be generated through cloning techniques using fragments isolated from native sources (Green & Sambrook, *Molecular Cloning: A Laboratory Manual*, (4th ed., 2012); U.S. Pat. No. 4,683,202 (incorporated by reference)). Alternatively, elements can be generated synthetically using known methods (Gene 164:49-53 (1995)).

B. Homologous Recombination

Homologous recombination is the ability of complementary DNA sequences to align and exchange regions of homology. Transgenic DNA ("donor") containing sequences homologous to the genomic sequences being targeted ("template") is introduced into the organism and then undergoes recombination into the genome at the site of the corresponding homologous genomic sequences.

The ability to carry out homologous recombination in a host organism has man practical implications for what can be carried out at the molecular genetic level and is useful in the generation of a microbe that can produce a desired product. By its nature homologous recombination is a precise gene targeting event and, hence, most transgenic lines generated with the same targeting sequence will be essentially identical in terms of phenotype, necessitating the screening of far fewer transformation events. Homologous recombination also targets gene insertion events into the host chromosome, potentially resulting in excellent genetic stability, even in the absence of genetic selection. Because different chromosomal loci will likely impact gene expression, even from exogenous promoters/UTRs, homologous recombination can be a method of querying loci in an unfamiliar gnome environment and to assess the impact of these environments on gene expression.

A particularly useful genetic engineering approach using homologous recombination is to co-opt specific host: regulatory elements, such as promoters/UTRs, to drive heterologous gene expression in a highly specific fashion.

Because homologous recombination is a precise gene targeting event, it can be used to precisely modify any nucleotide(s) within a gene or region of interest, so long as sufficient flanking regions have been identified. Therefore, homologous recombination can be used as a means to modify regulatory sequences impacting gene expression of RNA and/or proteins. It can also be used to modify protein coding regions in an effort to modify enzyme activities such as substrate specificity, affinities and Km, thereby affecting a desired change in the metabolism of the host cell. Homologous recombination provides a powerful means to manipulate the host genome resulting in gene targeting, gene conversion, gene deletion, gene duplication, gene inversion, and exchanging gene expression regulatory elements such as promoters, enhancers and 3'UTRs.

Homologous recombination can be achieved by using targeting constructs containing pieces of endogenous sequences to "target" the gene or region of interest within the endogenous host cell genome. Such targeting sequences can either be located 5' of the gene or region of interest, 3' of the gene/region of interest or even flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) by cutting the transgenic DNA with a restriction enzyme. This step can increase the recombination efficiency and decrease the occurrence of undesired events. Other methods of increasing recombination efficiency include using PCR to generate transforming transgenic DNA containing linear ends homologous to the genomic sequences being targeted.

C. Vectors and Vector Components

Vectors for transforming microorganisms in accordance with the present invention can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell.

1. Control Sequences

Control sequences are nucleic acids that regulate the expression of a coding sequence or direct as gene product to a particular location in or outside as cell. Control sequences that regulate expression include, for example, promoters that regulate transcription of a coding sequence and terminators that terminate transcription of a coding sequence. Another control sequence is a 3' untranslated sequence located at the end off coding sequence that encodes a polyadenylation signal. Control sequences that direct gene products to particular locations include those that encode signal peptides, which direct the protein to which they are attached to a particular location inside or outside the cell.

Thus, an exemplary vector design for expression of a gene in a microbe contains a coding sequence for a desired gene product (for example, a selectable marker, or an enzyme) in operable linkage with a promoter active in yeast. Alternatively, if the vector does not contain a promoter in table linkage with the coding sequence of interest, the coding sequence can be transformed into the cells such that it becomes operably linked to an endogenous promoter at the point of vector integration.

The promoter used to express a gene can be the promoter naturally linked to that gene or a different promoter.

A promoter can generally be characterized as constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the invention. Inducible promoters useful in the invention include those that mediate transcription of an operably linked gene in response to a stimulus, such as an exogenously provided small molecule, temperature (heat or cold), lack of nitrogen in culture media, etc. Suitable promoters can activate transcription of an essentially silent gene or upregulate, e.g., substantially, transcription of an operably linked gene that is transcribed at a low level.

Inclusion of termination region control sequence is optional, and if employed, then the choice is primarily one of convenience, as the termination region is relatively interchangeable. The termination region may be native to the transcriptional initiation region (the promoter), may be native to the DNA sequence of interest, or may be obtainable from another source (See, e.g., Chem & Orozco, Nucleic Acids Research 16:5411 (1988)).

2. Genes and Codon Optimization

Typically, a gene includes a promoter, a coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated (e.g., an episome), in which ease, the vector typically includes an origin of replication, which is capable of providing for replication of the vector DNA.

A common gene present on a vector is a gene that codes for a protein, the expression of which allows the recombinant cell containing the protein to be differentiated from cells that do not express the protein. Such a gene, and its corresponding gene product, is called a selectable marker or selection marker. An of a wide variety of selectable markers can be employed in a transgene construct useful for transforming the organisms of the invention.

For optimal expression of a recombinant protein, it is beneficial to employ coding sequences that produce mRNA with codons optimally used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized hi the cell, coupled with more efficient translation of the transgenic messenger RNA (RNA) when this need is met. When codon usage in the transgene is not optimized, available tRNA pools are not sufficient to allow for efficient translation of the transgenic mRNA resulting in ribosomal stalling and termination and possible instability of the transgenic mRNA.

Transformation

Cells can be transformed by any suitable technique including, e.g., biolistics, electroporation, glass bead transformation, and silicon carbide whisker transformation. Any convenient technique for introducing a transgene into a microorganism can be employed in the present invention. Transformation can be achieved by, for example, the method of D. M. Morrison (Methods in Enzymology 68:326 (1979)), the method by increasing permeability of recipient cells for DNA with calcium chloride (Mandel & Higa, J. Molecular Biology, 53:159 (1970)), or the like.

Examples of expression of transgenes in oleaginous yeast (e.g., *Yarrowia lipolytica*) can be found in the literature (Bordes et al., *J. Microbiological Methods,* 70:493 (2007); Chen et al., Applied Microbiology & Biotechnology 48:232 (1997)). Examples of expression of exogenous genes in bacteria such as *E. coli* are well known (Green & Sambrook, *Molecular Cloning: A Laboratory Manual*, (4th ed., 2012)).

Vectors for transformation of microorganisms in accordance with the present invention can be prepared by known techniques familiar to those skilled in the art. In one embodiment, an exemplary vector design for expression of a gene in a microorganism contains a gene encoding an enzyme in operable linkage with a promoter active in the microorganism. Alternatively, if the vector does not contain a promoter in operable linkage with the gene of interest, the gene can be transformed into the cells such that it becomes operably linked to a native promoter at the point of vector integration. The vector can also contain a second gene that encodes a protein. Optionally, one or both gene(s) is/are followed by a 3' untranslated sequence containing a polyadenylation signal. Expression cassettes encoding the two genes can be physically linked in the vector or on separate vectors, Co-transformation of microbes can also be used, in which distinct vector molecules are simultaneously used to transform cells (Protist 155:381-93 (2004)). The transformed cells can be optionally selected based upon the ability to grow in the presence of the antibiotic or other selectable marker under conditions in which cells lacking the resistance cassette would not grow.

Exemplary Cells. Nucleic Acids, and Methods

A. Transformed Cell

In some embodiments, the transformed cell is a prokaryotic coil, such as a bacterial cell. In some embodiments, the cell is a eukaryotic cell, such as a mammalian cell, a yeast cell, a filamentous fungi cell, a protist cell, an algae cell, an avian cell, a plant cell, or an insect cell. In some embodiments, the cell is a yeast. Those with skill in the art will recognize that many forms of filamentous fungi produce yeast-like growth, and the definition of yeast herein encompasses such cells.

The cell may be selected from the group consisting of *Arxula, Aspegillus, Adrontiochyrrizen, Candida, Claviceps, Cryptococcus, Cunninghamella, Geotrichum, Hansenula, Kluyveromyces, Kodamaea, Leucosporidiella, Lipomyces, Mortierella, Orataea, Pichia, Prototheca, Rhizoptus, Rhodosporidium, Rhodotorula, Saccharomyces, Schizosaecharomyces, Tremella, Trichosporon, Wickerhamomyces*, and *Yarrowia.*

In some embodiments, the cell is selected from the group of consisting of *Arxula adeninivorans, Aspergillus niger, Aspergillus orzyae, Aspergillus terreus, Aurantiochytrium limacinum, Candida utilis, Claviceps purpurea, Cryptococcus albidus, Cryptococcus curvatus, Cryptococcus ramirezgomezianus, Cryptococcus terreus, Cryptococcus wieringae, Cunninghamella echinulata, Cunninghamella japonica, Geotrichum fermentans, Hansemula polymorpha, Kluyveromyces lactis, Kluyveromyces marxianus, Kodamaea ohmeri, Leucosporidiella creatinivora, Lipomyces lipofer, Lipomyces starkeyi, Lipomyces tetrasporus, Mortierella isabellina, Mortierella alphina, Ogatanea polymorpha, Pichia ciferrii, Pichia guilliermondii, Pichia pastoris, Pichia stipites, Prototheca zopfii, Rhizopus arrhizus, Rhodosporidium babjevae, Rhodosporidium toruioides, Rhodosporidium paludigenum, Rhodotorula glutinis, Rhodotorula mucilaginosa, Saccharomyces cerevisiae, Schizosaccharomyces pombe, Tremella enchepala, Trichosporon cutaneum, Trichosporon fermentans, Wickerhamomyces ciferrii*, and *Yarrowia lipolytica.*

In certain embodiments, the cell is *Saccharomyces cerevisiae, Yarrowia lipolytica*, or *Arxula adeninivorans.*

In some embodiments, the cell is t yeast, fungus, or yeast-like algae. The cell may be selected from thraustochytrids (Aurantiochytrium) and achlorophylic unicellular algae (Prototheca).

In certain embodiments, the transformed cell comprises at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, or more lipid as measured by % dry cell weight. In some embodiments, the transformed cell comprises C18 fatty acids at a concentration of at least 80%, 81%, 82%, 83%, 84%, 85%, 86%, 87%, 88%, 89%, 90%, 91%, 92%, 93%, 94%, 95%, or higher as a percentage of total C16 and C18 fatty acids in the cell. In some embodiments, the transformed cell comprises oleic, acid at a concentration of at least 50%, 51%, 52%, 53%, 54%, 55%, 56%, 57%, 58%, 59%, 60%, 61%, 62%, 63%, 64%, 65%, 66%, 67%, 68%, 69%, 70% 71%, 72%, 73%, 74%, 75%, 76%, 77%, 78%, 79%, 80%, 81%, 82%, 83%, 84%, 85%, 86%, 87%, 88%, 89%, 90%, or higher as a percentage of total C16 and C18 fatty acids in the cell.

B. Nucleic Acids and Methods for Increasing the Activity of a Protein

The genes of the invention may comprise conservative substitutions, deletions and/or insertions while still encoding a protein that has activity. For example, codons may be optimized for a particular host cell, different codons may be substituted for convenience, such as to introduce a restriction site or to create optimal. PCR primers, or codons may be substituted for another purpose. Similarly, the nucleotide sequence may be altered to create conservative amino acid substitutions, deletions, and/or insertions.

Proteins may comprise conservative substitutions, deletions, and/or insertions while still maintaining activity. Conservative substitution tables are well known in the art (Creighton, *Proteins* (2d. ed., 1992)).

Amino acid substitutions, deletions and/or insertions may readily be made using recombinant DNA manipulation techniques. Methods for the manipulation of DNA sequences to produce substitution, insertion or deletion variants of a protein are well known in the art. These methods include M13 mutagenesis, T7-Gen in vitro mutagenesis (USB, Cleveland, Ohio), Quick Change Site Directed mutagenesis (Stratagene, San Diego, Calif.), PCR-mediated site-directed mutagenesis, and other site-directed mutagenesis protocols.

To determine the percent identity of two amino acid sequences or two nucleic acid sequences, the sequences can be aligned for optimal comparison purposes (e.g., gaps can be introduced in one or both of a first and a second amino acid or nucleic acid sequence for optimal alignment and non-identical sequences can be disregarded for comparison purposes). The length of a reference sequence aligned for comparison purposes can be at least 95% of the length of the reference sequence. The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithin. In one embodiment, the percent identity between two amino acid sequences can be determined using the Needleman and Wunsch (J. Molecular Biology 48:444-453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences can be determined using the algorithm of E. Meyers and W. Miller (Computer Applications in the Biosciences 4:11-17 (1988)) which has been incorporated into the ALIGN program (version 2.0 or 2.0U), using a PAM120 weight residue table, a gap length penalty of 12 and a gap penalty of 4.

Exemplary computer programs which can be used to determine identity between two sequences include, but are not limited to, the suite of BLAST programs, e.g., BLASTN, MEGABLAST, BLASTX, TBLASTN, TBLASTX, and BLASTP, and Clustal programs, e.g. ClustalW, ClustalX, and Clustal Omega.

Sequence searches are typically carried out using the BLASTN program. When evaluating a given nucleic acid sequence relative to nucleic acid sequences in the GenBank DNA Sequences and other public databases. The BLASTX program is effective for searching nucleic acid sequences that have been translated in all reading frames against amino acid sequences in the GenBank Protein Sequences and other public databases.

An alignment of selected sequences in order to determine "% identity" between two or more sequences is performed using for example, the CLUSTAL-W program.

A "coding sequence" or "coding region" refers to a nucleic acid molecule having sequence information necessary to produce a protein product, such as an amino acid or polypeptide, when the sequence is expressed. The coding sequence may comprise and/or consist of untranslated sequences (including introns or 5' or 3' untranslated regions) within translated regions, or may lack such intervening untranslated sequences (e.g., as in cDNA).

The abbreviation used throughout the specification to refer to nucleic acids comprising and/or consisting of nucleotide sequences are the conventional one-letter abbreviations. Thus when included in a nucleic acid, the naturally occurring encoding nucleotides are abbreviated as follows: adenine (A), guanine (G), cytosine (C), thymine (T) and uracil (U). Also, unless otherwise specified, the nucleic acid sequences presented herein is the 5'→3'direction.

As used herein, the term "complementary" and derivatives thereof are used in reference to pairing of nucleic acids by the well-known rules that A pairs with T or U and C pairs with G. Complement can be "partial" or "complete" h partial compleinent, only some of the nucleic acid bases are matched according to the base pairing rules; while in complete or total complement, all the bases are matched according to the pairing rule. The degree of complement between the nucleic acid strands may have significant effects on the efficiency and strength of hybridization between nucleic acid strands as well known in the art. The efficiency and strength of said hybridization depends upon the detection method.

Amino acid and nucleotide sequences may be derived from oleaginous organisms having high, native levels of lipid accumulation, (Bioresource Technology 144:360-69 (2013); Progress Lipid Research. 52:395-408 (2013); Applied Microbiology & Biotechnology 90:1219-27 (2011); European Journal Lipid Science & Technology 113:1031-51 (2011); Food Technology & Biotechnology 47:215-20 (2009); Advances Applied Microbiology 51:1-51 (2002); Lipids 11:837-44 (1976)). A list of organisms with a reported lipid content of about 50% and higher is shown in Table 1. *R. toruloides* and *L. starkeyi* have the highest lipid content.

TABLE 1

| List of oleaginous fungi with reported lipid contents of about 50% and above. |
|---|
| *Aspergillus terreus* |
| *Aurantiochytrium limacinum* |
| *Claviceps purpurea* |
| *Cryptococcus albidus* |
| *Cryptococcus curvatus* |
| *Cryptococcus ramirezgomezianus* |
| *Cryptococcus terreus* |
| *Cryptococcus wieringae* |
| *Cunninghamella echinulata* |
| *Cunninghamella japonica* |
| *Leucosporidiella creatinivora* |
| *Lipomyces lipofer* |
| *Lipomyces starkeyi* |
| *Lipomyces tetrasporus* |
| *Mortierella isabellina* |
| *Prototheca zopfil* |
| *Rhizopus arrhizus* |
| *Rhodosporidium babjevae* |
| *Rhodosporidium paludigenum* |
| *Rhodosporidium toruloides* |
| *Rhodotorula glutinis* |
| *Rhodotorula mucilaginosa* |
| *Tremella enchepala* |
| *Trichosporon cutaneum* |
| *Trichosporon fermentans* |

A protein's activity may be increased by overexpressing the protein. Proteins may be overexpressed in a cell using a variety of genetic modifications. In some embodiments, the genetic modification increases the expression of a native protein A native protein may be overexpressed by modifying the upstream transcription regulators of the gene that encodes the protein, for example, by increasing the expression of a transcription activator or decreasing the expression of a transcription repressor. Alternatively, the promoter of a native gene may be substituted with a constitutively active or inducible promoter by recombination with an exogenous nucleic acid.

In some embodiments, a genetic modification that increases the activity of a protein comprises transformation with a nucleic acid that comprises a gene that encodes the protein. The gene may be native to the cell or from a different: species. In certain embodiments, the gene is inheritable to the progeny of a transformed cell. In some embodiments, the gene is inheritable because it resides on a plasmid. In certain embodiments, the gene is inheritable because it is integrated into the genome of the transformed cell.

1. Increasing the Activity of a Δ9 Desaturase

In some aspects, the invention relates to a transformed cell comprising a genetic modification, wherein the genetic modification increases the activity of a Δ9 desaturase protein in the cell. The genetic modification may be transformation with a nucleic acid. In certain embodiments, the invention relates to a method of modifying the lipid content of a cell, comprising transforming the cell with a nucleic acid that increases the activity of a Δ9 desaturase protein in the cell.

The nucleic acid may encode a Δ9 desaturase gene. In some embodiments, the gene is Δ9. In some embodiments, the gene is from *Arxula adeninivorans, Gloeophyllum trabeum, Microbotryum violaceum, Puccinia graminis, Rhodosporidium toruloides, Rhodotorula glutinis, Rhodotorula graminis*, or *Yarrowia lipolytica*. The gene may be from *Arxula adeninivorans* or *Puccinia graminis.*

In some embodiments, the nucleic acid comprises a nucleotide sequence that has at least 70%, 71%, 72%, 73%, 74%, 75%, 76%, 77%, 78%, 79%, 80%, 81%, 82%. 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:4; SEQ ID NO:8; SEQ ID NO:10; SEQ ID NO:12; SEQ ID NO:14; SEQ ID NO:16; SEQ ID NO:112; or SEQ ID NO:114. The nucleic acid may comprise the nucleotide sequence set forth in SEQ ID NO:4; SEQ ID NO:8; SEQ ID NO:10, SEQ ID NO:12: SEQ ID NO:14; SEQ ID NO:16; SEQ ID NO:112; or SEQ ID NO:114. In some embodiments, the nucleic acid comprises a nucleotide sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:8 or SEQ NO:14. The nucleic acid may comprise the nucleotide sequence set forth in SEQ ID NO:8 SEQ ID NO:14.

In some embodiments, the nucleic acid encodes an ainino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:3; SEQ ID NO:7; SEQ ID NO:9; SEQ ID NO:11; SEQ ID NO:13; SEQ ID NO:15; SEQ ID NO:111; or SEQ ID NO:113, or a biologically active portion thereof. The nucleic acid may encode the amino acid sequence set forth in SEQ ID NO:3; SEQ ID NO:7; SEQ ID NO:9; SEQ ID NO:11: SEQ ID NO:13; SEQ ID NO:15; SEQ ID NO:111; or SEQ ID NO:113. In some embodiments, the nucleic acid encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:7 or SEQ ID NO:13, or a biologically active portion thereof. The nucleic acid may encode the amino acid sequence set forth in SEQ ID NO:7 or SEQ ID NO:13.

The nucleic acid that comprises a gene encoding a Δ9 desaturase protein may comprise a nucleotide sequence set forth in SEQ ID NO:4; SEQ ID NO:8; SEQ ID NO:10; SEQ ID NO:12; SEQ ID NO:14; SEQ ID NO:16; SEQ ID NO:112; or SEQ ID NO:114. In other embodiments, the gene is substantially identical to SEQ ID NO:4; SEQ ID NO:8; SEQ ID NO:10; SEQ ID NO:12; SEQ ID NO:14; SEQ ID NO:16; SEQ ID NO:112; or SEQ ID NO:114 and the nucleotide sequence encodes a protein that retains the Δ9 desaturase activity of a protein encoded by SEQ ID NO:3: SEQ ID NO:7; SEQ ID NO:9; SEQ ID NO:11; SEQ ID NO:13; SEQ ID NO:15; SEQ ID NO:111; or SEQ ID NO:113, yet differs in nucleotide sequence, e.g., due to natural allelic variation or mutagenesis.

The Δ9 desaturase protein may have an amino acid sequence set forth in SEQ ID NO:3; SEQ ID NO:7; SEQ ID NO:9; SEQ. ID NO:11: SEQ ID NO:13; SEQ ID NO:15; SEQ ID NO:111; or SEQ ID NO:113. In other embodiments, the Δ9 desaturase protein is substantially identical to SEQ ID NO:3; SEQ ID NO:7; SEQ ID NO:9; SEQ ID NO:11; SEQ ID NO:13; SEQ ID NO:15; SEQ ID NO:111; or SEQ ID NO:113, and retains the functional activity of the protein of SEQ ID NO:3; SEQ ID NO:7; SEQ ID NO:9; SEQ ID NO:11; SEQ ID NO:13; SEQ ID NO:15; SEQ ID NO:111; or SEQ ID NO:113, yet differs in amino acid sequence, e.g., due to natural allelic variation or mutagenesis.

In some embodiments, the transformed cell further comprises a genetic modification that increases the activity of an elongase, diacylglycerol acyltransferase, glycerol-3-phosphate acyltransferase, sn-2 acylglycerol fatty acyltransferase, lysophosphatidie acid acyltransferase, phosphatidate phosphatase, glycerol-3-phosphate/dihydroxyacetone phosphate sn-1 acyltransferase, and/or phospholipid:diacylglycerol acyltransferase. In some embodiments, the transformed cell further comprises a genetic modification that decreases the activity of a native Δ9 desaturase, native Δ12 desaturase, native diacylglycerol acyltransferase, native triacylglycerol lipase, native sn-2 acylglycerol fatty acyltransferase, native lysophosphatidic acid acyltransferase, native phosphatidate phosphatase, native glycerol-3-phosphate acyltransferase, native glycerol-3-phosphate/dihydroxyacetone phosphate sn-1 acyltransferase, and/or native phospholipid:diacylglycerol acyltransferase. For example, the transformed cell may comprise (1) a genetic modification that consists of transformation with a nucleic acid that encodes an exogenous Δ9 desaturase protein and (2) a knockout mutation in the native Δ9 desaturase gene.

2. Increasing the Activity of an Elongase

In some aspects, the invention relates to a transformed cell comprising a genetic modification, wherein the genetic modification increases the activity of an elongase protein in the cell. The genetic modification may be transformation with a nucleic acid. In certain embodiments, the invention relates to a method of modifying the lipid content of a cell, comprising transforming the cell with a nucleic acid that increases the activity of an elongase protein in the cell.

The nucleic acid may encode an elongase gene. In some embodiments, the gene is ELO1 or ELO2. In some embodiments, the gene is from *Arxula adeninivorans, Ratius norvegicus, Saccharomyces cerevisiae*, or *Yarrowia lipolytica.*

In some embodiments, the nucleic acid comprises a nucleotide sequence that has at least 70%, 71%, 72%, 73%, 74%, 75%, 76%, 77%, 78%, 79%, 80%, 81%, 82%, 83%, 84%, 85% 86%, 87%, 88%, 89%, 90%, 91%, 92%, 93%, 94%, 95%, 96%, 97% 98% 99%, 99.1%, 99.2%, 99.3%, 99.4%, 99.5%, 99.6%, 99.7%, 99.8%, 99.9% or more sequence homology with the sequence set forth in SEQ ID NO:6;SEQ ID NO: 108; SEQ ID NO:156; SEQ ID NO:158; or SEQ ID NO:160. The nucleic acid may comprise the nucleotide sequence set forth in SEQ ID NO:6; SEQ ID NO:108; SEQ ID NO:156; SEQ ID NO:158; or SEQ ID NO:160.

In some embodiments, the nucleic acid encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:5, SEQ ID NO:107; SEQ ID NO:155; SEQ ID NO:157; or SEQ ID NO:159, or a biologically active portion thereof. The nucleic acid may encode the amino acid sequence set forth in SEQ ID NO:5; SEQ ID NO:107; SEQ ID NO:155; SEQ ID NO:157; or SEQ ID NO:159.

The nucleic acid that comprises a gene encoding an elongase protein may comprise a nucleotide sequence set finth in SEQ ID NO:6; SEQ ID NO:108; SEQ ID NO:156, SEQ ID NO:158; or SEQ ID NO:160. In other embodiments, the gene is substantially identical to SEQ ID NO:6; SEQ ID NO:108; SEQ ID NO:156; SEQ ID NO:158; or SEQ ID NO:160 and the nucleotide sequence encodes a protein that retains the elongase activity of a protein encoded by SEQ ID NO:5, SEQ ID NO:107: SEQ ID NO:155; SEQ ID NO:157; Or SEQ ID NO:159, yet differs in nucleotide sequence, e.g., due to natural allelic variation or mutagenesis.

The elongate protein may have an amino acid sequence set forth in SEQ ID NO:5; SEQ ID NO:107; SEQ ID NO:155; SEQ ID NO:157; or SEQ ID NO:159. In other embodiments, the elongase protein is substantially identical to SEQ ID NO:5; SEQ ID NO:107; SEQ ID NO:155; SEQ ID NO:157; or SEQ ID NO:159, and retains the functional activity of the protein of SEQ ID NO:5; SEQ ID NO:107; SEQ ID NO:155; SEQ NO:157; or SEQ ID NO:159, yet differs m amino acid sequence, e.g., due to natural allelic variation or mutagenesis.

In some embodiments, the transformed cell further comprises a genetic modification that increases the activity of a Δ9 desaturase, dtacylglycerol acyltransferase, glycerol-3-phosphate acyltransferase, sn-2 acyhtlyeerol fatty acyltransferase, lysophosphatidie acid acyltransferase, phosphatidate phosphatase, glycerol-3-phosphate/dihydroxyacetone phosphate sn-1 acyltransferase, and/or phospholipid:diacylglycerol acyltransferase. In some embodiments, the transfOrmed cell further comprises a genetic modification that decreases the activity of a native Δ9 desaturase, native Δ12 desaturase, native diacylglycerol acyltransferase, native triacylglycerol lipase, native sn-2 acylglycerol fatty acyltransferase, native lysophosphatidic acid acyltransferase, native phosphatidate phosphatase, native glycerol-3-phosphate acyltransferase, native glycerol-3-phosphate/dihydroxyacetone phosphate sn-1 acyltransferase, and/or native phospholipid:diacylglycerol acyltransferase. For example, the transformed cell may comprise (1) a genetic modification that increases the activity of an elongase protein and (2) a genetic modification that decreases the activity native Δ12 desaturase gene. Similarly, the transformed cell may comprise (1) a genetic modification that increases the activity of an elongase protein and (2) a genetic modification that increases the activity of a diacylalycerol acyltransferase protein.

3. Increasing the Activity of an Acyltransferase

In some aspects, the invention relates to a transformed cell comprising a genetic modification, wherein the genetic modification increases the activity of an acyltransferase protein in the cell.

a. Increasing the Activity of a Type 1 Diacylglycerol Acyltransferase

In some embodiments, the acyltransferase protein is a type 1 diacylglycerol acyltransferase protein. The genetic modification may be transformation with a nucleic acid. In certain embodiments, the invention relates to a method of modifying the lipid content of a cell, comprising transforming the cell with a nucleic acid that increases the activity of a type 1 diacylglycerol acyltransferase protein in the cell.

The nucleic acid may encode a type 1 diacylglycerol acyltransferase gene. In some embodiments, the gene is DGAT1. In some embodiments, the gene is from *Arxula adeninivorans, Yarrowia lipolytica, Rhodosporidium toruloides, Lipomyces starkeyi, Aspergillus terreus, Claviceps purpurea, Metarhizium acridum, Ophiocordyceps sinensis, Phaeodactylum iricornutum, Pichia guilliermondii, Rhodotorula graminis, Rhodosporidham toruloides, Trichoderma virens*, and *Chaetomium globosum*. For example, the gene may be from *Cloviceps purpurea*.

In some embodiments, the nucleic acid composes a nucleotide sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:32; SEQ ID NO:34; SEQ ID NO:36; SEQ ID NO:38: SEQ ID NO:40: SEQ ID NO:94; SEQ ID NO:98; SEQ ID NO:102; SEQ ID NO:104; SEQ ID NO:144; SEQ ID NO:146; SEQ ID NO:148; or SEQ ID NO:150. The nucleic acid may comprise the nucleotide sequence set forth in SEQ ID NO:32; SEQ ID NO:34; SEQ ID NO:36; SEQ ID NO:38; SEQ ID NO:40; SEQ ID NO:94; SEQ ID NO:98; SEQ ID NO:102: SEQ ID NO:104: SEQ ID NO:144; SEQ ID NO:146; SEQ ID NO:148; or SEQ ID NO:150. In some embodiments, the nucleic acid comprises a nucleotide sequence that has ar least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:38. The nucleic acid may comprise the nucleotide sequence set forth in SEQ ID NO:38.

In some embodiments, the nucleic acid encodes an amino acid sequence having at least 80%, 81%, 82%, 83%, 84%, 85%, 86%, 87%, 88%, 89%, 90%, 91%, 92%, 93%, 94%, 95%, 97%, 98%, 99.1% 99.2%, 99.3%, 99.4%, 99.5%, 99.6%, 99.7%, 99.8%, 99.9% or more sequence homology with the sequence set forth in SEQ ID NO:31; SEQ ID NO:33, SEQ ID NO:35: SEQ ID NO:37; SEQ ID NO:39; SEQ ID NO93; SEQ ID NO:97; SEQ ID NO:101; SEQ ID NO:103; SEQ ID NO:143; SEQ ID NO:145; SEQ ID NO:147; or SEQ ID NO:149, or a biologically active portion thereof. The nucleic acid may encode the amino acid sequence set forth in SEQ ID NO:31; SEQ ID NO:33; SEQ ID NO:35; SEQ ID NO:37; SEQ ID NO:39; SEQ ID NO:93; SEQ ID NO:97, SEQ ID NO:101; SEQ ID NO:103; SEQ ID NO:143; SEQ ID NO:145; SEQ ID NO:147; or SEQ ID NO:149. In some embodiments, the nucleic acid encodes an amino acid sequence having at least 80%, 81%, 87%, 83%, 84%, 85%, 86%, 87%, 88%, 89%, 90%, 91%, 92%, 93%, 94% 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:37, or a biologically active portion thereof. The nucleic acid may encode the amino acid sequence set forth in SEQ ID NO:37.

The nucleic acid that comprises a gene encoding a type 1 diacylglycerol acyltransferase protein may comprise a nucleotide sequence set forth in SEQ ID NO:32; SEQ ID NO:34; SEQ ID NO:36; SEQ ID NO:38; SEQ ID NO:40; SEQ ID NO:94; SEQ ID NO:98; SEQ ID NO:102; SEQ ID NO:104; SEQ ID NO:144; SEQ ID NO:146; SEQ ID NO:148; or SEQ ID NO:150. In other embodiments, the gene is substantially identical to SEQ ID NO:32; SEQ ID NO:34; SEQ ID NO:36; SkQ ID NO:38, SEQ ID NO:40; SEQ ID NO:94; SEQ ID NO:98; SEQ ID NO:102; SEQ ID NO:104; SEQ ID NO:144; SEQ ID NO:146; SEQ ID NO:148; or SEQ ID NO:150 and the nucleotide sequence encodes a protein that retains the diacylglycerol acyltransferase activity of a protein encoded by SEQ ID NO:31 SEQ ID NO:33; SEQ ID NO:35; SEQ ID NO:37; SEQ ID NO:39, SEQ ID NO:93; SEQ ID NO:97; SEQ ID NO:101; SEQ ID NO:103; SEQ ID NO:143; SEQ ID NO:145; SEQ ID NO:147; or SEQ ID NO:149, yet differs in nucleotide sequence, e.g., due to natural allelic variation or mutagenesis.

The type I diacylglycerol acyltransferase protein may have an amino acid sequence set forth SEQ ID NO:31; SEQ ID NO:33; SEQ ID NO:35; SEQ ID NO:37; SEQ ID NO:39; SEQ ID NO:93; SEQ ID NO:97; SEQ ID NO:101; SEQ ID NO: 103; SEQ ID NO:143; SEQ ID NO:145; SEQ ID NO:147; or SEQ ID NO:149. In other embodiments, the type 1 diacylnlycerol acyltransferase protein is substantially identical to SEQ ID NO:31; SEQ ID NO:33; SFQ ID NO:35; SEQ ID NO:37; SEQ ID NO:39; SEQ ID NO:93; SEQ ID NO:97, SEQ ID NO:101; SEQ ID NO:103; SEQ ID NO:143; SEQ ID NO:145; SEQ ID NO:147; or SEQ ID NO:149, and retains the functional activity of the protein of SEQ ID NO:31; SEQ ID NO:33; SEQ ID NO:35; SEQ ID NO:37; SEQ ID NO:39; SEQ ID NO:93; SEQ ID NO:97; SEQ ID NO:101; SEQ ID NO:103, SEQ ID NO:143; SEQ ID NO:145; SEQ ID NO:147, or SEQ ID NO:149, yet differs in amino acid sequence, e.g., due to natural allelic variation or mutagenesis.

In some embodiments, the transformed cell further comprises a genetic modification that increases the activity of a Δ9 desaturase, elongase, diacylglycerol acyltransferase, glycerol-3-phosphate acyltransferase, sn-2 acylglycerol fatty acyltransferase, lysophosphatidic acid acyltransferase, phosphatidate phosphatase, glycerol-3-phosphate/dihydroxyacetone phosphate sn-1 acyltransferase, and/or phospholipid:diacylglycerol acyltransferase. For example, the transformed cell may comprise a genetic modification that increases the activity of a DGA1 protein and a genetic modification that increases the activity of a DGA2 protein. In some embodiments, the transformed cell further comprises a genetic modification that decreases the activity of a native Δ9 desaturase, native Δ12 desaturase, native diacylglycerol acyltransferase, native triacylglycerol lipase, native sn-2 acylglycerol fatty acyltransferase, native lysophosphatidic acid acyltransferase native phosphatidate phosphatase, native glycerol-3-phosphate acyltransferase, native glycerol-3-phosphate/dihydroxyacetone phosphate sn-1 acyltransferase, and/or native phospholipid:diacylglycerol acyltransferase. For example, the transformed cell may comprise (1) a genetic modification that consists of transformation with a nucleic acid that encodes an exogenous DGA2 protein and (2) a knockout mutation in the native DGAT1 gene. Similarly, the transformed cell may comprise (1) a genetic modification that consists of transformation with a nucleic acid that encodes an exogenous DGA2 protein and (2) a genetic modification that decreases the activity of a native Δ12 desaturase protein.

b. Increasing the Actively of Type 2 Diacylglycerol Acyltransferase

In some embodiments, the acyltransferase protein is a type 2 diacylglycerol acyltransferase protein. The genetic modification may be transformation with a nucleic acid. In certain embodiments, the invention relates to a method of modifying the lipid content of a cell, comprising transforming the cell with a nucleic acid that increases the activity of a type 2 diacylglycerol acyltransferase protein in the cell.

The nucleic acid may encode a type 2 diacylglycerol acyltransferase gene. In some embodiments, the gene is DGAT2. In some embodiments, the gene is from *Aspergillus terreus, Aurantiochytrium limacinum, Arxula adeninivorans, Claviceps purpurea, Gloeophythan trabeum, Lipomyces starkeyi, Microbotryum violaceum, Phaeodactylum tricornutum, Pichia guilliermondii, Puccinia graminis, Rhodosporidium diobovatum, Rhodosporidium toruloides, Rhodotorula graminis*, or *Yarrowia lipolytica*. The gene may be from *Yarrowia lipolytica.*

In some embodiments, the nucleic acid comprises a nucleotide sequence that has at least 70% 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99:1%, 99.2%, 99.3%, 99.4%. 99.5%, 99.6%, 99.7%, 99.8%, 99.9% or more sequence homology with the sequence set forth in SEQ ID NO:20; SEQ ID NO:22; SEQ ID NO:24; SEQ ID NO:26; SEQ ID NO:28; SEQ ID NO:30; SEQ ID NO:52; SEQ ID NO:96; SEQ ID NO:100; SEQ ID NO:128; SEQ ID NO:130; SEQ ID NO:132; SEQ ID NO:134; SEQ ID NO:136; SEQ. ID NO:138; SEQ ID NO:140; or SEQ ID NO:142. The nucleic acid may comprise the nucleotide sequence set forth in SEQ ID NO:20; SEQ ID NO:22; SEQ ID NO:24, SEQ ID NO:26; SEQ ID NO:28; SEQ ID NO:30; SEQ ID NO:52; SEQ ID NO:96; SEQ ID NO:100; SEQ ID NO:128; SEQ ID NO:130; SEQ ID NO:132; SEQ ID NO:134; SEQ ID NO:136; SEQ ID NO:138; SEQ ID NO:140; or SEQ ID NO:142. In some embodiments, the nucleic acid comprises a nucleotide sequence that has at least 70%, 71%, 72%, 73%, 74%, 75%, 76%, 77%, 78%, 79%, 80%, 81%, 82%, 83%, 84%, 85%, 86%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:20. The nucleic acid may comprise the nucleotide sequence set forth in SEQ ID NO:20.

In some embodiments, the nucleic acid encodes an amino acid sequence having at least 80%, 81%, 82%, 83%, 84%, 85%, 86%, 87%, 88%, 89%, 90% 91% 92%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:19; SEQ ID NO:21; SEQ ID NO:23; SEQ ID NO:25; SEQ ID NO:27; SEQ ID NO:29; SEQ ID NO:51; SEQ ID NO:95;

SEQ ID NO:99; SEQ ID NO:127; SEQ ID NO:129; SEQ ID NO:131; SEQ ID NO:133; SEQ ID NO:135, SEQ ID NO:137, SEQ ID NO:139; or SEQ ID NO:141, or a biologically active portion thereof. The nucleic acid may encode the amino acid sequence set forth in SEQ ID NO:19; SEQ ID NO21; SEQ ID NO:23; SEQ ID NO:25; SEQ ID NO:27; SEQ ID NO:29; SEQ ID NO:51; SEQ ID NO:95; SEQ ID NO:99; SEQ ID NO:127; SEQ ID NO:129; SEQ ID NO:131; SEQ ID NO:133; SEQ ID NO:135; SEQ ID NO:137; SEQ ID NO:139; or SEQ ID NO:141. In some embodiments, the nucleic acid encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:19, or a biologically active portion thereof. The nucleic acid may encode the amino acid sequence set forth in SEQ ID NO:19.

The nucleic acid that comprises a gene encoding a type 2 diacylglycerol acyltransferase protein may comprise a nucleotide sequence set forth in SEQ ID NO:20; SEQ ID NO:22; SEQ ID NO:24; SEQ ID NO:26; SEQ ID NO:28; SEQ ID NO:30; SEQ ID NO:52; SEQ ID NO:96; SEQ ID NO:100, SEQ ID NO:128; SEQ ID NO:130; SEQ ID NO:132; SEQ ID NO:134; SEQ ID NO: 136; SEQ ID NO:138; SEQ ID NO:140: or SEQ ID NO:142. In other embodiments, the gene is substantially identical to SEQ ID NO:20; SEQ ID NO:22; SEQ ID NO:24; SEQ ID NO:26; SEQ ID NO:28; SEQ ID NO:30; SEQ ID NO:52; SEQ ID NO:96; SEQ ID NO:100; SEQ ID NO:128; SEQ ID NO:130; SEQ ID NO:132; SEQ ID NO:134; SEQ ID NO:136; SEQ ID NO:138; SEQ ID NO:140; or SEQ ID NO:142, and the nucleotide sequence encodes a protein that retains the type 2 diacylglyeerol acyltransferase activity of a protein encoded by SEQ ID NO:19; SEQ NO:21; SEQ ID NO:23; SEQ ID NO:25; SEQ ID NO:27; SEQ ID NO:29; SEQ ID NO:51; SEQ ID NO:95; SEQ ID NO:99, SEQ ID NO:127; SEQ ID NO:129; SEQ ID NO:131; SEQ ID NO:133; SEQ ID NO:135; SEQ ID NO:137; SEQ ID NO:139; or SEQ ID NO:141, yet differs in nucleotide sequence, e.g., due to natural allelic variation or mutagenesis.

The type 2 diacylglycerol acyltransferase protein may have an amino acid sequence set forth in SEQ ID NO:19; SEQ ID NO:21; SEQ ID NO:23; SEQ ID NO:25; SEQ ID NO:27; SEQ ID NO:29; SEQ ID NO:51; SEQ ID NO:95; SEQ ID NO:99; SEQ ID NO:127; SEQ ID NO:129, SEQ ID NO:131; SEQ ID NO:133; SEQ ID NO:135; SEQ ID NO:137; SEQ ID NO:139: or SEQ ID NO:141. In other embodiments, the type 2 diacylglycerol acyltransferase protein is substantially identical to SEQ ID NO:19; SEQ ID NO:21; SEQ ID NO:23; SEQ ID NO;25; SEQ ID NO:27; SEQ ID NO:29; SEQ ID NO:51; SEQ ID NO:95; SEQ ID NO:99; SEQ ID NO:127; SEQ ID NO:129; SEQ ID NO:131; SEQ ID NO:133; SEQ ID NO:135; SEQ ID NO:137; SEQ ID NO:139; or SEQ ID NO:141, and retains the functional activity of the protein of SEQ ID NO:19; SEQ ID NO:21; SEQ ID NO:23, SEQ ID NO:25; SEQ ID NO:27; SEQ ID NO:29; SEQ ID NO:51; SEQ ID NO:95; SEQ ID NO:99; SEQ ID NO:127; SEQ ID NO:129: SEQ ID NO:131: SEQ ID NO:133; SEQ ID NO:135; SEQ ID NO:137; SEQ ID NO:139; or SEQ ID NO:141, yet differs in amino acid sequence, e.g., due to natural allelic, variation or mutagenesis.

In some embodiments, the transformed cell further comprises a genetic, modification that increases the activity of a Δ9 desaturase, elongase, diacylglycerol acyltransferase, glycerol-3-phosphate acyltransferase, sn-2 acylglycerol fatty acyltransferase, lysophosphatidic acid acyltransferase, phosphatidate phosphatase, glycerol-3-phosphate/dihydroxyacetone phosphate sn-1 acyltransferase, and/or phospholipid:diacylglycerol acyltransferase. For example, the transformed cell may comprise a genetic modification that increases the activity of a DGA1 protein and a genetic modification that increases the activity of a DGA2 protein. In some embodiments, the transformed cell further comprises a genetic modification that decreases the activity of a native Δ9 desaturase, native Δ12 desaturase, native diacylglycerol acyltransferase, native triacylglycerol lipase, native sn-2 acylglycerol fatty acyltransferase, native lysophosphatidic acid acyltransferase, native phosphatidate phosphatase, native glycerol-3-phosphate acyltransferase, native ttlyeerol-3-phosphateldihydroxyacetone phosphate sn-1 acyltransferase, and/or native phospholipid:diacylglycerol acyltransferase. For example, the transformed cell may comprise (1) a genetic modification that consists of transformation with a nucleic acid that encodes an exogenous DGA1 protein and (2) a knockout mutation in the native DGAT2 gene. Similarly, the transformed cell may comprise (1) a genetic modification that consists of transformation with a nucleic acid that encodes an exogenous DOA1 protein and (2) a genetic modification that decreases the activity of a native Δ12 desaturase protein.

c. Increasing the Activity of a Type 3 Diacylglycerol Acyltransferase

In some embodiments, the acyltransferase protein is a type 3 diticylglycerol acyltransferase protein. The genetic modification may be transformation with a nucleic acid. In certain embodiments, the invention relates to a method of modifying the lipid content of a cell, comprising transforming the cell with a nucleic acid that increases the activity of a type 3 diacylglycerol acyltransferase protein in the cell.

The nucleic acid may encode a type 3 diacylglycerol acyltransferase gene. In some embodiments, the gene is DGAT3. In some embodiments, the gene is from *Ricinus communis* or *Arachis hypogaea.*

In some embodiments, the nucleic acid comprises a nucleotide sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:152 or SEQ ID NO:154. The nucleic acid may comprise the nucleotide sequence set forth in SEQ ID NO:152 or SEQ ID NO:154.

In some embodiments, the nucleic acid encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:151 or SEQ ID NO:153, or a biologically active portion thereof. The nucleic acid may encode the amino acid sequence set forth in SEQ ID NO:151 or SEQ ID NO:153.

The nucleic acid that comprises a gene encoding a type 3 diacylglycerol acyltransferase protein may comprise a nucleotide sequence set forth in SEQ ID NO:152 or SEQ ID NO:154. In other embodiments, the gene is substantially identical to SEQ ID NO:4; SEQ ID NO:8; SEQ ID NO:152 or SEQ ID NO:154, and the nucleotide sequence encodes a protein that retains the type 3 diacylglycerol acyltransferase activity of a protein encoded by SEQ ID NO:151 or SEQ ID NO:153, yet differs in nucleotide sequence, e.g., due to natural allelic variation or mutagenesis.

The type 3 diacylglycerol acyltransferase protein may have an amino acid sequence set forth in SEQ ID NO:151 or SEQ ID NO:153. In other embodiments, the type 3 diacylglycerol acyltransferase protein is substantially identical to SEQ ID NO:151 SEQ ID NO:153, and retains the functional activity of the protein of SEQ ID NO:151 or SEQ ID NO:153, yet differs in amino acid sequence, e.g., the to natural allelic variation or mutagenesis.

In some embodiments, the transformed cell further comprises a genetic modification that increases the activity of a Δ9 desaturase, elongase diacylglycerol acyltransferase, glycerol-3-phosphate acyltransferase, sn-2 acylalyeerol fatty acyltransferase, lysophosphatidic acid acyltransferase, phosphatidate phosphatase, glyecrol-3-phosphate/dihydroxyaeetone phosphate sn-1 acyltransferase, and/or phospholipid: diacylglycerol acyltransferase. In some embodiments, the transformed cell further comprises a genetic modification that decreases the activity of a native Δ9 desaturase, native Δ12 desaturase, native diacylglycerol acyltransferase, native triacylglycerol lipase, native sn-2 acylglycerol fatty acyltransferase, native lysophosphatidic acid acyltransferase, native phosphatidate phosphatase, native glycerol-3-phosphate acyltransferase, native glycerol-3-phosphate/dihydroxyacetone phosphate sn-1 acyltransferase, and/or native phospholipid:diacylglycerol acyltransferase.

d. Increasing the Activity of a Glycerol-3-phosphate Acyltransferase

In some embodiments, the acyltransferase protein is a glycerol-3-phosphate acyltransferase protein. The genetic modification may be transformation with a nucleic acid. In certain embodiments, the invention relates to a method of modifying the lipid content of a cell, comprising transforming the cell with a nucleic acid that increases the activity of a glycerol-3-phosphate acyltransferase protein in the cell.

The nucleic acid may encode a glycerol-3-phosphate acyltransferase gene. In some embodiments, the gene is SCT1. In some embodiments, the gene is from, *Arxula adeninivorans, Phaeodactylum tricornutum, Rhodosphoridium toruloides, Rhodotorula glutinis, Rhodotorula graminis, Saccharomyces cerevisiae*, or *Yarrowia lipolytica*. The gene may be from *Arxula adeninivorans* or *Saccharomyces cerevisiae.*

In some embodiments, the nucleic acid comprises a nucleotide sequence that has at least 70%, 71%, 72%, 73%, 74%, 75%, 76%, 77%, 78%, 79%, 80%, 81%, 82%, 83%, 84%, 85% 86%, 87%, 88%, 89%, 90%, 91% 92%, 93%, 94%, 95% 96%, 97% 98%, 99%, 99.1%, 99.2%, 99.3%, 99.4%, 99.5%, 99.6%, 99.7%, 99.8%, 99.9% or more sequence homology with the sequence set forth in SEQ ID NO:18; SEQ ID NO:42; SEQ ID NO:44; SEQ ID NO:46; SEQ ID NO:48; SEQ ID NO:116; or SEQ ID NO:118. The nucleic acid may comprise the nucleotide sequence set forth in SEQ ID NO:18: SEQ ID NO:42; SEQ ID NO:44; SEQ ID NO:46; SEQ ID NO:48: SEQ ID NO:116; or SEQ ID NO:118. In some embodiments, the nucleic acid comprises a nucleotide sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%. 99.4%, 99.5%, 996%, 99.7%, 99.8%, 99.9% or more sequence homology with the sequence set forth in SEQ ID NO:42 or SEQ ID NO:44. The nucleic acid may comprise the nucleotide sequence set forth in SEQ ID NO:42 or SEQ ID NO:44.

In some embodiments, the nucleic acid encodes an amino acid sequence having at least 80%, 81%, 82%, 83%, 84%, 85%, 86%, 87%, 88%, 89%, 90%, 91%, 92%, 93%, 94%, 95%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:17; SEQ ID NO:41; SEQ ID NO:43; SEQ ID NO:45; SEQ ID NO:47; SEQ ID NO:115; or SEQ ID NO:117, or a biologically active portion thereof. The nucleic acid may encode the amino acid sequence set forth its SEQ ID NO:17; SEQ ID NO:41; SEQ ID NO:43; SEQ ID NO:45; SEQ ID NO:47; SEQ ID NO:115; or SEQ ID NO:117. In some embodiments, the nucleic acid encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:41 or SEQ ID NO:43, or a biologically active portion thereof. The nucleic acid may encode the amino acid sequence set forth in SEQ ID NO:41 or SEQ ID NO:43.

The nucleic acid that comprises a gene encoding a glycerol-3-phosphate acyltransferase protein may comprise a nucleotide sequence set forth in SEQ ID NO:18; SEQ ID NO:42; SEQ ID NO:44; SEQ ID NO:46; SEQ ID NO:48; SEQ ID SEQ:116; or SEQ ID NO:118. In other embodiments, the gene is substantially identical to SEQ ID NO:18; SEQ ID NO:42; SEQ ID NO:44; SEQ ID NO:46; SEQ ID NO:48; SEQ ID NO:116; or SEQ ID NO:118, and the nucleotide sequence encodes a protein that retains the glycerol-3-phosphate acyltransferase activity of a protein encoded by SEQ ID NO:17; SEQ ID NO:41; SEQ ID NO:43; SEQ ID NO:45; SEQ ID NO:47; SEQ ID NO:115; or SEQ ID NO:117, yet differs m nucleotide sequence, e.g., due to natural allelic variation or matagenesis.

The glycerol-3-phosphate acyltransferase protein may have an amino acid sequence set forth in SEQ ID NO:17; SEQ ID NO:41; SEQ ID NO:43; SEQ ID NO:45; SEQ ID NO:47; SEQ ID NO:115; or SEQ ID NO:117. In other embodiments, the glycerol-3-phosphate acyltransferase protein is substantially identical to SEQ ID NO:17; SEQ ID NO:41; SEQ ID NO:43; SEQ ID NO:45; SEQ ID NO:47; SEQ ID NO:115; or SEQ ID NO:117, and retains the functional activity of the protein of SEQ ID NO:17; SEQ ID NO:41; SEQ ID NO:43; SEQ ID NO;45; SEQ ID NO:47; SEQ ID NO:115; or SEQ ID NO:117, yet differs in ainino acid sequence, e.g., due to natural allelic variation or mutnenesis.

In some embodiments, the transformed cell further comprises a genetic modification that increases the activity of a Δ9 desaturase, elongase, diacylglycerol acyltransferase, sn-2 acylglycerol fatty acyltransferase, lysophosphatidie acid acyltransferase, phosphatidate phosphatase, glycerol-3-phosphate/dihydroxyacetone phosphate sn-1 acyltransferase, and/or phospholipid:diacylglycerol acyltransferase, in some embodiments, the transformed cell further comprises a genetic modification that decreases the activity of a native Δ9 desaturase, native Δ12 desaturase native diacylglycerol acyltransferase, native triacylglyccrol lipase, native, sn-2 acylglycerol fluty acyltransferase, native lysophosphatidic acid acyltransferase, native phosphatidate phosphatase, native glycerol-3-phosphate acyltransferase, native alyccrol-3-phosphateldihydioxyacetone phosphate sn-1 acyltransferase, and/or native phospholipid:diacylglycerol acyltransferase. For example, the transformed cell may comprise (1) a genetic modification that consists of transformation with a nucleic acid that encodes an exogenous glycerol-3-phosphate acyltransferase protein and (2) a knockout mutation in a native SCT1 gene. Similarly, the transformed cell may comprise (1) a genetic modification that increases the expression of a glycerol-3-phosphate acyltransferase protein and (2) a genetic modification that decreases the activity of a native Δ12 desaturase protein.

e. Increasing the Activity of a Phospholipid:diacylglycerol Acyltransferase

In some embodiments, the acyltransferase protein is a phospholipid:diacylglycerol acyltransferase protein. The genetic modification may be transformation with a nucleic acid. In certain embodiments, the invention relates to a method of modifying the lipid content of a cell, comprising transforming the cell with a nucleic acid that increases the activity of a phospholipid:diacylglycerol acyltransferase protein in the cell.

The nucleic acid may encode a phospholipid:diacylglycerol acyltransferase gene. In some embodiments, the gene is LRO1. In some embodiments, the gene is from *Arxula adeninivorans* or *Yarrowia lipolytica*

In some embodiments, the nucleic acid comprises a nucleotide sequence that has at least 70%, 71%, 72%, 74%, 75%, 76%, 77%, 79%, 80%, 81%, 82%, 83%, 84%, 85%, 86%, 87%, 88%, 89%, 90%, 91%, 92%, 93%, 94%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:106 or SEQ ID NO:110. The nucleic acid may comprise the nucleotide sequence set forth in SEQ ID NO:106 or SEQ ID NO:110.

In some embodiments, the nucleic acid encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:105 or SEQ ID NO:109, or a biologically active portion thereof. The nucleic acid may encode the amino acid sequence set forth in SEQ ID NO:105 or SEQ ID NO:109.

The nucleic acid that comprises a gene encoding a phospholipid:diacylglycerol acyltransferase protein may comprise a nucleotide sequence set forth in SEQ ID NO:106 or SEQ ID NO:110. In other embodiments, the gene is substantially identical to SEQ ID NO:106 or SEQ ID NO:110, and the nucleotide sequence encodes a protein that retains the phospholipid/diacylglycerol acylnansferase activity of a protein encoded by SEQ ID NO:105 or SEQ ID NO:109, yet differs in nucleotide sequence, e.g., due to natural allelic variation or mutasenesis.

The phospholipid:diacylglycerol acyhransferase protein may have an amino acid sequence set forth in SEQ ID NO:105 or SEQ ID NO:109. In other embodiments, the phospholipid:diacylglycerol acyltransferase protein is substantially identical to SEQ ID NO:105 or SEQ ID NO:109, and retains the functional activity of the protein of SEQ ID NO:105 or SEQ ID NO:109, yet differs in amino acid sequence, e.g., due to natural allelic variation or mutagenesis.

In some embodiments, the transformed cell further comprises a genetic modification that increases the activity of a Δ9 desaturase, elongase, diacylglycerol acyltransferase, sn-2 acylglyceml fatty acyltransferase, lysophosphatidic acid acyltransferase, phosphatidate phosphatase, glycerol-3-phosphate/dihydroxyacetone phosphate sn-1 acyltransferase, and/or glycerol-3-phosphate acyltransferase. In some embodiments, the transformed cell further comprises a genetic modification that decreases the activity of a native Δ9 desaturase, native Δ12 desaturase, native diacylglycerol acyltransferase, native triacylglycerol lipase, native sn-2 acylglycerol fatty acyltransferase, native lysophosphatidic acid acyltransferase, native phosphatidate phosphatase, native glycerol-3-phosphate acyltransferase, native glycerol-3-phosphate/dihydroxyacetone phosphate sn-1 acyltransferase, and/or native phospholipid:diacylglyecrol acyltransferase.

f. Increasing the Activity of a Glycerol-3-phosphate/dihydroxyacetone Phosphate sn-1 Acyltransferase In some embodiments, the acyltransferase protein is a glyeerol-3-phosphate/dihydroxyacetone phosphate acyltransferase protein. The genetic modification may be transformation with a nucleic acid. In certain embodiments, the invention relates to a method of modifying the lipid content of a cell, comprising transforming the cell with a nucleic acid that increases the activity of a glycerol-3-phosphate/dihydroxyacetone phosphate sn-1 acyltransferase protein in the cell.

The nucleic acid may encode a glycerol-3-phosphate/dihydroxyacetone phosphate sn-1 acyltransferase gene. In some embodiments, the gene is GPT2. In some embodiments, the gene is from *Saccharomyces cerevisiae, Naumovozyma dairenensis, Torulaspora delbrueckii*, or *Naumovozyma castellii.*

In some embodiments, the nucleic acid comprises a nucleotide sequence that has at least 70%, 71%, 72%, 73%, 74%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%. 99%, 99.1%, 99.2%, 99.3%, 99.4%, 99.5%, 99.6%, 99.7%, 99.8%, 99.9% or more sequence homology with the sequence set forth in SEQ ID NO:120; SEQ ID NO:122; SEQ ID NO:124; or SEO ID NO:126. The nucleic acid may comprise the nucleotide sequence set forth in SEQ ID NO:120, SEQ ID NO:122; SEQ ID NO:124; or SEQ ID NO:126.

In some embodiments, the nucleic acid encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:119; SEQ ID NO:121; SEQ ID NO:123; or SEQ ID NO:125, or a biologically active portion thereof. The nucleic acid may encode the amino acid sequence set forth in SEQ ID NO:119; SEQ ID NO:121; SEQ ID NO:123; or SEQ ID NO:125.

The nucleic acid that comprises a gene encoding a glycerol-3-phosphate/dihydroxyacetone phosphate sn-1 acyltransferase protein may comprise a nucleotide sequence set forth in SEQ ID NO:120; SEQ ID NO:122; SEQ ID NO:124; or SEQ ID NO:126. In other embodiments, the gene is substantially identical to SEQ ID NO:120; SEQ ID NO:122; SEQ ID NO:124; or SEQ ID NO:126, and the nucleotide sequence encodes a protein that retains the glycerol-3-phosphate/dihydroxyacetone phosphate sn-1 acyltransferase activity of a protein encoded by SEQ ID NO:119;

SEQ ID NO:121; SEQ ID NO:123; or SEQ ID NO:125, yet differs in nucleotide sequence, e.g., due to natural allelic variation or mutagenesis.

The glycerol-3-phosphate/dihydroxyacetone phosphate sn-1 acyltransferase protein may have an amino acid sequence set forth in SEQ ID NO:119; SEQ ID NO:121; SEQ ID NO:123; or SEQ ID NO:125. In other embodiments, the glycerol-3-phosphate/dihydroxyacetone phosphate sn-1 acyltransferase protein is substantially identical to SEQ ID NO:119; SEQ ID NO:121; SEQ ID NO:123; or SEQ ID NO:125, and retains the functional activity of the protein of SEQ ID NO:119; SEQ ID NO:121; SEQ ID NO:123; or SEQ ID NO:125, yet differs in amino acid sequence, e.g., due to natural allelic variation or mutagenesis.

In some embodiments, the transformed cell further comprises a genetic modification that increases the activity of a Δ9 desaturase, elongase, diacylglycerol acyltransferase, sn-2 acylglycerol fatty acyltransferase, lysophosphatidic acid acyltransferase, phosphatidate phosphatase, phospholipid: diacylglycerol acyltransfrase, and/or glycerol-3-phosphate acyltransferase. In some embodiments, the transformed cell, further comprises a genetic modification that decreases the activity of a native Δ9 desaturase, native Δ12 desaturase, native diacylglycerol acyltransferase, native triacylglycerol lipase, native sn-2 acylglycerol fatty acyltransferase, native lysophosphatidic acid acyltransferase, native phosphatidate phosphatase, native glycerol-3-phosphate acyltransterase, native glycerol-3-phosphate/dihydroxyacetone phosphate sn-1 acyltransferase, and/or native phospholipid:diacylglycerol acyltransferase. For example, the transformed cell may comprise (1) a genetic modification that consists of transformation with a nucleic acid that encodes an exogenous glycerol-3-phosphate/dihydroxyacetone phosphate sn-1 acyltransferase protein and (2) a knockout mutation in a native GPT2 gene.

g. Increasing the Activity of a sn-2 Acylglycerol Fatty Acyltransferase

In some embodiments, the acyltransferase protein is a sn-2 acylglycerol fatty acyltranstrase protein. The genetic modification may be transformation with a nucleic acid. In certain embodiments, the invention relates to a method of modifying the lipid content of a cell, comprising transforming the cell with a nucleic acid that increases the activity of a sn-2 acylglycerol fatty acyltransferase protein in the cell.

The nucleic acid may encode a sn-2 acylglycerol fatty acyltransferase gene. In some embodiments, the gene is SLC1 or SLC4. In some embodiments, the gene is from *Arxula adeninivorans, Saccharomyces cerevisiae, Phaendactylum tricornutum, Rhodosporidium toruloides, Rhodonorula minuta, Rhodotorula graminis*, or *Yarrowia lipolytica.*

In some embodiments, the nucleic acid comprises a nucleotide sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:60, SEQ ID NO:62; SEQ ID NO:64; SEQ ID NO:66; SEQ ID NO:68; SEQ ID NO:70; SEQ ID NO:72; SEQ ID NO:74; SEQ ID NO:76; or SEQ ID NO:78. The nucleic acid may comprise the nucleotide sequence set forth in SEQ ID NO:60; SEQ ID NO:62; SEQ ID NO:64; SEQ ID NO:66; SEQ ID NO:68; SEQ ID NO:70; SEQ ID NO:72; SEQ ID NO:74; SEQ ID NO:76; or SEQ ID NO:78.

In some embodiments, the nucleic acid encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%. 99.1%, 99.2%, 99.3%, 99.4%, 99.5%, 99.6%, 99.7%, 99.8%, 99.9% or more sequence homology with the sequence set forth in SEQ ID NO:59; SEQ ID NO:61; SEQ ID NO:63; SEQ ID NO:65; SEQ ID NO:67; SEQ ID NO:69; SEQ ID NO:71; SEQ ID NO:73; SEQ ID NO:75; or SEQ ID NO:77, ora biologically active portion thereof. The nucleic acid may encode the amino acid sequence set forth in SEQ ID NO:59; SEQ ID NO:61; SEQ ID NO:63; SEQ ID NO:65; SEQ ID NO:67; SEQ ID NO:69; SEQ ID NO:71; SEQ ID NO:73; SEQ ID NO:75; or SEQ ID NO:77.

The nucleic acid that comprises a gene encoding a sn-2 acylglycerol thtty acyltransferase protein may comprise a nucleotide sequence set forth in SEQ ID NO:60; SEQ ID NO:62; SEQ ID NO:64; SEQ ID NO:66; SEQ ID NO:68; SEQ ID NO:70; SEQ ID NO:72; SEQ ID NO:74; SEQ ID NO:76; or SEQ ID NO:78. In other embodiments, the gene is substimtially identical to SEQ ID NO:60; SFQ ID NO:62; SEQ ID NO:64; SEQ ID NO:66; SEQ ID NO:68; SEQ ID NO:70; SEQ ID NO:72; SEQ ID NO:74; SEQ ID NO:76; of SEQ ID NO:78, and the nucleotide sequence encodes a protein that retains the sn-2 acylglycerol fatty acyltransferase actiity of a protein encoded by SEQ ID NO:59; SEQ ID NO:61; SEQ ID NO:63; SEQ ID NO:65:SEQ ID NO:67; SEQ ID NO:69; SEQ ID NO:71; SEQ ID NO:73; SEQ ID NO175; cr SEQ ID NO:77, yet differs in nucleotide sequence, e.g., due to natural allelic variation or mutagenesis.

The sn-2 acyiglycerol fatty acyltransferase protein may have an amino acid sequence set forth in SEQ ID NO:59; SEQ ID NO:61; SEQ ID NO:63; SEQ ID NO:65; SEQ ID NO:67; SEQ ID NO:69; SEQ ID NO:71; SEQ ID NO:73; SEQ ID NO:75; or SEQ ID NO:77. In other embodiments, the sn-2 acylglycerol fatty acyltransferase protein is substantially identical to SEQ ID NO:59; SEQ ID NO:61; SEQ ID NO:63: SEQ ID NO:65; SEQ ID NO:67; SEQ ID NO:69; SEQ ID NO:71; SEQ ID NO:73; SEQ ID NO:75; or SEQ ID NO:77, and retains the functional activity of the protein of SEQ ID NO:59, SEQ ID NO:61; SEQ ID NO:63; SEQ ID NO:65; SEQ ID NO:67; SEQ ID NO:69; SEQ ID NO:71; SEQ ID NO:73; SEQ ID NO:75; or SEQ ID NO:77, yet diffeTs in amino acid sequence, eg., due to natural allelic variation or mutagenesis.

In some embodiments, the transformed cell further comprises a genetic modification that increases the activity of a Δ9 desaturase, elongase, diacylgiycerol acyltransferase, lysophosphatidic acid acyltransferase, phosphatidate phosphatase, phospholipid:diacylglycerol acyltransferase, glycerol-3-phosphate/dihydroxyacetone phosphate sn-1 acyltransferase, and/or glycerol-3-phosphate acyltransferase. In some embodiments, the transformed cell further comprises a genetic modification that decreases the activity of a native Δ9 desaturase, native Δ12 desaturase, native diacylglycerol acyltransferase, native triacylglyccrol lipase, native sn-2 acylglycerol fatty acyltransferase, native lysophosphatidic acid acyltransferase, native phosphatidate phosphatase, native glycerol-3-phosphate acyltransferase, native glycerol-3-phosphate/dihydroxyacetone phosphate sn-1 acyltransferase, and/or native phospholipid:diacylglycerol acyltransferase.

h. Increasing the Activity of a Lysophosphatidic Acid Acyltransferase

In some embodiments, the acyltransferase protein is a lysophosphatidic acid acyltransferase protein. The genetic modification may be transformation with a nucleic acid. In certain embodiments, the invention relates to a method of modifying the lipid content of a cell, comprising transforming the cell with a nucleic acid that increases the activity of a lysophosphatidic acid acyltransferase protein in the cell.

The nucleic acid may encode a lysophosphatidic acid acyltransferase gene. In some embodiments, the gene is LOA1. In some embodiments, the gene is from *Arxula adeninivorans, Saccharomyces cerevisiae*, or *Yarrowia lipolytica.*

In some embodiments, the nucleic acid comprises a nucleotide sequence that has at least 70%, 71%, 72%, 73%, 74%, 75%, 76%, 77%, 78%, 79%, 80%, 81%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:80; SEQ ID NO:821 or SEQ NO:84. The nucleic acid may comprise the nucleotide sequence set forth in SEQ ID NO:80; SEQ ID NO:82; or SEQ ID NO:84.

In some embodiments, the nucleic acid encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:79; SEQ ID NO:81; or SEQ ID NO:83, or a biologically active portion thereof. The nucleic acid may encode the amino acid sequence set forth in SEQ ID NO:79; SEQ ID NO:81; or SEQ ID NO:83.

The nucleic acid that comprises a gene encoding a lysophosphatidic acid acyltransferase protein may comprise a nucleotide sequence set forth in SEQ ID NO:80; SEQ ID NO:82; or SEQ ID NO:84. In other embodiments, the gene is substantially identical to SEQ ID NO:80; SEQ ID NO:82, SEQ ID NO:84, and the nucleotide sequence encodes a protein that retains the lysophosphatidic acid acyltransferase activity of a protein encoded by SEQ ID NO:79; SEQ ID NO:81; or SEQ ID NO:83, yet differs in nucleotide sequence, e.g., due to natural allelic variation or mutagenesis.

The lysophosphatidic acid acyltransferase protein may have an amino acid sequence set forth in SEQ ID NO:79; SEQ ID NO:81; SEQ ID NO:83. In other embodiments, the lysophosphatidic acid acyltransferase protein is substantially identical to SEQ ID NO:79; SEQ ID NO:81; or SEQ ID NO:83, and retains the functional activity of the protein of SEQ ID NO:79; SEQ ID NO:81; or SEQ ID NO:83, yet differs in amino acid sequence, e.g., due to natural allelic variation or mutagenesis.

In some embodiments, the transformed cell further comprises a genetic modification that increases the activity of a Δ9 desaturase, elongase, diacylglycerol acyltransferase, sn-2 acylglycerol fatty acyltransferase, phosphatidate phosphatase, phospholipid:diacylglycerol acyltransferase, glycerol-3-phosphate/dihydroxyacetone phosphate sn-1 acyltransferase, and/or glycerol-3-phosphate acyltransferase. In some embodiments, the transformed cell further comprises a genetic modification that decreases the activity of a native Δ9 desaturase, native Δ12 desaturase, native diacylglycerol acyltransferase, native triacylglycerol lipase, native sn-2 acylglycerol fatty acyltransferase, native lysophosphatidic acid acyltransferase, native phosphatidate phosphatase, native glycerol-3-phosphate acyltransferase, native glycerol-3-phosphate/dihydroxyacetone phosphate sn-1 acyltransferase, and/or native phospholipid:diacylglycerol acyltransferase.

4. Increasing the Activity of a Phosphatidate Phosphatase

In some aspects, the invention relates to a transformed cell comprising a genetic modification, wherein the genetic modification increases the activity of a phosphatidate phosphatase protein in the cell. The genetic modification may be transformation with a nucleic acid. In certain embodintents, the invention relates to a method of modifying the lipid content of a cell, comprising transforming the cell with a nucleic acid that increases the activity of a phosphatidate phosphatase protein in the cell.

The nucleic acid may eilcode a phosphatidate phosphatase gene. In some embodiments, the gene is PAH1. In some embodiments, the gene is from *Arxula adeninivorans, Saccharomyces cerevisiae*, or *Yarrowia lipolytica.*

In some embodiments, the nucleic acid comprises a nucleotide sequence that has at least 70%, 71%, 72%, 73%, 74%, 75%, 76%, 77%, 78%, 79%, 80%, 81%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:54; SEQ ID NO:56; or SEQ ID NO:58. The nucleic acid may comprise the nucleotide sequence set forth in SEQ ID NO:54; SEQ ID NO:56; SEQ ID NO:58.

In some embodiments, the nucleic acid encodes an amino acid sequence having at least 80%, 81%, 82%, 83%, 84%, 85%, 86%, 87%, 88%, 89%, 90%, 91%, 92%, 93%, 94%, 95%, 97%, 98%, 99%, 99.1%, 99.2%, 99.4%, 99.5%, 99.6%, 99.7%, 99.8%, 99.9% or more sequence homology with the sequence set forth in SEQ ID NO:53; SEQ ID NO:55; or SEQ ID NO:57, or a biologically active portion thereof. The nucleic acid may encode the amino acid sequence set forth in SEQ ID NO:53; SEQ ID NO:55; or SEQ ID NO:57.

The nucleic acid that comprises a gene encoding a phosphatidate phosphatase protein may comprise a nucleotide sequence set forth in SEQ ID NO:54; SEQ ID NO:56; or SEQ ID NO:58. In other embodiments, the gene is substantially identical to SEQ ID NO:54; SEQ ID NO:56; or SEQ ID NO:58, and the nucleotide sequence encodes a protein that retains the phosphatidate phosphatase activity of a protein encoded by SEQ ID NO:53; SEQ ID NO:55; or SEQ ID NO:57, yet differs in nucleotide sequence due to natural allelic variation or mutagenesis.

The phosphatidate phosphatase protein may have an amino acid sequence set forth in SEQ ID NO:53, SEQ ID NO:55; or SEQ ID NO:57. In other embodiments, the phosphatidate phosphatase protein is substantially identical to SEQ ID NO:53, SEQ ID NO:55; or SEQ ID NO:57, and retains the functional activity of the protein of SEQ NO:53; SEQ ID NO:55; or SEQ ID NO:57, yet differs in amino acid sequence, e.g., due to natural allelic; variation or mutagenesis.

In some embodiments, the transformed cell further comprises a genetic modification that increases the activity of a Δ9 desaturase, elongase, diacylglycerol acyltransferase, sn-2 acylglyeerol fatty acyltransferase, lysophosphatidic acid acyltransferase, phospholipid:diacylglycerol acyltransferase, glycerol-3-phosphate/dihydroxyacetone phosphate sn-1 acyltransferase, and/or glycerol-3-phosphate acyltransferase. In some embodiments, the transformed cell further comprises a genetic modification that decreases the activity of a native Δ9 desaturase, native Δ12 desaturase, native diacylglycerol acyltransferase, native triacylglycerol lipase, native sn-2 acylglycerol fatty acyltransferase, native lysophosphatidic acid acyltransferase, native phosphatidate phosphatase, native alycerol-3-phosphate acyltransferase, native glycerol-3-phosphate/dihydroxyacetone phosphate sn-1 acyltransferase, and/or native phospholipid:diacylglycerol acyltransferase.

C. Nucleic Acids and Methods for Decreasing the Activity of a Native Protein

In some embodiments, the transformed oleaginous cell comprises a genetic modification that decreases the activity of a native protein. Such genetic modifications may affect a protein that regulates the transcription of the native protein, including modifications that decrease the expression of a transcription activator and/or increase the expression of a transcription repressor. Modifications that affect a regulator protein may both decrease the expression of the native protein and alter other gene expression profiles that shift the cellular equilibrium toward increased oleic acid accumulation. Alternatively, the genetic modification may be the introduction of an interfering nucleic acid, such as a smart interfering RNA, or a nucleic acid that encodes an interfering nucleic acid. In other embodiments, the genetic modification consists of the homologous recombination of a nucleic acid and the regulatory region of a gene that encodes the native protein. The regulatory region of the gene may include an operator, promoter, sequences upstream from the promoter, enhancers, and/or sequences downstream of the gene.

In some embodiments the transformed oleaginous cell comprises a genetic modification consisting of a homologous recombination event. In certain embodiments, the transformed cell comprises a genetic modification consisting of a homologous recombination event between a native gene and a nucleic acid. Thus, the genetic modification deletes the native gene, prevents its transcription, or prevents the transcription of a gene that can be translated into a fully-active protein. A homologous recombination event may mutate or delete a portion of a native gene. For example, the homologous recombination event may mutate one or more residues in the active site of a native enzyme, thereby reducing the efficiency of the enzyme or rendering it inactive. Alternatively, the homologous recombination event may affect post-translational modification, folding, stability, or localization within the cell. In some embodiments, the homologous recombination event replaces the promoter with a promoter that drives less transcription. In other embodiments, the homologous recombination event mutates the promoter to impair its ability to drive transcription. In certain embodiments, the genetic modification is a knockout mutation.

A knockout mutation may delete one or more genes. Additionally, the knockout mutation may substitute a native gene with an exogenous gene that encodes a different protein. The exogenous gene may be operably linked to an exogenous promoter. In certain embodiments, the gene is not linked to an exogenous promoter, and instead, the gene is configured to recombine with the native gene such that the native gene's promoter drives transcription of the exogenous gene. Thus, the gene is less likely to be expressed if it randomly integrates into the cell's genome. Methods for creating knockouts are well-known in the art (See, e.g., Fickers et al., J. Microbiological Methods 55:727 (2003)).

In certain embodiments, the genetic modification comprises two homologous recombination events. In the first event, a nucleic acid encoding a portion of a gene recombines with the native gene, and in the second event, a nucleic acid encoding the remaining portion of the gene recombines with the native gene. The two portions of the gene are designed such that neither portion is functional unless they recombine with each other. These two events further reduce the likelihood that the gene can be expressed following random integration events.

In certain embodiments, the gene encodes a marker protein, such as a dominant selectable marker. Thus, knockout cells may be selected by screening for the marker. In some embodiments, the dominant selectable marker is a drug resistance marker. A drug resistance marker is a dominant selectable marker that, when expressed by a cell, allows the cell to grow and/or survive in the presence of a drug that would normally inhibit cellular growth and/or survival. Cells expressing a drug resistance marker can be selected by growing the cells in the presence of the drug. In some embodiments, the drug resistance marker is an antibiotic resistance marker. In some embodiments, the drug resistance marker confers resistance to a drug selected from the group consisting of Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naltifine, Terbinafine, Anidalafungin, Caspofungin, Micafungin, Benzoic acid, Ciclopirox, Flucytosine, 5-fluorocytosine, Griscofulvin, Haloprogin, Polygodial, Tolnaftate, Crystal violet, Amikacin, Gentamicin, Kanamycin, Neomycin, Netilmicin, Tobramycin, Paromomycin, Spectinomycin, Geldanamycin, Herbimycin, Rifaximin, Streptomycin, Loracarbef, Ertapenem, Doripenem, Imipenem, Meropenem, Cefadroxil, Cefazolin, Cefalotin, Cefalexin, Cofaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Cefepime, Ceftaroline fosamil, Ceftobiprole, Teicoplanin, Vancomycin, Telavancin, Clindamycin, Lincomycin, Daptomycin, Azithromycin, Clarithromycin, Dirithromycin, Erythromycin, Roxithromycin, Troleandomycin, Telithromycin, Spiramycin, Aztreonam, Furazolidone, Nitrofurantoin, Linezolid, Posizolid, Radezolid, Torezolid, Amoxicillin, Ampicillin, Azlocillin, Carbenicillin, Cloxacillin, Dieloxacillin, Flucloxacillin, Methicillin, Nafcillin, Oxacillin, Penicillin G, Penicillin V, Piperacillin, Penicillin G, Temocillin, Ticarcillin, clavulanate, sulbactam, tazobactam, clavulanate, Bacitracin, Colistin, Polymyxin B, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Trimethoprim-Sulfamethoxazole, Co-trimoxazole, Sulfonamidochrysoidine, Demeclocycline, Doxycycline, Minocycline, Oxytetracycline, Tetracycline, Clofazimine, Dapsone, Capreomycin, Cycloserine, Ethambutol, Ethionamide, Isoniazid, Pyrazinamide, Rifampicin, Rifabutin, Rifapentine, Streptomycin, Arsphenamine, Chloramphenicol, Fosfomycin, Fusidic acid, Metronidazole, Mupirocin, Platensimycin, Quinupristin, Dalfopristin, Thiamphenicol, Tigecycline, Tinidazole, Trimethoprim, Geneticin, Nourseothricin, Hygramycin, Bleomycin, and Puromycin.

In some embodiments, the dominant selectable marker is a nutritional marker. A nutritional marker is a dominant selectable marker that, when expressed by the cell, enables the cell to grow or survive using one or more particular nutrient sources. Cells expressing a nutritional marker can be selected by growing the cells under limiting nutrient conditions in which cells expressing the nutritional marker can survive and/or grow, but cells lacking the nutrient marker cannot. In some embodiments, the nutritional marker is selected from the group consisting of Orotidine 5-phosphate decarboxylase, Phosphite specific oxidoreductase, Alpha-keloglatarate-dependent hypophosphite dioxygenase, Alkaline phosphatase, Cyanamide hydratase, Melamine deaminase, Cyanurate amidohydrolase, Biuret hydrolyase, Urea amidolyase, Ammelide aminohydrolase, Guanine deaminase, Phosphodiesterase, Phosphotriesterase, Phosphite hydrogenase, Glycerophosphodiesterase, Parathion hydrolyase, Phosphite dehydrogenase, Dibenzothiophene desulfurization enzyme, Aromatic desulfinase, NADH-dependent FMN reductase, Aminopurine transporter, Hydroxylamine oxidoreductase, Invertase, Beta-glucosidase, Alpha-glucosidase, Beta-galactosidase, Alpha-galactosidase, Amylase, Cellulase, and Pullulonase.

Different approaches may be used to knockout a gene in a yeast cell (See, e.g., Dulermo et al., Biochimica Biophysiea Acta 1831:1486 (2013)). The methods disclosed herein and other methods known in the art may be used to knockout different genes in other species, such as *Arxula adeninivorans.*

In some embodiments, a genetic modification decreases the expression of a native gene by 0.1, 0.2, 0.3, 0.4, 0.5, 0.6, 0.7, 0.8, 0.9, 1, 2, 3, 4, 5, 6, 7, 8, 9, 10, 25, 30, 35, 40, 45, 50, 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8, 99.9, or 100 percent.

In some embodiments, a genetic modification decreases the efficiency of a native protein by 0.1, 0.2, 0.3, 0.4, 0.5, 0.6, 0.7, 0.8, 0.9, 1, 2, 3, 4, 5, 6, 7, 8, 9, 10, 25, 30, 35, 40, 45, 50, 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8, 99.9, or 100 percent.

In some embodiments, a genetic modification decreases the activity of a native protein by 0.1, 0.2, 0.3, 0.4, 0.5, 0.6, 0.7, 0.8, 0.9, 1, 2, 3, 4, 5, 6, 7, 8, 9, 10, 25, 30, 35, 40, 45, 50, 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8, 99.9, or 100 percent.

1. Decreasing the Activity of a Native Δ12 Desaturase

In some aspects, the invention relates to a transformed cell comprising a genetic modification, wherein the genetic modification decreases the activity of a native Δ12 desaturase protein. In some embodiments, the genetic modification is a knockout mutation.

The genetic modification may be transformation with a nucleic acid. In certain embodiments, the invention relates to a method of modifying the lipid content of a cell, comprising transforming the cell with a nucleic acid that decreases the activity of a native Δ12 desaturase protein in the cell. The nucleic acid may be capable of recombining with a native Δ12 desaturase gene and/or a nucleotide sequence in the regulatory region of a native Δ12 desaturase gene. In some embodiments, the native Δ12 desaturase protein is encoded by the Δ12 gene.

In certain embodiments, the cell is *Yarrowia lipolytica* and the native Δ12 desaturase protein has the amino acid sequence set forth in SEQ ID NO:1. In some embodiments, the cell is *Yarrowia lipolytica*, and the native Δ12 desaturase protein is encoded by the nucleotide sequence set forth in SEQ ID NO:2.

In certain embodiments, the cell is *Arxula adeninivorans* and the native Δ12 desaturase protein has the amino acid sequence set forth in SEQ ID NO:49. In some embodiments, the cell is *Arxula adeninivorans*, and the native Δ12 desaturase protein is encoded by the nucleotide sequence set forth in SEQ ID NO:50.

In some embodiments, the transformed cell further comprises a genetic modification that increases the activity of a Δ9 desaturase, elongase, diacylglycerol acyltransferase, sn-2 acylglycerol fatty acyltransferase, lysophosphatidic acid acyltransferase, phosphatidate phosphatase, phospholipid: diacylglycerol acyltransferase, glycerol-3-phosphate/dihydroxyacetone phosphate sn-1 acyltransferase, and/or glycerol-3-phosphate acyltransferase. For example, the transformed cell may comprise (1) a genetic modification that decreases the activity of a native Δ12 desaturase protein and (2) a genetic modification that increases the activity of a Δ9 desaturase protein. Similarly, the transformed cell may comprise (1) a genetic modification that decreases the activity of a native Δ12 desaturase protein and (2) a genetic modification that increases the activity of a diacylglycerol acyltransferase protein. In some embodiments, the transformed cell further comprises a genetic modification that decreases the activity of a native Δ9 desaturase, native diacylglycerol acyltransferase, native triacylglycerol lipase, native sn-2 acylglycerol fatty acyltransfense, native lysophosphatidic acid acyltransferase, native phosphatidate phosphatase, native glycerol-3-phosphate acyltransferase, native glycerol-3-phosphate/dihydroxyacetone phosphate sn-1 acyltransferase, and/or native phospholipid:diacylycerol acyltransferase.

2. Decreasing the Activity of Native Δ9 Desaturase

In some aspects, the invention relates to a transformed cell comprising a genetic modification, wherein the genetic modification decreases the activity of a native Δ9 desaturase protein. In some embodiments, the genetic modification is a knockout mutation.

The genetic modification may be transformation with a nucleic acid. In certain embodiments, the invention relates to a method of modifying the lipid content of a cell, comprising transforming the cell with a nucleic acid that decreases the activity of a native Δ9 desaturase protein in the cell. The nucleic acid may be capable of recombining with a native Δ9 desaturase gene and/or a nucleotide sequence in the regulatory region of a native Δ9 desaturase gene. In some embodiments, the native Δ9 desaturase protein is encoded by the Δ9, OLE1, or FADI gene.

In certain embodiments, the cell is *Yarrowia lipolytica* and the native Δ9 desaturase protein has the amino acid sequence set forth in SEQ ID NO:3. In some embodiments, the cell is *Yarrowia lipolytica, and the native* Δ9 desaturase protein is encoded by the nucleotide sequence set forth in SEQ ID NO:4.

In certain embodiments, the cell is *Arxula adeninivorans* and the native Δ9 desaturase protein has the amino acid sequence set firth in SEQ ID NO:7. In some embodiments, the cell is *Arxula adeninivorans*, and the native Δ9 desaturase protein is encoded by the nucleotide sequence set forth in SEQ ID NO:8.

In some embodiments, the transformed cell further comprises a genetic modification that increases the activity of a Δ9 desaturase (e.g., an exogenous Δ9 desaturase), elongase, diacylglycerol acyltransferase, sn-2 acylglycerol fatty acyltransferase, lysophosphatidic acid acyltransferase, phosphatidate phosphatase, phospholipid:diacylglycerol acyltransferase, glycerol-3-phosphate/dihydroxyacetone phosphate sn-1 acyltransferase, and/or glycerol-3-phosphate acyltransferase. For example, the transformed cell may comprise (1) a genetic modification that decreases the activity of a native Δ9 desaturase protein and (2) a genetic modification that consists of transformation with a nucleic acid encoding a Δ9 desaturase protein, e.g., a Δ9 desaturase protein from a different species. In some embodiments, the transformed cell further comprises a genetic modification that decreases the activity of a native Δ12 desaturase, native diacylglycerol acyltransferase, native triacylglycerol lipase, native sn-2 acylglycerol fatty acyltransferase, native lysophosphatidic acid acyltransferase, native phosphatidate phosphatase, native glycerol-3-phosphate acyltransferase, native glycerol-3-phosphate/dihydroxyacetone phosphate sn-1 acyltransferase, and/or native phospholipid:diacylglycerol acyltransferase.

3. Decreasing the Activity of a Native Diacylglycerol Acyltransferase

In some aspects, the invention relates to a transformed cell comprising a genetic modification, wherein the genetic modification decreases the activity of a native diacylglycerol acyltransferase protein. In some embodiments, the genetic modification is a knockout mutation.

The genetic modification may be transformation with a nucleic acid. In certain embodiments, the invention relates to a method of modifying the lipid content of a cell, comprising transforming the cell with a nucleic acid that decreases the activity of a native diacylglycerol acyltransferase protein in the cell. The nucleic acid may be capable of recombining with a native diacylglycerol acyltransferase gene and/or a nucleotide sequence in the regulatory region of a native diacylglycerol acyltransferase gene. In some embodiments, the native diacylglycerol acyltransferase protein is encoded by the DGAT1 or DGAT2 gene.

In certain embodiments, the cell is *Yarrowia lipolytica* and the native diacylglycerol acyltransferase protein has the amino acid sequence set forth in SEQ ID NO:19 or SEQ ID NO:93. In some embodiments, the cell is *Yarrowia lipolytica*, and the native diacylglycerol acyltransferase protein is encoded by the nucleotide sequence set forth in SEQ ID NO:20 or SEQ ID NO:94.

In certain embodiments, the cell is *Arxula adeninivorans* and the native diacylglycerol acyltransferase protein has the amino acid sequence set forth in SEQ ID NO:51 or SEQ ID NO:103. In some embodiments, the cell is *Arxula adeninivorans*, and the native diacylglycerol acyltransferase protein is encoded by the nucleotide sequence set forth in SEQ ID NO:52 or SEQ ID NO:104.

In some embodiments, the transformed cell further comprises a genetic modification that increases the activity of a Δ9 desaturase, elongase, diacylglycerol acyltransferase (e.g., an exogenous diacylglycerol acyltransferase), srt-2 acylglycerol fatty acyltransferase, lysophosphatidic acid acyltransferase, phosphatidate phosphatase, phospholipid: diacylglycerol acyltransferase, glycerol-3-phosphate/dihydroxyacetone phosphate sn-1 acyltransferase, and/or glycerol-3-phosphate acyltransferase. For example, the transformed cell may comprise (1) a genetic modification that decreases the activity of a native diacylglycerol acyltransferase protein and (2) a genetic modification that consists of transformation with a nucleic acid encoding a diacylglycerol acyltransferase protein, e.g., a diacylglycerol acyltransferase protein from a different species. Similarly, the transformed cell may comprise (1) a genetic modification that decreases the activity of a native diacylglycerol acyltransferase protein and (2) a genetic modification that increases the activity of a Δ9 desaturase protein. In some embodiments, the transformed cell further comprises a genetic modification that decreases the activity of a native Δ9 desaturase, native Δ12 desaturase, native diacylglycerol acyltransferase (e.g., a different diacylidycerol acyltransferase), native triacylglycerol lipase, native sn-2 acylglycorol fatty acyltransferase, native lysophosphatidic acid acyltransferase, native phosphatidate phosphatase, native glycerol-3-phosphate acyltransferase, native glycerol-3-phosphate/dihydroxyacetone phosphate sn-1 acyltransferase and/or native phospholipid:diacylglycerol acyltransferase. For example, the transformed cell may comprise (1) a genetic modification that decreases the activity of a native DGA1 protein and (2) a genetic modification that decreases the activity of a native DGA2 protein. Similarly, the transformed cell may comprise (1) a genetic modification that decreases the activity of a native diacylglycerol acyltransferase protein and (2) a genetic modification that decreases the activity of a native Δ12 desaurase protein.

4. Decreasing the Activity of a Native Triacylglycerol Lipase

In some aspects, the invention relates to a transformed cell comprising a genetic modification wherein the genetic modification decreases the activity of a native triacylglycerol lipase protein. In some embodiments, the genetic modification is a knockout mutation.

The genetic modification may be transformation with a nucleic acid. In certain embodiments, the invention relates to a method of modifying the lipid content of a cell, comprising transforming the cell with a nucleic acid that decreases the activity of a native triacylglycerol lipase protein in the cell. The nucleic acid may be capable of recombining with a native triacylglycerol lipase gene and/or a nucleotide sequence in the regulatory region of a native triacylglyeerol lipase gene. In some embodiments, the native triacylglycerol lipase is encoded by the TGL3, TGL3/4, or TGT4 gene.

In certain embodiments, the cell is *Yarrowia lipolytica* and the native triacylglycerol lipase protein has the amino acid sequence set forth in SEQ ID NO:91. In some embodiments, the cell is *Yarrowia lipolytica*, and the native triacylglycerol lipase protein is encoded by the nucleotide sequence set forth in SEQ ID NO:92.

In certain embodiments, the cell is *Arxula adeninivorans* and the native triacylglycerol lipase protein has the amino acid sequence set forth in SEQ ID NO:85; SEQ ID NO:87; or SEQ ID NO:89. In some embodiments, the cell is *Arxula adeninivorans*, and the native triacylglycerol lipase protein is encoded by the nucleotide sequence set forth in SEQ ID NO:86; SEQ ID NO:88; or SEQ ID NO:90.

In some embodiments, the transformed cell further comprises a genetic modification that increases the activity of a Δ9 desaturase, elongase, diacylglycerol acyltransferase, sn-2 acylglycerol fatty acyltransferase, lysophosphatidic acid acyltransferase, phosphatidate phosphatase, phospholipid: diacylglycerol acyltransferase, glycerol-3-phosphate/dihydroxyacetone phosphate sn-1 acyltransferase, and/or glycerol-3-phosphate acyltransferase. For example, the transformed cell may comprise (1) a genetic modification that decreases the activity of a native triacylglycerol lipase protein and (2) a genetic modification that increases the activity of a diacylglycerol acyltransferase protein. In some embodiments, the transformed cell further comprises a genetic modification that decreases the activity of a native Δ9 desaturase, native Δ12 desaturase, native diacylslycerol acyltransferase, native sn-2 acylglycerol fatty acyltransferase, native lysophosphatidic acid acyltransferase, native phosphatidate phosphatase, native glycerol-3-phosphate acyltransferase, native glycerol-3-phosphate/dihydroxacetone phosphate sn-1 acyltransferase and/or native phospholipid:diacylglyecrol acyltransferase.

Triacylglycerol lipase depletes a cell's triacylglycerol by removing one or more fatty acid chains. Thus, decreasing the net triacylglycerol lipase activity of a cell may increase the cell's oleic acid. This decrease may be accomplished by reducing the efficiency of the enzyme, e.g., by mutating amino acids in its active site, or by reducing the expression of the enzyme. For example, a TGL3 knockout mutation will decrease the activity of a triacylglycerol lipase because it prevents the cell from transcribing TGL3. Triacylglycerol lipase knockouts are described in WO 2015/168531 and U.S. Ser. No. 61/987,098 (both of which are incorporated by reference).

In some embodiments, the triacylglycerol lipase is TGL3. In other embodiments, the triacylglycerol lipase is TGL3/4 or TGL4.

The TGL3 gene in *Y. lipolytica* encodes the triacylglycerol lipase protein TGL3 (SEQ ID NO:91). SEQ ID NO:92 contains the TGL3 nucleotide sequence. 100 upstream nucleotides, and 100 downstream. Thus, the SEQ ID NO:92 nucleotide sequence may be used to design a nucleic acid capable of recombining with a nucleic acid sequence in the native *Y. lipolytica* triacylglycerol lipase gene.

Knockout cassettes SEQ ID NOs: 167 and 168 are capable of recombining with the native TGL3 gene in *Y. lipolytica*. Thus, in some embodiments, the nucleic acids encoded by SEQ ID NOs: 167 and 168 may be used to generate a triacylglycerol lipase knockout mutation in *Y. lipolytica*. SEQ ID NOs: 167 and 168 each contain portions of a hygromycin resistance aene hph. Neither isolated sequence encodes a functional protein, but the two sequences are capable of encoding a functional kinase that confers hygromycin resistance upon successful recombination. Further, neither SEQ ID NO:167 nor SEQ ID NO:168 contains a promoter or terminator, and thus, they rely on homologous recombination with the *Y. lipolytica* TGL3 gene in order for the hph gene to be transcribed and translated. In this way, successfully transformed oleaginous cells may be selected by growing, the cells on medium containing hygromycin.

Knockout cassette SEQ ID NO:167 may be prepared by amplifying a hygromycin resistance gene hph (SEQ ID NO:162) with primer NP1798 (SEQ ID NO:165) and primer NP656 (SEQ ID NO:164). Knockout cassette SEQ ID NO:50 may be prepared by amplifying a hygromycin resistance gene hph (SEQ ID NO:162) with printer NP655 (SEQ ID NO:163) and primer NP1799 (SEQ ID NO:166).

Different approaches may be used to design nucleic acids that reduce the activity of TGL3 in *Y. lipolytica* (Biochimica Biophysica Acta 1831:1486-95 (2013)). The methods disclosed herein and other methods known in the art may be used to reduce triacylglycerol lipase activity in other species. For example, these methods may be used to reduce the activity of the TGL3 gene of *Arxula adeninivorans* (SEQ ID NO:86), the TGL3/4 gene of *Arxula adeninivorans* (SEQ ID NO:88), or the TGL4 gene of *Arxula adeninivorans* (SEQ ID NO:90). Similarly, these methods are generally applicable to reduce the activity of a protein in yeast and other organism.

5. Decreasing the Activity of a Native sn-2 Acylglycerol Fatty Acyltransferase

In some aspects, the invention relates to a transformed cell comprising a genetic modification, wherein the genetic modification decreases the activity of a native sn-2 acylglycerol fatty acyltransferase protein. In some embodiments, the genetic modification is a knockout mutation.

The genetic modification may be transformation with a nucleic acid. In certain embodiments, the invention relates to a method of modifying the lipid content of a cell, comprising transforming the cell with a nucleic acid that decreases the activity of a native sn-2 acylglycerol fatty acyltransferase protein in the cell. The nucleic acid may be capable of recombining with a native sn-2 acylglycerol fatty acyltransferase gene and/or a nucleotide sequence in the regulatory region of a native sn-2 acylglycerol fatty acyltransferase gene. In some embodiments, the native sn-2 acylglycerol fatty acyltransferase protein is encoded by the SLC1 or SLC4 gene.

In certain embodiments, the cell is *Yarrowia lipolytica* and the native sn-2 acylglycerol fatty acyltransferase protein has the amino acid sequence set forth in SEQ ID NO:59 or SEQ ID NO:65. In some embodiments, the cell is *Yarrowia lipolytica*, and the native sn-2 acylglycerol fatty acyltransferase protein is encoded by the nucleotide sequence set forth in SEQ ID NO:60 or SEQ ID NO:66.

In certain embodiments the cell is *Arxula adeninivorans* and the native sn-2 acylglycerol fatty acyltransferase protein has the amino acid sequence set forth in SEQ ID NO:61 or SEQ ID NO:63. In some embodiments, the cell is *Arxula adeninivorans*, and the native sn-2 acylglycerol fatty acyltransferase protein is encoded by the nucleotide sequence set forth in SEQ ID NO:62 or SEQ ID NO:64.

In some embodiments, the transformed cell further comprises a genetic modification that increases the activity of a Δ9 desaturase, elongase, diacylglycerol acyltransferase, sn-2 acylglycerol fatty acyltransferase (e.g., an exogenous sn-2 acylglycerol fatty acyltransferase), lysophosphatidic acid acyltransferase, phosphatidate phosphatase, phospholipid: diacylglycerol acyltransferase, glycerol-3-phosphate/dihydroxyacetone phosphate sn-1 acyltransferase, and/or glycerol-3-phosphate acyltransferase. In some embodiments, the transformed cell further comprises a genetic modification that decreases the activity of a native Δ9 desaturase, native Δ12 desaturase, native diacylglycerol acyltransferase, native triacylglycerol lipase, native lysophosphatidic acid acyltransferase, native phosphatidate phosphatase, native glycerol-3-phosphate acyltransferase native glycerol-3-phosphate/dihydroxyacetone phosphate sn1 acyltransferase, and/or native phospholipid:diacylglycerol acyltransferase.

6. Decreasing the Activity of a Native Lysophosphatidic Acid Acyltransferase

In some aspects, the invention relates to a transformed cell comprising a genetic modification, wherein the genetic modification decreases the activity of a native lysophosphatidic acid acyltransferase protein. In some embodiments, the genetic modification is a knockout mutation.

The genetic modification may be transformation with a nucleic acid. In certain embodiments, the invention relates to a method of modifying the lipid content of a cell, comprising transforming the cell with a nucleic acid that decreases the activity of a native lysophosphatidic acid acyltransferase protein in the cell. The nucleic acid may be capable of recombining with a native lysophosphatidic acid acyltransferase gene and/or a nucleotide sequence in the regulatory region of a native lysophosphatidic acid acyltransferase gene. In some embodiments, the native lysophosphatidic acid acyltransferase protein is encoded by the LOA1 gene.

In certain embodiments, the cell is *Yarrowia lipolytica* and the native lysophosphatidic acid acyltransferase protein has the amino acid sequence set forth in SEQ ID NO:83. In some embodiments, the cell is *Yarrowia lipolytica*, and the native lysophosphatidic acid acyltransferase protein is encoded by the nucleotide sequence set forth in SEQ ID NO:84.

In certain embodiments, the cell is *Arxula adeninivorans and the native lysophosphatidic acid acyltransferase protein has the amino acid sequence set forth in SEQ ID NO:*81. In some embodiments, the cell is *Arxula adeninivorans*, and the native lysophosphatidic acid acyltransferase protein is encoded by the nucleotide sequence set forth in SEQ ID NO:82.

In some embodiments, the transformed cell further comprises a genetic modification that increases the activity of a Δ9 desaturase elongase, diacylglycerol acyltransferase, sn-2 acylglycerol fatty acyltransferase, lysophosphatidic acid acyltransferase (e.g., an exogenous lysophosphatidic acid acyltransferase), phosphatidate phosphatase, phospholipid: diacylglycerol acyltransferase, glycerol-3-phosphate/dihydroxyacetone phosphate sn-1 acyltransferase, and/or glycerol-3-phosphate acyltransferase. In some embodiments, the transformed cell further comprises a genetic modification that decreases the activity of a native Δ9 desaturase, native Δ12 desaturase, native diacylglycerol acyltransferase, native triacylglycerol lipase, native sn-2 acylglycerol fatty acyltransferase, native phosphatidate phosphatase, as glycerol-3-phosphate acyltransferase, native glycerol-3-phosphate/dihydroxyacetone phosphate sn-1 acyltransferase, and/or native phospholipid:diacylglycerol acyltransferase.

7. Decreasing the Activity of a Native Phosphatidate Phosphatase

In some aspects, the invention relates to a transformed cell comprising a genetic modification, wherein the genetic modification decreases the activity of a native phosphatidate phosphatase protein. In some embodiments, the genetic modification is a knockout mutation.

The genetic modification may be transformation with a nucleic acid. In certain embodiments, the invention relates to a method of modifying the lipid content of a cell, comprising transforming the cell with a nucleic acid that decreases the activity of a native phosphatidate phosphatase protein in the cell. The nucleic acid may be capable of recombining with a native phosphatidate phosphatase gene and/or a nucleotide sequence in the regulatory region of a native phosphatidate phosphatase gene. In some embodiments, the native phosphatidate phosphatase protein is encoded by the PAH1 gene.

In certain embodiments, the cell is *Yarrowia lipolytica* and the native phosphatidate phosphatase protein has the amino acid sequence set forth in SEQ ID NO:5 in some embodiments, the cell is *Yarrowia lipolytica*, and the native phosphatidate phosphatase protein is encoded by the nucleotide sequence set forth in SEQ ID NO:58.

In certain embodiments, the cell is *Arxula adeninivorans* and the native phosphatidate phosphatase protein has the amino acid sequence set forth in SEQ ID NO:55. In some embodiments, the cell is *Arxula adeninivorans*, and the native phosphatidate phosphatase protein is encoded by the nucleotide sequence set forth in SEQ ID NO:56.

In some embodiments, the transformed cell further comprises a genetic modification that increases the activity of a Δ9 desaturase, elongase, diacylglycerol acyltransferase, sn-2 acylglycerol fatty acyltransferase, lysophosphatidic acid acyltransferase, phosphatidate phosphatase. (e.g., an exogenous phosphatidate phosphatase), phospholipid:diacylglycerol acyltransferase, glycerol-3-phosphate/dihydroxyacetone phosphate sn-1 acyltransferase, and/or glycerol-3-phosphate acyltransferase. In some embodiments, the transformed cell further comprises a genetic modification that decreases the activity of a native Δ9 desaturase, native Δ12 desaturase, native diacylglycerol acyltransferase, native triacylglycerol lipase, native sn-2 acylglycerol fatty acyltransferase, native lysophosphatidic acid acyltransferase, native glycerol-3-phosphate acyltransferase, native glycerol-3-phosphate/dihydroxyacetone phosphate sn-1 acyltransferase, and/or native phospholipid:diacylglycerol acyltransferase.

8. Decreasing the Activity of a Native Glycerol-3-phosphate Acyltransferase

In some aspects, the invention relates to a transformed cell comprising a genetic modification, wherein the genetic modification decreases the activity of a native glycerol-3-phosphate acyltransferase protein. In some embodiments, the genetic modification is a knockout mutation.

The genetic modification may be transformation with a nucleic acid. In certain embodiments, the invention relates to a method of modifying the lipid content of a cell, comprising transforming the cell with a nucleic acid that decreases the activity of a native glycerol-3-phosphate acyltransferase protein in the cell. The nucleic acid may be capable of recombining with a native glycerol-3-phosphate acyltransferase gene and/or a nucleotide sequence in the regulatory region of a native glycerol-3-phosphate acyltransferase gene. In some embodiments, the native glycerol-3-phosphate acyltransferase is encoded by the SCT1 gene.

In certain embodiments, the cell is *Yarrowia lipolytica* and the native glycerol-3-phosphate acyltransferase protein has the amino acid sequence set forth in SEQ ID NO:17. In some embodiments, the cell is *Yarrowia lipolytica*, and the native glycerol-3-phosphate acyltransferase protein is encoded by the nucleotide sequence set forth in SEQ ID NO:18.

In certain embodiments, the cell is *Arxula adeninivorans* and the native glycerol-3-phosphate acyltransferase protein has the amino acid sequence set forth in SEQ ID NO:43. In some embodiments, the cell is *Arxula adeninivorans*, and the native glycerol-3-phosphate acyltransferase protein is encoded by the nucleotide sequence set forth in SEQ ID NO:44.

In some embodiments, the transformed cell further comprises a genetic modification that increases the activity at Δ9 desaturase, elongase, diacylglycerol acyltransferase, sn-2 acylglycerol fatty acyltransferase, lysophosphatidic acid acyltransferase, phosphatidate phosphatase, phospholipid: diacylglycerol acyltransferase, glycerol-3-phosphate/dihydroxyacetone phosphate sn-1 acyltransferase, and/or glycerol-3-phosphate acyltransferase (e.g., an exogenous glycerol-3-phosphate acyltransferase). For example, the transformed cell may comprise (1) a genetic modification that decreases the activity of a native glycerol-3-phosphate acyltransferase protein and (2) a genetic modification that consists of transformation with a nucleic acid that encodes an exogenous glycerol-3-phosphate acyltransferase protein. In some embodiments, the transformed cell further comprises a genetic modification that decreases the activity of a native Δ9 desaturase, native Δ12 desaturase, native diacylglycerol acyltransferase, native triacylglycerol lipase, native sn-2 acylglycerol fatty acyltransferase, native lysophosphatidic acid acyltransferase, native phosphatidate phosphatase, native glycerol-3-phosphate/dihydroxyacetone phosphate sn-1 acyltransferase, and/or native phospholipid: diacylglycerol acyltransferase. For example, the transformed cell may comprise (1) a genetic modification that decreases the activity of a native glycerol-3-phosphate acyltransferase protein and (2) a genetic modification that decreases the activity of a native Δ12 desaturase protein.

9. Decreasing the Activity of a Native Phospholipid: diacylglycerol Acyltransferase In some aspects, the invention relates to a transformed cell comprising a genetic modification, wherein the genetic modification decreases the activity of a native phospholipid:

diacylglycerol acyltransferase protein. In some embodiments, the genetic modification is a knockout mutation.

The genetic modification may be transformation with a nucleic acid. In certain embodiments, the invention relates to a method of modifying the lipid content of a cell, comprising transforming the cell with a nucleic acid that decreases the activity of a native phospholipid:diacylglycerol acyltransferase protein in the cell. The nucleic acid may be capable of recombining with a native phospholipid:diacylglycerol acyltransferase gene and/or a nucleotide sequence in the regulatory region of a native phospholipid:diacylglycerol acyltransferase gene. In some embodiments, the native phospholipid:diacylglycerol acyltransferase protein is encoded by the LRO1 gene.

In certain embodiments, the cell is *Yarrowia lipolytica* and the native phospholipid:diacylglycerol acyltransferase protein has the amino acid sequence set forth in SEQ ID NO:109. In some embodiments, the cell is *Yarrowia lipolytica and the native phospholipid:diacylglycerol acyltransferase protein is encoded by the nucleotide sequence set forth in SEQ ID NO:*110.

In certain embodiments, the cell is *Arxula adeninivorans* and the native phospholipid:diacylglycerol acyltransferase protein has the amino acid sequence set forth in SEQ ID NO:105. In some embodiments, the cell is *Arxula adeninivorans*, and the native phospholipid:diacylglycerol acyltransferase protein is encoded by the nucleotide sequence set forth in SEQ ID NO:106.

In some embodiments, the transformed cell further comprises a genetic modification that increases the activity of a Δ9 desaturase, elongase, diacylglycerol acyltransferase, sn-2 acylglycerol fatty acyltransferase, lysophosphatidic acid acyltransferase, phosphatidate phosphatase, phospholipid: diacylglycerol acyltransferase (e.g., an exogenous phospholipid:diacylglycerol acyltransferase), glycerol-3-phosphate/dihydroxyacetone phosphate sn-1 acyltransferase, and/or glycerol-3-phosphate acyltransferase. In some embodiments, the transformed cell further comprises a genetic modification that decreases the activity of a native Δ9 desaturase, native Δ12 desaturase, native diacylglycerol acyltransferase, native triacylglycerol lipase, native sn-2 acylglycerol fatty acyltransferase, native lysophosphatidic acid acyltransferase, native phosphatidate phosphatase, native glycerol-3-phosphate/dihydroxyacetone phosphate so-1 acyltransferase, and/or native glycerol-3-phosphate acyltransferase.

10. Decreasing the activity of a native glycerol-3-phosphate/dihydroxyacetone phosphate sn-1 acyltransferase In some aspects, the invention relates to a transformed cell comprising a genetic modification, wherein the genetic modification decreases the activity of a native glycerol-3-phosphate/dihydroxyacetone phosphate sn-1 acyltransferase protein. In some embodiments, the genetic modification is a knockout mutation.

The genetic modification may be transformation with a nucleic acid. In certain embodiments, the invention relates to a method of modifying the lipid content of a cell, comprising transforming the cell with a nucleic acid that decreases the activity of a native glycerol-3-phosphate/dihydroxyacetone phosphate sn-1 acyltransferase protein in the cell. The nucleic acid may be capable of recombining with a native glycerol-3-phosphate/dihydroxyacetone phosphate sn-1 acyltransferase gene and/or a nucleotide sequence in the regulatory region of a native glycerol-3-phosphate/dihydroxyacetone phosphate sn-1 acyltransferase gene. In some embodiments, the native glycerol-3-phosphate/dihydroxyacetone phosphate sn-1 acyltransferase protein is encoded by the GPT2 gene.

In certain embodiments, the cell is *Saccharomyces cerevisiae* and the native glycerol-3-phosphate/dihydroxyacetone phosphate sn-1 acyltransferase protein has the amino acid sequence set forth in SEQ ID NO:119. In some embodiments, the cell is *Saccharomyces cerevisiae*, and the native glycerol-3-phosphate/dihydroxyacetone phosphate sn-1 acyltransferase protein is encoded by the nucleotide sequence set forth in SEQ ID NO:120.

In some embodiments, the transformed cell further comprises a genetic modification that increases the activity of a Δ9 desaturase, elongase, diacylglycerol acyltransferase, sn-2 acylglycerol fatty acyltransferase, lysophosphatidic acid acyltransferase, phosphatidate phosphatase, phospholipid: diacylglycerol acyltransferase, glycerol-3-phosphate/dihydroxyacetone phosphate sn-1 acyltransferase (e.g., an exogenous glycerol-3-phosphate/dihydroxyacetone phosphate sn-1 acyltransferase), and/or glycerol-3-phosphate acyltransferase. For example, the transformed cell may comprise (1) a genetic modification that decreases the activity of a native glycerol-3-phosphate/dihydroxyacetone phosphate sn-1 acyltransferase protein and (2) a genetic modification that consists of transformation with a nucleic, acid that encodes an exogenous glycerol-3-phosphate/dihydroxyacetone phosphate sn-1 acyltransferase protein. In some embodiments, the transformed cell further comprises a genetic modification that decreases the activity of a native Δ9 desaturase, native Δ12 desaturase, native diacylglycerol acyltransferase, native triacylglycerol lipase, native sn-2 acylglycerol fatty acyltransferase, native lysophosphatidic acid acyltransferase, native phosphatidate phosphatase, native phosphatidate phosphatase, and/or native glycerol-3-phosphate acyltransferase.

D. Products

In certain embodiments, the transformed cells are grown in the presence of exogenous fatty acids, glucose, ethanol, xylose, sucrose, starch, starch dextrin, glycerol, cellulose, and/or acetic acid. These substrates may be added during cultivation to increase lipid production. The exogenous fatty acids may include stearate, oleic acid, linoleic acid, γ-linolenic acid, dihomo-γ-lisolenic acid, arachidonic acid, α-linolenic acid, stearidonic acid, eicosatetraenoic acid, eicosapenteaenoic acid, docosapentaenoic acid, eicosadienoic acid, and/or eicosatrienoic acid.

In certain embodiments, the present invention relates to a product produced by a modified host cell described herein. In certain embodiments, the product is an oil, lipid, or triacylglycerol. In some embodiments, the product is palmitic acid, palmitoleic acid, stearic acid, oleic acid, or linoleic acid. In certain embodiments, the product is a saturated fat acid. Thus, the product may be caprylic acid, capric acid, lauric acid, myristic acid, palmitic acid, stearic acid, arachidic acid, behenic acid, lignoceric acid, or cerotic acid. In some embodiments, the product is an unsaturated fatty acid. Thus, the product may be myristoleic acid, palmitoleic acid, sapienic acid, oleic acid, elaidic acid, vaccenic acid, linoleic acid, linoelaidic acid, α-linolenic acid, arachidonic acid, eicosapenteaenoic acid, erucic acid, or docosahexaenoic acid.

In some embodiments, the product comprises an 18-carbon fatty acid. In some embodiments, the product comprises oleic acid, stearic acid, or linoleic acid. For example, the product may be oleic acid.

One skilled in the art will readily appreciate that the present invention is well adapted to carry out the objects and obtain the ends and advantages mentioned, as well as those inherent therein. The embodiments described herein are not intended as limitations on the scope of the invention.

EXEMPLIFICATION

The present description is further illustrated by the following examples, which should not be construed as limiting in any way. The contents of all cited references (including literature references, issued patents, published patent applications and GenBank Accession numbers as cited throughout this application) are hereby expressly incorporated by reference. When definitions of terms in documents that are incorporated by reference herein conflict with those used herein, the definitions used herein govern.

EXAMPLE 1

Method to Increase the Activity of a DGA1 Protein (DGAT2 Gene)

Figure 2:
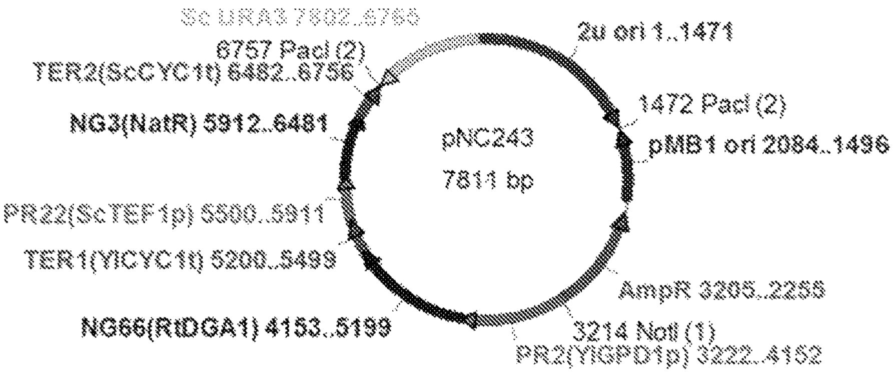
FIG. 2 depicts a map of the pNC243 construct used to overexpress the diacylglycerol acyltransferase DGA1 gene NG66 in *Y. lipolytica* strain NS18 (obtained from ARS Culture Collection, NRRL #YB 392). Vector pNC243 was linearized by a PacI/NotI restriction digest before transformation. "2u ori" denotes the *S. cerevisiae* origin of replication from the 2 μm circle plasmid; "pMB1 ori" denotes the *E. coli* pMB1 origin of replication from the pBR322 plasmid; "AmpR" denotes the bla gene used as a marker for selection with ampicillin: "PR2" denotes the *Y. lipolytica* GPD1 promoter −931 to −1; "NG66" denotes the native *Rhodosporidium toruloides* DGA1 cDNA synthesized by GenScript; "TER1" denotes the *Y. lipolytica* CYC1 terminator 300 base pairs after stop; "PR22" denotes the *S. cerevisiae* TEF1 promoter −412 to −1; "NG3" denotes the *Streptomyces noursei* Nat1 gene used as a marker for selection with nourseothricin; "TER2" denotes the *S. cerevisiae* CYC1 terminator 275 base pairs after stop; and "Sc URA3" denotes the *S. cerevisiae* URA 3 auxotrophic marker for selection in yeast.

Exemplary nucleic acid constructs for overexpressing DGA1 were described in U.S. Ser. No. 61/943,664 (hereby incorporated by reference). FIG. 2 shows expression construct pNC243 used for overexpression of the *R. toruioides* DGA1 gene NG66 (SEQ ID NO:22) in *Y. lipolytica*. DGA1 expression constructs were linearized before transformation by a PacI/NotI restriction digest. The linear expression constructs each included an expression cassette for the DGAT2 gene and for the Nat1 gene, used as a marker for selection with nomsecithricin (NAT).

DGA1 expression constructs were randomly integrated into the genome of *Y. lipolytica* strain NS18 (obtained from ARS Culture Collection, NRRL #YB 392) using a transformation protocol as described in Chen (Applied Microbiology & Biotechnology 48:232-35 (1997)). Transformants were selected on YPD plates with 500 μg/mL NAT.

For most constructs, there was significant colony variation between the transformants, likely due to the lack of a functional DGA1 expression cassette in cells that only obtained a functional Nat1 cassette, or due to a negative effect of the site of DGA1 integration on DGA1 expression. All transformants had a significant increase in lipid content.

In certain experiments, the effect of native *R. toruloides* DGA1 overexpression on lipid production in *Y. lipolytica* was not as high as the effect of synthetic versions of *R. toruloides* DGAT2 genes that did not contain introns. This result may indicate that the gene splicing of the *R. toruloides* DGAT2 gene in *Y. lipolytica* was not very efficient. In certain experiments, codon optimization of the *R. toruloides* DGA1 gene for expression in *Y. lipolytica* did not have a positive effect on lipid production.

The skilled artisan will recognize that similar methods may be used to increase the activity of other proteins in a range of organisms.

EXAMPLE 2

Method to Decrease the Activity of a Native Triacylglycerol Lipase Protein

Exemplary nucleic acid constructs for knocking out the *Y. lipolytica* TGL3 gene while overexpressing the DGA2 gene were described in WO 2015/168531 and U.S. Ser. No. 61/987,098 (both of which are incorporated by reference). The TGL3 gene was knocked out of *Y. lipolytica* wild-type strain NS18 (obtained from NRLL #YB-392) and its DGA1 overexpressing derivative NS281. NS281 overexpresses the DGA1 gene from *Rhodosporidium toruloides* as described above. The *Y. lipolytica* TGL3 gene (YALI0D17534g, SEQ ID NO: 92) was deleted as follows: A two-fragment deletion cassette was amplified by PCR from a plasmid containing the hygromycin resistance gene ("hph," SEQ ID NO: 162) using primer pairs NP1798-NP656 and NP655-NP1799 (SEQ ID NOs: 163-166). The resulting PCR fragments (SEQ ID NOs: 167 & 168) were co-transformed into NS18 and NS281 according to the protocol developed in WO 2014/182657 and U.S. Ser. No. 61/819,746 (both of which are incorporated by reference). The omission of a promoter and terminator in the hph cassette and the splitting of the hph coding sequence into two PCR fragments reduce the probability that random integration of these pieces will confer hygromycin resistance. The hph gene should only be expressed if it integrates at the TGL3 locus by homologous recombination so that the TGL3 promoter and terminator can direct its transcription. Hygromycin resistant colonies were screened by PCR to confirm the absence of TGL3 and the presence of a tgl3::hyg specific product.

The skilled artisan will recognize that similar methods may be used to decrease the activity of other proteins in a range of organisms.

EXAMPLE 3

Decreasing Δ12 Desaturase Activity in *Y. lipolytica*

Figure 3:
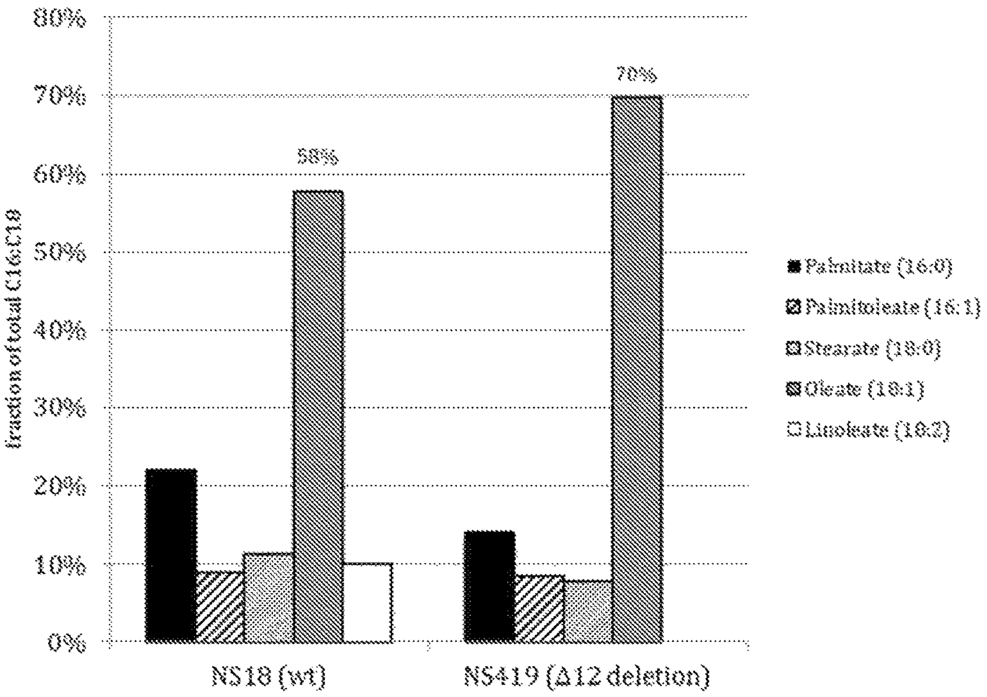
FIG. 3 depicts the percentage of C16 and C18 fatty acids that are palmitate, palmitoleate, stearate, oleate, and linoleate for a *Y. lipolytica* strain before (NS18) and after (NS419) deletion of a native Δ12 desaturase gene.

Δ12 desaturase is responsible for the production of linoleic acid through the desaturation of oleic acid, converting C18:1 fatty acid to C18:2. The Δ12 gene (SEQ ID NO:2) was deleted in *Y. Lipolytica* strain NS18 to produce strain NS419. Lipid accumulation was induced in NS419 and lipid composition was analyzed. Deletion of the Δ12 gene led to a complete elimination of linoleic acid production and a concomitant increase in oleic acid (FIG. 3).

EXAMPLE 4

Increasing Δ9 Desaturase Activity in *Y. lipolytica*

Figure 4:
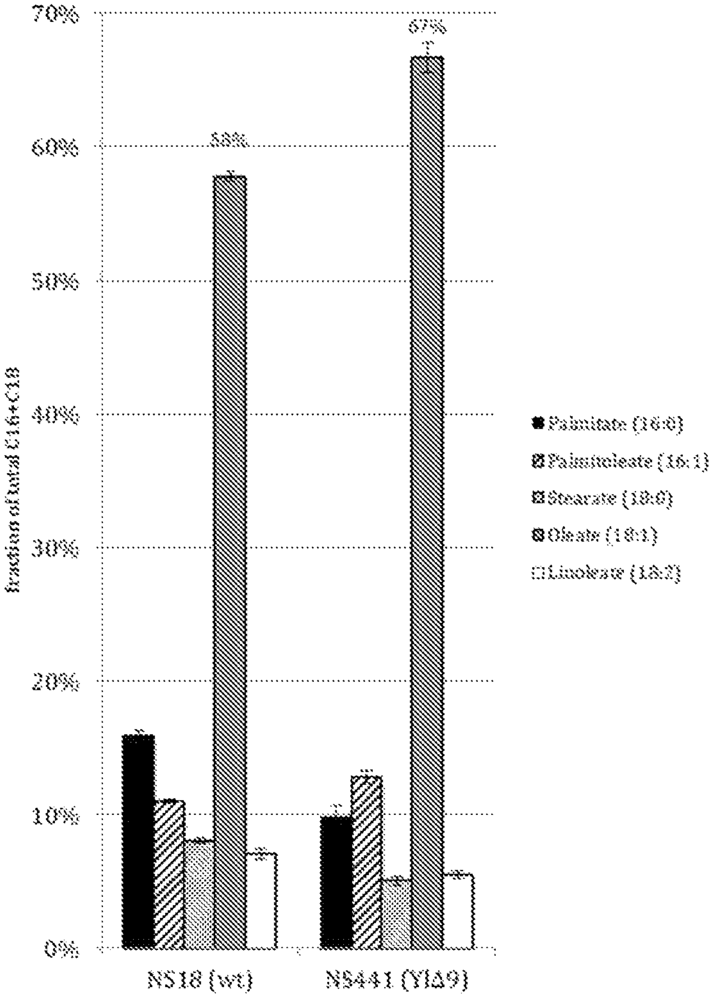
FIG. 4 depicts the percentage of C16 and C18 fatty acids that are palmitate, palmitoleate, stearate, oleate, and linoleate for a *Y. lipolytica* strain before (NS18) and after NS441) transformation with a nucleic acid that encodes an additional copy of the *Y. lipolytica* Δ9 desaturase gene.

Δ9 desaturase is responsible for the production of oleic acid through the desaturation of stearie acid, converting C18:0 fatty acid to C18:1. The Δ9 gene (SEQ ID NO:4) was overexpressed in *Y. Lipolytica* strain NS18 to produce strain NS441. Lipid accumulation was induced and lipid composition was analyzed. Overexpression of the Δ9 gene led to an increase in oleic (and paimitoleic) acids (FIG. 4).

EXAMPLE 5

Increasing Elongase Activity in *Y. lipolytica*

Elongases extend the carbon chain of fatty acids beyond the length produced by fatty, acid synthases. YALI0F06754 (SEQ ID NO:6) was identified as a *Y. lipolytica* gene with limited homology to *S. cerevisiae* elongases. Although this gene has not been annotated as an elongase, its function was assessed in *Y. lipolytica, and KALI*0F06754 was found to play a role in the elongation of C16 to C18 fatty acids, YALI0F06754 was thus termed ELO1.

Figure 5:
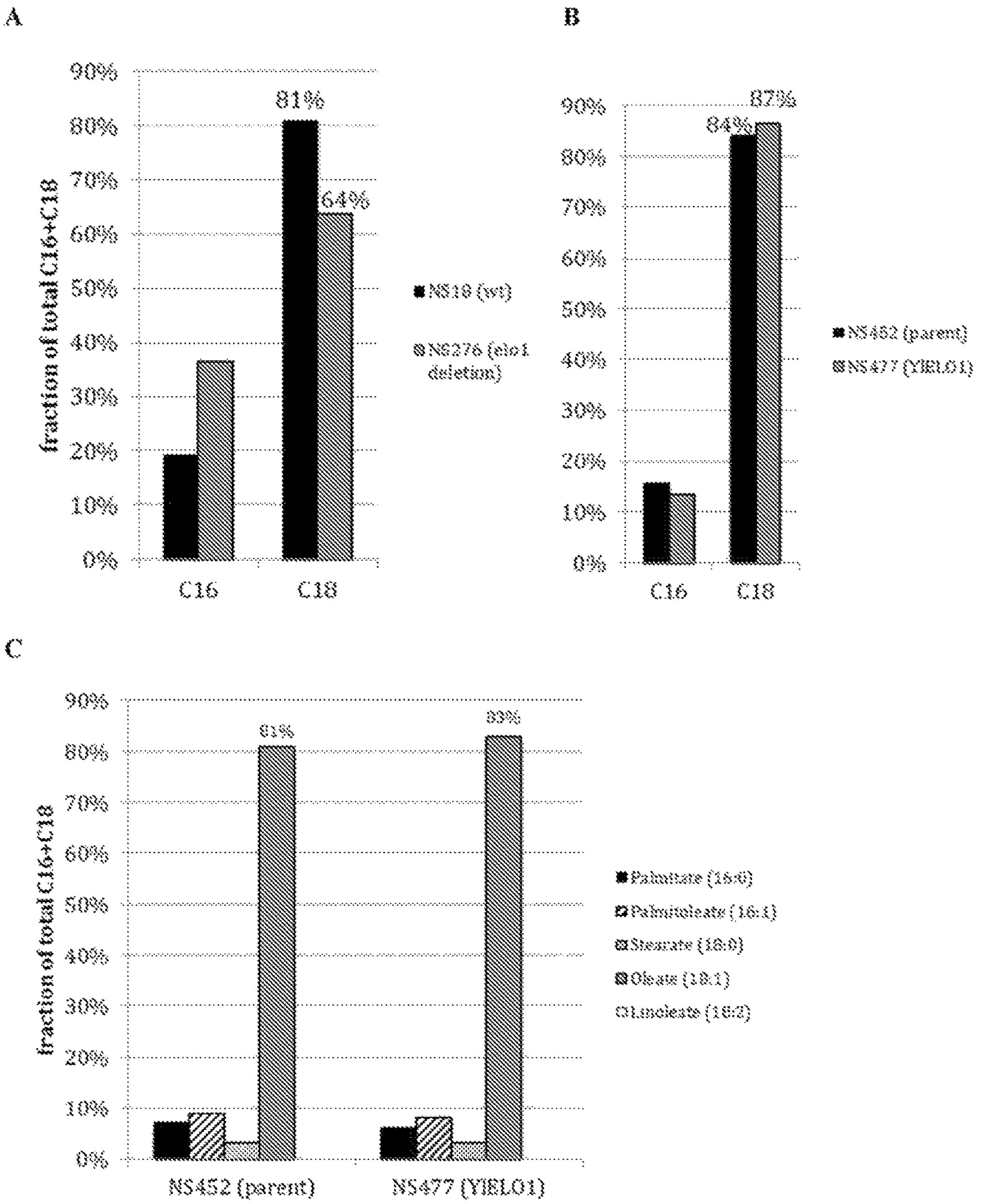
FIG. 5 (consisting of panels A-C) depicts experiments on *Y. lipolytica* cells comprising genetic modifications that increase or decrease the activity of an elongase protein. (A) The percentage of fatty acids that are either C16 or C18 fatty acids for *Y. lipolytica* strain before (NS18) and after (NS276) deletion of a native ELO1 gene. (B) The percentage of fatty acids that are either C16 or C18 fatty acids for a *Y. lipolytica* strain before (NS452) and after (NS477) transformation with a nucleic acid that encodes an additional copy of the *Y. lipolytica* ELO1 gene, (C) The percentage of fatty acids that are palmitate, palmitoleate, stearate, oleate, and linoleate for a *Y. lipolytica* strain before (NS452) and after (NS477) transformation with a nucleic acid that encodes an additional copy of the *Y. lipolytica* ELO1 gene. Strain NS452 comprises an additional copy of the *Y. lipolytica* DGAT2 gene, which encodes a DCA1 protein, and a copy of the *Claviceps purpurea* DGAT1 gene, which encodes a DGA2 protein, and a deletion of the native Δ12 desaturase gene.

The deletion of ELO1 in *Y. lipolytica* strain NS18 led to a decrease in C18 levels (FIG. 5A). The ELO1 knockout in *Y. lipolytica* strain NS 18 was named NS276. In contrast, overexpression of ELO1 led to an increase in C18 levels (FIG. 5B), and specifically, the overexpression of ELO1 increased oleic acid levels (FIG. 5C). ELO1 overexpression was performed in strain NS452, which overexpresses *Y. lipolytica* DGA1 and *Claviceps purpurea* DGA2 and contains a Δ12 desaturase deletion, resulting in strain NS477.

EXAMPLE 6

Switching Δ9 Desaturase Specificity in *Y. lipolytica*

Figure 6:
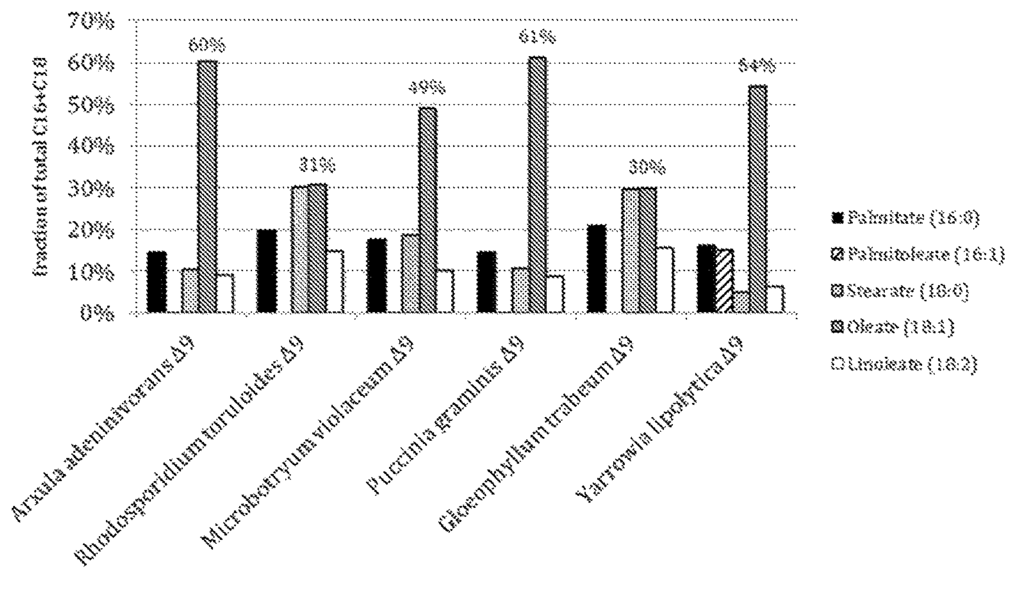
FIG. 6 depicts the percentage of C16 and C18 fatty acids that are palmitate, palmitoleate, stearate, oleate, and linoleate for *Y. lipolytica* strain NS418, which comprises a deletion of a native Δ9 desaturase gene, after transforming the strain with nucleic acids comprising a Δ9 desaturase gene from other organisms.

The native Δ9 desaturase of *Y. lipolytica* uses both C16 and C18 saturated fatty acids as substrates. Exogenous Δ9 enzymes were screened for higher C18 specificity by introducing the genes (SEQ ID NOs: 8, 10, 12, 14, & 16) as the sole Δ9 activity in *Y. lipolytica. This was achieved by first deleting Y. lipolytica* Δ9 in NS18 to produce strain NS418. NS418 required supplementation with unsaturated fatty acids, such as oleic acid and/or Tween-80, for growth due to the absence of Δ9 activity. The exogenous Δ9 genes were then inserted into the native locus through targeted integration and selected for the ability to grow without supplementation. Expression of Δ9 enzymes from the source organisms shown here in the absence of the native enzyme resulted in a switch in substrate specificity to overwhelmingly C18:0 substrate, thus reducing C16:1 content to minimal levels. Δ9 enzymes from *A. adeninivorans* (SEQ ID NO:8) and *Puccinia graminis* (SEQ ID NO:14) resulted in the highest oleic acid levels (FIG. 6).

EXAMPLE 7

Decreasing Acyltransferase Activity in *Y. lipolytica*

Figure 7:
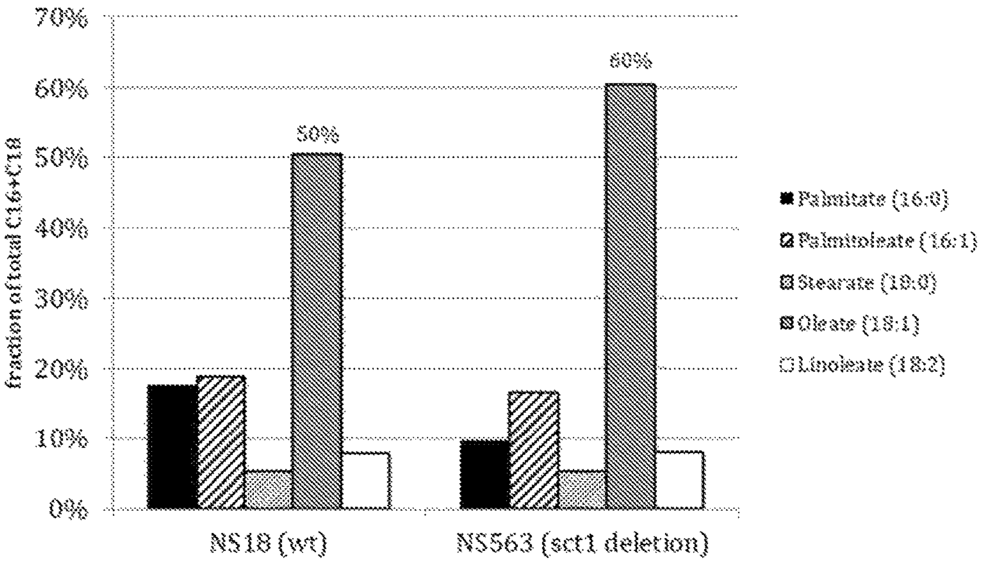
FIG. 7 depicts the percentage of C16 and C18 fatty acids that are palmitate, palmitoleate, stearate, oleate, and linoleate for a *Y. lipolytica* strain before (NS18) and after (NS563) deletion of a native glycerol acyltransferase gene (SCT1).

When a native acyltransferase activity exhibits substrate preference for fatty acids, deletion of the gene can affect fatty acid composition. The glycerol acyltransferase SCT1 (SEQ ID NO:18) was deleted is NS18 to produce strain NS563. Lipid accumulation was induced and lipid composition was analyzed. Deletion of SCT1 led to an increase in the oleic acid lipid fraction (FIG. 7).

EXAMPLE 8

Increasing Acyltransferase Activity in *Y. lipolytica*

Figure 8:
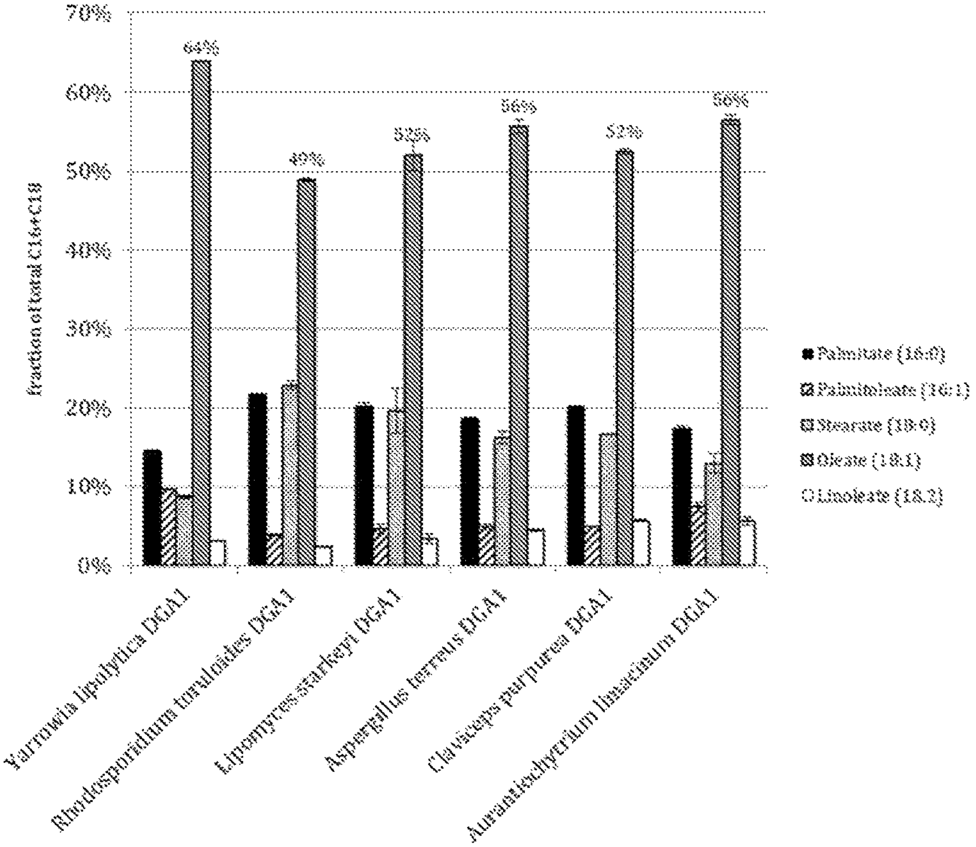
FIG. 8 depicts the percentage of C16 and C18 fatty acids that are palmitate, palmitoleate, stearate, oleate, and linoleate for *Y. lipolytica* strain NS18 after transforming the strain with nucleic acids comprising a DGAT2 gene from various species. The DGAT2 gene encodes the DGA1 protein.
Figure 9:
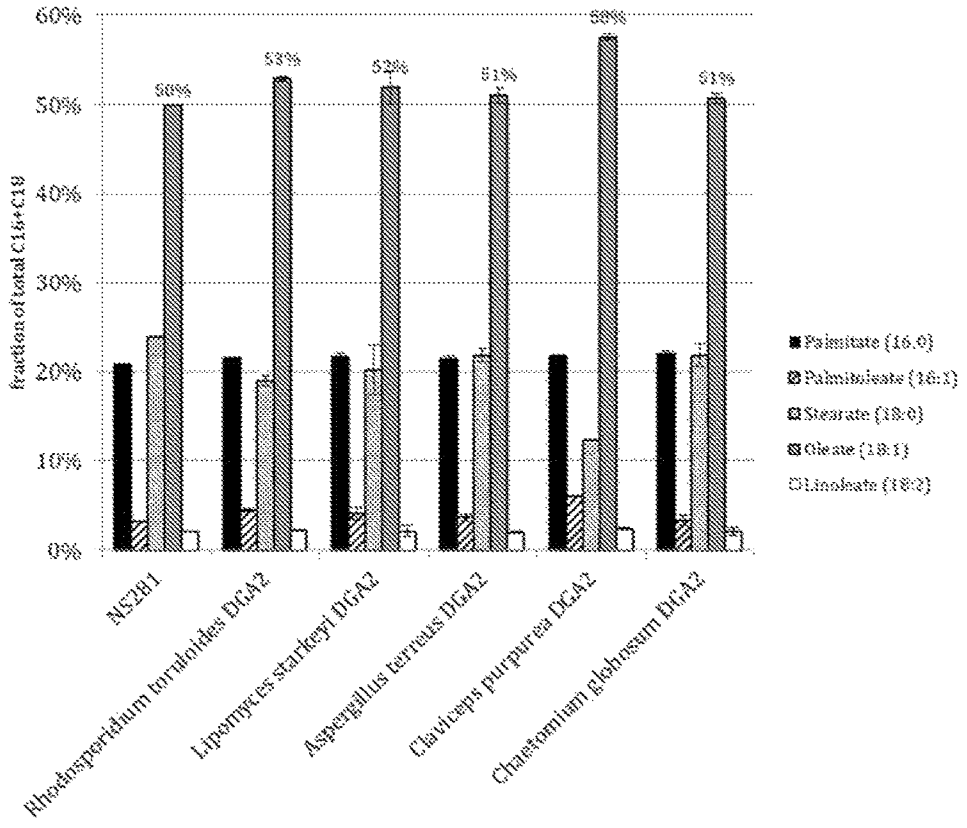
FIG. 9 depicts the percentage of C16 and C18 fatty acids that are palmitate, palmitoleate, stearate, oleate, and linoleate for *Y. lipolytica* strain NS281, which comprises a nucleic acid that encodes the DGA1 protein from *R. toruloides*, after transforming the strain with nucleic acids comprising a DGAT1 gene from various species. The DGAT1 gene encodes the DGA2 protein.
Figure 10:
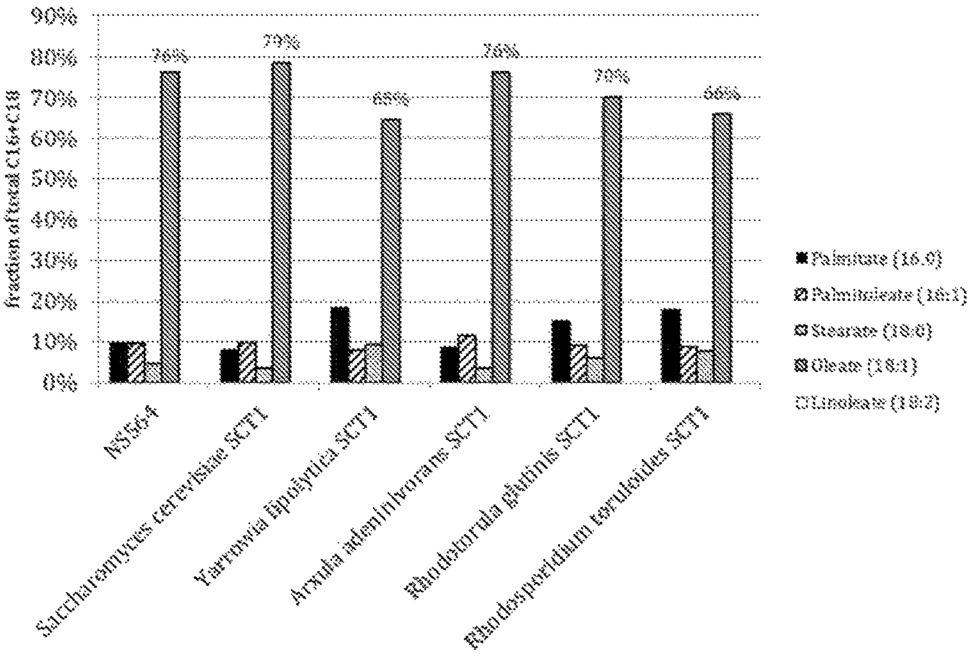
FIG. 10 depicts the percentage of C16 and C18 fatty acids that are palmitate, palmitoleate, stearate, oleate, and linoleate for *Y. lipolytica* strain NS564, which comprises a deletion of a native Δ12 desaturase gene and a native SCT1 gene, after transforming the strain with a nucleic acid comprising a SCT1 gene from various species.

The overexpression of an acyltransferase can improve total lipid levels to achieve high lipid yields. It is important that the overexpressed acyltransferase have a desirable substrate specificity to maintain or increase the oleic acid content of the cell. Overexpression can be in the wild-type acyltransferase background or in a strain that comprises a deletion of a native acyltransferase. The type 2 diacylglycerol acyltransferases from various species (SEQ ID NOs: 20, 22, 24, 26, 28 & 30) were expressed in NS18. The DGAT2 gene from *Y. lipolytica, which encodes the DOA*1 protein, resulted in the highest oleic-acid levels (FIG. 8). Similarly, type 1 diacylglycerol acyltransferases from different species (SEQ ID NOs: 32, 34, 36, 38, & 40) wore expressed in NS281 (made by overexpressing *R. toruloides DGA*1 in NS18). The DGA2 gene from *C. purpurea* resulted in the highest oleic acid levels (FIG. 9). Additionally, glycerol-3-phosphate acyltransferases from different species (SEQ ID NOs: 18, 42, 44, 46, & 48) were expressed in a strain carrying deletions of native SCT1 and Δ12 genes (NS564). The SCT1 genes from *S. cerevisiae* and *A. adeninivorans* resulted in the highest oleic acid levels (FIG. 10).

EXAMPLE 9

Decreasing Δ12 Desaturase Activity in *A. adeninivorans*

Figure 11:
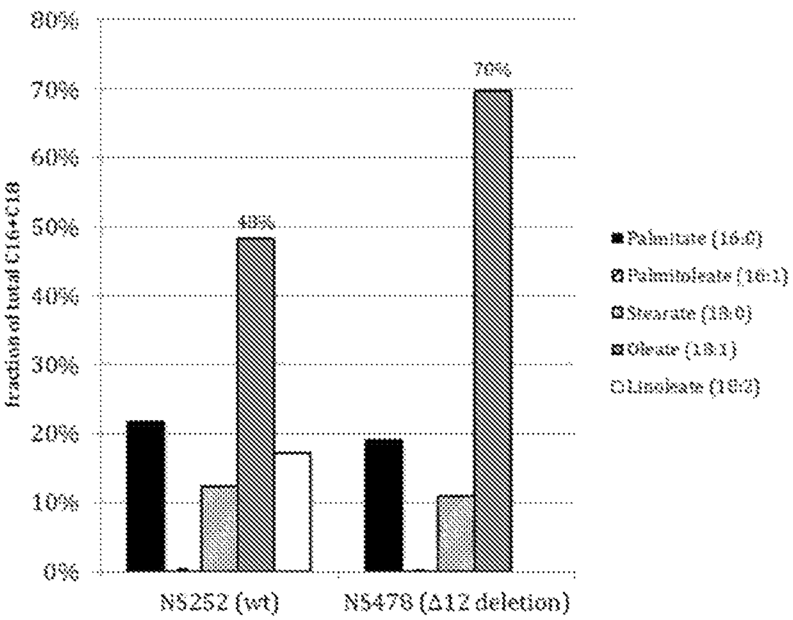
FIG. 11 depicts the percentage of C16 and C18 fatty acids that are palmitate, palmitoleate, stearate, oleate, and linoleate for an *A. adeninivorans* strain before (NS252) and after (NS478) deletion of a native Δ12 desaturase gene.

The Δ12 gone (SEQ ID NO:50) was deleted from *A. adeninivorans* strain NS252 (ATCC 76597) to produce strain NS478. Lipid accumulation was induced and lipid composition was analyzed. Deletion of Δ12 led to a complete elimination of linoleic acid production and a concomitant increase in oleic acid (FIG. 11).

EXAMPLE 10

Increasing Acyltransferase Activity in *A. adeninivorans*

Figure 12:
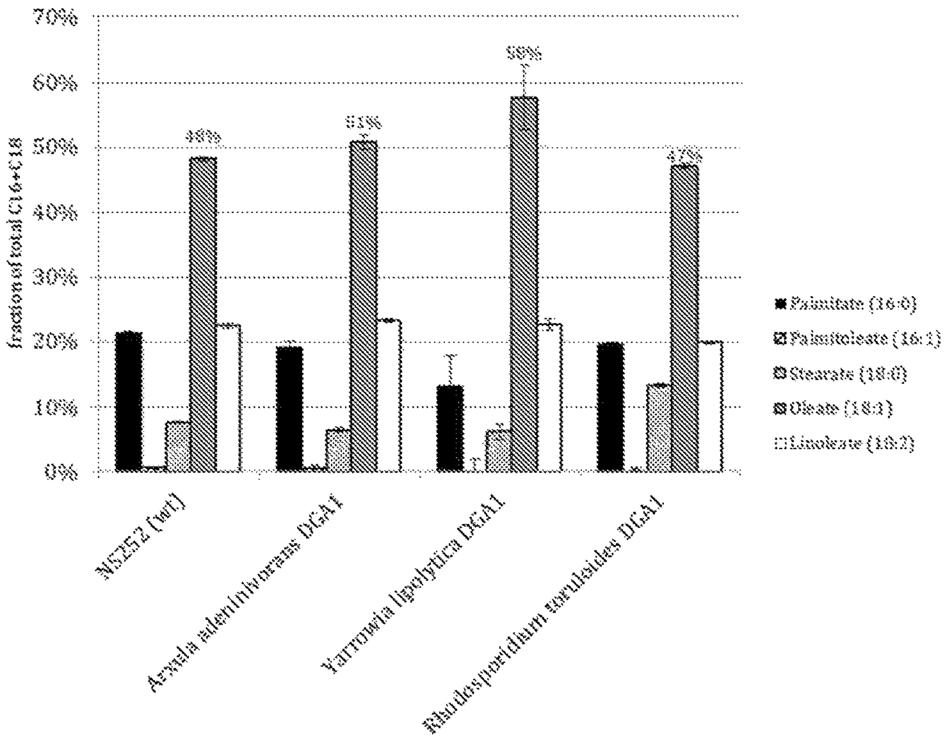
FIG. 12 depicts the percentage of C16 and C18 fatty acids that are palmitate, palmitoleate, stearate, oleate, and linoleate for *A. adeninivorans* strain NS252 after transforming the strain with nucleic acids comprising a DGAT2 gene from various species. The DGAT2 gene encodes the DGA1 protein.

As in *Y. lipolytica*, overexpression of an acyltransferase *A. adeninivorans* can improve total lipid levels to achieve high lipid yields. It is important that the overexpressed acyltransferase have a desirable substrate specificity to maintain or increase the oleic acid content of the cell. Overexpression can be in the wild-type acyltransferase background or a strain deleted for a native acyltransferase. Type 2 diacylglycerol acyltransferases from different specks (SEQ ID NOs: 20, 22, & 52) were expressed in *A. adeninivorans* strain NS252. The DGA1 gene from *Y. lipolytica* (SEQ ID NO:20) resulted in the highest oleic acid levels (FIG. 12).

EXAMPLE 11

Increasing Δ9 Desaturase Activity in *Y. lipolytica*

Figure 13:
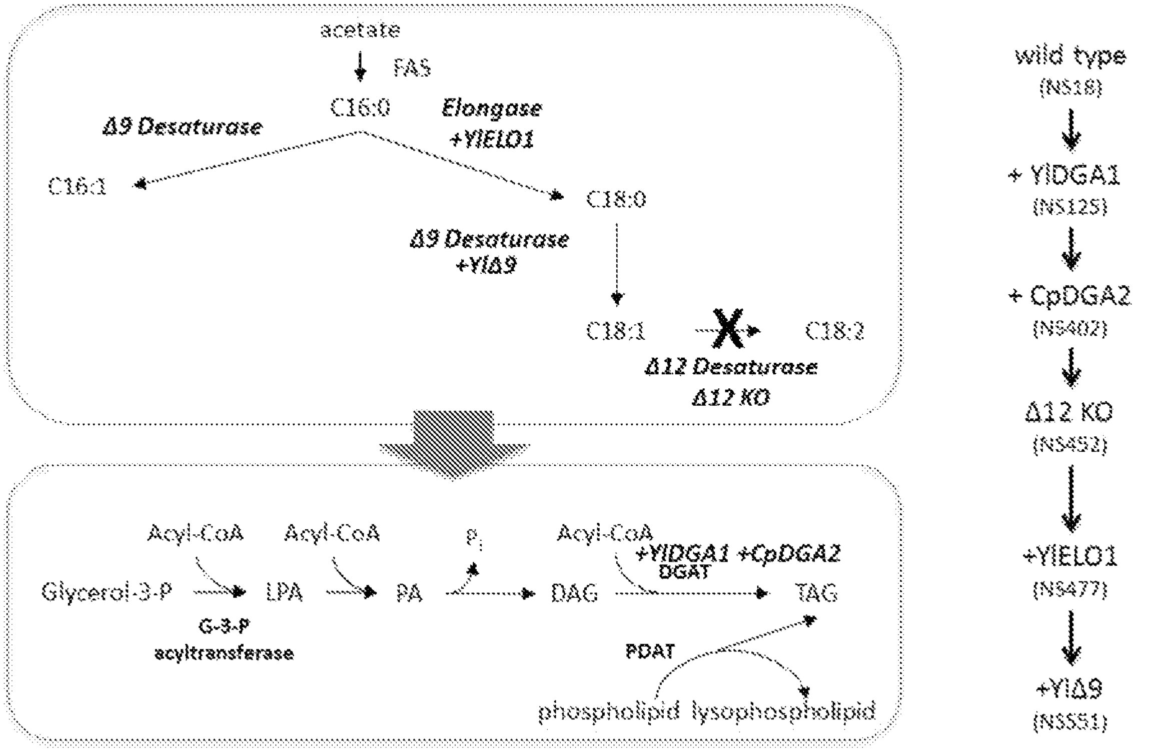
FIG. 13 depicts the strategy for engineering *Y. lipolytica* strain NS551.

The *Y. lipolytica* Δ9 desaturase gene was overexpressed in strain NS477, which is described in Example 5, resulting in strain NS551. Strain NS551 expresses *Y. lipolytica* DGA1, *C. purpurea* DGA2, *Y. lipolytica* ELO1, *Y. lipolytica* Δ9, and comprises a Δ12 knockout. This strain contains approximately 87% oleic acid as a percentage of total C16 and C18 fatty acids. FIG. 13 provides an overview of the bioengineering of strain NS551.

EXAMPLE 12

Increasing Elongase Activity in *A. adeninivorans*

Figure 14:
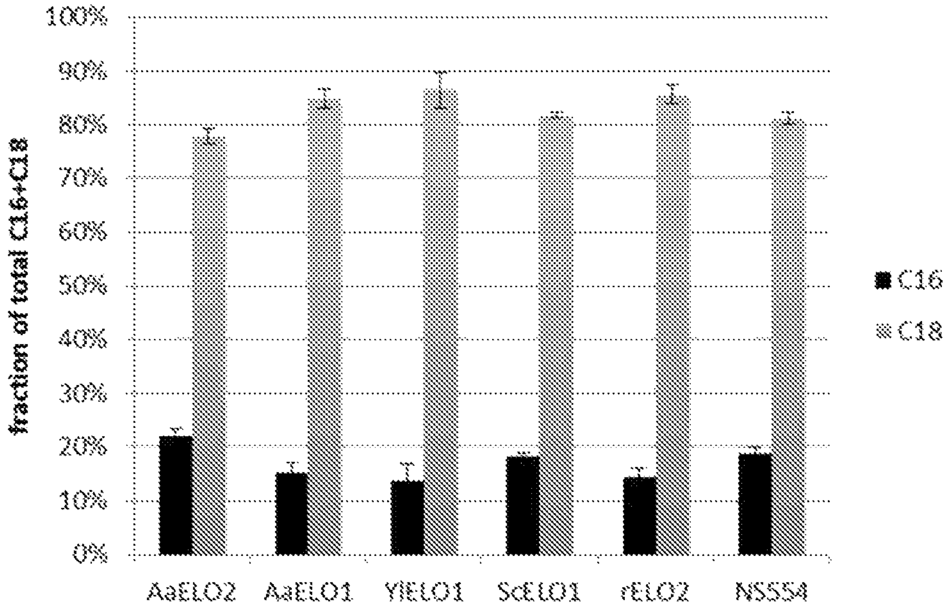
FIG. 14 depicts the percentage of C16 and C18 fatty acids that are either C16 or C18 fatty acids for an *A. adeninivorans* strain comprising a Δ1.2 desaturase knockout and the addition of various elongase genes. Each elongase gene was added to *A. adeninivorans* strain NS554, which comprises a Δ12 desaturase knockout and is shown as a control.

Elongase genes from *A. adeninivorans* (AaELO1, SEQ ID NO:108; AaELO2, SEQ ID NO:160), *Y. lipolytica* (Y1 ELO1, SEQ ID NO:6), *S. cerevisiae* (ScELO1, SEQ ID NO:158), and *R. norvegicus* (rELO2, SEQ ID NO:156) were expressed in *A. adeninivorans* strain NS554 via random genomic integration of a linear expression cassette. NS554 carries deletion of the Δ12 desaturase gene (SEQ ID NO:50) in wild-type *A. adeninivorans*. The expression of AaELO1, YlELO1, and rELO2 all increased the C18 fatty acid content of the cells, suggesting increased elongation of C16 fatty acids (FIG. 14). AaELO1, YlELO1, and rELO2 expression in NS554 also increased oleic acid content (FIG. 15).

EXAMPLE 13

Switching Elongase Specificity in *Y. lipolytica*

Elongase genes from *A. adeninivorans* (AaELO1, SEQ ID NO:108; AaELO2, SEQ ID NO:160), *Y. lipolytica* (Y1 ELO1, SEQ ID NO:6), *S. cerevisiae* (ScELO1, SEQ ID NO:158) and *R. norvegicus* (rELO2, SEQ ID NO:156) were expressed in *Y. lipolytica* strain NS276 via random genomie integration of a linear expression cassette. NS276 carries deletion of the ELO1 gene (SEQ ID NO:6) in wild-type *Y. lipolytica*. Expression of rELO2 increased the C18 fatty acid content of the cells, suggesting increased elongation of C16 fatty acids (FIG. 16). Additionally, rELO2 expression in NS276 also increased oleic acid content (FIG. 15).

EXAMPLE 14

Increasing Elongase Activity in *A. adeninivorans*

The elongase 1 gene from *Y. lipolytica* (Y1 ELO1, SEQ ID NO:6) was expressed in *A. adeninivorans* strain NS557 via random genomics integration of a linear expression cassette. NS557 carries a deletion of the Δ12 desaturase gene (SEQ ID NO:50) in wild-type *A. adeninivorans* and the *Y. lipolytica* gene for DGA1 (SEQ ID NO:20). Most transormants produced increased C18 fatty acids, suggesting that C16 fatty acids were elongated by the elongase (FIG. 17). Ninty-five total isolates were screened, and FIG. 17 depicts representative results. The top performing isolate was named NS776, and its lipid composition was further analyzed. Approximately 87% of the C16 and C18 fatty acids in strain NS776 were oleic acid (FIG. 18).

EXAMPLE 15

Combinations of Genetic Modifications in *Y. lipolytica*

Various combinations of genetic modifications were introduced into *Y. lipolytica*. The strategy for introducing some of modifications is shown in FIG. 19. Wild type *Y. lipolytica* strain NS18 was used as the parent strain (obtained from ARS Culture Collection, NRRL #YB 392), Strain NS804 was prepared from strain NS 18 by first deleting the SCT1 gene (SEQ ID NO:18) and then adding the SCT1 gene from *A. adeninivorans* (SEQ ID NO:44). Strain NS809 was prepared from strain NS804 by first deleting the Δ9 desaturase gene (SEQ ID NO:4) and then adding, the 19 desaturase gene from *Puccino graminis* (SEQ ID NO:14). Strain NS810 was prepared from strain NS804 by first deleting the Δ9 desaturase gene (SEQ ID NO:4) and then adding the Δ9 desaturase gene from *A. adeninivorans* (SEQ. ID NO:8).

Strain NS813 was prepared from strain NS18 deleting, the Δ12 desaturase gene (SEQ ID NO:2), overexpressing the DGA1 gene from *Y. lipolytica* (SEQ ID NO:20), adding the DGA2 gene from *C. purpurea* (SEQ ID NO:38), and adding the ELO2 gene from *R. norvegicus* (SEQ ID NO:156).

Strain NS814 was prepared from strain NS18 by deleting the Δ12 desaturase gene (SEQ ID NO:2), deleting the Δ9 desaturase gene (SEQ ID NO:4), adding the Δ9 desaturase gene from *A. adeninivorans* (SEQ ID NO:8), deleting the SCT1 gene (SEQ ID NO:18), adding the SCT1 gene from *A. adeninivorans* (SEQ ID NO:44), and adding the ELO2 gene from *R. norvegicus* (SEQ ID NO:156).

The fatty acid profies for strains NS18, NS804, NS809, NS810, NS813, and NS814 are shown in FIG. 20. Each modified strain produced more oleic acid (C18:1) than the wild type strain.

Strain NS968 was prepared from strain NS809 by deleting the Δ12 gene (SEQ ID NO:2). Strain NS975 was prepared from strain NS968 by adding the ELO2 gene from *R. norvegicus* (SEQ ID NO:156), and adding the DGA1 gene from *R. toruloides* (SEQ ID NO:22). Strains NS992, NS993, and NS994 are three isolates prepared from strain NS975 by adding the Δ9 desaturase gene from *Puccinia graminis* (SEQ ID NO:14), adding an additional copy of the DGA1 gene from *R. toruloides* (SEQ ID NO:22), and adding the DOA2 gene from *C. purpurea* (SEQ ID NO:38).

Strain NS812 was prepared from strain NS810 by deleting the Δ12 gene (SEQ ID NO:12). Strain NS969 was prepared from strain NS812 by adding the Δ9 desaturase gene from *Puccinia graminis* (SEQ ID NO:14), adding the DGA1 gene from *R. toruloides* (SEQ ID NO:22), adding the ELO2 gene from *R. norvegicus* (SEQ ID NO:156), and adding the DGA2 gene from *C. purpurea* (SEQ ID NO:38).

Strain NS662 was prepared from strain NS18 by deleting the Δ12 gene (SEQ ID NO:2) deleting the SCT1 gene (SEQ ID NO:18), and adding the SCT1 gene from *A. adeninivorans* (SEQ ID NO:44).

The fatty acid profiles for strains NS18, NS804, NS809, NS968, NS975, NS992, NS993, NS994, NS810, NS812, NS969, NS987, NS988, NS551 (described in Example 11), and NS622 are shown in FIG. 21. Each modified strain produced more oleic acid (18:1) than the wild type strain. Additionally, each strain modified with the DGA2 gene from *C. purpurea* (SEQ ID NO:38) comprised more lipids than the wild type NS18 strain.

INCORPORATION BY REFERENCE

Each of the patents, published patent applications, and non-patent references cited herein is hereby incorporated by reference in its entirety.

EQUIVALENTS

Those skilled in the art will recognize, or be able to ascertain usurp, no more than routine experimentation, many equivalents to the specific embodiments of the invention described herein. Such equivalents are intended to be encompassed by the following claims.

What is claimed is:

1. A yeast cell comprising:

a first genetic modification, wherein the first genetic modification is a knockout mutation of a native Δ12 desaturase protein;

a second genetic modification, wherein the second genetic modification increases the expression of an elongase protein, a diacylglycerol acyltransferase protein, or a glycerol-3-phosphate acyltransferase protein; and a third genetic modification, wherein the third genetic modification results from a transformation with a nucleic acid comprising a gene encoding an exogenous fungal Δ9 desaturase protein.

2. The yeast cell of claim 1, wherein the second genetic modification results from a transformation with a nucleic acid comprising a gene encoding an elongase protein, a diacylglycerol acyltransferase protein, or a glycerol-3-phosphate acyltransferase protein.

3. The yeast cell of claim 1, wherein:

the exogenous Δ9 desaturase protein is a *Puccinia graminis, Arxula adeninivorans* or *Microbotryum violaceum* Δ9 desaturase protein.

4. The yeast cell of claim 1, wherein the yeast cell is selected from the group consisting of *Arxula, Aspergillus, Aurantiochytrium, Candida, Claviceps, Cryptococcus, Cunninghamella, Geotrichum, Hansenula, Kluyveromyces, Kodamaea, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Wickerhamomyces*, and *Yarrowia*.

5. The yeast cell of claim 1, wherein the yeast cell is selected from the group consisting of *Arxula adeninivorans, Saccharomyces cerevisiae*, and *Yarrowia lipolytica*.

6. The yeast cell of claim 1, wherein:

the yeast cell is *Yarrowia lipolytica*; and the native Δ12 desaturase protein has the amino acid sequence set forth in SEQ ID NO: 1.

7. The yeast cell of claim 1, wherein the yeast cell comprises at least 50% lipid as measured by % dry cell weight.

8. The yeast cell of claim 1, wherein the yeast cell comprises oleic acid at a concentration of at least 70% as a percentage of total C16 and C18 fatty acids in the yeast cell.

9. The yeast cell of claim 1, wherein the second genetic modification increases the expression of a glycerol-3-phosphate acyltransferase protein.

10. The yeast cell of claim 2, wherein the glycerol-3-phosphate acyltransferase protein is an exogenous glycerol-3-phosphate acyltransferase protein.

11. The yeast cell of claim 1, wherein the second genetic modification increases the expression of an elongase protein.

12. The yeast cell of claim 1, wherein the second genetic modification increases the expression of a diacylglycerol acyltransferase protein.

13. The yeast cell of claim 1, wherein the yeast cell comprises a knockout mutation of a native Δ9 desaturase protein.

14. The yeast cell of claim 1, wherein the exogenous Δ9 desaturase protein has an increased specificity for C18 saturated fatty acids relative to a native Δ9 desaturase protein of the yeast cell.

15. The yeast cell of claim 10, wherein the exogenous glycerol-3-phosphate acyltransferase protein is an *Arxula adeninivorans* glycerol-3-phosphate acyltransferase.

16. The yeast cell of claim 2, wherein the elongase protein is an exogenous elongase protein.

17. The yeast cell of claim 16, wherein the exogenous elongase protein is a *Rattus norvegicus* or *Yarrowia lipolytica* elongase.

18. The yeast cell of claim 2, wherein the diacylglycerol acyltransferase protein is an exogenous diacylglycerol acyltransferase protein.

19. The yeast cell of claim 18, wherein the exogenous diacylglycerol acyltransferase protein is a *Rhodosporidium toruloides, Yarrowia lipolytica, Arxula adeninivorans*, or *Claviceps purpurea* diacylglycerol acyltransferase.

20. The yeast cell of claim 1, wherein the second genetic modification results from transformation with a nucleic acid comprising a gene encoding a diacylglycerol acyltransferase type 1 protein, a gene encoding a diacylglycerol acyltransferase type 2 protein, or a gene encoding a diacylglycerol acyltransferase type 1 protein and a gene encoding a diacylglycerol acyltransferase type 2 protein.

21. The yeast cell of claim 1, wherein the second genetic modification results from a transformation with one or more nucleic acids comprising a gene encoding an elongase protein, a diacylglycerol acyltransferase protein, and a glycerol-3-phosphate acyltransferase protein.

22. The yeast cell of claim 21, wherein the elongase protein is a *Rattus norvegicus* or *Yarrowia lipolytica* elongase, the diacylglycerol acyltransferase protein is a *Rhodosporidium toruloides, Yarrowia lipolytica, Arxula adeninivorans* and/or *Claviceps purpurea* diacylglycerol acyltransferase, and the glycerol-3-phosphate acyltransferase protein is an *Arxula adeninivorans* glycerol-3-phosphate acyltransferase.

* * * * *